(12) United States Patent
Kamal et al.

(10) Patent No.: US 8,883,809 B2
(45) Date of Patent: Nov. 11, 2014

(54) ISOXAZOLE/ISOXAZOLINE/COMBRETASTATIN LINKED DIHYDROQUINAZOLINONE HYBRIDS AS POTENTIAL ANTICANCER AGENTS AND PROCESS FOR THE PREPARATION THEREOF

(75) Inventors: Ahmed Kamal, Hyderabad (IN); Earla V. Bharathi, Hyderabad (IN); Jonnala S. Reddy, Hyderabad (IN); Dudekula Dastagiri, Hyderabad (IN); Arutla Viswanath, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 557 days.

(21) Appl. No.: 13/129,974

(22) PCT Filed: Sep. 8, 2009

(86) PCT No.: PCT/IN2009/000490
§ 371 (c)(1),
(2), (4) Date: Jan. 2, 2012

(87) PCT Pub. No.: WO2010/058417
PCT Pub. Date: May 27, 2010

(65) Prior Publication Data
US 2012/0283439 A1 Nov. 8, 2012

(30) Foreign Application Priority Data
Nov. 19, 2008 (IN) .......................... 2602/DEL/2008

(51) Int. Cl.
A01N 43/54 (2006.01)
A61K 31/517 (2006.01)
C07D 239/72 (2006.01)
C07D 401/00 (2006.01)

(52) U.S. Cl.
USPC ......... 514/266.2; 544/284; 548/240; 514/378

(58) Field of Classification Search
USPC ............................ 514/378; 548/240; 544/284
See application file for complete search history.

(56) References Cited

FOREIGN PATENT DOCUMENTS

WO  WO-9520567 A1  8/1995

OTHER PUBLICATIONS

McMahon et al. (2000) Pinedo et al (2000).*
Hamel E et al.: "Antitumor 2,3-Dihydro-2-(aryl)-4(1H)-Quinazolinone Derivatives Interactions with Tubulin" Biochemical Pharmacology, Pergamon, Oxford, GB LNKD-DOI:10.1016/0006-2952(95)02156-6, vol. 51, No. 1, Jan. 1, 1996, pp. 53-59.
Kaffy J et al.: "Isoxazole-type derivatives related to combretastatin A-4, synthesis and biological evaluation" Bioorganic & Medicinal Chemistry, Pergamon, GB LNKD-DOI: 10.1016/J.BMC.2006.02.001, vol. 14, No. 12, Jun. 15, 2006, pp. 4067-4077.
Gian Cesare Tron et al.: "Medicinal Chemistry of Combretastatin A4: Present and future directions" Journal of Medicinal Chemistry, vol. 49, No. 11, Jun. 1, 2006, pp. 3033-3044.
Simoni D et al: "Heterocyclic and phenyl double-bond-locked combretastatin analogues possessing potent apoptosis-inducing activity in HL60 and in MDR cell lines" Journal of Medicinal Chemistry, American Chemical Society, Washington, US LNKD-DOI:10.1021/JM049622B, vol. 48, No. 3, Feb. 10, 2005, pp. 723-736.
Kamal A et al: Synthesis and biological activity of fluoroquinolone-pyrrolo[2,1-c][1,4] benzodiazepine conjugates: Bioorganic & Medicinal Chemistry, Pergamon, GB LNKD- DOI: 10.1016/J.BMC.2005.01.010, vol. 13, No. 6, Mar. 15, 2005, pp. 2021-2029.
Kamal A et al: "Design, Synthesis, and Evaluation of New Non-Crosslinking Pyrrolobenzodiazepine Dimers with Efficient DNA Binding Ability and Potent Antitumor Activity" Journal of Medicinal Chemistry, American Chemical Society, Washington, US LNKD-DOI:10.1021/JM020124H, vol. 45, Jan. 1, 2002, pp. 4679-4688.

* cited by examiner

Primary Examiner — Paul V. Ward
(74) Attorney, Agent, or Firm — Edwards Wildman Palmer LLP; Barry Kramer; Nicholas J. DiCeglie, Jr.

(57) ABSTRACT

The present invention provides a compound of general formulae 3a-i to 6a-i, 7a-i to 10a-i, 12a-i to 15a-i, 16a-i to 19a-i, 21a-i to 24a-i, 25a-i to 28a-i, 30a-i to 33a-i, 34a-i to 37a-i and 39a-i to 42a-i, 43a-i to 46a-i useful as potential antitumour agents against human cancer cell lines and a process for the preparation thereof.

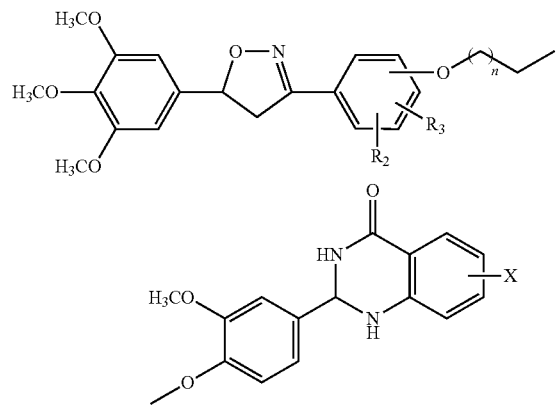

3a-1 to 6a-1 R$_3$ = 2-OCH$_3$, H; H = Cl, X = CH$_3$, MK
7a-1 to 10a-1 R$_3$ = 2-OCH$_3$ R$_3$ = U-OCH$_3$ X = H, Cl, CH$_3$, OCH$_1$ n = 1-9

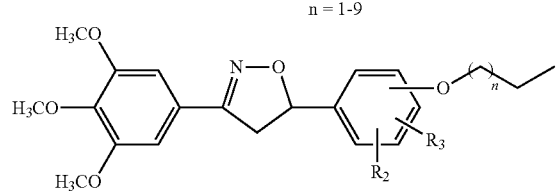

-continued
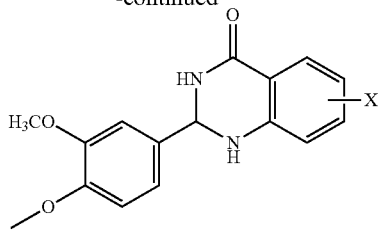
12a-1 to 10a-1 R₃ = 2-OCH₃, R₃ H; X = H, Cl, CH₃, OCH₃
10a-1 to 10a-1 R₃ = 2-OCH₃ R₃ = COCH₃ R₃ = COCl X H, Cl, CH₃ OCH₁
n = 1-9
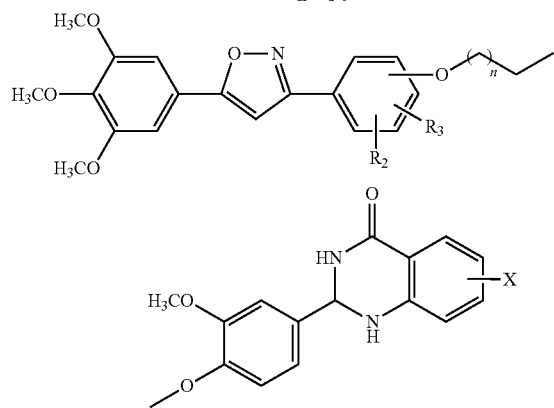
21a-1 to 24a-1 R₃ = 2-OCH₃, R₃ = ClH; X = H, Cl, CH₃, OCH₃
28a-1 to 28a-1 R₃ = 2-OCH₃, R₃ = 2OCH₃, X = H, Cl, CH₃ OCH₃
n = 1-9
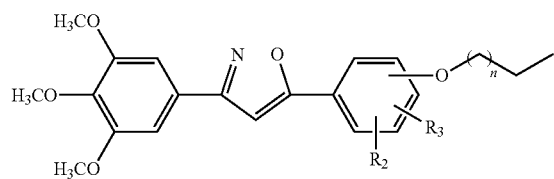
-continued
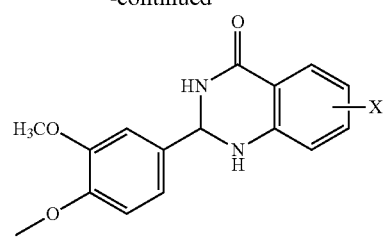
30a-1 to 33a-1 R₃ = 2-OCH₃, R₃ = CH; K = H, Cl, CH₃, OCH₃
34a-i to 37a-i R₃ = 2-OCH₃, R₃ = 2OCH₃, X = H, Cl, CH₃ OCH₃
n = 1-9
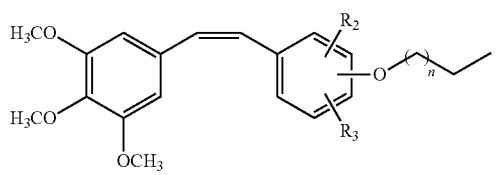
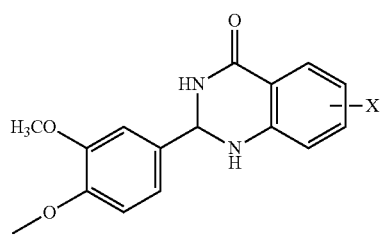
39a-1 to 42a-1 R₂ = 2-OCH₃, R₃ = CH; X = H, Cl, CH₃, OCH₃
42a-i to 44a-i R₂ = 2-OCH₃, R₃ = 2-OCH₃, X = H, Cl, CH₃ OCH₃
n = 1-9
8 Claims, No Drawings

ISOXAZOLE/ISOXAZOLINE/COMBRETASTATIN LINKED DIHYDROQUINAZOLINONE HYBRIDS AS POTENTIAL ANTICANCER AGENTS AND PROCESS FOR THE PREPARATION THEREOF

CROSS REFERENCE TO RELATED APPLICATIONS

This application is a U.S. National Stage application under 35 U.S.C. §371 of International Patent Application Serial No. PCT/IN2009/000490, filed Sep. 8, 2009, which claims the benefit of the Indian Patent Application No. 2602/DEL/2008, filed Nov. 19, 2008, the disclosures of each of which are expressly incorporated by reference in their entireties.

FIELD OF THE INVENTION

The present invention relates to Isoxazole/isoxazoline/combretastatin linked dihydroquinazolinone hybrids as anticancer agents. Particularly, the present invention relates to Isoxazole/isoxazoline/combretastatin linked dihydroquinazolinone hybrids of general formula A.

Formula A

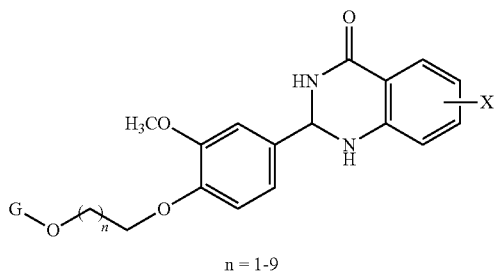

n = 1-9

Where in G=

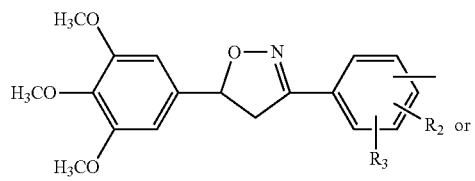

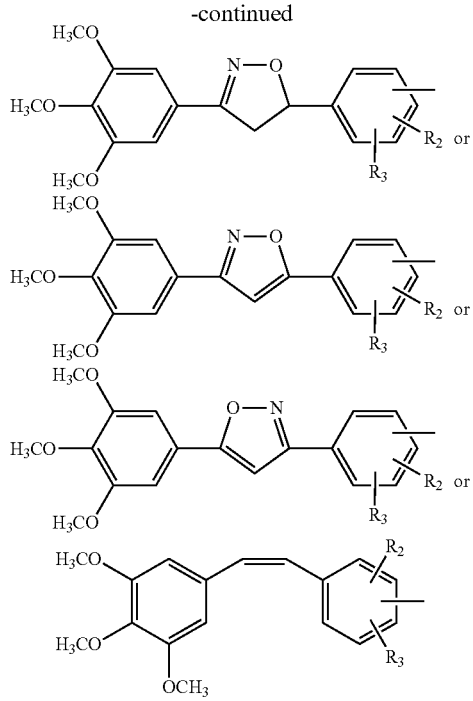

If $R_2$ = 2-OCH$_3$, $R_3$ = 6-OCH$_3$
If $R_2$ = 2-OCH$_3$, $R_3$ = 6-H
X = H, Cl, CH$_3$, OCH$_3$

More particularly the present invention relates to 2-[4-(5-{2,6-Dimethoxy-4-[5-(3,4,5-trimethoxy Phenyl)-4,5-dihydro-isoxazol-3-yl]-phenoxy}-pentyloxy)-3-methoxy-phenyl]-2,3-dihydro-1H quinazolin-4-one, 2-[4-(5-{2,6-Dimethoxy-4-[3-(3,4,5-trimethoxy-phenyl)-4,5-dihydro-isoxazol-5-yl]-phenoxy}-pentyloxy-3-methoxy-phenyl]-2,3-dihydro-1H-quinazolin-4-one, 2-(4-(5-(2,6-dimethoxy-4-(5-(3,4,5-trimethoxy-phenyl isoxazol-3-yl)phenoxy)pentyloxy)-3-methoxyphenyl)-2,3-dihydroquinazolin-4(1H)-one, 2-(4-(5-(2,6-dimethoxy-4-(3-(3,4,5-trimethoxy phenyl) isoxazol-5-yl)phenoxy)pentyloxy)-3-methoxyphenyl)-2,3-dihydroquinazolin-4(1H)-one, (Z)-2-(4-(5-(2,6-dimethoxy-4-(3,4,5-trimethoxystyryl)phenoxy)pentyloxy)-3-methoxyphenyl)-2,3 dihydroquinazolin-4(1H)-one with aliphatic chain length variations useful as anticancer (antitumour) agents. The structural formulae of these isoxazole/isoxazoline/combretastatin-dihydroquinazolinone hybrids is given below.

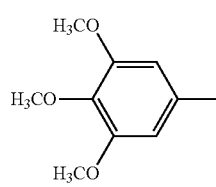

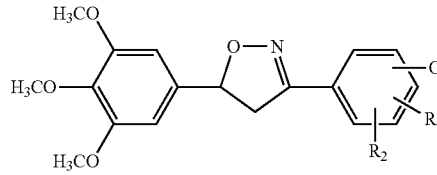

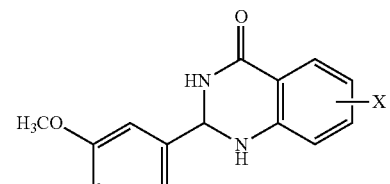

3a-i to 6a-i $R_2$ = 2-OCH$_3$, $R_3$ = 6-H; X = H, Cl, CH$_3$, OCH$_3$
7a-i to 10a-i $R_2$ = 2-OCH$_3$, $R_3$ = 6-OCH$_3$; X = H, Cl, CH$_3$, OCH$_3$, n = 1-9

-continued
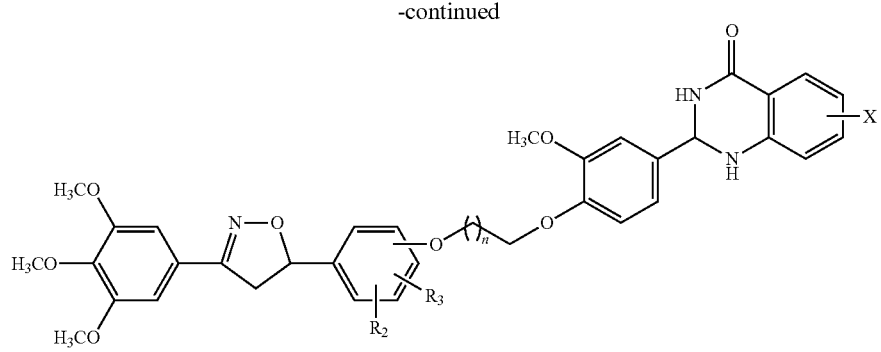
12a-i to 15a-i R₂ = 2-OCH₃, R₃ = 6-H; X = H, Cl, CH₃, OCH₃
16a-i to 19a-i R₂ = 2-OCH₃, R₃ = 6-OCH₃; X = H, Cl, CH₃, OCH₃,
n = 1-9
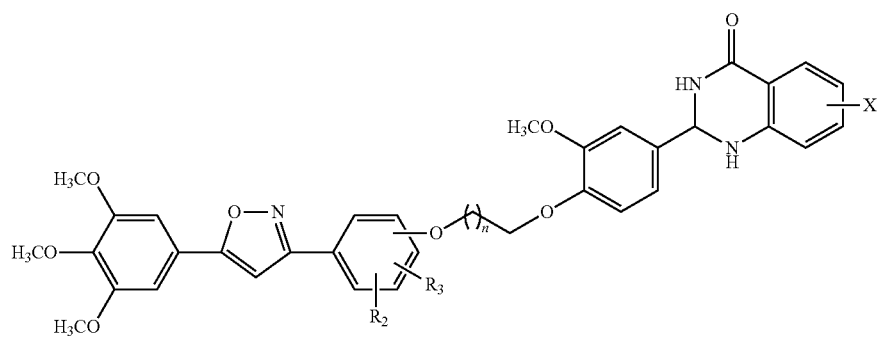
21a-i to 24a-i R₂ = 2-OCH₃, R₃ = 6-H; X = H, Cl, CH₃, OCH₃
25a-i to 28a-i R₂ = 2-OCH₃, R₃ = 6-OCH₃; X = H, Cl, CH₃, OCH₃,
n = 1-9
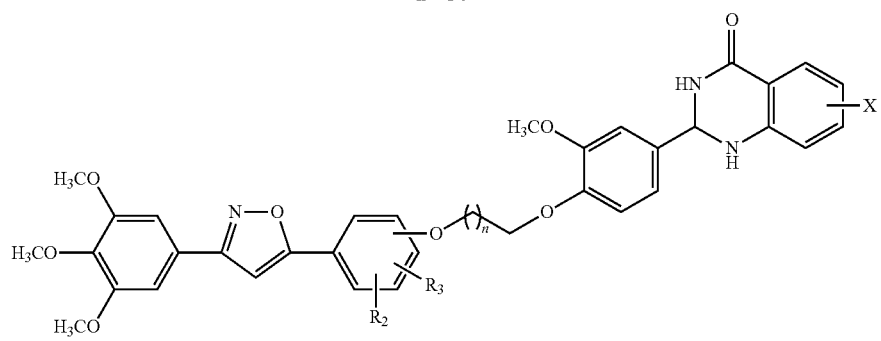
30a-i to 33a-i R₂ = 2-OCH₃, R₃ = 6-H; X = H, Cl, CH₃, OCH₃
34a-i to 37a-i R₂ = 2-OCH₃, R₃ = 6-OCH₃; X = H, Cl, CH₃, OCH₃,
n = 1-9
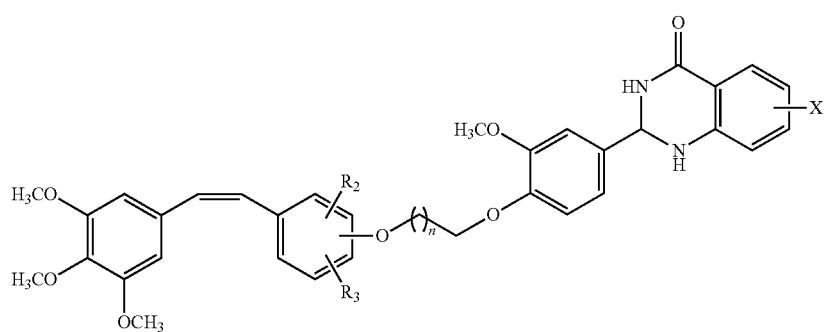
39a-i to 42a-i R₂ = 2-OCH₃, R₃ = 6-H; X = H, Cl, CH₃, OCH₃
43a-i to 46a-i R₂ = 2-OCH₃, R₃ = 6-OCH₃; X = H, Cl, CH₃, OCH₃,
n = 1-9

BACKGROUND OF THE INVENTION

Inhibition of tubulin polymerization is the target of many antitumoural agents known as antimitotic agents or spindle poisons colchicines, podophyllo-toxins and combretastatins are representative examples of compounds that inhibit microtubule assembly by binding to tubulin. 2-Aryl- and 2-styrylquinazolin-4(3H)-ones (SQZ) and 2,3-dihydro-2-aryl-4-quinazolinones (DHPQ) are compounds that possess this common structural feature for an effective interaction with tubulin. The antitumor activities of 2,3-dihydro-2-aryl-4-quinazolinones (DHPQZ) were reported around 1970 (Yale H L, Kalkstein M. Substituted 2,3-dihydro-4(1H)-quinazolinones, a new class of inhibitors_of cell multiplication. *J Med Chem* 1967 10, 334-336, Neil, G. L.; Li, L. H.; Buskirk, H. H.; Moxlcy, T. E. *Cancer Chemother.* 1972, 56, 163-173. and Hamel, E.; Lin, C. M.; Plowman, J.; Wang, H. K.; Lee, K. H.; Paull, K. D. Antitumor 2,3-dihydro-2-(aryl)-4(1H)-quinazolinone derivatives. Interactions with tubulin. *Biochem. Pharmacol.* 1996, 51, 53-59). A more recent reevaluation of this type of compound by NCI against human tumor cell lines reconfirmed that, like colchicine, they are effective inhibitors of tubulin polymerization. Many isoxazole, isoxazoline type moieties related to combretastain A-4 showed potential biological properties particularly anticancer activity (Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. J. Med. Chem. 2005, 48, 723, Julia Kaffy, a Renée Pontikis,a,* Danièle Carrez,b Alain Croisy, Claude Monnereta and Jean-Claude Florent. Bioorg. Med. Chem. 2006, 14, 4067-4077, Gian Ceasure Tron, Tracy Pirali, Giovanni sorba, Francesca pagliai, Sara Buasacca and Armado A. Genazzani. J. Med. Chem. 2006, 49, 3033-3044. and Tracey Pirali, Sara buasacca, Lorena Beltrami, Daniela Imovilli, Francesca Paliai, Gianluca Migilio, Alberto Massrotti, Luisella Verotta, Gian Cesare Tron, Givanni Sorba, and Armado A. Genazzani. J. Med. Chem. 2006, 49, 5372-5376). Some of the heterocyclic bridged Combretastains showed an attractive profile cytotoxicity and were able to induce apoptosis at lower concentrations.

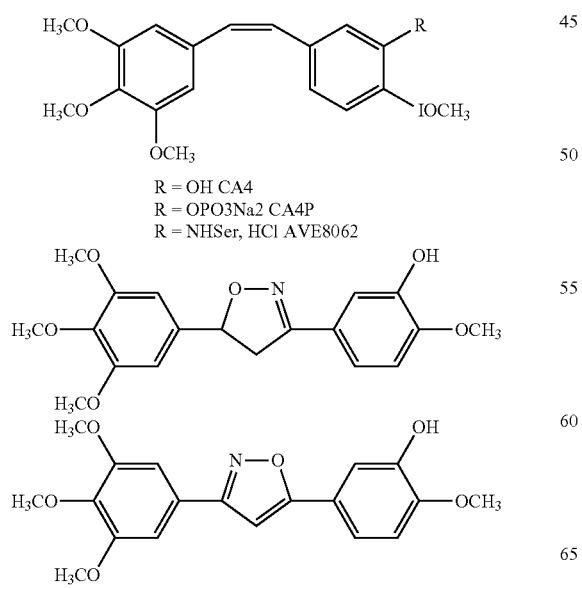

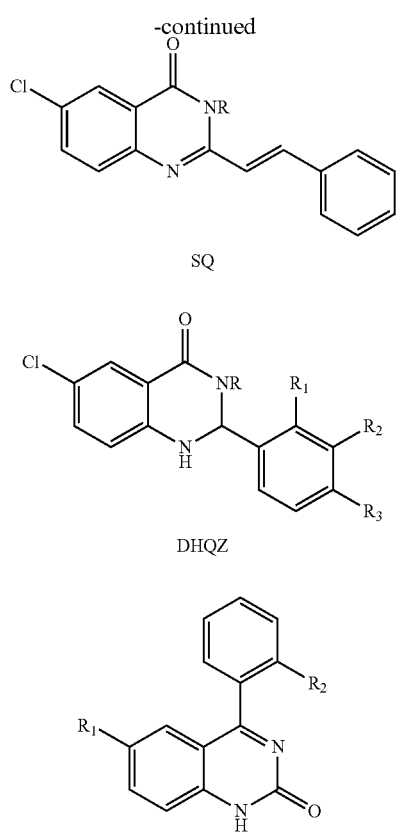

OBJECTIVES OF THE INVENTION

The main objective of the present invention is to provide novel isoxazole/isoxazoline/combretastatin linked dihydroquinazolinone hybrids useful as antitumour agents.

Yet another object of this invention is to provide a process for the preparation of novel isoxazole/isoxazoline/combretastatin linked dihydroquinazolinone hybrids.

SUMMARY OF THE INVENTION

Accordingly the present invention provides a novel isoxazole/isoxazoline/combretastatin linked dihydroquinazolinone hybrids of general formulae A

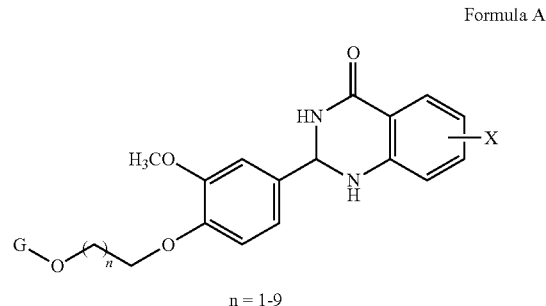

Formula A n = 1-9

Where in G=

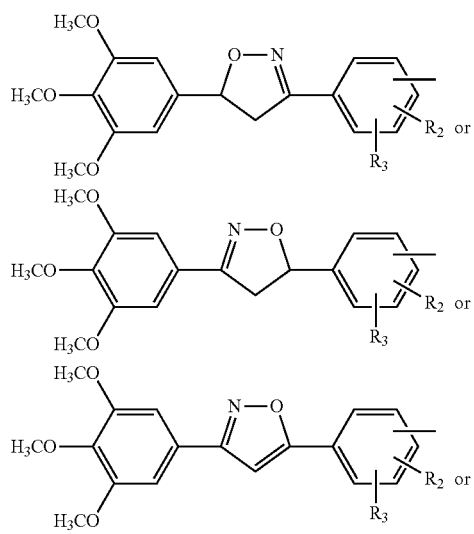

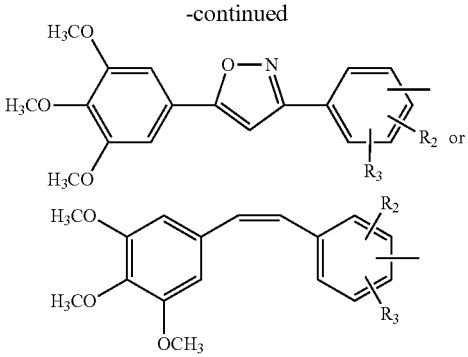

If R$_2$ = 2-OCH$_3$, R$_3$ = 6-OCH$_3$
If R$_2$ = 2-OCH$_3$, R$_3$ = 6-H
X = H, Cl, CH$_3$, OCH$_3$

In an embodiment of the present invention the novel isoxazole/isoxazoline/combretastatin linked dihydroquinazolinone hybrids of formulae A is represented by the compounds of general formulae 3a-i to 6a-i, 7a-i to 10a-i, 12a-i to 15a-i, 16a-i to 19a-i, 21a-i to 24a-i, 25a-i to 28a-i, 30a-i to 33a-i, 34a-i to 37a-i and 39a-i to 42a-i, 43a-i to 46a-i.

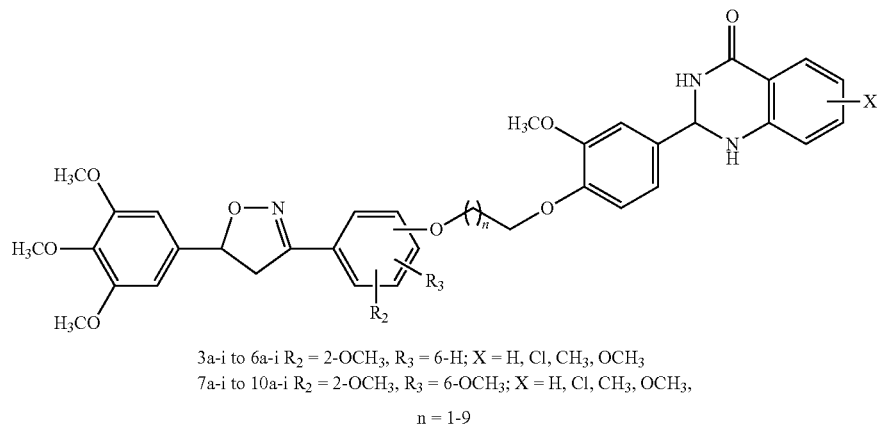

3a-i to 6a-i R$_2$ = 2-OCH$_3$, R$_3$ = 6-H; X = H, Cl, CH$_3$, OCH$_3$
7a-i to 10a-i R$_2$ = 2-OCH$_3$, R$_3$ = 6-OCH$_3$; X = H, Cl, CH$_3$, OCH$_3$, n = 1-9

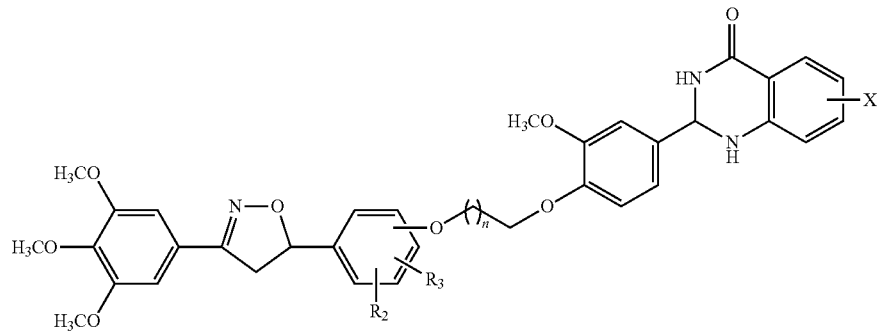

12a-i to 15a-i R$_2$ = 2-OCH$_3$, R$_3$ = 6-H; X = H, Cl, CH$_3$, OCH$_3$
16a-i to 19a-i R$_2$ = 2-OCH$_3$, R$_3$ = 6-OCH$_3$; X = H, Cl, CH$_3$, OCH$_3$, n = 1-9

-continued

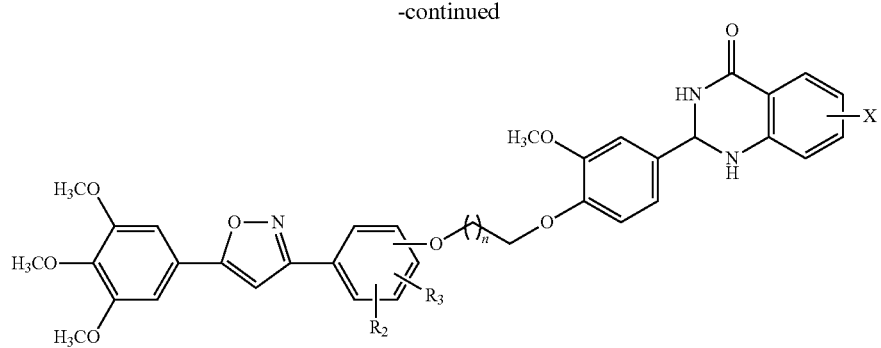

21a-i to 24a-i R₂ = 2-OCH₃, R₃ = 6-H; X = H, Cl, CH₃, OCH₃
25a-i to 28a-i R₂ = 2-OCH₃, R₃ = 6-OCH₃; X = H, Cl, CH₃, OCH₃, n = 1-9

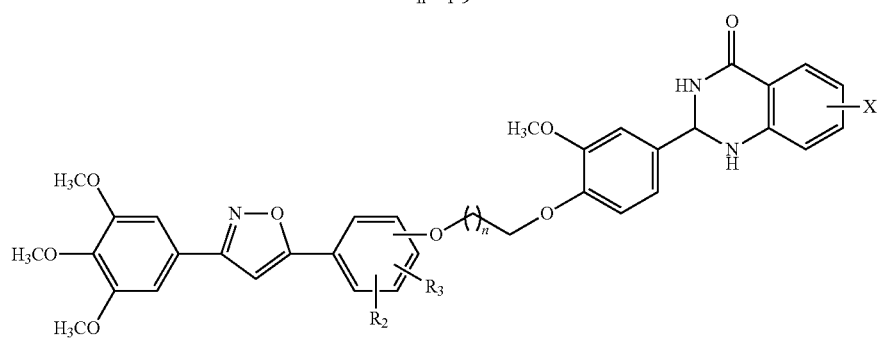

30a-i to 33a-i R₂ = 2-OCH₃, R₃ = 6-H; X = H, Cl, CH₃, OCH₃
34a-i to 37a-i R₂ = 2-OCH₃, R₃ = 6-OCH₃; X = H, Cl, CH₃, OCH₃, n = 1-9

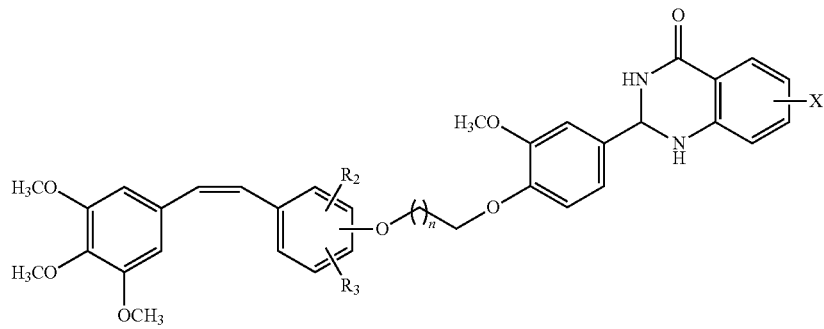

39a-i to 42a-i R₂ = 2-OCH₃, R₃ = 6-H; X = H, Cl, CH₃, OCH₃
43a-i to 46a-i R₂ = 2-OCH₃, R₃ = 6-OCH₃; X = H, Cl, CH₃, OCH₃, n = 1-9

In yet another embodiment the isoxazole/isoxazoline/combretastatin linked dihydroquinazolinone hybrids are represented by the group of the following compounds:

2-[3-Methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (3a)
2-[3-Methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (3b)
2-[3-Methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (3c)
2-[3-Methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (3d)
2-[3-Methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (3e)
2-[3-Methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (3f)
2-[3-Methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (3g)
2-[3-Methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (3h)
2-[3-Methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (3i)

6-Chloro-2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (4a)

6-Chloro-2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (4b)

6-Chloro-2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (4c)

6-Chloro-2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (4d)

6-Chloro-2-[3-methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (4e)

6-Chloro-2-[3-Methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (4f)

6-Chloro-2-[3-methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (4g)

6-Chloro-2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (4h)

6-Chloro-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (4i)

6-Methyl 2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (5a)

6-Methyl 2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (5b)

6-Methyl 2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (5c)

6-Methyl 2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (5d)

6-Methyl 2-[3-methoxy-4-(6-{2-methoxy-5-[5-(3,4,5-trimethoxy-phenyl)-4,5-dihydro-isoxazol-3-yl]-hexyloxy}-butoxy)-phenyl]-2,3-dihydro-1H-quinazolin-4-one (5e)

6-Methyl 2-[3-methoxy-4-(7-{2-methoxy-5-[5-(3,4,5-trimethoxy-phenyl)-4,5-dihydro-isoxazol-3-yl]-phenoxy}-heptoxy)-phenyl]-2,3-dihydro-1H-quinazolin-4-one (5f)

6-Methyl 2-[3-methoxy-4-(8-{2-methoxy-5-[5-(3,4,5-trimethoxy-phenyl)-4,5-dihydro-isoxazol-3-yl]-phenoxy}-octoxy)-phenyl]-2,3-dihydro-1H-quinazolin-4-one (5g)

6-Methyl 2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (5h)

6-Methyl-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (5i)

6-Methoxy-2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (6a)

6-Methoxy-2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (6b)

6-Methoxy-2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (6c)

6-Methoxy-2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (6d)

6-Methoxy-2-[3-methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (6e)

6-Methoxy-2-[3-methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (6f)

6-Methoxy-2-[3-methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (6g)

6-Methoxy-2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (6h)

6-Methoxy-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (6i)

2-[4-(2-{2,6-Dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (7a)

2-[4-(3-{2,6-Dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (7b)

2-[4-(4-{2,6-Dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (7c)

2-[4-(5-{2,6-Dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (7d)

2-[4-(6-{2,6-Dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (7e)

2-[4-(7-{2,6-Dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (7f)

2-[4-(8-{2,6-Dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (7g)

2-[4-(9-{2,6-Dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (7h)

2-[4-(10-{2,6-Dimethoxy-4-[5-(3,4,5-trimethoxy-phenyl)-4,5-dihydro isoxazol-3-yl]-phenoxy}-decyloxy)-3-methoxy-phenyl]-2,3-dihydro 1H-quinazolin-4-one (7i)

6-Chloro-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (8a)

6-Chloro-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (8b)

6-Chloro-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (8c)

6-Chloro-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro 1H-quinazolin-4-one (8d)

6-Chloro-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (8e)

6-Chloro-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (8f)

6-Chloro-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (8g)

6-Chloro-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (8h)

6-Chloro-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (8i)

6-Methyl-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (9a)

6-Methyl-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (9b)

6-Methyl-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (9c)

6-Methyl-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (9d)

6-Methyl-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (9e)

6-Methyl-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (9f)

6-Methyl-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (9g)

6-Methyl-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (9h)

6-Methyl-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (9i)

6-Methoxy-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (10a)

6-Methoxy-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (10b)

6-Methoxy-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (10c)

6-Methoxy-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (10d)

6-Methoxy-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (10e)

6-Methoxy-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (10f)

6-Methoxy-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (10g)

6-Methoxy-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (10h)

6-Methoxy-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (10i)

2-[3-Methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (12a)

2-[3-Methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (12b)

2-[3-Methoxy-4-(4-{2-methoxy-5-[3-(3,4,5-trimethoxy-phenyl)-4,5-dihydro-isoxazol-5-yl]-phenoxy}-butoxy)-phenyl]-2,3-dihydro-1H-quinazolin-4-one (12c)

2-[3-Methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (12d)

2-[3-Methoxy-4-(6-{2-methoxy-5-[3-(3,4,5-trimethoxy-phenyl)-4,5 dihydro-isoxazol-5-yl]-phenoxy}-heptyloxy)-phenyl]-2,3-dihydro-1H-quinazolin-4-one (12e)

2-[3-Methoxy-4-(7-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (12f)

2-[3-Methoxy-4-(8-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (12g)

2-[3-Methoxy-4-(9-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (12h)

2-[3-Methoxy-4-(10-{2-methoxy-5-[3-(3,4,5-trimethoxy-phenyl)-4,5-dihydro-isoxazol-5-yl]-phenoxy}-dedyloxy)-phenyl]-2,3-dihydro-1H-quinazolin-4-one (12i)

6-Chloro-2-[3-methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (13a)

6-Chloro-2-[3-methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (13b)

6-Chloro-2-[3-methoxy-4-(4-{2-methoxy-5-[3-(3,4,5-trimethoxy-phenyl)-4,5-dihydro-isoxazol-5-yl]-phenoxy}-butyloxy)-phenyl]-2,3-dihydro-1H-quinazolin-4-one (13c)

6-Chloro-2-[3-methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (13d)

6-Chloro-2-[3-methoxy-4-(6-{2-methoxy-5-[3-(3,4,5-trimethoxy-phenyl)-4,5-dihydro-isoxazol-5-yl]-phenoxy}-hexyloxy)-phenyl]-2,3-dihydro-1H-quinazolin-4-one (13e)

6-Chloro-2-[3-methoxy-4-(7-{2-methoxy-5-[3-(3,4,5-trimethoxy-phenyl)-4,5-dihydro-isoxazol-5-yl]-phenoxy}-heptyloxy)-phenyl]-2,3-dihydro-1H-quinazolin-4-one (13f)

6-Chloro-2-[3-methoxy-4-(8-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (13g)

6-Chloro-2-[3-methoxy-4-(9-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (13h)

6-Chloro-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (13i)

6-Methyl-2-[3-methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (14a)

6-Methyl-2-[3-methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (14b)

6-Methyl-2-[3-methoxy-4-(4-{2-methoxy-5-[3-(3,4,5-trimethoxy-phenyl)-4,5-dihydro-isoxazol-5-yl]-phenoxy}-butyloxy)-phenyl]-2,3-dihydro-1H-quinazolin-4-one (14c)

6-Methyl-2-[3-methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (14d)

6-Methyl-2-[3-methoxy-4-(6-{2-methoxy-5-[3-(3,4,5-trimethoxy-phenyl)-4,5-dihydro-isoxazol-5-yl]-phenoxy}-hexyloxy)-phenyl]-2,3-dihydro-1H-quinazolin-4-one (14e)

6-Methyl-2-[3-methoxy-4-(7-{2-methoxy-5-[3-(3,4,5-trimethoxy-phenyl)-4,5-dihydro-isoxazol-5-yl]-phenoxy}-heptyloxy)-phenyl]-2,3-dihydro-1H-quinazolin-4-one (14f)

6-Methyl-2-[3-methoxy-4-(8-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (14g)

6-Methyl-2-[3-methoxy-4-(9-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (14h)

6-Methyl-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (14i)

6-Methoxy-2-[3-methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (15a)

6-Methoxy-2-[3-methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (15b)

6-Methoxy-2-[3-methoxy-4-(4-{2-methoxy-5-[3-(3,4,5-trimethoxy-phenyl)-4,5-dihydro-isoxazol-5-yl]-phenoxy}-butyloxy)-phenyl]-2,3-dihydro-1H-quinazolin-4-one (15c)

6-Methoxy-2-[3-methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (15d)

6-Methoxy-2-[3-methoxy-4-(6-{2-methoxy-5-[3-(3,4,5-trimethoxy-phenyl)-4,5-dihydro-isoxazol-5-yl]-phenoxy}-hexyloxy)-phenyl]-2,3-dihydro-1H quinazolin-4-one (15e)

6-Methoxy-2-[3-methoxy-4-(7-{2-methoxy-5-[3-(3,4,5-trimethoxy-phenyl)-4,5-dihydro-isoxazol-5-yl]-phenoxy}-heptyloxy)-phenyl]-2,3-dihydro-1H-quinazolin-4-one (15f)

6-Methoxy-2-[3-methoxy-4-(8-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (15g)

6-Methoxy-2-[3-methoxy-4-(9-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (15h)

6-Methoxy-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (15i)

2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (16a)

2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (16b)

2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (16c)

2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]-2,3-dihydro-1H-quinazolin-4-one (16d)

2-[4-(6-{2,6-Dimethoxy-4-[3-(3,4,5-trimethoxy-phenyl)-4,5-dihydro-isoxazol-5-yl]-phenoxy}hexyloxy)-3-methoxy-phenyl]-2,3-dihydro-1H-quinazolin-4-one (16e)

2-[4-(7-{2,6-Dimethoxy-4-[3-(3,4,5-trimethoxy-phenyl)-4,5-dihydro-isoxazol-5-yl]-phenoxy}-heptyloxy)-3-methoxy-phenyl]-2,3-dihydro-1H-quinazolin-4-one (16f)

2-[4-(8-{2,6-Dimethoxy-4-[3-(3,4,5-trimethoxy-phenyl)-4,5-dihydro-isoxazol-5-yl]-phenoxy}-octyloxy)-3-methoxy-phenyl]-2,3-dihydro-1H-quinazolin-4-one (16g)

2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]-2,3-dihydro-1H-quinazolin-4-one (16h)

2-[4-(10-{2,6-Dimethoxy-4-[3-(3,4,5-trimethoxy-phenyl)-4,5-dihydro-isoxazol-5-yl]-phenoxy}-decyloxy)-3-methoxy-phenyl]-2,3-dihydro-1H-quinazolin-4-one (16i)

6-Chloro-2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (17a)

6-Chloro-2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (17b)

6-Chloro-2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (17c)

6-Chloro-2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (17d)

6-Chloro-2-[4-(6-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (17e)

6-Chloro-2-[4-(7-{2,6-Dimethoxy-4-[3-(3,4,5-trimethoxy-phenyl)-4,5-dihydro-isoxazol-5-yl]-phenoxy}-hexyloxy)-3-methoxy-phenyl]2,3-dihydro-1H-quinazolin-4-one (17f)

6-Chloro-2-[4-(8-{2,6-Dimethoxy-4-[3-(3,4,5-trimethoxy-phenyl)-4,5-dihydro-isoxazol-5-yl]-phenoxy}-heptyloxy)-3-methoxy-phenyl]2,3-dihydro-1H-quinazolin-4-one (17g)

6-Chloro-2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]2,3-dihydro-1H-quinazolin-4-one (17h)

6-Chloro-2-[4-(10-{2,6-Dimethoxy-4-[3-(3,4,5-trimethoxy-phenyl)-4,5-dihydro-isoxazol-5-yl]-phenoxy}-decyloxy)-3-methoxy-phenyl]2,3-dihydro-1H-quinazolin-4-one (17i)

6-Methyl-2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (18a)

6-Methyl-2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (18b)

6-Methyl-2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (18c)

6-Methyl-2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (18d)

6-Methyl-2-[4-(6-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (18e)

6-Methyl-2-[4-(7-{2,6-Dimethoxy-4-[3-(3,4,5-trimethoxy-phenyl)-4,5-dihydro-isoxazol-5-yl]-phenoxy}-hexyloxy)-3-methoxy-phenyl]2,3-dihydro-1H-quinazolin-4-one (18f)

6-Methyl-2-[4-(8-{2,6-Dimethoxy-4-[3-(3,4,5-trimethoxy-phenyl)-4,5-dihydro-isoxazol-5-yl]-phenoxy}-heptyloxy)-3-methoxy-phenyl]2,3-dihydro-1H-quinazolin-4-one (18g)

6-Methyl-2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]2,3-dihydro-1H-quinazolin-4-one (18h)

6-Methyl-2-[4-(10-{2,6-Dimethoxy-4-[3-(3,4,5-trimethoxy-phenyl)-4,5-dihydro-isoxazol-5-yl]-phenoxy}-decyloxy)-3-methoxy-phenyl]2,3-dihydro-1H-quinazolin-4-one (18i)

6-Methoxy-2-[4-(2-{2,6-dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (19a)

6-Methoxy-2-[4-(3-{2,6-dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (19b)

6-Methoxy-2-[4-(4-{2,6-dimethoxy-4-[3-(3,4,5-trimethoxy-phenyl)-4,5-dihydro-isoxazol-5-yl]=phenoxy}-butoxy)-3-methoxy-phenyl]-2,3-dihydro-1H-quinazolin-4-one (19c)

6-Methoxy-2-[4-(5-{2,6-dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (19d)

6-Methoxy-2-[4-(6-{2,6-dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (19e)

6-Methoxy-2-[4-(7-{2,6-dimethoxy-4-[3-(3,4,5-trimethoxy-phenyl)-4,5-dihydro-isoxazol-5-yl]-phenoxy}-hexyloxy)-3-methoxy-phenyl]2,3-dihydro-1H-quinazolin-4-one (19f)

6-Methoxy-2-[4-(8-{2,6-dimethoxy-4-[3-(3,4,5-trimethoxy-phenyl)-4,5-dihydro-isoxazol-5-yl]-phenoxy}-heptyloxy)-3-methoxy-phenyl]2,3-dihydro-1H-quinazolin-4-one (19g)

6-Methoxy-2-[4-(9-{2,6-dimethoxy-4-[3-(3,4,5-trimethoxy-phenyl)-4,5-dihydro-isoxazol-5-yl]-phenoxy}-nonyloxy)-3-methoxy-phenyl]2,3-dihydro-1H-quinazolin-4-one (19h)

6-Methoxy-2-[4-(10-{2,6-dimethoxy-4-[3-(3,4,5-trimethoxy-phenyl)-4,5-dihydro-isoxazol-5-yl]-phenoxy}-decyloxy)-3-methoxy-phenyl]2,3-dihydro-1H-quinazolin-4-one (19i)

2-(3-methoxy-4-(2-(2-methoxy-5-(5-(3,4,5-trimethoxyphenyl)isoxazol-3-yl)phenoxy)ethoxy)phenyl)-2,3-dihydroquinazolin-4(1H)-one (21a)

2-(3-methoxy-4-(3-(2-methoxy-5-(5-(3,4,5-trimethoxyphenyl)isoxazol-3-yl)phenoxy)propoxy)phenyl)-2,3-dihydroquinazolin-4(1H)-one (21b)

2-(3-methoxy-4-(4-(2-methoxy-5-(5-(3,4,5-trimethoxyphenyl) isoxazol-3-yl)phenoxy)butoxy)phenyl)-2,3-dihydroquinazolin-4(1H)-one (21c)

2-(3-methoxy-4-(5-(2-methoxy-5-(5-(3,4,5-trimethoxyphenyl)isoxazol-3-yl)phenoxy)pentyloxy)phenyl)-2,3-dihydroquinazolin-4(1H)-one (21d)

2-(3-methoxy-4-(6-(2-methoxy-5-(5-(3,4,5-trimethoxyphenyl) isoxazol-3-yl)phenoxy)hexyloxy)phenyl)-2,3-dihydroquinazolin-4(1H)-one (21e)

2-(3-methoxy-4-(7-(2-methoxy-5-(5-(3,4,5-trimethoxyphenyl)isoxazol-3-yl)phenoxy)heptyloxy)phenyl)-2,3-dihydroquinazolin-4(1H)-one (21f)

2-(3-methoxy-4-(8-(2-methoxy-5-(5-(3,4,5-trimethoxyphenyl)isoxazol-3-yl)phenoxy)octyloxy)phenyl)-2,3-dihydroquinazolin-4(1H)-one (21g)

2-(3-methoxy-4-(9-(2-methoxy-5-(5-(3,4,5-trimethoxyphenyl)isoxazol-3-yl)phenoxy)nonyloxy)phenyl)-2,3-dihydroquinazolin-4(1H)-one (21h)

2-(3-methoxy-4-(10-(2-methoxy-5-(5-(3,4,5-trimethoxyphenyl)isoxazol-3-yl)phenoxy)decyloxy)phenyl)-2,3-dihydroquinazolin-4(1H)-one (21i)

6-Chloro-2-[3-methoxy-4-(2-{2-methoxy-5-[5-(3,4,5-trimethoxy-phenyl)-isoxazol-3-yl]-phenoxy}-ethoxy)-phenyl]-2,3-dihydro-1H-quinazolin-4-one (22a)

6-Chloro-2-[3-methoxy-4-(3-{2-methoxy-5-[5-(3,4,5-trimethoxy-phenyl)-isoxazol-3-yl]-phenoxy}-propoxy)-phenyl]-2,3-dihydro-1H-quinazolin-4-one (22b)

6-Chloro-2-[3-methoxy-4-(4-{2-methoxy-5-[5-(3,4,5-trimethoxy-phenyl)-isoxazol-3-yl]-phenoxy}-butyloxy)-phenyl]-2,3-dihydro-1H-quinazolin-4-one (22c)

6-Chloro-2-[3-methoxy-4-(5-{2-methoxy-5-[5-(3,4,5-trimethoxy-phenyl)-isoxazol-3-yl]-phenoxy}-pentyloxy)-phenyl]-2,3-dihydro-1H-quinazolin-4-one (22d)

6-Chloro-2-[3-methoxy-4-(6-{2-methoxy-5-[5-(3,4,5-trimethoxy-phenyl)-isoxazol-3-yl]-phenoxy}-hexyloxy)-phenyl]-2,3-dihydro-1H-quinazolin-4-one (22e)

6-Chloro-2-[3-methoxy-4-(7-{2-methoxy-5-[5-(3,4,5-trimethoxy-phenyl)-isoxazol-3-yl]-phenoxy}-heptyloxy)-phenyl]-2,3-dihydro-1H-quinazolin-4-one (22f)

6-Chloro-2-[3-methoxy-4-(8-{2-methoxy-5-[5-(3,4,5-trimethoxy-phenyl)-isoxazol-3-yl]-phenoxy}-octyloxy)-phenyl]-2,3-dihydro-1H-quinazolin-4-one (22g)

6-Chloro-2-[3-methoxy-4-(9-{2-methoxy-5-[5-(3,4,5-trimethoxy-phenyl)-isoxazol-3-yl]-phenoxy}-nonyloxy)-phenyl]-2,3-dihydro-1H-quinazolin-4-one (22h)

6-Chloro-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (22i)

6-Methyl-2-[3-methoxy-4-(2-{2-methoxy-5-[5-(3,4,5-trimethoxy-phenyl)-isoxazol-3-yl]-phenoxy}-ethoxy)-phenyl]-2,3-dihydro-1H-quinazolin-4-one (23a)

6-Methyl-2-[3-methoxy-4-(3-{2-methoxy-5-[5-(3,4,5-trimethoxy-phenyl)-isoxazol-3-yl]-phenoxy}-propoxy)-phenyl]-2,3-dihydro-1H-quinazolin-4-one (23b)

6-Methyl-2-[3-methoxy-4-(4-{2-methoxy-5-[5-(3,4,5-trimethoxy-phenyl)-isoxazol-3-yl]-phenoxy}-butyloxy)-phenyl]-2,3-dihydro-1H-quinazolin-4-one (23c)

6-Methyl-2-[3-methoxy-4-(5-{2-methoxy-5-[5-(3,4,5-trimethoxy-phenyl)-isoxazol-3-yl]-phenoxy}-pentyloxy)-phenyl]-2,3-dihydro-1H-quinazolin-4-one (23d)

6-Methyl-2-[3-methoxy-4-(6-{2-methoxy-5-[5-(3,4,5-trimethoxy-phenyl)-isoxazol-3-yl]-phenoxy}-hexyloxy)-phenyl]-2,3-dihydro-1H-quinazolin-4-one (23e)

6-Methyl-2-[3-methoxy-4-(7-{2-methoxy-5-[5-(3,4,5-trimethoxy-phenyl)-isoxazol-3-yl]-phenoxy}-heptyloxy)-phenyl]-2,3-dihydro-1H-quinazolin-4-one (23f)

6-Methyl-2-[3-methoxy-4-(8-{2-methoxy-5-[5-(3,4,5-trimethoxy-phenyl)-isoxazol-3-yl]-phenoxy}-octyloxy)-phenyl]-2,3-dihydro-1H-quinazolin-4-one (23g)

6-Methyl-2-[3-methoxy-4-(9-{2-methoxy-5-[5-(3,4,5-trimethoxy-phenyl)-isoxazol-3-yl]-phenoxy}-nonyloxy)-phenyl]-2,3-dihydro-1H-quinazolin-4-one (23h)

6-Methyl-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (23i)

6-Methoxy-2-[3-methoxy-4-(2-{2-methoxy-5-[5-(3,4,5-trimethoxy-phenyl)-isoxazol-3-yl]-phenoxy}-ethoxy)-phenyl]-2,3-dihydro-1H-quinazolin-4-one (24a)

6-Methoxy-2-[3-methoxy-4-(3-{2-methoxy-5-[5-(3,4,5-trimethoxy-phenyl)-isoxazol-3-yl]-phenoxy}-propoxy)-phenyl]-2,3-dihydro-1H-quinazolin-4-one (24b)

6-Methoxy-2-[3-methoxy-4-(4-{2-methoxy-5-[5-(3,4,5-trimethoxy-phenyl)-isoxazol-3-yl]-phenoxy}-butyloxy)-phenyl]-2,3-dihydro-1H-quinazolin-4-one (24c)

6-Methoxy-2-[3-methoxy-4-(5-{2-methoxy-5-[5-(3,4,5-trimethoxy-phenyl)-isoxazol-3-yl]-phenoxy}-pentyloxy)-phenyl]-2,3-dihydro-1H-quinazolin-4-one (24d)

6-Methoxy-2-[3-methoxy-4-(6-{2-methoxy-5-[5-(3,4,5-trimethoxy-phenyl)-isoxazol-3-yl]-phenoxy}-hexyloxy)-phenyl]-2,3-dihydro-1H-quinazolin-4-one (24e)

6-Methoxy-2-[3-methoxy-4-(7-{2-methoxy-5-[5-(3,4,5-trimethoxy-phenyl)-isoxazol-3-yl]-phenoxy}-heptyloxy)-phenyl]-2,3-dihydro-1H-quinazolin-4-one (24f)

6-Methoxy-2-[3-methoxy-4-(8-{2-methoxy-5-[5-(3,4,5-trimethoxy-phenyl)-isoxazol-3-yl]-phenoxy}-octyloxy)-phenyl]-2,3-dihydro-1H-quinazolin-4-one (24g)

6-Methoxy-2-[3-methoxy-4-(9-{2-methoxy-5-[5-(3,4,5-trimethoxy-phenyl)-isoxazol-3-yl]-phenoxy}-nonyloxy)-phenyl]-2,3-dihydro-1H-quinazolin-4-one (24h)

6-Methoxy-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (24i)

2-(4-(2-(2,6-dimethoxy-4-(5-(3,4,5-trimethoxyphenyl)isoxazol-3-yl)phenoxy)ethoxy)-3-methoxyphenyl)-2,3-dihydroquinazolin-4(1H)-one (25a)

2-(4-(3-(2,6-dimethoxy-4-(5-(3,4,5-trimethoxyphenyl)isoxazol-3-yl)phenoxy)propoxy)-3-methoxyphenyl)-2,3-dihydroquinazolin-4(1H)-one (25b)

2-(4-(4-(2,6-dimethoxy-4-(5-(3,4,5-trimethoxyphenyl)isoxazol-3-yl)phenoxy)butoxy)-3-methoxyphenyl)-2,3-dihydroquinazolin-4(1H)-one (25c)

2-(4-(5-(2,6-dimethoxy-4-(5-(3,4,5-trimethoxyphenyl)isoxazol-3-yl)phenoxy)pentyloxy)-3-methoxyphenyl)-2,3-dihydroquinazolin-4(1H)-one (25d)

2-(4-(6-(2,6-dimethoxy-4-(5-(3,4,5-trimethoxyphenyl)isoxazol-3-yl)phenoxy)hexyloxy)-3-methoxyphenyl)-2,3-dihydroquinazolin-4(1H)-one (25e)

2-(4-(7-(2,6-dimethoxy-4-(5-(3,4,5-trimethoxyphenyl)isoxazol-3-yl)phenoxy)heptyloxy)-3-methoxyphenyl)-2,3-dihydroquinazolin-4(1H)-one (25f)

2-(4-(8-(2,6-dimethoxy-4-(5-(3,4,5-trimethoxyphenyl)isoxazol-3-yl)phenoxy)octyloxy)-3-methoxyphenyl)-2,3-dihydroquinazolin-4(1H)-one (25g)

2-(4-(7-(2,6-dimethoxy-4-(5-(3,4,5-trimethoxyphenyl)isoxazol-3-yl)phenoxy)heptyloxy)-3-methoxyphenyl)-2,3-dihydroquinazolin-4(1H)-one (25h)

2-(4-(8-(2,6-dimethoxy-4-(5-(3,4,5-trimethoxyphenyl)isoxazol-3-yl)phenoxy)octyloxy)-3-methoxyphenyl)-2,3-dihydroquinazolin-4(1H)-one (25i)

2-(4-(9-(2,6-dimethoxy-4-(5-(3,4,5-trimethoxyphenyl)isoxazol-3-yl)phenoxy)nonyloxy)-3-methoxyphenyl)-2,3-dihydroquinazolin-4(1H)-one (25h)

2-(4-(10-(2,6-dimethoxy-4-(5-(3,4,5-trimethoxyphenyl)isoxazol-3-yl)phenoxy)decyloxy)-3-methoxyphenyl)-2,3-dihydroquinazolin-4(1H)-one (25i)

6-Chloro-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (26a)

6-Chloro-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (26b)

6-Chloro-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (26c)

6-Chloro-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (26d)

6-Chloro-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (26e)

6-Chloro-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (26f)

6-Chloro-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (26g)

6-Chloro-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (26h)

6-Chloro-2-[4-(10-{2,6-dimethoxy-4-[5-(3,4,5-trimethoxy-phenyl)-isoxazol-3-yl]-phenoxy}-decyloxy)-3-methoxy-phenyl]-2,3-dihydro-1H-quinazolin-4-one (26i)

6-Methyl-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (27a)

6-Methyl-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (27b)

6-Methyl-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (27c)

6-Methyl-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (27d)

6-Methyl-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (27e)

6-Methyl-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (27f)

6-Methyl-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (27g)

6-Methyl-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (27h)

6-Methyl-2-[4-(10-{2,6-dimethoxy-4-[5-(3,4,5-trimethoxy-phenyl)-isoxazol-3-yl]-phenoxy}-decyloxy)-3-methoxy-phenyl]-2,3-dihydro-1H-quinazolin-4-one (27i)

6-Methoxy-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (28a)

6-Methoxy-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (28b)

6-Methoxy-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (28c)

6-Methoxy-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (28d)

6-Methoxy-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (28e)

6-Methoxy-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (28f)

6-Methoxy-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (28g)

6-Methoxy-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (28h)

6-Methoxy-2-[4-(10-{2,6-dimethoxy-4-[5-(3,4,5-tri-methoxy-phenyl)-isoxazol-3-yl]-phenoxy}-decyloxy)-3-methoxy-phenyl]-2,3-dihydro-1H-quinazolin-4-one (28i)

2-(3-methoxy-4-(2-(2-methoxy-5-(3-(3,4,5-trimethoxyphenyl)isoxazol-5-yl)phenoxy)ethoxy)phenyl)-2,3-dihydro-quinazolin-4(1H)-one (30a)

2-(3-methoxy-4-(3-(2-methoxy-5-(3-(3,4,5-trimethoxyphenyl)isoxazol-5-yl)phenoxy)propoxy)phenyl)-2,3-dihydroquinazolin-4(1H)-one (30b)

2-(3-methoxy-4-(4-(2-methoxy-5-(3-(3,4,5-trimethoxyphenyl)isoxazol-5-yl)phenoxy)butoxy)phenyl)-2,3-dihydroquinazolin-4(1H)-one (30c)

2-(3-methoxy-4-(5-(2-methoxy-5-(3-(3,4,5-trimethoxyphenyl)isoxazol-5-yl)phenoxy)pentyloxy)phenyl)-2,3-dihydroquinazolin-4(1H)-one (30d)

2-(3-methoxy-4-(6-(2-methoxy-5-(3-(3,4,5-trimethoxyphenyl)isoxazol-5-yl)phenoxy)hexyloxy)phenyl)-2,3-dihydroquinazolin-4(1H)-one (30e)

2-(3-methoxy-4-(7-(2-methoxy-5-(3-(3,4,5-trimethoxyphenyl)isoxazol-5-yl)phenoxy)heptyloxy)phenyl)-2,3-dihydroquinazolin-4(1H)-one (30f)

2-(3-methoxy-4-(8-(2-methoxy-5-(3-(3,4,5-trimethoxyphenyl)isoxazol-5-yl)phenoxy)octyloxy)phenyl)-2,3-dihydroquinazolin-4(1H)-one (30g)

2-(3-methoxy-4-(9-(2-methoxy-5-(3-(3,4,5-trimethoxyphenyl)isoxazol-5-yl)phenoxy)nonyloxy)phenyl)-2,3-dihydroquinazolin-4(1H)-one (30h)

2-(3-methoxy-4-(10-(2-methoxy-5-(3-(3,4,5-trimethoxyphenyl)isoxazol-5-yl)phenoxy)decyloxy)phenyl)-2,3-dihydroquinazolin-4(1H)-one (30i)

6-Chloro-2-[3-methoxy-4-(2-{2-methoxy-5-[3-(3,4,5-tri-methoxy-phenyl)-isoxazol-5-yl]-phenoxy}-ethoxy)-phenyl]-2,3-dihydro-1H-quinazolin-4-one (31a)

6-Chloro-2-[3-methoxy-4-(3-{2-methoxy-5-[3-(3,4,5-tri-methoxy-phenyl)-isoxazol-5-yl]-phenoxy}-propoxy)-phenyl]-2,3-dihydro-1H-quinazolin-4-one (31b)

6-Chloro-2-[3-methoxy-4-(4-{2-methoxy-5-[3-(3,4,5-tri-methoxy-phenyl)-isoxazol-5-yl]-phenoxy}-butoxy)-phenyl]-2,3-dihydro-1H-quinazolin-4-one (31c)

6-Chloro-2-[3-methoxy-4-(5-{2-methoxy-5-[3-(3,4,5-tri-methoxy-phenyl)-isoxazol-5-yl]-phenoxy}-pentyloxy)-phenyl]-2,3-dihydro-1H-quinazolin-4-one (31d)

6-Chloro-2-[3-methoxy-4-(6-{2-methoxy-5-[3-(3,4,5-tri-methoxy-phenyl)-isoxazol-5-yl]-phenoxy}-hexyloxy)-phenyl]-2,3-dihydro-1H-quinazolin-4-one (31e)

6-Chloro-2-[3-methoxy-4-(7-{2-methoxy-5-[3-(3,4,5-tri-methoxy-phenyl)-isoxazol-5-yl]-phenoxy}-heptyloxy)-phenyl]-2,3-dihydro-1H-quinazolin-4-one (31f)

6-Chloro-2-[3-methoxy-4-(8-{2-methoxy-5-[3-(3,4,5-tri-methoxy-phenyl)-isoxazol-5-yl]-phenoxy}-octyloxy)-phenyl]-2,3-dihydro-1H-quinazolin-4-one (31g)

6-Chloro-2-[3-methoxy-4-(9-{2-methoxy-5-[3-(3,4,5-tri-methoxy-phenyl)-isoxazol-5-yl]-phenoxy}-nonyloxy)-phenyl]-2,3-dihydro-1H-quinazolin-4-one (31h)

6-Chloro-2-[3-methoxy-4-(10-{2-methoxy-5-[3-(3,4,5-tri-methoxy-phenyl)-isoxazol-5-yl]-phenoxy}-decyloxy)-phenyl]-2,3-dihydro-1H-quinazolin-4-one (31i)

6-Methyl-2-[3-methoxy-4-(2-{2-methoxy-5-[3-(3,4,5-tri-methoxy-phenyl)-isoxazol-5-yl]-phenoxy}-ethoxy)-phenyl]-2,3-dihydro-1H-quinazolin-4-one (32a)

6-Methyl-2-[3-methoxy-4-(3-{2-methoxy-5-[3-(3,4,5-tri-methoxy-phenyl)-isoxazol-5-yl]-phenoxy}-propoxy)-phenyl]-2,3-dihydro-1H-quinazolin-4-one (32b)

6-Methyl-2-[3-methoxy-4-(4-{2-methoxy-5-[3-(3,4,5-tri-methoxy-phenyl)-isoxazol-5-yl]-phenoxy}-butoxy)-phenyl]-2,3-dihydro-1H-quinazolin-4-one (32c)

6-Methyl-2-[3-methoxy-4-(5-{2-methoxy-5-[3-(3,4,5-tri-methoxy-phenyl)-isoxazol-5-yl]-phenoxy}-pentyloxy)-phenyl]-2,3-dihydro-1H-quinazolin-4-one (32d)

6-Methyl-2-[3-methoxy-4-(6-{2-methoxy-5-[3-(3,4,5-tri-methoxy-phenyl)-isoxazol-5-yl]-phenoxy}-hexyloxy)-phenyl]-2,3-dihydro-1H-quinazolin-4-one (32e)

6-Methyl-2-[3-methoxy-4-(7-{2-methoxy-5-[3-(3,4,5-tri-methoxy-phenyl)-isoxazol-5-yl]-phenoxy}-heptyloxy)-phenyl]-2,3-dihydro-1H-quinazolin-4-one (32f)

6-Methyl-2-[3-methoxy-4-(8-{2-methoxy-5-[3-(3,4,5-tri-methoxy-phenyl)-isoxazol-5-yl]-phenoxy}-octyloxy)-phenyl]-2,3-dihydro-1H-quinazolin-4-one (32g)

6-Methyl-2-[3-methoxy-4-(9-{2-methoxy-5-[3-(3,4,5-tri-methoxy-phenyl)-isoxazol-5-yl]-phenoxy}-nonyloxy)-phenyl]-2,3-dihydro-1H-quinazolin-4-one (32h)

6-Methyl-2-[3-methoxy-4-(10-{2-methoxy-5-[3-(3,4,5-tri-methoxy-phenyl)-isoxazol-5-yl]-phenoxy}-decyloxy)-phenyl]-2,3-dihydro-1H-quinazolin-4-one (32i)

6-Methoxy-2-[3-methoxy-4-(2-{2-methoxy-5-[3-(3,4,5-tri-methoxy-phenyl)-isoxazol-5-yl]-phenoxy}-ethoxy)-phenyl]-2,3-dihydro-1H-quinazolin-4-one (33a)

6-Methoxy-2-[3-methoxy-4-(3-{2-methoxy-5-[3-(3,4,5-tri-methoxy-phenyl)-isoxazol-5-yl]-phenoxy}-propoxy)-phenyl]-2,3-dihydro-1H-quinazolin-4-one (33b)
6-Methoxy-2-[3-methoxy-4-(4-{2-methoxy-5-[3-(3,4,5-tri-methoxy-phenyl)-isoxazol-5-yl]-phenoxy}-butoxy)-phenyl]-2,3-dihydro-1H-quinazolin-4-one (33c)
6-Methoxy-2-[3-methoxy-4-(5-{2-methoxy-5-[3-(3,4,5-tri-methoxy-phenyl)-isoxazol-5-yl]-phenoxy}-pentyloxy)-phenyl]-2,3-dihydro-1H-quinazolin-4-one (33d)
6-Methoxy-2-[3-methoxy-4-(6-{2-methoxy-5-[3-(3,4,5-tri-methoxy-phenyl)-isoxazol-5-yl]-phenoxy}-hexyloxy)-phenyl]-2,3-dihydro-1H-quinazolin-4-one (33e)
6-Methoxy-2-[3-methoxy-4-(7-{2-methoxy-5-[3-(3,4,5-tri-methoxy-phenyl)-isoxazol-5-yl]-phenoxy}-heptyloxy)-phenyl]-2,3-dihydro-1H-quinazolin-4-one (33f)
6-Methoxy-2-[3-methoxy-4-(8-{2-methoxy-5-[3-(3,4,5-tri-methoxy-phenyl)-isoxazol-5-yl]-phenoxy}-octyloxy)-phenyl]-2,3-dihydro-1H-quinazolin-4-one (33g)
6-Methoxy-2-[3-methoxy-4-(9-{2-methoxy-5-[3-(3,4,5-tri-methoxy-phenyl)-isoxazol-5-yl]-phenoxy}-nonyloxy)-phenyl]-2,3-dihydro-1H-quinazolin-4-one (33h)
6-Methoxy-2-[3-methoxy-4-(10-{2-methoxy-5-[3-(3,4,5-trimethoxy-phenyl)-isoxazol-5-yl]-phenoxy}-decyloxy)-phenyl]-2,3-dihydro-1H-quinazolin-4-one (33i)
2-(4-(2-(2,6-dimethoxy-4-(3-(3,4,5-trimethoxyphenyl)isoxazol-5-yl)phenoxy)ethoxy)-3-methoxyphenyl)-2,3-dihydroquinazolin-4(1H)-one (34a)
2-(4-(3-(2,6-dimethoxy-4-(3-(3,4,5-trimethoxyphenyl)isoxazol-5-yl)phenoxy)propoxy)-3-methoxyphenyl)-2,3-dihydroquinazolin-4(1H)-one (34b)
2-(4-(4-(2,6-dimethoxy-4-(3-(3,4,5-trimethoxyphenyl)isoxazol-5-yl)phenoxy)butoxy)-3-methoxyphenyl)-2,3-dihydroquinazolin-4(1H)-one (34c)
2-(4-(5-(2,6-dimethoxy-4-(3-(3,4,5-trimethoxyphenyl)isoxazol-5-yl)phenoxy)pentyloxy)-3-methoxyphenyl)-2,3-dihydroquinazolin-4(1H)-one (34d)
2-(4-(6-(2,6-dimethoxy-4-(3-(3,4,5-trimethoxyphenyl)isoxazol-5-yl)phenoxy)hexyloxy)-3-methoxyphenyl)-2,3-dihydroquinazolin-4(1H)-one (34e)
2-(4-(7-(2,6-dimethoxy-4-(3-(3,4,5-trimethoxyphenyl)isoxazol-5-yl)phenoxy)heptyloxy)-3-methoxyphenyl)-2,3-dihydroquinazolin-4(1H)-one (34f)
2-(4-(8-(2,6-dimethoxy-4-(3-(3,4,5-trimethoxyphenyl)isoxazol-5-yl)phenoxy)octyloxy)-3-methoxyphenyl)-2,3-dihydroquinazolin-4(1H)-one (34g)
2-(4-(9-(2,6-dimethoxy-4-(3-(3,4,5-trimethoxyphenyl)isoxazol-5-yl)phenoxy)nonyloxy)-3-methoxyphenyl)-2,3-dihydroquinazolin-4(1H)-one (34h)
2-(4-(10-(2,6-dimethoxy-4-(3-(3,4,5-trimethoxyphenyl)isoxazol-5-yl)phenoxy)decyloxy)-3-methoxyphenyl)-2,3-dihydroquinazolin-4(1H)-one (34i)
6-Chloro-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (35a)
6-Chloro-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (35b)
6-Chloro-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (35c)
6-Chloro-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (35d)
6-Chloro-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (35e)
6-Chloro-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (35f)
6-Chloro-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (35g)
6-Chloro-2-[4-(9-{2,6-dimethoxy-4-[3-(3,4,5-trimethoxy-phenyl)-isoxazol-5-yl]-phenoxy}-nonyloxy)-3-methoxy-phenyl]-2,3-dihydro-1H-quinazolin-4-one (35h)
6-Chloro-2-[10-(4-{2,6-dimethoxy-4-[3-(3,4,5-trimethoxy-phenyl)-isoxazol-5-yl]-phenoxy}-decyloxy)-3-methoxy-phenyl]-2,3-dihydro-1H-quinazolin-4-one (35i)
6-Methyl-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (36a)
6-Methyl-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (36b)
6-Methyl-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (36c)
6-Methyl-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (36d)
6-Methyl-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (36e)
6-Methyl-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (36f)
6-Methyl-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (36g)
6-Methyl-2-[4-(9-{2,6-dimethoxy-4-[3-(3,4,5-trimethoxy-phenyl)-isoxazol-5-yl]-phenoxy}-nonyloxy)-3-methoxy-phenyl]-2,3-dihydro-1H-quinazolin-4-one (36h)
6-Methyl-2-[10-(4-{2,6-dimethoxy-4-[3-(3,4,5-trimethoxy-phenyl)-isoxazol-5-yl]-phenoxy}-decyloxy)-3-methoxy-phenyl]-2,3-dihydro-1H-quinazolin-4-one (36i)
6-Methoxy-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (37a)
6-Methoxy-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (37b)
6-Methoxy-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (37c)
6-Methoxy-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (37d)
6-Methoxy-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (37e)
6-Methoxy-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (37f)
6-Methoxy-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (37g)
6-Methoxy-2-[4-(9-{2,6-dimethoxy-4-[3-(3,4,5-trimethoxy-phenyl)-isoxazol-5-yl]-phenoxy}-nonyloxy)-3-methoxy-phenyl]-2,3-dihydro-1H-quinazolin-4-one (37h)
6-Methoxy-2-[10-(4-{2,6-dimethoxy-4-[3-(3,4,5-tri-methoxy-phenyl)-isoxazol-5-yl]-phenoxy}-decyloxy)-3-methoxy-phenyl]-2,3-dihydro-1H-quinazolin-4-one (37i)

(Z)-2-(3-methoxy-4-(2-(2-methoxy-5-(3,4,5-trimethoxystyryl)phenoxy)ethoxy)phenyl)-2,3-dihydroquinazolin-4(1H)-one (39a)

(Z)-2-(3-methoxy-4-(3-(2-methoxy-5-(3,4,5-trimethoxystyryl)phenoxy)propoxy)phenyl)-2,3-dihydroquinazolin-4(1H)-one (39b)

(Z)-2-(3-methoxy-4-(4-(2-methoxy-5-(3,4,5-trimethoxystyryl)phenoxy)butoxy)phenyl)-2,3-dihydroquinazolin-4(1H)-one (39c)

(Z)-2-(3-methoxy-4-(5-(2-methoxy-5-(3,4,5-trimethoxystyryl)phenoxy)pentyloxy)phenyl)-2,3-dihydroquinazolin-4(1H)-one (39d)

(Z)-2-(3-methoxy-4-(6-(2-methoxy-5-(3,4,5-trimethoxystyryl)phenoxy)hexyloxy)phenyl)-2,3-dihydroquinazolin-4(1H)-one (39e)

(Z)-2-(3-methoxy-4-(7-(2-methoxy-5-(3,4,5-trimethoxystyryl)phenoxy)heptyloxy)phenyl)-2,3-dihydroquinazolin-4(1H)-one (39f)

(Z)-2-(3-methoxy-4-(8-(2-methoxy-5-(3,4,5-trimethoxystyryl)phenoxy)octyloxy)phenyl)-2,3-dihydroquinazolin-4(1H)-one (39g)

(Z)-2-(3-methoxy-4-(9-(2-methoxy-5-(3,4,5-trimethoxystyryl)phenoxy)nonyloxy)phenyl)-2,3-dihydroquinazolin-4(1H)-one (39h)

(Z)-2-(3-methoxy-4-(10-(2-methoxy-5-(3,4,5-trimethoxystyryl)phenoxy)decyloxy)phenyl)-2,3-dihydroquinazolin-4(1H)-one (39i)

6-Chloro-2-[3-methoxy-4-(2-{2-methoxy-5-[2-(3,4,5-trimethoxy-phenyl)-vinyl]-phenoxy}-ethoxy)-phenyl]-2,3-dihydro-1H-quinazolin-4-one (40a)

6-Chloro-2-[3-Methoxy-4-(3-{2-methoxy-5-[2-(3,4,5-trimethoxy-phenyl)-vinyl]-phenoxy}-propoxy)-phenyl]-2,3-dihydro-1H-quinazolin-4-one (40b)

6-Chloro-2-[3-Methoxy-4-(4-{2-methoxy-5-[2-(3,4,5-trimethoxy-phenyl)-vinyl]-phenoxy}-butoxy)-phenyl]-2,3-dihydro-1H-quinazolin-4-one (40c)

6-Chloro-2-[3-methoxy-4-(5-{2-methoxy-5-[2-(3,4,5-trimethoxy-phenyl)-vinyl]-phenoxy}-pentyloxy)-phenyl]-2,3-dihydro-1H-quinazolin-4-one (40d)

6-Chloro-2-[3-Methoxy-4-(6-{2-methoxy-5-[2-(3,4,5-trimethoxy-phenyl)-vinyl]-phenoxy}-hexyloxy)-phenyl]-2,3-dihydro-1H-quinazolin-4-one (40e)

6-Chloro-2-[3-Methoxy-4-(7-{2-methoxy-5-[2-(3,4,5-trimethoxy-phenyl)-vinyl]-phenoxy}-heptyloxy)-phenyl]-2,3-dihydro-1H-quinazolin-4-one (40f)

6-Chloro-2-[3-methoxy-4-(8-{2-methoxy-5-[2-(3,4,5-trimethoxy-phenyl)-vinyl]-phenoxy}-octyloxy)-phenyl]-2,3-dihydro-1H-quinazolin-4-one (40g)

6-Chloro-2-[3-Methoxy-4-(9-{2-methoxy-5-[2-(3,4,5-trimethoxy-phenyl)-vinyl]-phenoxy}-nonyloxy)-phenyl]-2,3-dihydro-1H-quinazolin-4-one (40h)

6-Chloro-2-[3-Methoxy-4-(10-{2-methoxy-5-[2-(3,4,5-trimethoxy-phenyl)-vinyl]-phenoxy}-decyloxy)-phenyl]-2,3-dihydro-1H-quinazolin-4-one (40i)

6-Methyl-2-[3-methoxy-4-(2-{2-methoxy-5-[2-(3,4,5-trimethoxy-phenyl)-vinyl]-phenoxy}-ethoxy)-phenyl]-2,3-dihydro-1H-quinazolin-4-one (41a)

6-Methyl-2-[3-Methoxy-4-(3-{2-methoxy-5-[2-(3,4,5-trimethoxy-phenyl)-vinyl]-phenoxy}-propoxy)-phenyl]-2,3-dihydro-1H-quinazolin-4-one (41b)

6-Methyl-2-[3-Methoxy-4-(4-{2-methoxy-5-[2-(3,4,5-trimethoxy-phenyl)-vinyl]-phenoxy}-butoxy)-phenyl]-2,3-dihydro-1H-quinazolin-4-one (41c)

6-Methyl-2-[3-methoxy-4-(5-{2-methoxy-5-[2-(3,4,5-trimethoxy-phenyl)-vinyl]-phenoxy}-pentyloxy)-phenyl]-2,3-dihydro-1H-quinazolin-4-one (41d)

6-Methyl-2-[3-Methoxy-4-(6-{2-methoxy-5-[2-(3,4,5-trimethoxy-phenyl)-vinyl]-phenoxy}-hexyloxy)-phenyl]-2,3-dihydro-1H-quinazolin-4-one (41e)

6-Methyl-2-[3-Methoxy-4-(7-{2-methoxy-5-[2-(3,4,5-trimethoxy-phenyl)-vinyl]-phenoxy}-heptyloxy)-phenyl]-2,3-dihydro-1H-quinazolin-4-one (41f)

6-Methyl-2-[3-methoxy-4-(8-{2-methoxy-5-[2-(3,4,5-trimethoxy-phenyl)-vinyl]-phenoxy}-octyloxy)-phenyl]-2,3-dihydro-1H-quinazolin-4-one (41g)

6-Methyl-2-[3-Methoxy-4-(9-{2-methoxy-5-[2-(3,4,5-trimethoxy-phenyl)-vinyl]-phenoxy}-nonyloxy)-phenyl]-2,3-dihydro-1H-quinazolin-4-one (41h)

6-Methyl-2-[3-Methoxy-4-(10-{2-methoxy-5-[2-(3,4,5-trimethoxy-phenyl)-vinyl]-phenoxy}-decyloxy)-phenyl]-2,3-dihydro-1H-quinazolin-4-one (41i)

6-Methoxy-2-[3-methoxy-4-(2-{2-methoxy-5-[2-(3,4,5-trimethoxy-phenyl)-vinyl]-phenoxy}-ethoxy)-phenyl]-2,3-dihydro-1H-quinazolin-4-one (42a)

6-Methoxy-2-[3-Methoxy-4-(3-{2-methoxy-5-[2-(3,4,5-trimethoxy-phenyl)-vinyl-]phenoxy}-propoxy)-phenyl]-2,3-dihydro-1H-quinazolin-4-one (42b)

6-Methoxy-2-[3-Methoxy-4-(4-{2-methoxy-5-[2-(3,4,5-trimethoxy-phenyl)-vinyl]-phenoxy}-butoxy)-phenyl]-2,3-dihydro-1H-quinazolin-4-one (42c)

6-Methoxy-2-[3-methoxy-4-(5-{2-methoxy-5-[2-(3,4,5-trimethoxy-phenyl)-vinyl]-phenoxy}-pentyloxy)-phenyl]-2,3-dihydro-1H-quinazolin-4-one (42d)

6-Methoxy-2-[3-Methoxy-4-(6-{2-methoxy-5-[2-(3,4,5-trimethoxy-phenyl)-vinyl]-phenoxy}-hexyloxy)-phenyl]-2,3-dihydro-1H-quinazolin-4-one (42e)

6-Methoxy-2-[3-Methoxy-4-(7-{2-methoxy-5-[2-(3,4,5-trimethoxy-phenyl)-vinyl]-phenoxy}-heptyloxy)-phenyl]-2,3-dihydro-1H-quinazolin-4-one (42f)

6-Methoxy-2-[3-methoxy-4-(8-{2-methoxy-5-[2-(3,4,5-trimethoxy-phenyl)-vinyl-]phenoxy}-octyloxy)-phenyl]-2,3-dihydro-1H-quinazolin-4-one (42g)

6-Methoxy-2-[3-Methoxy-4-(9-{2-methoxy-5-[2-(3,4,5-trimethoxy-phenyl)-vinyl]-phenoxy}-nonyloxy)-phenyl]-2,3-dihydro-1H-quinazolin-4-one (42h)

6-Methoxy-2-[3-Methoxy-4-(10-{2-methoxy-5-[2-(3,4,5-trimethoxy-phenyl)-vinyl]-phenoxy}-decyloxy)-phenyl]-2,3-dihydro-1H-quinazolin-4-one (42i)

(Z)-2-(4-(2-(2,6-dimethoxy-4-(3,4,5-trimethoxystyryl)phenoxy)ethoxy)-3-methoxy phenyl)-2,3-dihydroquinazolin-4(1H)-one (43a)

(Z)-2-(4-(3-(2,6-dimethoxy-4-(3,4,5-trimethoxystyryl)phenoxy)propoxy)-3-methoxy phenyl)-2,3-dihydroquinazolin-4(1H)-one (43b)

(Z)-2-(4-(4-(2,6-dimethoxy-4-(3,4,5-trimethoxystyryl)phenoxy)butoxy)-3-methoxy phenyl)-2,3-dihydroquinazolin-4(1H)-one (43c)

(Z)-2-(4-(5-(2,6-dimethoxy-4-(3,4,5-trimethoxystyryl)phenoxy)pentyoxy)-3-methoxy phenyl)-2,3-dihydroquinazolin-4(1H)-one (43d)

(Z)-2-(4-(6-(2,6-dimethoxy-4-(3,4,5-trimethoxystyryl)phenoxy)hexyloxy)-3-methoxy phenyl)-2,3-dihydroquinazolin-4(1H)-one (43e)

(Z)-2-(4-(7-(2,6-dimethoxy-4-(3,4,5-trimethoxystyryl)phenoxy)heptyloxy)-3-methoxy phenyl)-2,3-dihydroquinazolin-4(1H)-one (43f)

(Z)-2-(4-(8-(2,6-dimethoxy-4-(3,4,5-trimethoxystyryl)phenoxy)octyloxy)-3-methoxy phenyl)-2,3-dihydroquinazolin-4(1H)-one (43g)

(Z)-2-(4-(9-(2,6-dimethoxy-4-(3,4,5-trimethoxystyryl)phenoxy)nonyloxy)-3-methoxy phenyl)-2,3-dihydroquinazolin-4(1H)-one (43h)

(Z)-2-(4-(10-(2,6-dimethoxy-4-(3,4,5-trimethoxystyryl)phenoxy)decyloxy)-3-methoxy phenyl)-2,3-dihydroquinazolin-4(1H)-one (43i)

6-Chloro-2-[4-(2-{2,6-dimethoxy-4-[2-(3,4,5-trimethoxy-phenyl)-vinyl]-phenoxy}-ethoxy)-3-methoxy-phenyl]-2,3-dihydro-1H-quinazolin-4-one (44a)

6-Chloro-2-[4-(3-{2,6-dimethoxy-4-[2-(3,4,5-trimethoxy-phenyl)-vinyl]-phenoxy}-propoxy)-3-methoxy-phenyl]-2,3-dihydro-1H-quinazolin-4-one (44b)

6-Chloro-2-[4-(4-{2,6-dimethoxy-4-[2-(3,4,5-trimethoxy-phenyl)-vinyl]-phenoxy}-butoxy)-3-methoxy-phenyl]-2,3-dihydro-1H-quinazolin-4-one (44c)

6-Chloro-2-[4-(5-{2,6-dimethoxy-4-[2-(3,4,5-trimethoxy-phenyl)-vinyl]-phenoxy}-pentyloxy)-3-methoxy-phenyl]-2,3-dihydro-1H-quinazolin-4-one (44d)

6-Chloro-2-[4-(6-{2,6-dimethoxy-4-[2-(3,4,5-trimethoxy-phenyl)-vinyl]-phenoxy}-hexyloxy)-3-methoxy-phenyl]-2,3-dihydro-1H-quinazolin-4-one (44e)

6-Chloro-2-[4-(7-{2,6-dimethoxy-4-[2-(3,4,5-trimethoxy-phenyl)-vinyl]-phenoxy}-heptyloxy)-3-methoxy-phenyl]-2,3-dihydro-1H-quinazolin-4-one (44f)

6-Chloro-2-[4-(8-{2,6-dimethoxy-4-[2-(3,4,5-trimethoxy-phenyl)-vinyl]-phenoxy}-octyloxy)-3-methoxy-phenyl]-2,3-dihydro-1H-quinazolin-4-one (44g)

6-Chloro-2-[4-(9-{2,6-dimethoxy-4-[2-(3,4,5-trimethoxy-phenyl)-vinyl]-phenoxy}-nonyloxy)-3-methoxy-phenyl]-2,3-dihydro-1H-quinazolin-4-one (44h)

6-Chloro-2-[4-(10-{2,6-dimethoxy-4-[2-(3,4,5-trimethoxy-phenyl)-vinyl]-phenoxy}-decyloxy)-3-methoxy-phenyl]-2,3-dihydro-1H-quinazolin-4-one (44i)

6-Methyl-2-[4-(2-{2,6-dimethoxy-4-[2-(3,4,5-trimethoxy-phenyl)-vinyl]-phenoxy}-ethoxy)-3-methoxy-phenyl]-2,3-dihydro-1H-quinazolin-4-one (45a)

6-Methyl-2-[4-(3-{2,6-dimethoxy-4-[2-(3,4,5-trimethoxy-Phenyl)-vinyl]-phenoxy}-propoxy)-3-methoxy-phenyl]-2,3-dihydro-1H-quinazolin-4-one (45b)

6-Methyl-2-[4-(4-{2,6-dimethoxy-4-[2-(3,4,5-trimethoxy-phenyl)-vinyl]-phenoxy}-butoxy)-3-methoxy-phenyl]-2,3-dihydro-1H-quinazolin-4-one (45c)

6-Methyl-2-[4-(5-{2,6-dimethoxy-4-[2-(3,4,5-trimethoxy-phenyl)-vinyl]-phenoxy}-pentyloxy)-3-methoxy-phenyl]-2,3-dihydro-1H-quinazolin-4-one (45d)

6-Methyl-2-[4-(6-{2,6-dimethoxy-4-[2-(3,4,5-trimethoxy-phenyl)-vinyl]-phenoxy}-hexyloxy)-3-methoxy-phenyl]-2,3-dihydro-1H-quinazolin-4-one (45e)

6-Methyl-2-[4-(7-{2,6-dimethoxy-4-[2-(3,4,5-trimethoxy-phenyl)-vinyl]-phenoxy}-heptyloxy)-3-methoxy-phenyl]-2,3-dihydro-1H-quinazolin-4-one (45f)

6-Methyl-2-[4-(8-{2,6-dimethoxy-4-[2-(3,4,5-trimethoxy-phenyl)-vinyl]-phenoxy}-octyloxy)-3-methoxy-phenyl]-2,3-dihydro-1H-quinazolin-4-one (45g)

6-Methyl-2-[4-(9-{2,6-dimethoxy-4-[2-(3,4,5-trimethoxy-phenyl)-vinyl]-phenoxy}-nonyloxy)-3-methoxy-phenyl]-2,3-dihydro-1H-quinazolin-4-one (45h)

6-Methyl-2-[4-(10-{2,6-dimethoxy-4-[2-(3,4,5-trimethoxy-phenyl)-vinyl]-phenoxy}-decyloxy)-3-methoxy-phenyl]-2,3-dihydro-1H-quinazolin-4-one (45i)

6-Methoxy-2-[4-(2-{2,6-dimethoxy-4-[2-(3,4,5-trimethoxy-phenyl)-vinyl]-phenoxy}-ethoxy)-3-methoxy-phenyl]-2,3-dihydro-1H-quinazolin-4-one (46a)

6-Methoxy-2-[4-(3-{2,6-dimethoxy-4-[2-(3,4,5-trimethoxy-phenyl)-vinyl]-phenoxy}-propoxy)-3-methoxy-phenyl]-2,3-dihydro-1H-quinazolin-4-one (46b)

6-Methoxy-2-[4-(4-{2,6-dimethoxy-4-[2-(3,4,5-trimethoxy-phenyl)-vinyl]-phenoxy}-butoxy)-3-methoxy-phenyl]-2,3-dihydro-1H-quinazolin-4-one (46c)

6-Methoxy-2-[4-(5-{2,6-dimethoxy-4-[2-(3,4,5-trimethoxy-phenyl)-vinyl]-phenoxy}-pentyloxy)-3-methoxy-phenyl]-2,3-dihydro-1H-quinazolin-4-one (46d)

6-Methoxy-2-[4-(6-{2,6-dimethoxy-4-[2-(3,4,5-trimethoxy-phenyl)-vinyl]-phenoxy}-hexyloxy)-3-methoxy-phenyl]-2,3-dihydro-1H-quinazolin-4-one (46e)

6-Methoxy-2-[4-(7-{2,6-dimethoxy-4-[2-(3,4,5-trimethoxy-phenyl)-vinyl]-phenoxy}-heptyloxy)-3-methoxy-phenyl]-2,3-dihydro-1H-quinazolin-4-one (46f)

6-Methoxy-2-[4-(8-{2,6-dimethoxy-4-[2-(3,4,5-trimethoxy-phenyl)-vinyl]-phenoxy}-octyloxy)-3-methoxy-phenyl]-2,3-dihydro-1H-quinazolin-4-one (46g)

6-Methoxy-2-[4-(9-{2,6-dimethoxy-4-[2-(3,4,5-trimethoxy-phenyl)-vinyl]-phenoxy}-nonyloxy)-3-methoxy-phenyl]-2,3-dihydro-1H-quinazolin-4-one (46h)

6-Methoxy-2-[4-(10-{2,6-dimethoxy-4-[2-(3,4,5-trimethoxy-phenyl)-vinyl]-phenoxy}-decyloxy)-3-methoxy-phenyl]-2,3-dihydro-1H-quinazolin-4-one (46i)

The present invention further provides a process for preparation of novel isoxazole/isoxazoline/combretastatin linked dihydroquinazolinone hybrids of general formulae 3a-i to 6a-i, 7a-i to 10a-i, 12a-i to 15a-i, 16a-i to 19a-i, 21a-i to 24a-i, 25a-i to 28a-i, 30a-i to 33a-i, 34a-i to 37a-i and 39a-i to 42a-i, 43a-i to 46a-i which comprises Reacting 2-[4-(n-Bromo-alkyloxy)-3-methoxy-phenyl]-2,3-dihydro-1H-quinazolin-4-one of formula 2 with the compounds of formulae 1a, 1b, 11a, 11b, 20a, 20b, 29a, 29b, 38a, 38b respectively in an aprotic water miscible organic solvent, in the presence of anhydrous mild inorganic base, under room temperature for a period of about 48 hrs, followed by the removal of inorganic base by filtration and evaporating the organic solvent to obtain the resultant crude product and purifying it by column chromatography to obtain the desired products of formulae 3a-i to 6a-i, 7a-i to 10a-i, 12a-i to 15a-i, 16a-i to 19a-i, 21a-i to 24a-i, 25a-i to 28a-i, 30a-i to 33a-i, 34a-i to 37a-i and 39a-i to 42a-i, 43a-i to 46a-i respectively.

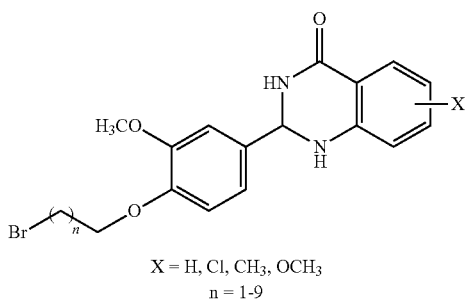

X = H, Cl, CH$_3$, OCH$_3$
n = 1-9

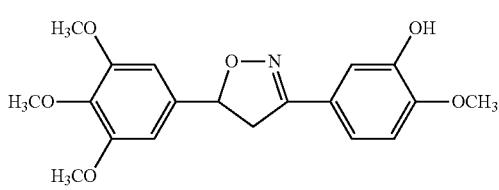

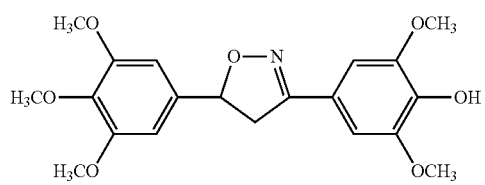

1b

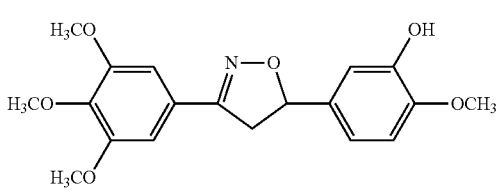

11a

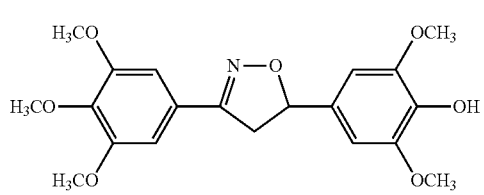

11b

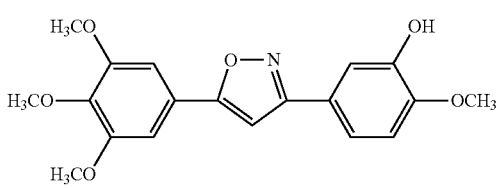

20a

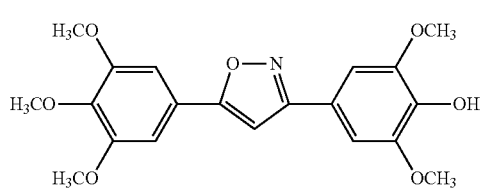

20b

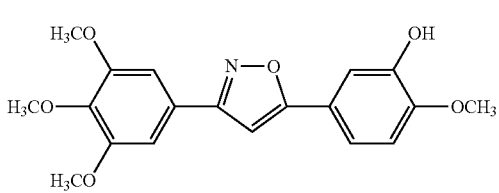

29a

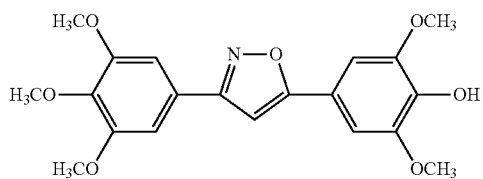

29b

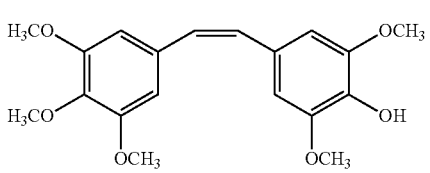

38a

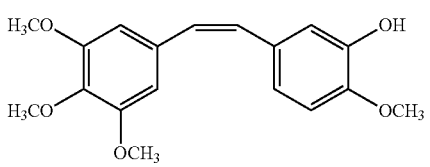

38b

DETAILED DESCRIPTION OF THE INVENTION

The precursor dihydroquinazolinone of formula 2, has been prepared using literature method (Mann-Jen Hour, † Li-Jiau Huang, † Sheng-Chu Kuo, *, † Yi Xia, ‡ Kenneth Bastow, § Yuka Nakanishi, § Ernest Hamel, | and Kuo-Hsiung Lee*, ‡ J. Med. Chem. 2000, 43, 4479-4487). The precursors isoxazoles, isoxazolines and combretastatins of formulae 1(a&b), 11(a&b), 20(a&b), 29(a&b) and 38(a&b) have been prepared using literature methods (Julia kaffy, Renee Pontikis, Daniele Carrez, Alain Croisy, Claude Monneret and Jean-Claude Florent. Bioorg. Med. Chem. 2006, 14, 4067-4077, Simoni, D.; Grisolia, G.; Giannini, G.; Roberti, M.; Rondanin, R.; Piccagli, L.; Baruchello, R.; Rossi, M.; Romagnoli; R.; Invidiata, F. P.; Grimaudo, S.; Jung, M. K.; Hamel, E.; Gebbia, N.; Crosta, L.; Abbadessa, V.; DiCristina, A.; Dusonchet, L.; Meli, M.; Tolomeo, M. J. Med. Chem. 2005, 48, 723)

These new analogues of isoxazole/isoxazoline/combretastatin linked dihydro-quinazolinone hybrids have shown promising anticancer activity in various cell lines. The molecules synthesized are of immense biological significance. This resulted in design and synthesis of new congener's as illustrated in schemes 1-5 which comprise:

The ether linkage between dihydroquinazolinone of formula 2 and isoxazole/isoxazoline/combretastatins of formulae 1(a&b), 11(a&b), 20(a&b), 29(a&b) and 38(a&b)
1. Stirring the reaction mixtures at a temperature of 35° C. for 30 h.
2. Synthesis of isoxazole/isoxazoline/combretastatin linked dihydroquinazolinone hybrids.
3. Purification by column chromatography using different solvents like ethyl acetate, hexane, dichloromethane and methanol.

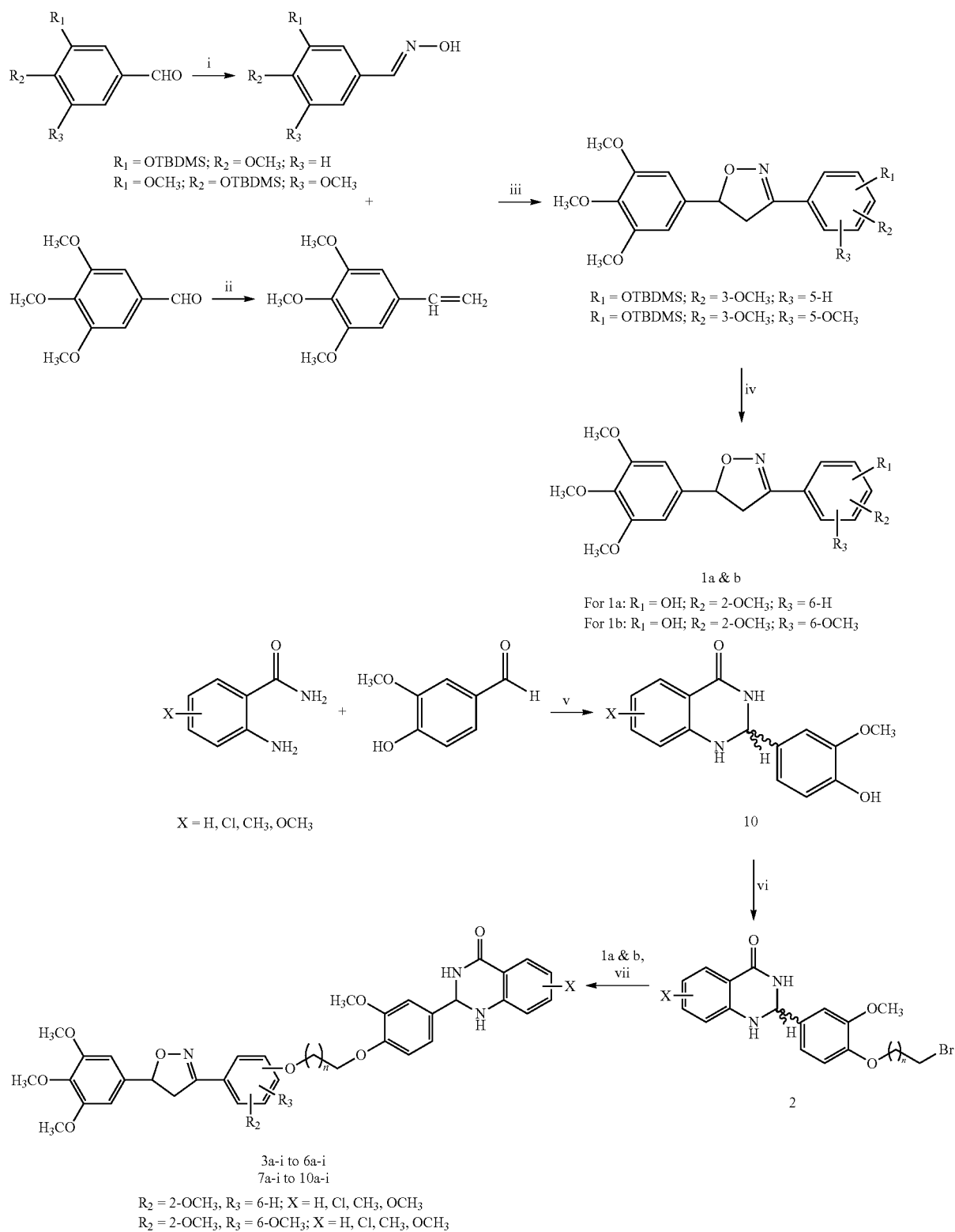
scheme-1
3a-i to 6a-i
7a-i to 10a-i
$R_2 = 2\text{-OCH}_3, R_3 = 6\text{-H}; X = H, Cl, CH_3, OCH_3$
$R_2 = 2\text{-OCH}_3, R_3 = 6\text{-OCH}_3; X = H, Cl, CH_3, OCH_3$
n = 1-9
Reagents and conditions i) $NH_2OH \cdot HCl$, $NaHCO_3$, $CH_3OH$, $H_2O$; ii) $CH_3P(Ph_3)_3^+Br^-$, KOtBu, THF; iii) NaOCl, $Et_3N$, DCM,; iv) TBAF, THF; v) PTSA, DMA; vi) $Br(CH_2)_nBr$, $K_2CO_3$, DMF vii) 2, $K_2CO_3$, DMF.
OTBDMS = Tertiary Butyl Dimethyl Silyloxy

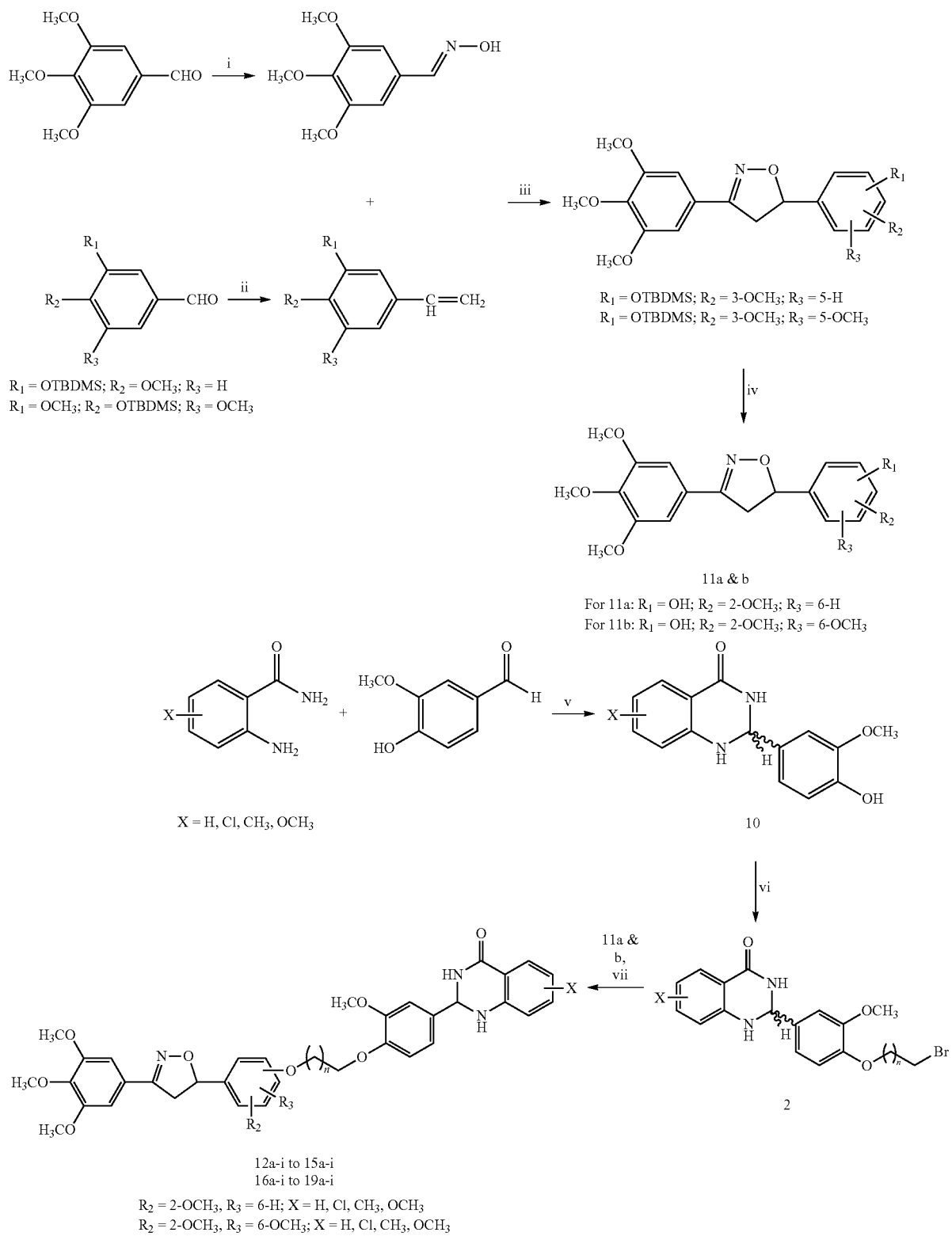

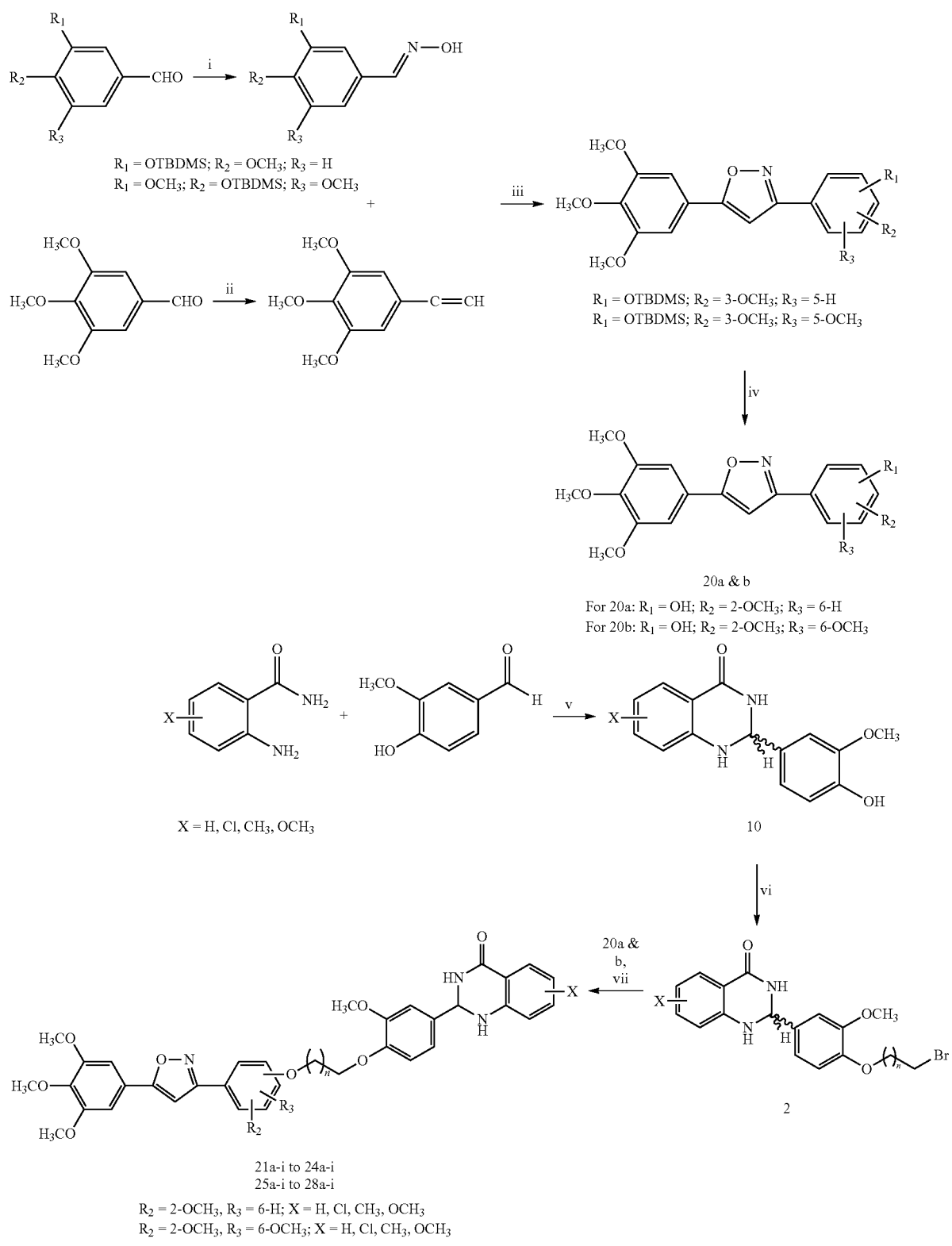

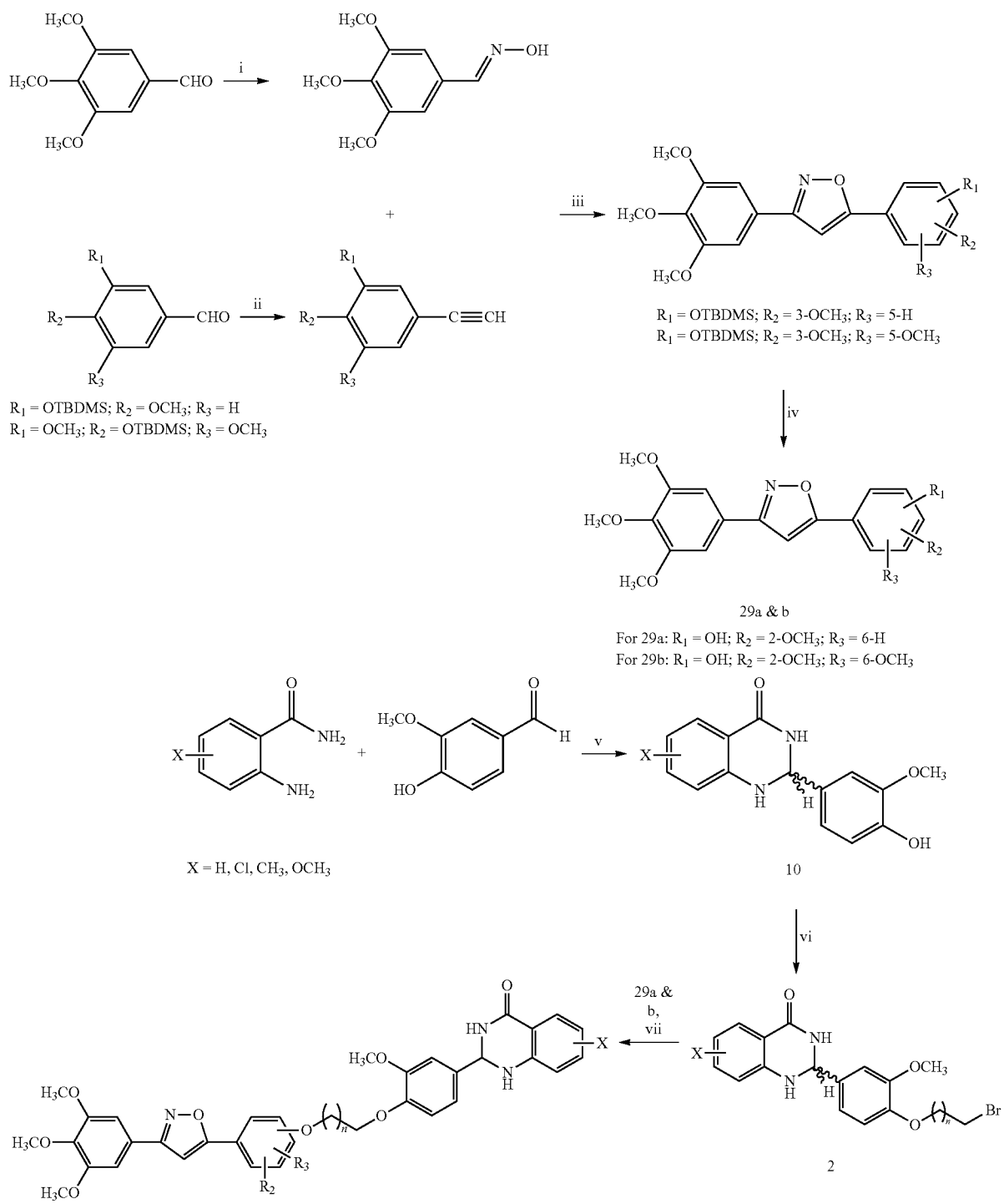

scheme-5
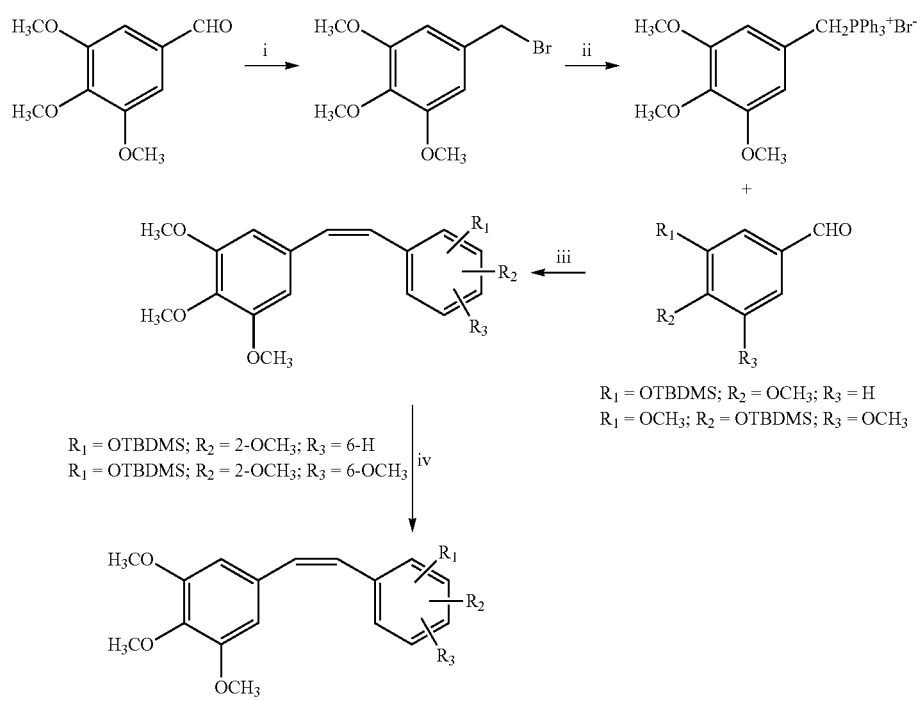
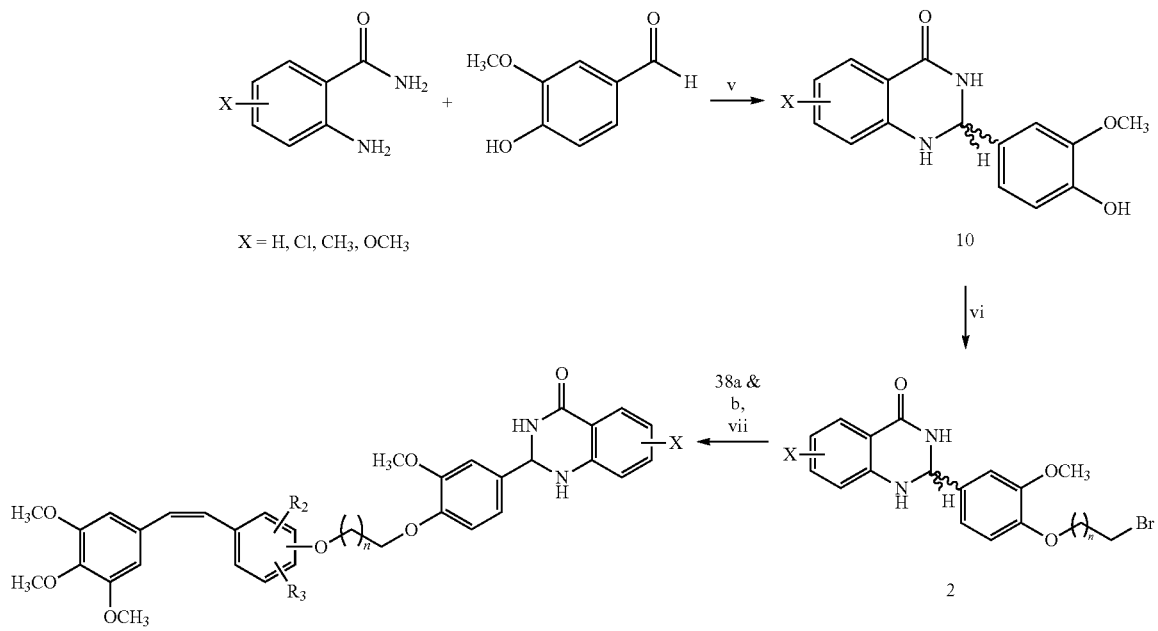
39a-i to 42a-i
43a-i to 46a-i
$R_2 = 2\text{-OCH}_3$, $R_3 = 6\text{-H}$; X = H, Cl, $CH_3$, $OCH_3$
$R_2 = 2\text{-OCH}_3$, $R_3 = 6\text{-OCH}_3$; X = H, Cl, $CH_3$, $OCH_3$
n = 1-9
Reagents and conditions i) $NaBH_4$, $CH_3OH$; ii) TPP, toluene, reflux; iii) KOtBu, THF;
iv) TBAF, THF, v) PTSA, DMA; vi) $Br(CH_2)_nBr$, $K_2CO_3$, DMF vii) 2, $K_2CO_3$, DMF.
OTBDMA = Tertiary Butyl Dimethyl Silyloxy The following examples are given by way of illustration and therefore should not be construed to the present limit of the scope of invention.

Example 1

2-[3-Methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (3d)

2-Methoxy-5-[5-(3,4,5-trimethoxy-phenyl)-4,5-dihydro-isoxazol-3-yl]-phenol (1a) (359.37 mg, 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.31 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (3d) (557 mg, 80% yield).
$^1$H NMR (CDCl$_3$): δ 1.70-1.80 (m, 2H), 1.89-2.02 (m, 4H), 3.69-3.82 (dd, 1H, J=10.7 Hz, J=16.4 Hz), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 5.63-5.73 (t, 1H, J=10.1 Hz, J=9.2 Hz), 5.77 (s, 1H), 6.57-6.61 (d, 1H, J=7.9 Hz), 6.63 (s, 1H) 6.76-6.79 (d, 1H, J=8.1 Hz), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.87 (dd, 1H, J=7.74 Hz J=7.55 Hz) FABMS: 698.75 (M+H)$^-$.

Example 2

2-[4-(5-{2,6-Dimethoxy-4-[5-(3,4,5-trimethoxyphenyl)-4,5-dihydro-isoxazol-3-yl]-phenoxy}pentyloxy)-3-methoxy-phenyl]-2,3-dihydro-1H-quinazolin-4-one (7d) 2,6-Dimethoxy-4-[5-(3,4,5-trimethoxy-phenyl)-4,5-dihydro-isoxazol-3-yl]-phenol (1b)

(389.15 mg, 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.31 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (7d) (583 mg, 80% yield).
$^1$H NMR (CDCl$_3$): δ 1.70-1.80 (m, 2H), 1.89-2.02 (m, 4H), 3.69-3.82 (dd, 1H, J=10.7 Hz, J=16.4 Hz), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 5.63-5.73 (t, 1H, J=10.1 Hz, J=9.2 Hz), 5.77 (s, 1H), 6.62 (s, 2H), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.92 (dd, 1H, J=7.74 Hz J=7.55 Hz) FABMS: 728.78M+H)$^+$.

Example 3

2-[3-Methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (12d)

2-Methoxy-5-[3-(3,4,5-trimethoxy-phenyl)-4,5-dihydro-isoxazol-5-yl]phenol (11a) (359.37 mg, 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.31 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (12d) (546 mg, 80% yield).
$^1$H NMR (CDCl$_3$): δ 1.70-1.80 (m, 2H), 1.89-2.02 (m, 4H), 3.69-3.82 (dd, 1H, J=10.7 Hz, J=16.4 Hz), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 5.63-5.73 (t, 1H, J=10.1 Hz, J=9.2 Hz), 5.77 (s, 1H), 6.57-6.61 (d, 1H, J=7.9 Hz), 6.63 (s, 1H) 6.76-6.79 (d, 1H, J=8.1 Hz), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2Hz), 7.82-7.87 (dd, 1H, J=7.74 Hz J=7.55 Hz) FABMS: 698.75 (M+H)$^+$.

Example 4

2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]-2,3-dihydro-1H-quinazolin-4-one (16d)

2,6-Dimethoxy-4-[3-(3,4,5-trimethoxy-phenyl)-4,5-dihydro-isoxazol-5-yl]-phenol (11b) (389.40 mg, 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.31 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (16d) (570 mg, 80% yield).
$^1$H NMR (CDCl$_3$): δ 1.70-1.80 (m, 2H), 1.89-2.02 (m, 4H), 3.69-3.82 (dd, 1H, J=10.7 Hz, J=16.4 Hz), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 5.63-5.73 (t, 1H, J=10.1 Hz, J=9.2 Hz), 5.77 (s, 1H), 6.62 (s, 2H), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.92 (dd, 1H, J=7.74 Hz J=7.55 Hz) FABMS: 728.80 (M+H)$^+$.

Example 5

2-(3-methoxy-4-(5-(2-methoxy-5-(5-(3,4,5-trimethoxyphenyl)isoxazol-3-yl)phenoxy)pentyloxy)phenyl)-2,3-dihydroquinazolin-4(1H)-one (21d)

2-methoxy-5-(5-(3,4,5-trimethoxyphenyl)isoxazol-3-yl)phenol (20a) (357.36 mg 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (21d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 6.04 (s, 1H), 6.57-6.61 (d, 1H, J=7.9 Hz), 6.63 (s, 1H), 6.67 (s, 1H), 6.76-6.79 (d, 1H, J=8.1 Hz), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.87 (dd, 1H, J=7.74 Hz J=7.55 Hz) FABMS: 696.76 (M+H)$^+$.

Example 6

2-(4-(5-(2,6-dimethoxy-4-(5-(3,4,5-trimethoxyphenyl)isoxazol-3-yl)phenoxy)pentyloxy)-3-methoxyphenyl)-2,3-dihydroquinazolin-4(1H)-one (25d)

2,6-dimethoxy-4-(5-(3,4,5-trimethoxyphenyl)isoxazol-3-yl)phenol (20b) (387.38 mg, 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (25d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 6.04 (s, 1H), 6.62 (s, 2H), 6.67 (s, 1H) 6.82-6.85 (d, 1H, J=7.7 Hz), 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.92 (dd, 1H, J=7.74 Hz J=7.55 Hz) FABMS: 726.78 (M+H)$^+$.

Example 7

2-(3-methoxy-4-(5-(2-methoxy-5-(3-(3,4,5-trimethoxyphenyl)isoxazol-5-yl)phenoxy)pentyloxy)phenyl)-2,3-dihydroquinazolin-4(1H)-one (30d)

2-methoxy-5-(3-(3,4,5-trimethoxyphenyl)isoxazol-5-yl)phenol (29a) (357.36 mg 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (30d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 6.04 (s, 1H), 6.57-6.61 (d, 1H, J=7.9 Hz), 6.63 (s, 1H), 6.67 (s, 1H), 6.76-6.79 (d, 1H, J=8.1 Hz), 6.82-6.85 (d, 1H, J=7.7 Hz) 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.87 (dd, 1H, J=7.74 Hz J=7.55 Hz) FABMS: 696.76 (M+H)$^+$.

Example 8

2-(4-(5-(2,6-dimethoxy-4-(3-(3,4,5-trimethoxyphenyl)isoxazol-5-yl)phenoxy)pentyloxy)-3-methoxyphenyl)-2,3-dihydroquinazolin-4(1H)-one (34d)

2,6-dimethoxy-4-(3-(3,4,5-trimethoxyphenyl)isoxazol-5-yl)phenol (29b) (387.38 mg 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (34d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.94 (s, 3H), 4.02-4.08 (t, 2H, J=5. Hz), 4.10-4.16 (t, 2H, J=6.4 Hz), 4.39-4.42 (bs, NH), 6.04 (s, 1H), 6.62 (s, 2H), 6.67 (s, 1H) 6.82-6.85 (d, 1H, J=7.7 Hz), 6.88 (s, 2H), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.92 (dd, 1H, J=7.74 Hz J=7.55 Hz) FABMS: 726.78 (M+H)$^+$.

Example 9

(Z)-2-(3-methoxy-4-(5-(2-methoxy-5-(3,4,5-trimethoxystyryl)phenoxy)pentyloxy)phenyl)-2,3-dihydroquinazolin-4(1H)-one (39d)

(Z)-2-methoxy-5-(3,4,5-trimethoxystyryl)phenol (38a) (316.35 mg 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (39d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.94 (s, 3H), 4.02-4.08 (t, 2H, J=5.2 Hz), 4.10-4.16 (t, 2H, J=6.4 Hz), 4.39-4.42 (bs, NH), 6.04 (s, 1H), 6.39 (d, 2H, J=4.4 Hz), 6.47 (s, 2H) 6.73 (d, 1H, 2.2 Hz), 6.82-6.85 (d, 1H, J=7.7 Hz), 6.89 (d, 1H, J=2.2 Hz), 6.90 (s, 1H), 6.94-6.97 (d, 1H, J=7.7 Hz), 7.18-7.21 (m,

2H), 7.22-7.29 (dd, 1H, J=7.5 Hz J=15.2 Hz), 7.82-7.92 (dd, 1H, J=7.55 Hz J=7.74 Hz) FABMS: 655.75M+H)+.

Example 10

(Z)-2-(4-(5-(2,6-dimethoxy-4-(3,4,5-trimethoxy-styryl)phenoxy)pentyloxy)-3-methoxy phenyl)-2,3-dihydroquinazolin-4(1H)-one (43d)

(Z)-2,6-dimethoxy-4-(3,4,5-trimethoxystyryl)phenol (38b) (346.37.36 mg 1.0 mmol) in DMF (20 mL) was added anhydrous potassium carbonate (690 mg, 5.0 mmol) and 2-[4-(5-Bromo-pentyloxy)-3-methoxy-phenyl]-2,3-dihydro-1H-quinazolin-4-one (2d) (419.29 mg, 1.0 mmol). The reaction mixture was stirred at a temperature of 30° C. for 30 h and the reaction was monitored by TLC using ethyl acetate-hexane (6:4) as a solvent system. Then to this ice is added and extracted with ethyl acetate. The solvent was evaporated under vacuum to afford the crude product. This was further purified by column chromatography using ethyl acetate:hexane (6:4) as a solvent system to obtain the pure product (43d) (546 mg, 80% yield).

$^1$H NMR (CDCl$_3$): δ 1.70-1.80 (m, 2H), 1.89-2.02 (m, 4H), 3.84 (s, 6H), 3.87 (s, 3H), 3.92 (s, 3H), 3.89 (s, 6H), 3.94 (s, 3H), 4.02-4.08 (t, 2H, J=5.2 Hz), 4.10-4.16 (t, 21-1, J=6.4 Hz), 4.39-4.42 (bs, NH), 6.04 (s, 1H), 6.47 (s, 2H), 6.70 (s, 2H), 6.73 (d, 1H, J=2.2 Hz), 6.82-6.85 (d, 1H, J=7.7 Hz), 6.89 (d, 11-1, J=2.2 Hz), 6.90 (s, 1H), 6.94-6.97 (d, 1H, J=7.7 Hz), 7.18-7.21 (m, 2H), 7.22-7.29 (dd, 1H, J=7.5 Hz J=15.2 Hz), 7.82-7.92 (dd, 1H, J=7.55 Hz J=7.74 Hz): FABMS: 685.77M+H)+.

BIOLOGICAL ACTIVITY some of in vitro biological activity studies were carried out at the National Cancer Institute, Maryland, USA.

In Vitro Cytotoxicity

The isoxazole/isoxazoline/combretastatin linked dihydroquinazolinone hybrid (7d) has been tested against forty nine human tumour cell lines derived from nine cancer types (leukemia, non-small cell lung cancer, colon cancer, CNS cancer, melanoma, ovarian cancer, renal cancer, prostate cancer and breast cancer) as per NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. The concentration for 50% cell growth inhibition (GI$_{50}$), total cell growth inhibition (TGI, 0% growth) and 50% cell death (LC$_{50}$, 50% growth) compared with the control has been calculated (Table-1). Compound 7d has been evaluated for their in vitro cytotoxicity in forty nine cell lines from nine human cancer types of lung (Hop-62, NCI-H226, NCI-H522), leukemia (K-562, SR), colon (HCT-116, HCT-15, HCC-2998), CNS(SF-539), melanoma (SK-MEL-5, MDA-MB-435, UACC-62, M14), ovarian (IGROV1), renal (A498), prostate (PC3) breast (BT-549, HS578T) origin. The results are expressed as percent of cell growth determined relative to that of untreated control cells (Table 2). The representative compound 7d has shown significant cytotoxicity against some cancer cell lines.

TABLE 1

Log$_{10}$ GI$_{50}$ (concentration in mol/L causing 50% growth inhibition) values for quinazolinone-PBD hybrid(7d)

| | Log$_{10}$ GI50 | Log$_{10}$ LC50 |
|---|---|---|
| Leukemia | −6.17 | −4.15 |
| Non-small-celllung | −4.97 | −4.00 |
| Colon | −5.17 | −4.00 |
| CNS | −4.66 | −4.00 |
| Melanoma | −5.69 | −4.00 |
| Ovarian | −5.20 | −4.00 |
| Renal | −4.72 | −4.00 |
| Prostate | −5.39 | −4.00 |
| Breast | −5.82 | −4.00 |

Each cancer type represents the average of six to eight different cancer cell lines.

The compound 7d exhibits a wide spectrum of activity against forty nine cell lines in nine cell panels, with GI$_{50}$ value of <40 µm. In the non-small cell lung cancer panel, the growth of EKVX, NCI-H3 cell lines were affected by compound 7d with GI$_{50}$ values as 0.36 and 0.38 µM respectively. The GI$_{50}$ values of compound 7d against colon cancer HCC-2998, HCT-116 cell lines are 0.06 and 0.26 µm respectively. The GI$_{50}$ values for compound 7d against leukemia CCRF-CEM, K-562, MOLT-4 and RPMI-8226 cell lines are 0.62, 0.37, 0.68 and 0.06 µm respectively. The GI$_{50}$ values for compound 7d against melanoma SK-MEL-5, UACC-257, MDA-MB-435, and UACC-62 cell lines are 0.18, 0.29, 0.60 and 0.99 µm respectively. The GI$_{50}$ values for compound 7d against ovarian IGROV1 and OVCAR-4 cell lines are 0.32 and 0.49 µM. The GI$_{50}$ values for compound 7d against renal ACHN cell line is 0.95 µm The GI$_{50}$ values for compound 7d against prostate PC-3 cell line is 0.74 µm. The GI$_{50}$ values for compound 7d against breast MCF7, T-47D. MDA-MB-468 cell lines are 0.45, 0.30, 0.08 µm respectively.

Compound 7d exhibits activity against forty nine cell lines in nine cancer panels with GI$_{50}$ values of <40 µm. in vitro cytotoxicity of compound 7d in selected cancer cell lines has been illustrated in Table 2. The average GI$_{50}$ values for each cancer panel of compounds 7d have been illustrated in Tablet.

TABLE 2

In vitro cytotoxicity of compounds 7d in forty nine cancer cell lines

| Cancer panel/ cell line | GI$_{50}$ (µm) 7d |
|---|---|
| Leukemia | |
| CCRF-CEM | 0.62 |
| HL-60(TB) | 12.2 |
| K-562 | 0.37 |
| MOLT-4 | 0.68 |
| RPMI-8226 | 0.06 |
| Non-small cell lung | |
| A549/ATCC | 15.7 |
| EKVX | 0.36 |
| HOP-92 | 15.8 |
| NCI-H23 | 0.38 |
| NCI-H460 | 15.1 |
| NCI-H522 | 27.4 |
| Colon | |
| HCC-2998 | 0.06 |
| HCT-116 | 0.26 |
| HCT-15 | 15.9 |
| KM12 | 10.4 |
| SW-620 | 21.0 |

TABLE 2-continued

In vitro cytotoxicity of compounds 7d in forty nine cancer cell lines

| Cancer panel/ cell line | GI$_{50}$ (μm) 7d |
|---|---|
| CNS | |
| SF-268 | 20.2 |
| SF-295 | 16.4 |
| SF-539 | 21.2 |
| SNB-19 | 16.6 |
| SNB-75 | 34.2 |
| U251 | 25.2 |
| Melanoma | |
| LOX IMVI | 19.5 |
| M14 | 19.8 |
| Ovarian | |
| IGROV1 | 0.32 |
| OVCAR-3 | 12.4 |
| OVCAR-4 | 0.49 |
| OVCAR-5 | 31.7 |
| OVCAR-8 | 25.7 |
| SK-OV-3 | 38.5 |
| NCI/ADRRES | 10.6 |
| Renal | |
| 786-0 | 31.8 |
| A498 | 19.3 |
| ACHN | 0.95 |
| CAKI-1 | 18.0 |
| SN12C | 39.1 |
| UO-31 | 21.4 |
| Prostate | |
| PC-3 | 0.74 |
| DU-145 | 22.4 |
| Breast | |
| MCF7 | 0.45 |
| MDA-MB-231/ATCC | 14.7 |
| HS 578T | 15.0 |
| T-47D | 0.30 |
| MDA-MB-468 | 0.08 |
| Melanoma | |
| SK-MEL-28 | 3.24 |
| SK-MEL-5 | 0.18 |
| UACC-257 | 0.29 |
| UACC-62 | 0.99 |
| MDA-MB-435 | 0.60 |

The mean graph mid point values of $\log_{10}$ TGI and $\log_{10}$ LC$_{50}$ as well as $\log_{10}$ GI$_{50}$ for 7d is listed in Table-3. As demonstrated by mean graph pattern, compounds 7d exhibit an interesting profile of activity and selectivity for various cell lines. The mean graph mid points of $\log_{10}$ TGI and $\log_{10}$ LC$_{50}$ have shown similar pattern to the $\log_{10}$ GI$_{50}$ mean graph mid points.

TABLE 3

$\log_{10}$ GI$_{50}$, $\log_{10}$ TGI and $\log_{10}$ LC$_{50}$ mean graphs midpoints (MG_MID) of in vitro cytotoxicity data for the compound 7d.against human tumour cell lines.

| Compound | Log$_{10}$ GI$_{50}$ | Log$_{10}$ TGI | Log$_{10}$ LC$_{50}$ |
|---|---|---|---|
| 7d | −5.28 | −4.18 | −4.02 |

Significance of the Work Carried Out

The novel dihydroquinazolinone-isoxazole/isoxazoline/combretastatin hybrids that have been synthesized exhibited significant cytotoxic activity against forty nine human tumour cell lines.

ADVANTAGES OF THE INVENTION

1. The present invention provides a new dihydroquinazolinone-isoxazole/isoxazoline/combretastatin hybrids useful as antitumour agents.
2. It also provides a process for the preparation of novel dihydroquinazolinone-isoxazole/isoxazoline/combretastatin hybrids.

We claim:

1. An isoxazole/isoxazoline/combretastatin linked dihydroquinazolinone compound of general formulae A

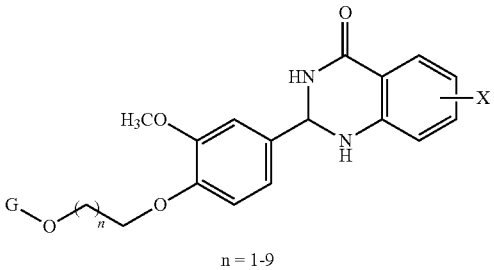

Formula A n = 1-9

Where in G=

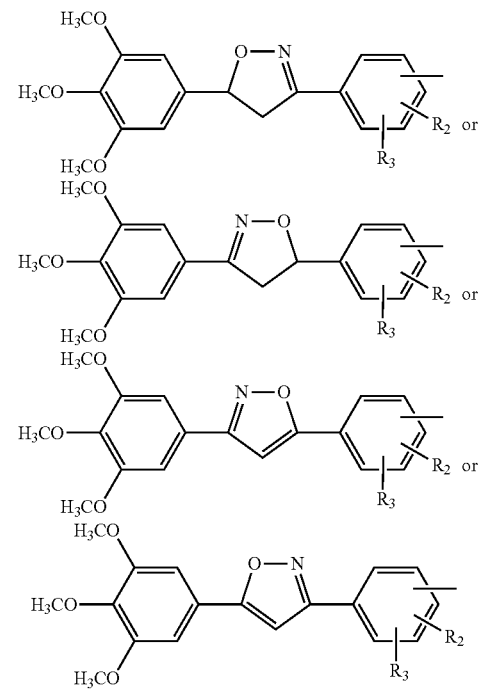

If R$_2$ = 2-OCH$_3$, R$_3$ = 6-OCH$_3$
If R$_2$ = 2-OCH$_3$, R$_3$ = 6-H
X = H, Cl, CH$_3$, OCH$_3$.

2. The isoxazole/isoxazoline/combretastatin linked dihydroquinazolinone compound as claimed in claim 1 wherein the isoxazole/isoxazoline/combretastatin linked dihydroquinazolinone compound of formula A wherein the compound is represented by general formulae 3a-i to 6a-1, 7a-i to 10a-1, 12a-i to 15a-1, 16a-i to 19a-1, 21a-i to 24a-1, 25a-i to 28a-1, 30a-i to 33a-1, 3-a-i to 37a-i and 39a-i to 42a-1, 43a-i to 46a-i

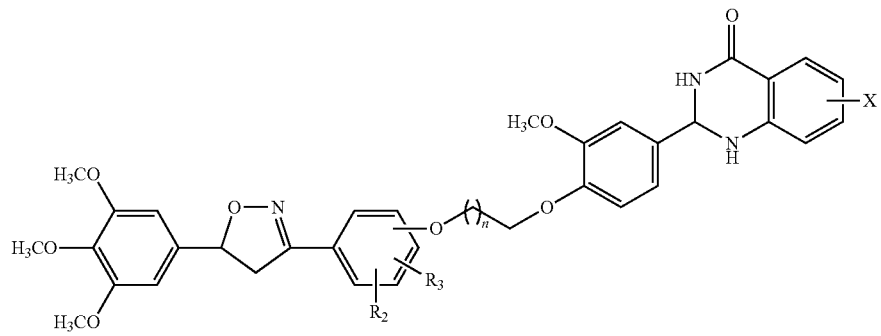
3a-i to 6a-i R$_2$ = 2-OCH$_3$, R$_3$ = 6-H; X = H, Cl, CH$_3$, OCH$_3$
7a-i to 10a-i R$_2$ = 2-OCH$_3$, R$_3$ = 6-OCH$_3$; X = H, Cl, CH$_3$, OCH$_3$
n = 1-9
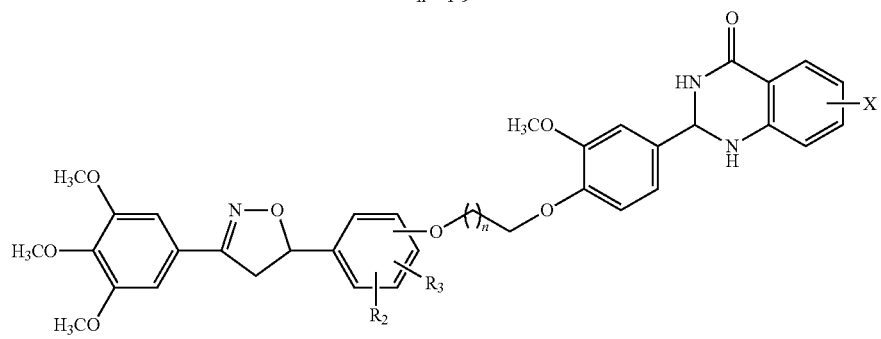
12a-i to 15a-i R$_2$ = 2-OCH$_3$, R$_3$ = 6-H; X = H, Cl, CH$_3$, OCH$_3$
16a-i to 19a-i R$_2$ = 2-OCH$_3$, R$_3$ = 6-OCH$_3$; X = H, Cl, CH$_3$, OCH$_3$
n = 1-9
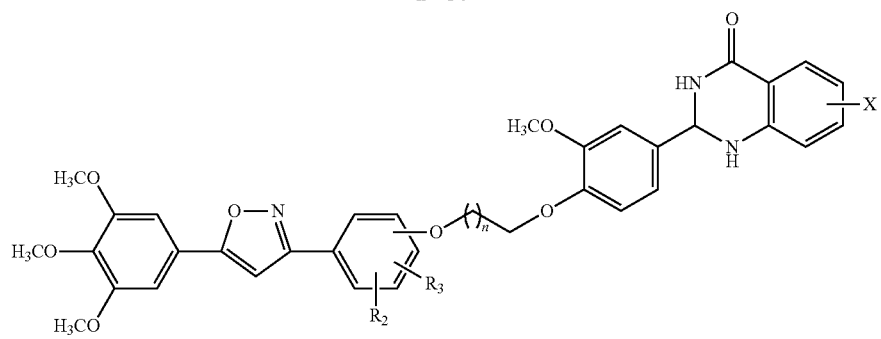
21a-i to 24a-i R$_2$ = 2-OCH$_3$, R$_3$ = 6-H; X = H, Cl, CH$_3$, OCH$_3$
25a-i to 28a-i R$_2$ = 2-OCH$_3$, R$_3$ = 6-OCH$_3$; X = H, Cl, CH$_3$, OCH$_3$
n = 1-9
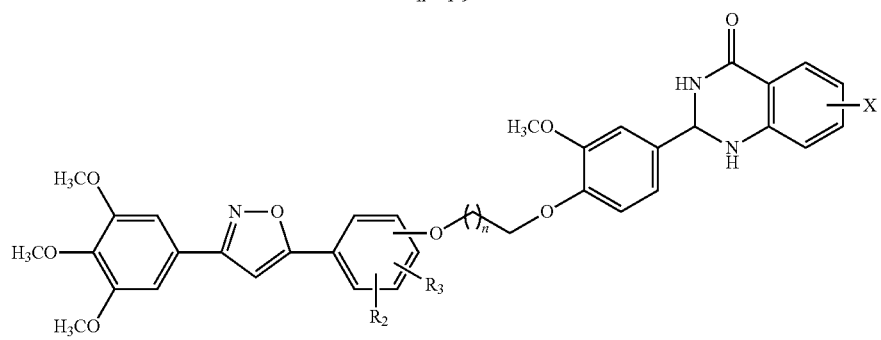
30a-i to 33a-i R$_2$ = 2-OCH$_3$, R$_3$ = 6-H; X = H, Cl, CH$_3$, OCH$_3$
34a-i to 37a-i R$_2$ = 2-OCH$_3$, R$_3$ = 6-OCH$_3$; X = H, Cl, CH$_3$, OCH$_3$
n = 1-9.

3. The isoxazole/isoxazoline/combretastatin linked dihydroquinazolinone compound as claimed in claim 1 wherein the compound is represented by the group of the following compounds:

2-[3-Methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (3a);

2-[3-Methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (3b);

2-[3-Methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (3c);

2-[3-Methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (3d);

2-[3-Methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (3e);

2-[3-Methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (3f);

2-[3-Methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (3g);

2-[3-Methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (3h);

2-[3-Methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (3i);

6-Chloro-2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (4a);

6-Chloro-2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (4b);

6-Chloro-2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (4c);

6-Chloro-2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (4d);

6-Chloro-2-[3-methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (4e);

6-Chloro-2-[3-methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (4f);

6-Chloro-2-[3-methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (4g);

6-Chloro-2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (4h);

6-Chloro-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (4i);

6-Methyl 2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (5a);

6-Methyl 2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (5b);

6-Methyl 2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (5c);

6-Methyl 2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (5d);

6-Methyl 2-[3-methoxy-4-(6-{2-methoxy-5-[5-(3,4,5-trimethoxy-phenyl)-4,5-dihydro-isoxazol-3-yl]-hexyloxy}-butoxy)-phenyl]-2,3-dihydro-1H-quinazolin-4-one (5e);

6-Methyl 2-[3-methoxy-4-(7-{2-methoxy-5-[5-(3,4,5-trimethoxy-phenyl)-4,5-dihydro-isoxazol-3-yl]-phenoxy}-heptoxy)-phenyl]-2,3-dihydro-1H-quinazolin-4-one (5f);

6-Methyl 2-[3-methoxy-4-(8-{2-methoxy-5-[5-(3,4,5-trimethoxy-phenyl)-4,5-dihydro-isoxazol-3-yl]-phenoxy}-octoxy)-phenyl]-2,3-dihydro-1H-quinazolin-4-one (5g);

6-Methyl 2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (5h);

6-Methyl-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (5i);

6-Methoxy-2-[3-methoxy-4-(2-{2-methoxy-5-[5-(3,4,5-trimethoxy-phenyl)-4,5-dihydro-isoxazol-3-yl]-phenoxy}-ethoxy)-phenyl]-2,3-dihydro-1H-quinazolin-4-one (6a);

6-Methoxy-2-[3-methoxy-4-(3-{2-methoxy-5-[5-(3,4,5-trimethoxy-phenyl)-4,5-dihydro-isoxazol-3-yl]-phenoxy}-propoxy)-phenyl]-2,3-dihydro-1H-quinazolin-4-one (6b);

6-Methoxy-2-[3-methoxy-4-(4-{2-methoxy-5-[5-(3,4,5-trimethoxy-phenyl)-4,5-dihydro-isoxazol-3-yl]-phenoxy}-butoxy)-phenyl]-2,3-dihydro-1H-quinazolin-4-one (6c);

6-Methoxy-2-[3-methoxy-4-(5-{2-methoxy-5-[5-(3,4,5-trimethoxy-phenyl)-4,5-dihydro-isoxazol-3-yl]-phenoxy}-pentyloxy)-phenyl]-2,3-dihydro-1H-quinazolin-4-one (6d);

6-Methoxy-2-[3-methoxy-4-(6-{2-methoxy-5-[5-(3,4,5-trimethoxy-phenyl)-4,5-dihydro-isoxazol-3-yl]-phenoxy}-hexyloxy)-phenyl]-2,3-dihydro-1H-quinazolin-4-one (6e);

6-Methoxy-2-[3-methoxy-4-(7-{2-methoxy-5-[5-(3,4,5-trimethoxy-phenyl)-4,5-dihydro-isoxazol-3-yl]-phenoxy}-heptyloxy)-phenyl]-2,3-dihydro-1H-quinazolin-4-one (6f);

6-Methoxy-2-[3-methoxy-4-(8-{2-methoxy-5-[5-(3,4,5-trimethoxy-phenyl)-4,5-dihydro-isoxazol-3-yl]-phenoxy}-octyloxy)-phenyl]-2,3-dihydro-1H-quinazolin-4-one (6g);

6-Methoxy-2-[3-methoxy-4-(9-{2-methoxy-5-[5-(3,4,5-trimethoxy-phenyl)-4,5-dihydro-isoxazol-3-yl]-phenoxy}-nonyloxy)-phenyl]-2,3-dihydro-1H-quinazolin-4-one (6h);

6-Methoxy-2-[3-methoxy-4-(10-{2-methoxy-5-[5-(3,4,5-trimethoxy-phenyl)-4,5-dihydro-isoxazol-3-yl]-phenoxy}-decyloxy)-phenyl]-2,3-dihydro-1H-quinazolin-4-one (6i);

2-[4-(2-{2,6-Dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (7a);

2-[4-(3-{2,6-Dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (7b);

2-[4-(4-{2,6-Dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (7c);

2-[4-(5-{2,6-Dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (7d);

2-[4-(6-{2,6-Dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (7e);

2-[4-(7-{2,6-Dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (7f);

2-[4-(8-{2,6-Dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (7g);

2-[4-(9-{2,6-Dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (7h);

2-[4-(10-{2,6-Dimethoxy-4-[5-(3,4,5-trimethoxy-phenyl)-4,5-dihydro isoxazol-3-yl]-phenoxy}-decyloxy)-3-methoxy-phenyl]-2,3-dihydro 1H-quinazolin-4-one (7i);

6-Chloro-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (8a);

6-Chloro-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (8b);

6-Chloro-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (8c);

6-Chloro-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro 1H-quinazolin-4-one (8d);

6-Chloro-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (8e);

6-Chloro-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (8f);

6-Chloro-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (8g);

6-Chloro-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (8h);

6-Chloro-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (8i);

6-Methyl-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (9a);

6-Methyl-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (9b);

6-Methyl-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (9c);

6-Methyl-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (9d);

6-Methyl-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (9e);

6-Methyl-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (9f);

6-Methyl-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (9g);

6-Methyl-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (9h);

6-Methyl-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (9i);

6-Methoxy-2-[4-(2-{2,6-dimethoxy-4-[5-(3,4,5-trimethoxy-phenyl)-4,5-dihydro-isoxazol-3-yl]-phenoxy}-ethoxy)-3-methoxy-phenyl]-2,3-dihydro-1H-quinazolin-4-one (10a);

6-Methoxy-2-[4-(3-{2,6-dimethoxy-4-[5-(3,4,5-trimethoxy-phenyl)-4,5-dihydro-isoxazol-3-yl]-phenoxy}-propoxy)-3-methoxy-phenyl]-2,3-dihydro-1H-quinazolin-4-one (10b);

6-Methoxy-2-[4-(4-{2,6-dimethoxy-4-[5-(3,4,5-trimethoxy-phenyl)-4,5-dihydro-isoxazol-3-yl]-phenoxy}-butoxy)-3-methoxy-phenyl]-2,3-dihydro-1H-quinazolin-4-one (10c);

6-Methoxy-2-[4-(5-{2,6-dimethoxy-4-[5-(3,4,5-trimethoxy-phenyl)-4,5-dihydro-isoxazol-3-yl]-phenoxy}-pentyloxy)-3-methoxy-phenyl]-2,3-dihydro-1H-quinazolin-4-one (10d);

6-Methoxy-2-[4-(6-{2,6-dimethoxy-4-[5-(3,4,5-trimethoxy-phenyl)-4,5-dihydro-isoxazol-3-yl]-phenoxy}-hexyloxy)-3-methoxy-phenyl]-2,3-dihydro-1H-quinazolin-4-one (10e);

6-Methoxy-2-[4-(7-{2,6-dimethoxy-4-[5-(3,4,5-trimethoxy-phenyl)-4,5-dihydro-isoxazol-3-yl]-phenoxy}-heptyloxy)-3-methoxy-phenyl]-2,3-dihydro-1H-quinazolin-4-one (10f);

6-Methoxy-2-[4-(8-{2,6-dimethoxy-4-[5-(3,4,5-trimethoxy-phenyl)-4,5-dihydro-isoxazol-3-yl]-phenoxy}-octyloxy)-3-methoxy-phenyl]-2,3-dihydro-1H-quinazolin-4-one (10g);

6-Methoxy-2-[4-(9-{2,6-dimethoxy-4-[5-(3,4,5-trimethoxy-phenyl)-4,5-dihydro-isoxazol-3-yl]-phenoxy}-nonyloxy)-3-methoxy-phenyl]-2,3-dihydro-1H-quinazolin-4-one (10h);

6-Methoxy-2-[4-(10-{2,6-dimethoxy-4-[5-(3,4,5-trimethoxy-phenyl)-4,5-dihydro-isoxazol-3-yl]-phenoxy}-decyloxy)-3-methoxy-phenyl]-2,3-dihydro-1H-quinazolin-4-one (10i);

2-[3-Methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (12a);

2-[3-Methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (12b);

2-[3-Methoxy-4-(4-{2-methoxy-5-[3-(3,4,5-trimethoxy-phenyl)-4,5-dihydro-isoxazol-5-yl]-phenoxy}-butoxy)-phenyl]-2,3-dihydro-1H-quinazolin-4-one (12c);

2-[3-Methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (12d);

2-[3-Methoxy-4-(6-{2-methoxy-5-[3-(3,4,5-trimethoxy-phenyl)-4,5 dihydro-isoxazol-5-yl]-phenoxy}-heptyloxy)-phenyl]-2,3-dihydro-1H-quinazolin-4-one (12e);

2-[3-Methoxy-4-(7-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (12f);

2-[3-Methoxy-4-(8-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (12g);

2-[3-Methoxy-4-(9-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (12h);

2-[3-Methoxy-4-(10-{2-methoxy-5-[3-(3,4,5-trimethoxy-phenyl)-4,5-dihydro-isoxazol-5-yl]-phenoxy}-dedyloxy)-phenyl]-2,3-dihydro-1H-quinazolin-4-one (12i);

6-Chloro-2-[3-methoxy-4-(2-{2-methoxy-5-[3-(3,4,5-tri-methoxy-phenyl)-4,5-dihydro-isoxazol-5-yl]-phenoxy}-ethoxy)-phenyl]-2,3-dihydro-1H-quinazolin-4-one (13a);

6-Chloro-2-[3-methoxy-4-(3-{2-methoxy-5-[3-(3,4,5-tri-methoxy-phenyl)-4,5-dihydro-isoxazol-5-yl]-phenoxy}-propoxy)-phenyl]-2,3-dihydro-1H-quinazolin-4-one (13b);

6-Chloro-2-[3-methoxy-4-(4-{2-methoxy-5-[3-(3,4,5-tri-methoxy-phenyl)-4,5-dihydro-isoxazol-5-yl]-phenoxy}-butyloxy)-phenyl]-2,3-dihydro-1H-quinazolin-4-one (13c);

6-Chloro-2-[3-methoxy-4-(5-{2-methoxy-5-[3-(3,4,5-tri-methoxy-phenyl)-4,5-dihydro-isoxazol-5-yl]-phenoxy}-pentyloxy)-phenyl]-2,3-dihydro-1H-quinazolin-4-one (13d);

6-Chloro-2-[3-methoxy-4-(6-{2-methoxy-5-[3-(3,4,5-tri-methoxy-phenyl)-4,5-dihydro-isoxazol-5-yl]-phenoxy}-hexyloxy)-phenyl]-2,3-dihydro-1H-quinazolin-4-one (13e);

6-Chloro-2-[3-methoxy-4-(7-{2-methoxy-5-[3-(3,4,5-tri-methoxy-phenyl)-4,5-dihydro-isoxazol-5-yl]-phenoxy}-heptyloxy)-phenyl]-2,3-dihydro-1H-quinazolin-4-one (13f);

6-Chloro-2-[3-methoxy-4-(8-{2-methoxy-5-[3-(3,4,5-tri-methoxy-phenyl)-4,5-dihydro-isoxazol-5-yl]-phenoxy}-octyloxy)-phenyl]-2,3-dihydro-1H-quinazolin-4-one (13g);

6-Chloro-2-[3-methoxy-4-(9-{2-methoxy-5-[3-(3,4,5-tri-methoxy-phenyl)-4,5-dihydro-isoxazol-5-yl]-phenoxy}-nonyloxy)-phenyl]-2,3-dihydro-1H-quinazolin-4-one (13h);

6-Chloro-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (13i);

6-Methyl-2-[3-methoxy-4-(2-{2-methoxy-5-[3-(3,4,5-tri-methoxy-phenyl)-4,5-dihydro-isoxazol-5-yl]-phenoxy}-ethoxy)-phenyl]-2,3-dihydro-1H-quinazolin-4-one (14a);

6-Methyl-2-[3-methoxy-4-(3-{2-methoxy-5-[3-(3,4,5-tri-methoxy-phenyl)-4,5-dihydro-isoxazol-5-yl]-phenoxy}-propoxy)-phenyl]-2,3-dihydro-1H-quinazolin-4-one (14b);

6-Methyl-2-[3-methoxy-4-(4-{2-methoxy-5-[3-(3,4,5-tri-methoxy-phenyl)-4,5-dihydro-isoxazol-5-yl]-phenoxy}-butyloxy)-phenyl]-2,3-dihydro-1H-quinazolin-4-one (14c);

6-Methyl-2-[3-methoxy-4-(5-{2-methoxy-5-[3-(3,4,5-tri-methoxy-phenyl)-4,5-dihydro-isoxazol-5-yl]-phenoxy}-pentyloxy)-phenyl]-2,3-dihydro-1H-quinazolin-4-one (14d);

6-Methyl-2-[3-methoxy-4-(6-{2-methoxy-5-[3-(3,4,5-tri-methoxy-phenyl)-4,5-dihydro-isoxazol-5-yl]-phenoxy}-hexyloxy)-phenyl]-2,3-dihydro-1H-quinazolin-4-one (14e);

6-Methyl-2-[3-methoxy-4-(7-{2-methoxy-5-[3-(3,4,5-tri-methoxy-phenyl)-4,5-dihydro-isoxazol-5-yl]-phenoxy}-heptyloxy)-phenyl]-2,3-dihydro-1H-quinazolin-4-one (14f);

6-Methyl-2-[3-methoxy-4-(8-{2-methoxy-5-[3-(3,4,5-tri-methoxy-phenyl)-4,5-dihydro-isoxazol-5-yl]-phenoxy}-octyloxy)-phenyl]-2,3-dihydro-1H-quinazolin-4-one (14g);

6-Methyl-2-[3-methoxy-4-(9-{2-methoxy-5-[3-(3,4,5-tri-methoxy-phenyl)-4,5-dihydro-isoxazol-5-yl]-phenoxy}-nonyloxy)-phenyl]-2,3-dihydro-1H-quinazolin-4-one (14h);

6-Methyl-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (14i);

6-Methoxy-2-[3-methoxy-4-(2-{2-methoxy-5-[3-(3,4,5-trimethoxy-phenyl)-4,5-dihydro-isoxazol-5-yl]-phenoxy}-ethoxy)-phenyl]-2,3-dihydro-1H-quinazolin-4-one (15a);

6-Methoxy-2-[3-methoxy-4-(3-{2-methoxy-5-[3-(3,4,5-trimethoxy-phenyl)-4,5-dihydro-isoxazol-5-yl]-phenoxy}-propoxy)-phenyl]-2,3-dihydro-1H-quinazolin-4-one (15b);

6-Methoxy-2-[3-methoxy-4-(4-{2-methoxy-5-[3-(3,4,5-trimethoxy-phenyl)-4,5-dihydro-isoxazol-5-yl]-phenoxy}-butyloxy)-phenyl]-2,3-dihydro-1H-quinazolin-4-one (15c);

6-Methoxy-2-[3-methoxy-4-(5-{2-methoxy-5-[3-(3,4,5-trimethoxy-phenyl)-4,5-dihydro-isoxazol-5-yl]-phenoxy}-pentyloxy)-phenyl]-2,3-dihydro-1H-quinazolin-4-one (15d);

6-Methoxy-2-[3-methoxy-4-(6-{2-methoxy-5-[3-(3,4,5-trimethoxy-phenyl)-4,5-dihydro-isoxazol-5-yl]-phenoxy}-hexyloxy)-phenyl]-2,3-dihydro-1H quinazolin-4-one (15e);

6-Methoxy-2-[3-methoxy-4-(7-{2-methoxy-5-[3-(3,4,5-trimethoxy-phenyl)-4,5-dihydro-isoxazol-5-yl]-phenoxy}-heptyloxy)-phenyl]-2,3-dihydro-1H-quinazolin-4-one (15f);

6-Methoxy-2-[3-methoxy-4-(8-{2-methoxy-5-[3-(3,4,5-trimethoxy-phenyl)-4,5-dihydro-isoxazol-5-yl]-phenoxy}-octyloxy)-phenyl]-2,3-dihydro-1H-quinazolin-4-one (15g);

6-Methoxy-2-[3-methoxy-4-(9-{2-methoxy-5-[3-(3,4,5-trimethoxy-phenyl)-4,5-dihydro-isoxazol-5-yl]-phenoxy}-nonyloxy)-phenyl]-2,3-dihydro-1H-quinazolin-4-one (15h);

6-Methoxy-2-[3-methoxy-4-(10-{2-methoxy-5-[3-(3,4,5-trimethoxy-phenyl)-4,5-dihydro-isoxazol-5-yl]-phenoxy}-decyloxy)-phenyl]-2,3-dihydro-1H-quinazolin-4-one (15i);

2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (16a);

2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (16b);

2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (16c);

2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]-2,3-dihydro-1H-quinazolin-4-one (16d);

2-[4-(6-{2,6-Dimethoxy-4-[3-(3,4,5-trimethoxy-phenyl)-4,5-dihydro-isoxazol-5-yl]-phenoxy}-hexyloxy)-3-methoxy-phenyl]-2,3-dihydro-1H-quinazolin-4-one (16e);

2-[4-(7-{2,6-Dimethoxy-4-[3-(3,4,5-trimethoxy-phenyl)-4,5-dihydro-isoxazol-5-yl]-phenoxy}-heptyloxy)-3-methoxy-phenyl]-2,3-dihydro-1H-quinazolin-4-one (16f);

2-[4-(8-{2,6-Dimethoxy-4-[3-(3,4,5-trimethoxy-phenyl)-4,5-dihydro-isoxazol-5-yl]-phenoxy}-octyloxy)-3-methoxy-phenyl]-2,3-dihydro-1H-quinazolin-4-one (16g);

2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]-2,3-dihydro-1H-quinazolin-4-one (16h);

2-[4-(10-{2,6-Dimethoxy-4-[3-(3,4,5-trimethoxy-phenyl)-4,5-dihydro-isoxazol-5-yl]-phenoxy}-decyloxy)-3-methoxy-phenyl]-2,3-dihydro-1H-quinazolin-4-one (16i);

6-Chloro-2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (17a);

6-Chloro-2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (17b);

6-Chloro-2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (17c);

6-Chloro-2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (17d);

6-Chloro-2-[4-(6-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (17e);

6-Chloro-2-[4-(7-{2,6-Dimethoxy-4-[3-(3,4,5-trimethoxy-phenyl)-4,5-dihydro-isoxazol-5-yl]-phenoxy}-hexyloxy)-3-methoxy-phenyl]2,3-dihydro-1H-quinazolin-4-one (17f);

6-Chloro-2-[4-(8-{2,6-Dimethoxy-4-[3-(3,4,5-trimethoxy-phenyl)-4,5-dihydro-isoxazol-5-yl]-phenoxy}-heptyloxy)-3-methoxy-phenyl]2,3-dihydro-1H-quinazolin-4-one (17g);

6-Chloro-2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]2,3-dihydro-1H-quinazolin-4-one (17h);

6-Chloro-2-[4-(10-{2,6-Dimethoxy-4-[3-(3,4,5-trimethoxy-phenyl)-4,5-dihydro-isoxazol-5-yl]-phenoxy}-decyloxy)-3-methoxy-phenyl]2,3-dihydro-1H-quinazolin-4-one (17i);

6-Methyl-2-[4-(2-{2,6-Dimethoxy-4-[3-(3,4,5-trimethoxy-phenyl)-4,5-dihydro-isoxazol-5-yl]-phenoxy}-ethoxy)-3-methoxy-phenyl]-2,3-dihydro-1H-quinazolin-4-one (18a);

6-Methyl-2-[4-(3-{2,6-Dimethoxy-4-[3-(3,4,5-trimethoxy-phenyl)-4,5-dihydro-isoxazol-5-yl]-phenoxy}-propoxy)-3-methoxy-phenyl]-2,3-dihydro-1H-quinazolin-4-one (18b);

6-Methyl-2-[4-(4-{2,6-Dimethoxy-4-[3-(3,4,5-trimethoxy-phenyl)-4,5-dihydro-isoxazol-5-yl]-phenoxy}-butoxy)-3-methoxy-phenyl]-2,3-dihydro-1H-quinazolin-4-one (18c);

6-Methyl-2-[4-(5-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (18d);

6-Methyl-2-[4-(6-{2,6-Dimethoxy-4-[3-(3,4,5-trimethoxy-phenyl)-4,5-dihydro-isoxazol-5-yl]-phenoxy}-pentyloxy)-3-methoxy-phenyl]2,3-dihydro-1H-quinazolin-4-one (18e);

6-Methyl-2-[4-(7-{2,6-Dimethoxy-4-[3-(3,4,5-trimethoxy-phenyl)-4,5-dihydro-isoxazol-5-yl]-phenoxy}-hexyloxy)-3-methoxy-phenyl]2,3-dihydro-1H-quinazolin-4-one (18f);

6-Methyl-2-[4-(8-{2,6-Dimethoxy-4-[3-(3,4,5-trimethoxy-phenyl)-4,5-dihydro-isoxazol-5-yl]-phenoxy}-heptyloxy)-3-methoxy-phenyl]2,3-dihydro-1H-quinazolin-4-one (18g);

6-Methyl-2-[4-(9-{2,6-Dimethoxy-4-[3-(3,4,5-trimethoxy-phenyl)-4,5-dihydro-isoxazol-5-yl]-phenoxy}-nonyloxy)-3-methoxy-phenyl]2,3-dihydro-1H-quinazolin-4-one (18h);

6-Methyl-2-[4-(10-{2,6-Dimethoxy-4-[3-(3,4,5-tri-methoxy-phenyl)-4,5-dihydro-isoxazol-5-yl]-phenoxy}-decyloxy)-3-methoxy-phenyl]2,3-dihydro-1H-quinazolin-4-one (18i);

6-Methoxy-2-[4-(2-{2,6-dimethoxy-4-[3-(3,4,5-tri-methoxy-phenyl)-4,5-dihydro-isoxazol-5-yl]-phenoxy}-ethoxy)-3-methoxy-phenyl]-2,3-dihydro-1H-quinazolin-4-one (19a);

6-Methoxy-2-[4-(3-{2,6-dimethoxy-4-[3-(3,4,5-tri-methoxy-phenyl)-4,5-dihydro-isoxazol-5-yl]-phenoxy}-propoxy)-3-methoxy-phenyl]-2,3-dihydro-1H-quinazolin-4-one (19b);

6-Methoxy-2-[4-(4-{2,6-dimethoxy-4-[3-(3,4,5-tri-methoxy-phenyl)-4,5-dihydro-isoxazol-5-yl]-phenoxy}-butoxy)-3-methoxy-phenyl]-2,3-dihydro-1H-quinazolin-4-one (19c);

6-Methoxy-2-[4-(5-{2,6-dimethoxy-4-[3-(3,4,5-tri-methoxy-phenyl)-4,5-dihydro-isoxazol-5-yl]-phenoxy}-pentyloxy)-3-methoxy-phenyl]2,3-dihydro-1H-quinazolin-4-one (19d);

6-Methoxy-2-[4-(6-{2,6-dimethoxy-4-[3-(3,4,5-tri-methoxy-phenyl)-4,5-dihydro-isoxazol-5-yl]-phenoxy}-pentyloxy)-3-methoxy-phenyl]2,3-dihydro-1H-quinazolin-4-one (19e);

6-Methoxy-2-[4-(7-{2,6-dimethoxy-4-[3-(3,4,5-tri-methoxy-phenyl)-4,5-dihydro-isoxazol-5-yl]-phenoxy}-hexyloxy)-3-methoxy-phenyl]2,3-dihydro-1H-quinazolin-4-one (19f);

6-Methoxy-2-[4-(8-{2,6-dimethoxy-4-[3-(3,4,5-tri-methoxy-phenyl)-4,5-dihydro-isoxazol-5-yl]-phenoxy}-heptyloxy)-3-methoxy-phenyl]2,3-dihydro-1H-quinazolin-4-one (19g);

6-Methoxy-2-[4-(9-{2,6-dimethoxy-4-[3-(3,4,5-tri-methoxy-phenyl)-4,5-dihydro-isoxazol-5-yl]-phenoxy}-nonyloxy)-3-methoxy-phenyl]2,3-dihydro-1H-quinazolin-4-one (19h);

6-Methoxy-2-[4-(10-{2,6-dimethoxy-4-[3-(3,4,5-tri-methoxy-phenyl)-4,5-dihydro-isoxazol-5-yl]-phenoxy}-decyloxy)-3-methoxy-phenyl]2,3-dihydro-1H-quinazolin-4-one (19i);

2-(3-methoxy-4-(2-(2-methoxy-5-(5-(3,4,5-trimethoxyphenyl)isoxazol-3-yl)phenoxy)ethoxy)phenyl)-2,3-dihydroquinazolin-4(1H)-one (21a);

2-(3-methoxy-4-(3-(2-methoxy-5-(5-(3,4,5-trimethoxyphenyl) isoxazol-3-yl)phenoxy)propoxy)phenyl)-2,3-dihydroquinazolin-4(1H)-one (21b);

2-(3-methoxy-4-(4-(2-methoxy-5-(5-(3,4,5-trimethoxyphenyl) isoxazol-3-yl)phenoxy)butoxy)phenyl)-2,3-dihydroquinazolin-4(1H)-one (21c);

2-(3-methoxy-4-(5-(2-methoxy-5-(5-(3,4,5-trimethoxyphenyl) isoxazol-3-yl)phenoxy)pentyloxy)phenyl)-2,3-dihydroquinazolin-4(1H)-one (21d);

2-(3-methoxy-4-(6-(2-methoxy-5-(5-(3,4,5-trimethoxyphenyl) isoxazol-3-yl)phenoxy)hexyloxy)phenyl)-2,3-dihydroquinazolin-4(1H)-one (21e);

2-(3-methoxy-4-(7-(2-methoxy-5-(5-(3,4,5-trimethoxyphenyl) isoxazol-3-yl)phenoxy)heptyloxy)phenyl)-2,3-dihydroquinazolin-4(1H)-one (21f);

2-(3-methoxy-4-(8-(2-methoxy-5-(5-(3,4,5-trimethoxyphenyl) isoxazol-3-yl)phenoxy)octyloxy)phenyl)-2,3-dihydroquinazolin-4(1H)-one (21g);

2-(3-methoxy-4-(9-(2-methoxy-5-(5-(3,4,5-trimethoxyphenyl) isoxazol-3-yl)phenoxy)nonyloxy)phenyl)-2,3-dihydroquinazolin-4(1H)-one (21h);

2-(3-methoxy-4-(10-(2-methoxy-5-(5-(3,4,5-trimethoxyphenyl) isoxazol-3-yl)phenoxy)decyloxy)phenyl)-2,3-dihydroquinazolin-4(1H)-one (21i);

6-Chloro-2-[3-methoxy-4-(2-{2-methoxy-5-[5-(3,4,5-tri-methoxy-phenyl)-isoxazol-3-yl]-phenoxy}-ethoxy)-phenyl]-2,3-dihydro-1H-quinazolin-4-one (22a);

6-Chloro-2-{3-methoxy-4-(3-[2-methoxy-5-[5-(3,4,5-tri-methoxy-phenyl)-isoxazol-3-yl]-phenoxy}-propoxy)-phenyl]-2,3-dihydro-1H-quinazolin-4-one (22b);

6-Chloro-2-{3-methoxy-4-(4-[2-methoxy-5-[5-(3,4,5-tri-methoxy-phenyl)-isoxazol-3-yl]-phenoxy}-butyloxy)-phenyl]-2,3-dihydro-1H-quinazolin-4-one (22c);

6-Chloro-2-{3-methoxy-4-(5-[2-methoxy-5-[5-(3,4,5-tri-methoxy-phenyl)-isoxazol-3-yl]-phenoxy}-pentyloxy)-phenyl]-2,3-dihydro-1H-quinazolin-4-one (22d);

6-Chloro-2-{3-methoxy-4-(6-[2-methoxy-5-[5-(3,4,5-tri-methoxy-phenyl)-isoxazol-3-yl]-phenoxy}-hexyloxy)-phenyl]-2,3-dihydro-1H-quinazolin-4-one (22e);

6-Chloro-2-{3-methoxy-4-(7-[2-methoxy-5-[5-(3,4,5-tri-methoxy-phenyl)-isoxazol-3-yl]-phenoxy}-heptyloxy)-phenyl]-2,3-dihydro-1H-quinazolin-4-one (22f);

6-Chloro-2-{3-methoxy-4-(8-[2-methoxy-5-[5-(3,4,5-tri-methoxy-phenyl)-isoxazol-3-yl]-phenoxy}-octyloxy)-phenyl]-2,3-dihydro-1H-quinazolin-4-one (22g);

6-Chloro-2-{3-methoxy-4-(9-[2-methoxy-5-[5-(3,4,5-tri-methoxy-phenyl)-isoxazol-3-yl]-phenoxy}-nonyloxy)-phenyl]-2,3-dihydro-1H-quinazolin-4-one (22h);

6-Chloro-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (22i);

6-Methyl-2-{3-methoxy-4-(2-[2-methoxy-5-[5-(3,4,5-tri-methoxy-phenyl)-isoxazol-3-yl]-phenoxy}-ethoxy)-phenyl]-2,3-dihydro-1H-quinazolin-4-one (23a);

6-Methyl-2-[3-methoxy-4-(3-{2-methoxy-5-[5-(3,4,5-tri-methoxy-phenyl)-isoxazol-3-yl]-phenoxy}-propoxy)-phenyl]-2,3-dihydro-1H-quinazolin-4-one (23b);

6-Methyl-2-[3-methoxy-4-(4-{2-methoxy-5-[5-(3,4,5-tri-methoxy-phenyl)-isoxazol-3-yl]-phenoxy}-butyloxy)-phenyl]-2,3-dihydro-1H-quinazolin-4-one (23c);

6-Methyl-2-[3-methoxy-4-(5-{2-methoxy-5-[5-(3,4,5-tri-methoxy-phenyl)-isoxazol-3-yl]-phenoxy}-pentyloxy)-phenyl]-2,3-dihydro-1H-quinazolin-4-one (23d);

6-Methyl-2-[3-methoxy-4-(6-{2-methoxy-5-[5-(3,4,5-tri-methoxy-phenyl)-isoxazol-3-yl]-phenoxy}-hexyloxy)-phenyl]-2,3-dihydro-1H-quinazolin-4-one (23e);

6-Methyl-2-[3-methoxy-4-(7-{2-methoxy-5-[5-(3,4,5-tri-methoxy-phenyl)-isoxazol-3-yl]-phenoxy}-heptyloxy)-phenyl]-2,3-dihydro-1H-quinazolin-4-one (23f);

6-Methyl-2-[3-methoxy-4-(8-{2-methoxy-5-[5-(3,4,5-tri-methoxy-phenyl)-isoxazol-3-yl]-phenoxy}-octyloxy)-phenyl]-2,3-dihydro-1H-quinazolin-4-one (23g);

6-Methyl-2-[3-methoxy-4-(9-{2-methoxy-5-[5-(3,4,5-tri-methoxy-phenyl)-isoxazol-3-yl]-phenoxy}-nonyloxy)-phenyl]-2,3-dihydro-1H-quinazolin-4-one (23h);

6-Methyl-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (23i);

6-Methoxy-2-[3-methoxy-4-(2-{2-methoxy-5-[5-(3,4,5-trimethoxy-phenyl)-isoxazol-3-yl]-phenoxy}-ethoxy)-phenyl]-2,3-dihydro-1H-quinazolin-4-one (24a);

6-Methoxy-2-[3-methoxy-4-(3-{2-methoxy-5-[5-(3,4,5-trimethoxy-phenyl)-isoxazol-3-yl]-phenoxy}-propoxy-phenyl]-2,3-dihydro-1H-quinazolin-4-one (24b);

6-Methoxy-2-[3-methoxy-4-(4-{2-methoxy-5-[5-(3,4,5-trimethoxy-phenyl)-isoxazol-3-yl]-phenoxy}-butyloxy)-phenyl]-2,3-dihydro-1H-quinazolin-4-one (24c);

6-Methoxy-2-[3-methoxy-4-(5-{2-methoxy-5-[5-(3,4,5-trimethoxy-phenyl)-isoxazol-3-yl]-phenoxy}-pentyloxy)-phenyl]-2,3-dihydro-1H-quinazolin-4-one (24d);

6-Methoxy-2-[3-methoxy-4-(6-{2-methoxy-5-[5-(3,4,5-trimethoxy-phenyl)-isoxazol-3-yl]-phenoxy}-hexyloxy)-phenyl]-2,3-dihydro-1H-quinazolin-4-one (24e);

6-Methoxy-2-[3-methoxy-4-(7-{2-methoxy-5-[5-(3,4,5-trimethoxy-phenyl)-isoxazol-3-yl]-phenoxy}-heptyloxy)-phenyl]-2,3-dihydro-1H-quinazolin-4-one (24f);

6-Methoxy-2-[3-methoxy-4-(8-{2-methoxy-5-[5-(3,4,5-trimethoxy-phenyl)-isoxazol-3-yl]-phenoxy}-octyloxy)-phenyl]-2,3-dihydro-1H-quinazolin-4-one (24g);

6-Methoxy-2-[3-methoxy-4-(9-{2-methoxy-5-[5-(3,4,5-trimethoxy-phenyl)-isoxazol-3-yl]-phenoxy}-nonyloxy)-phenyl]-2,3-dihydro-1H-quinazolin-4-one (24h);

6-Methoxy-2-[3-methoxy-4-(10-{2-methoxy-5-[5-(3,4,5-trimethoxy-phenyl)-isoxazol-3-yl]-phenoxy}-decyloxy)-phenyl]-2,3-dihydro-1H-quinazolin-4-one (24i);

2-(4-(2-(2,6-dimethoxy-4-(5-(3,4,5-trimethoxyphenyl)isoxazol-3-yl)phenoxy)ethoxy)-3-methoxyphenyl)-2,3-dihydroquinazolin-4(1H)-one (25a);

2-(4-(3-(2,6-dimethoxy-4-(5-(3,4,5-trimethoxyphenyl)isoxazol-3-yl)phenoxy)propoxy)-3-methoxyphenyl)-2,3-dihydroquinazolin-4(1H)-one (25b);

2-(4-(4-(2,6-dimethoxy-4-(5-(3,4,5-trimethoxyphenyl)isoxazol-3-yl)phenoxy) butoxy)-3-methoxyphenyl)-2,3-dihydroquinazolin-4(1H)-one (25c);

2-(4-(5-(2,6-dimethoxy-4-(5-(3,4,5-trimethoxyphenyl)isoxazol-3-yl)phenoxy) pentyloxy)-3-methoxyphenyl)-2,3-dihydroquinazolin-4(1H)-one (25d);

2-(4-(6-(2,6-dimethoxy-4-(5-(3,4,5-trimethoxyphenyl)isoxazol-3-yl)phenoxy) hexyloxy)-3-methoxyphenyl)-2,3-dihydroquinazolin-4(1H)-one (25e);

2-(4-(7-(2,6-dimethoxy-4-(5-(3,4,5-trimethoxyphenyl)isoxazol-3-yl)phenoxy) heptyloxy)-3-methoxyphenyl)-2,3-dihydroquinazolin-4(1H)-one (25f);

2-(4-(8-(2,6-dimethoxy-4-(5-(3,4,5-trimethoxyphenyl)isoxazol-3-yl)phenoxy) octyloxy)-3-methoxyphenyl)-2,3-dihydroquinazolin-4(1H)-one (25g);

2-(4-(9-(2,6-dimethoxy-4-(5-(3,4,5-trimethoxyphenyl)isoxazol-3-yl)phenoxy) nonyloxy)-3-methoxyphenyl)-2,3-dihydroquinazolin-4(1H)-one (25h);

2-(4-(10-(2,6-dimethoxy-4-(5-(3,4,5-trimethoxyphenyl)isoxazol-3-yl)phenoxy) decyloxy)-3-methoxyphenyl)-2,3-dihydroquinazolin-4(1H)-one (25i);

6-Chloro-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (26a);

6-Chloro-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (26b);

6-Chloro-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (26c);

6-Chloro-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (26d);

6-Chloro-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (26e);

6-Chloro-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (26f);

6-Chloro-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (26g);

6-Chloro-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (26h);

6-Chloro-2-[4-(10-{2,6-dimethoxy-4-[5-(3,4,5-trimethoxy-phenyl)-isoxazol-3-yl]-phenoxy}-decyloxy)-3-methoxy-phenyl]-2,3-dihydro-1H-quinazolin-4-one (26i);

6-Methyl-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (27a);

6-Methyl-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (27b);

6-Methyl-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (27c);

6-Methyl-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (27d);

6-Methyl-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (27e);

6-Methyl-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (27f);

6-Methyl-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (27g);

6-Methyl-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (27h);

6-Methyl-2-[4-(10-{2,6-dimethoxy-4-[5-(3,4,5-trimethoxy-phenyl)-isoxazol-3-yl]-phenoxy}-decyloxy)-3-methoxy-phenyl]-2,3-dihydro-1H-quinazolin-4-one (27i);

6-Methoxy-2-[4-(2-{2,6-dimethoxy-4-[5-(3,4,5-trimethoxy-phenyl)-isoxazol-3-yl]-phenoxy}-ethoxy)-3-methoxy-phenyl]-2,3-dihydro-1H-quinazolin-4-one (28a)

6-Methoxy-2-[4-(3-{2,6-dimethoxy-4-[5-(3,4,5-trimethoxy-phenyl)-isoxazol-3-yl]-phenoxy}-propoxy)-3-methoxy-phenyl]-2,3-dihydro-1H-quinazolin-4-one (28b);

6-Methoxy-2-[4-(4-{2,6-dimethoxy-4-[5-(3,4,5-trimethoxy-phenyl)-isoxazol-3-yl]-phenoxy}-butoxy)-3-methoxy-phenyl]-2,3-dihydro-1H-quinazolin-4-one (28c);

6-Methoxy-2-[4-(5-{2,6-dimethoxy-4-[5-(3,4,5-trimethoxy-phenyl)-isoxazol-3-yl]-phenoxy}-pentyloxy)-3-methoxy-phenyl]-2,3-dihydro-1H-quinazolin-4-one (28d);

6-Methoxy-2-[4-(6-{2,6-dimethoxy-4-[5-(3,4,5-trimethoxy-phenyl)-isoxazol-3-yl]-phenoxy}-hexyloxy)-3-methoxy-phenyl]-2,3-dihydro-1H-quinazolin-4-one (28e);

6-Methoxy-2-[4-(7-{2,6-dimethoxy-4-[5-(3,4,5-trimethoxy-phenyl)-isoxazol-3-yl]-phenoxy}-heptyloxy)-3-methoxy-phenyl]-2,3-dihydro-1H-quinazolin-4-one (28f);

6-Methoxy-2-[4-(8-{2,6-dimethoxy-4-[5-(3,4,5-trimethoxy-phenyl)-isoxazol-3-yl]-phenoxy}-octyloxy)-3-methoxy-phenyl]-2,3-dihydro-1H-quinazolin-4-one (28g);

6-Methoxy-2-[4-(9-{2,6-dimethoxy-4-[5-(3,4,5-trimethoxy-phenyl)-isoxazol-3-yl]-phenoxy}-nonyloxy)-3-methoxy-phenyl]-2,3-dihydro-1H-quinazolin-4-one (28h);

6-Methoxy-2-[4-(10-{2,6-dimethoxy-4-[5-(3,4,5-trimethoxy-phenyl)-isoxazol-3-yl]phenoxy}-decyloxy)-3-methoxy-phenyl]-2,3-dihydro-1H-quinazolin-4-one (28i);

2-(3-methoxy-4-(2-(2-methoxy-5-(3-(3,4,5-trimethoxyphenyl) isoxazol-5-yl)phenoxy)ethoxy)phenyl)-2,3-dihydroquinazolin-4(1H)-one (30a);

2-(3-methoxy-4-(3-(2-methoxy-5-(3-(3,4,5-trimethoxyphenyl) isoxazol-5-yl)phenoxy)propoxy)phenyl)-2,3-dihydroquinazolin-4(1H)-one (30b);

2-(3-methoxy-4-(4-(2-methoxy-5-(3-(3,4,5-trimethoxyphenyl) isoxazol-5-yl)phenoxy)butoxy)phenyl)-2,3-dihydroquinazolin-4(1H)-one (30c);

2-(3-methoxy-4-(5-(2-methoxy-5-(3-(3,4,5-trimethoxyphenyl) isoxazol-5-yl)phenoxy)pentyloxy)phenyl)-2,3-dihydroquinazolin-4(1H)-one (30d);

2-(3-methoxy-4-(6-(2-methoxy-5-(3-(3,4,5-trimethoxyphenyl) isoxazol-5-yl)phenoxy)hexyloxy)phenyl)-2,3-dihydroquinazolin-4(1H)-one (30e);

2-(3-methoxy-4-(7-(2-methoxy-5-(3-(3,4,5-trimethoxyphenyl) isoxazol-5-yl)phenoxy)heptyloxy)phenyl)-2,3-dihydroquinazolin-4(1H)-one (30f);

2-(3-methoxy-4-(8-(2-methoxy-5-(3-(3,4,5-trimethoxyphenyl) isoxazol-5-yl)phenoxy)octyloxy)phenyl)-2,3-dihydroquinazolin-4(1H)-one (30g);

2-(3-methoxy-4-(9-(2-methoxy-5-(3-(3,4,5-trimethoxyphenyl) isoxazol-5-yl)phenoxy)nonyloxy)phenyl)-2,3-dihydroquinazolin-4(1H)-one (30h);

2-(3-methoxy-4-(10-(2-methoxy-5-(3-(3,4,5-trimethoxyphenyl) isoxazol-5-yl)phenoxy)decyloxy)phenyl)-2,3-dihydroquinazolin-4(1H)-one (30i);

6-Chloro-2-[3-methoxy-4-(2-{2-methoxy-5-[3-(3,4,5-trimethoxy-phenyl)-isoxazol-5-yl]-phenoxy}-ethoxy)-phenyl]-2,3-dihydro-1H-quinazolin-4-one (31a);

6-Chloro-2-[3-methoxy-4-(3-{2-methoxy-5-[3-(3,4,5-trimethoxy-phenyl)-isoxazol-5-yl]-phenoxy}-propoxy)-phenyl]-2,3-dihydro-1H-quinazolin-4-one (31b);

6-Chloro-2-[3-methoxy-4-(4-{2-methoxy-5-[3-(3,4,5-trimethoxy-phenyl)-isoxazol-5-yl]-phenoxy}-butoxy)-phenyl]—2,3-dihydro-1H-quinazolin-4-one (31c);

6-Chloro-2-[3-methoxy-4-(5-{2-methoxy-5-[3-(3,4,5-trimethoxy-phenyl)-isoxazol-5-yl]-phenoxy}-pentyloxy)-phenyl]-2,3-dihydro-1H-quinazolin-4-one (31d);

6-Chloro-2-[3-methoxy-4-(6-{2-methoxy-5-[3-(3,4,5-trimethoxy-phenyl)-isoxazol-5-yl]-phenoxy}-hexyloxy)-phenyl]-2,3-dihydro-1H-quinazolin-4-one (31e);

6-Chloro-2-[3-methoxy-4-(7-{2-methoxy-5-[3-(3,4,5-trimethoxy-phenyl)-isoxazol-5-yl]-phenoxy}-heptyloxy)-phenyl]—2,3-dihydro-1H-quinazolin-4-one (31f);

6-Chloro-2-[3-methoxy-4-(8-{2-methoxy-5-[3-(3,4,5-trimethoxy-phenyl)-isoxazol-5-yl]-phenoxy}-octyloxy)-phenyl]-2,3-dihydro-1H-quinazolin-4-one (31g);

6-Chloro-2-{3-methoxy-4-(9-[2-methoxy-5-[3-(3,4,5-trimethoxy-phenyl)-isoxazol-5-yl]-phenoxy}-nonyloxy)-phenyl]-2,3-dihydro-1H-quinazolin-4-one (31h);

6-Chloro-2-[3-methoxy-4-(10-{2-methoxy-5-[3-(3,4,5-trimethoxy-phenyl)-isoxazol-5-yl]-phenoxy}-decyloxy)-phenyl]—2,3-dihydro-1H-quinazolin-4-one (31i);

6-Methyl-2-[3-methoxy-4-(2-{2-methoxy-5-[3-(3,4,5-trimethoxy-phenyl)-isoxazol-5-yl]-phenoxy}-ethoxy)-phenyl]-2,3-dihydro-1H-quinazolin-4-one (32a);

6-Methyl-2-[3-methoxy-4-(3-{2-methoxy-5-[3-(3,4,5-trimethoxy-phenyl)-isoxazol-5-yl]-phenoxy}-propoxy)-phenyl]-2,3-dihydro-1H-quinazolin-4-one (32b);

6-Methyl-2-[3-methoxy-4-(4-{2-methoxy-5-[3-(3,4,5-trimethoxy-phenyl)-isoxazol-5-yl]-phenoxy}-butoxy)-phenyl]-2,3-dihydro-1H-quinazolin-4-one (32c);

6-Methyl-2-[3-methoxy-4-(5-{2-methoxy-5-[3-(3,4,5-trimethoxy-phenyl)-isoxazol-5-yl]-phenoxy}-pentyloxy)-phenyl]-2,3-dihydro-1H-quinazolin-4-one (32d);

6-Methyl-2-[3-methoxy-4-(6-{2-methoxy-5-[3-(3,4,5-trimethoxy-phenyl)-isoxazol-5-yl]-phenoxy}-hexyloxy)-phenyl]-2,3-dihydro-1H-quinazolin-4-one (32e);

6-Methyl-2-[3-methoxy-4-(7-{2-methoxy-5-[3-(3,4,5-trimethoxy-phenyl)-isoxazol-5-yl]-phenoxy}-heptyloxy)-phenyl]-2,3-dihydro-1H-quinazolin-4-one (32f);

6-Methyl-2-[3-methoxy-4-(8-{2-methoxy-5-[3-(3,4,5-trimethoxy-phenyl)-isoxazol-5-yl]-phenoxy}-octyloxy)-phenyl]-2,3-dihydro-1H-quinazolin-4-one (32g);

6-Methyl-2-[3-methoxy-4-(9-{2-methoxy-5-[3-(3,4,5-trimethoxy-phenyl)-isoxazol-5-yl]-phenoxy}-nonyloxy)-phenyl]-2,3-dihydro-1H-quinazolin-4-one (32h);

6-Methyl-2-[3-methoxy-4-(10-{2-methoxy-5-[3-(3,4,5-trimethoxy-phenyl)-isoxazol-5-yl]-phenoxy}-decyloxy)-phenyl]-2,3-dihydro-1H-quinazolin-4-one (32i);

6-Methoxy-2-[3-methoxy-4-(2-{2-methoxy-5-[3-(3,4,5-trimethoxy-phenyl)-isoxazol-5-yl]-phenoxy}-ethoxy)-phenyl]-2,3-dihydro-1H-quinazolin-4-one (33a);

6-Methoxy-2-[3-methoxy-4-(3-{2-methoxy-5-[3-(3,4,5-trimethoxy-phenyl)-isoxazol-5-yl]-phenoxy}-propoxy)-phenyl]-2,3-dihydro-1H-quinazolin-4-one (33b);

6-Methoxy-2-[3-methoxy-4-(4-{2-methoxy-5-[3-(3,4,5-trimethoxy-phenyl)-isoxazol-5-yl]-phenoxy}-butoxy)-phenyl]-2,3-dihydro-1H-quinazolin-4-one (33c);

6-Methoxy-2-[3-methoxy-4-(5-{2-methoxy-5-[3-(3,4,5-trimethoxy-phenyl)-isoxazol-5-yl]-phenoxy}-pentyloxy)-phenyl]-2,3-dihydro-1H-quinazolin-4-one (33d);

6-Methoxy-2-[3-methoxy-4-(6-{2-methoxy-5-[3-(3,4,5-trimethoxy-phenyl)-isoxazol-5-yl]-phenoxy}-hexyloxy)-phenyl]-2,3-dihydro-1H-quinazolin-4-one (33e);

6-Methoxy-2-[3-methoxy-4-(7-{2-methoxy-5-[3-(3,4,5-trimethoxy-phenyl)-isoxazol-5-yl]-phenoxy}-heptyloxy)-phenyl]-2,3-dihydro-1H-quinazolin-4-one (33f);

6-Methoxy-2-[3-methoxy-4-(8-{2-methoxy-5-[3-(3,4,5-trimethoxy-phenyl)-isoxazol-5-yl]-phenoxy}-octyloxy)-phenyl]-2,3-dihydro-1H-quinazolin-4-one (33g);

6-Methoxy-2-[3-methoxy-4-(9-{2-methoxy-5-[3-(3,4,5-trimethoxy-phenyl)-isoxazol-5-yl]-phenoxy}-nonyloxy)-phenyl]-2,3-dihydro-1H-quinazolin-4-one (33h);

6-Methoxy-2-[3-methoxy-4-(10-{2-methoxy-5-[3-(3,4,5-trimethoxy-phenyl)-isoxazol-5-yl]-phenoxy}-decyloxy)-phenyl]-2,3-dihydro-1H-quinazolin-4-one (33i);

2-(4-(2-(2,6-dimethoxy-4-(3-(3,4,5-trimethoxyphenyl) isoxazol-5-yl)phenoxy)ethoxy)-3-methoxyphenyl)-2,3-dihydroquinazolin-4(1H)-one (34a);

2-(4-(3-(2,6-dimethoxy-4-(3-(3,4,5-trimethoxyphenyl) isoxazol-5-yl)phenoxy) propoxy)-3-methoxyphenyl)-2,3-dihydroquinazolin-4(1H)-one (34b);

2-(4-(4-(2,6-dimethoxy-4-(3-(3,4,5-trimethoxyphenyl) isoxazol-5-yl)phenoxy) butoxy)-3-methoxyphenyl)-2,3-dihydroquinazolin-4(1H)-one (34c);

2-(4-(5-(2,6-dimethoxy-4-(3-(3,4,5-trimethoxyphenyl) isoxazol-5-yl) phenoxy) pentyloxy)-3-methoxyphenyl)-2,3-dihydroquinazolin-4(1H)-one (34d);

2-(4-(6-(2,6-dimethoxy-4-(3-(3,4,5-trimethoxyphenyl) isoxazol-5-yl)phenoxy) hexyloxy)-3-methoxyphenyl)-2,3-dihydroquinazolin-4(1H)-one (34e);

2-(4-(7-(2,6-dimethoxy-4-(3-(3,4,5-trimethoxyphenyl) isoxazol-5-yl)phenoxy) heptyloxy)-3-methoxyphenyl)-2,3-dihydroquinazolin-4(1H)-one (34f);

2-(4-(8-(2,6-dimethoxy-4-(3-(3,4,5-trimethoxyphenyl) isoxazol-5-yl)phenoxy) octyloxy)-3-methoxyphenyl)-2,3-dihydroquinazolin-4(1H)-one (34g);

2-(4-(9-(2,6-dimethoxy-4-(3-(3,4,5-trimethoxyphenyl) isoxazol-5-yl)phenoxy) nonyloxy)-3-methoxyphenyl)-2,3-dihydroquinazolin-4(1H)-one (34h);

2-(4-(10-(2,6-dimethoxy-4-(3-(3,4,5-trimethoxyphenyl) isoxazol-5-yl)phenoxy) decyloxy)-3-methoxyphenyl)-2,3-dihydroquinazolin-4(1H)-one (34i);

6-Chloro-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (35a);

6-Chloro-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (35b);

6-Chloro-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (35c);

6-Chloro-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (35d);

6-Chloro-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (35e);

6-Chloro-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (35f);

6-Chloro-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (35g);

6-Chloro-2-[4-(9-{2,6-dimethoxy-4-[3-(3,4,5-trimethoxy-phenyl)-isoxazol-5-yl]-phenoxy}-nonyloxy)-3-methoxy-phenyl]-2,3-dihydro-1H-quinazolin-4-one (35h);

6-Chloro-2-[10-(4-{2,6-dimethoxy-4-[3-(3,4,5-trimethoxy-phenyl)-isoxazol-5-yl]-phenoxy}-decyloxy)-3-methoxy-phenyl]-2,3-dihydro-1H-quinazolin-4-one (35i);

6-Methyl-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (36a);

6-Methyl-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (36b);

6-Methyl-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (36c);

6-Methyl-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (36d);

6-Methyl-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (36e);

6-Methyl-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (36f);

6-Methyl-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (36g);

6-Methyl-2-[4-(9-{2,6-dimethoxy-4-[3-(3,4,5-trimethoxy-phenyl)-isoxazol-5-yl]-phenoxy}-nonyloxy)-3-methoxy-phenyl]-2,3-dihydro-1H-quinazolin-4-one (36h);

6-Methyl-2-[10-(4-{2,6-dimethoxy-4-[3-(3,4,5-trimethoxy-phenyl)-isoxazol-5-yl]-phenoxy}-decyloxy)-3-methoxy-phenyl]-2,3-dihydro-1H-quinazolin-4-one (36i);

6-Methoxy-2-[4-(2-{2,6-dimethoxy-4-[3-(3,4,5-trimethoxy-phenyl)-isoxazol-5-yl]-phenoxy}-ethoxy)-3-methoxy-phenyl]-2,3-dihydro-1H-quinazolin-4-one (37a);

6-Methoxy-2-[4-(3-{2,6-dimethoxy-4-[3-(3,4,5-trimethoxy-phenyl)-isoxazol-5-yl]-phenoxy}-propoxy)-3-methoxy-phenyl]-2,3-dihydro-1H-quinazolin-4-one (37b);

6-Methoxy-2-[4-(4-{2,6-dimethoxy-4-[3-(3,4,5-trimethoxy-phenyl)-isoxazol-5-yl]-phenoxy}-butyloxy)-3-methoxy-phenyl]-2,3-dihydro-1H-quinazolin-4-one (37c);

6-Methoxy-2-[4-(5-{2,6-dimethoxy-4-[3-(3,4,5-trimethoxy-phenyl)-isoxazol-5-yl]-phenoxy}-pentyloxy)-3-methoxy-phenyl]-2,3-dihydro-1H-quinazolin-4-one (37d);

6-Methoxy-2-[4-(6-{2,6-dimethoxy-4-[3-(3,4,5-trimethoxy-phenyl)-isoxazol-5-yl]-phenoxy}-hexyloxy)-3-methoxy-phenyl]-2,3-dihydro-1H-quinazolin-4-one (37e);

6-Methoxy-2-[4-(7-{2,6-dimethoxy-4-[3-(3,4,5-trimethoxy-phenyl)-isoxazol-5-yl]-phenoxy}-heptyloxy)-3-methoxy-phenyl]-2,3-dihydro-1H-quinazolin-4-one (37f);

6-Methoxy-2-[4-(8-{2,6-dimethoxy-4-[3-(3,4,5-trimethoxy-phenyl)-isoxazol-5-yl]-phenoxy}-octyloxy)-3-methoxy-phenyl]-2,3-dihydro-1H-quinazolin-4-one (37g);

6-Methoxy-2-[4-(9-{2,6-dimethoxy-4-[3-(3,4,5-tri-methoxy-phenyl)-isoxazol-5-yl]-phenoxy}-nonyloxy)-3-methoxy-phenyl]-2,3-dihydro-1H-quinazolin-4-one (37h); or 6-Methoxy-2-[10-(4-{2,6-dimethoxy-4-[3-(3,4,5-tri-methoxy-phenyl)-isoxazol-5-yl]-phenoxy}-decyloxy)-3-methoxy-phenyl]-2,3-dihydro-1H-quinazolin-4-one (37i).

4. The isoxazole/isoxazoline/combretastatin linked dihydroquinazolinone compound as claimed in claim 1 wherein the compound is:

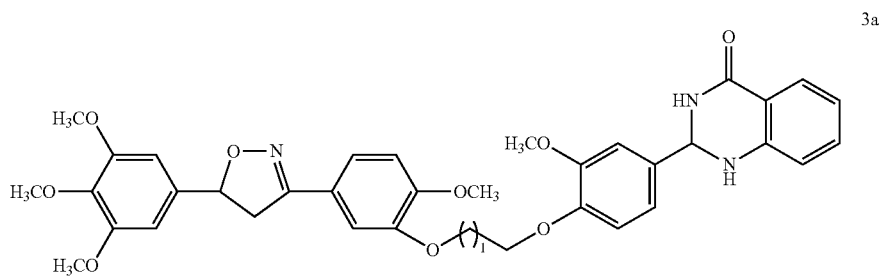

3a

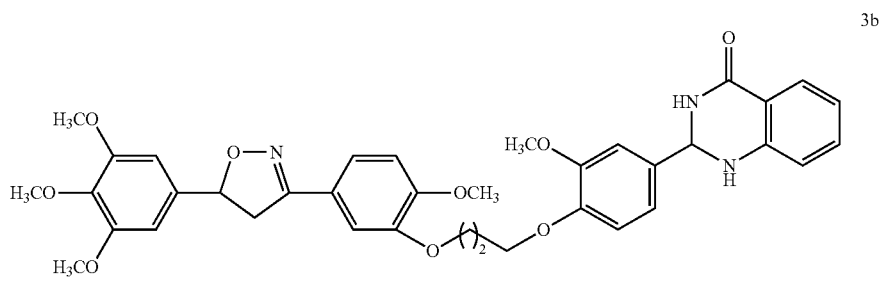

3b

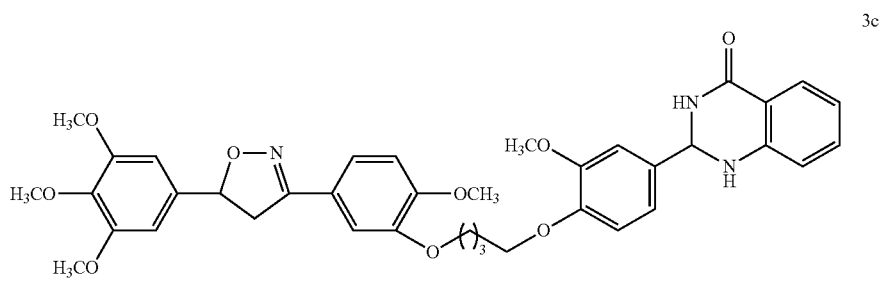

3c

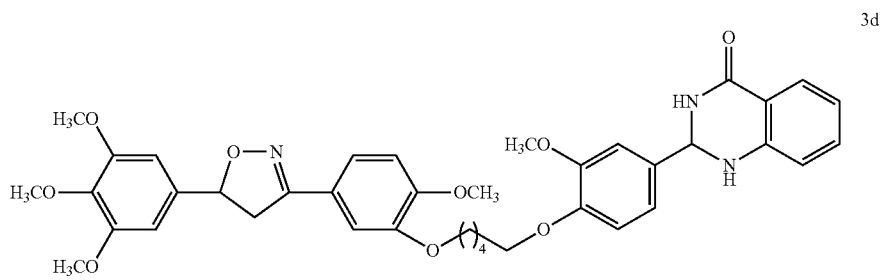

3d

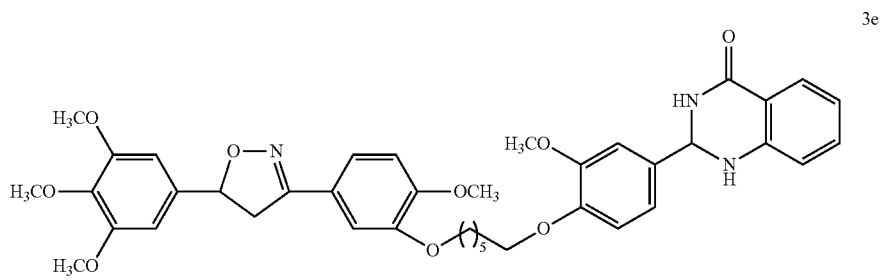

3e

-continued
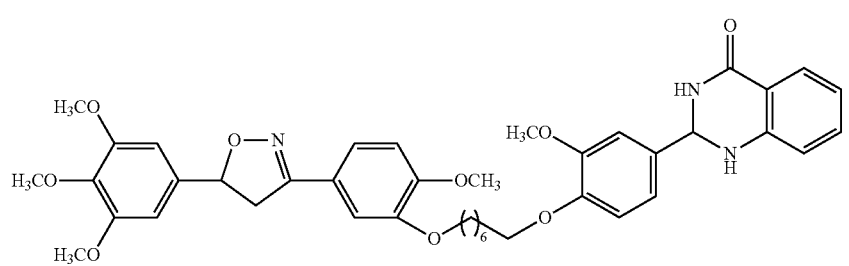
3f
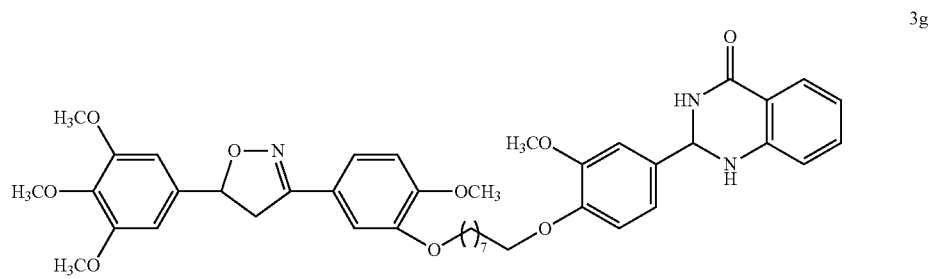
3g
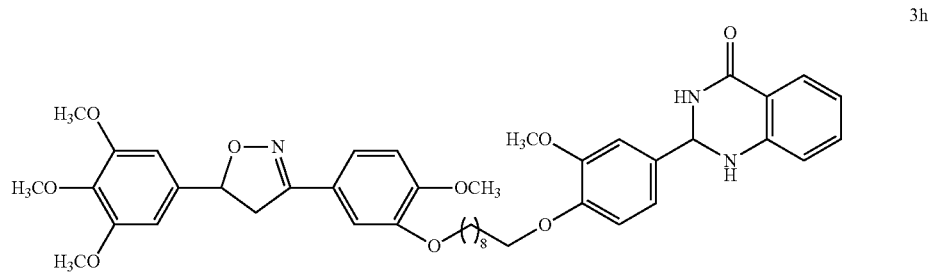
3h
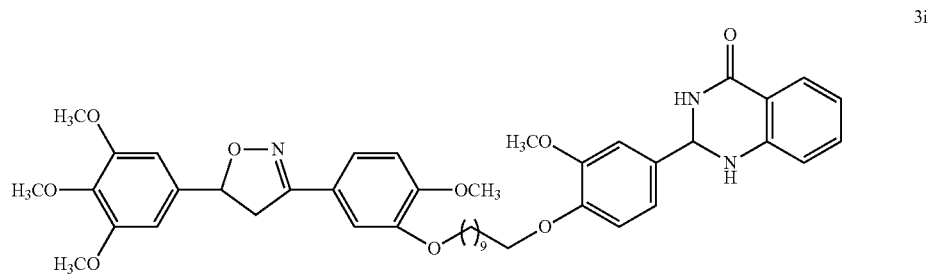
3i
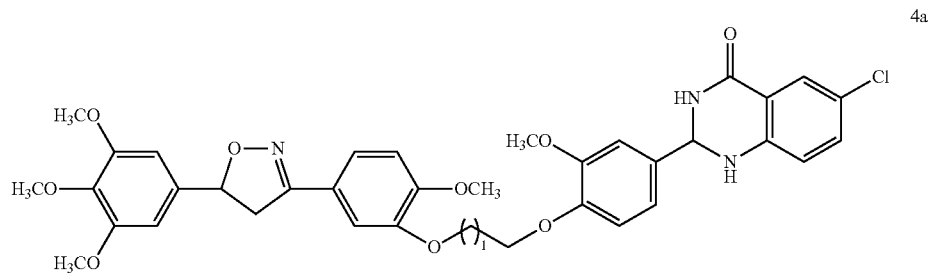
4a
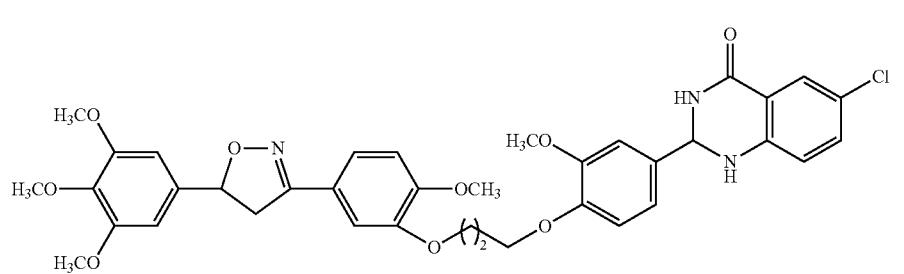
4b -continued
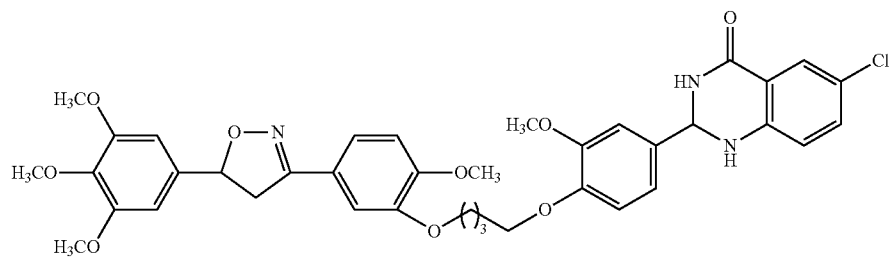
4c
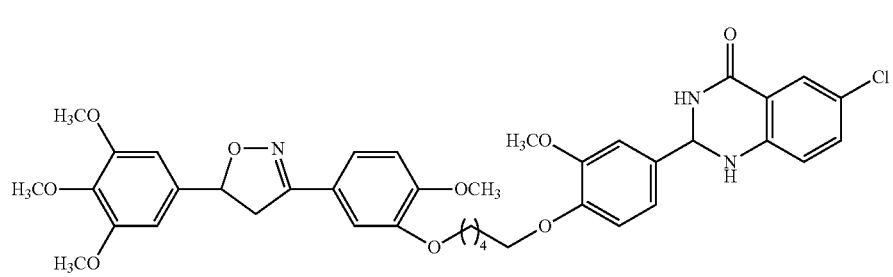
4d
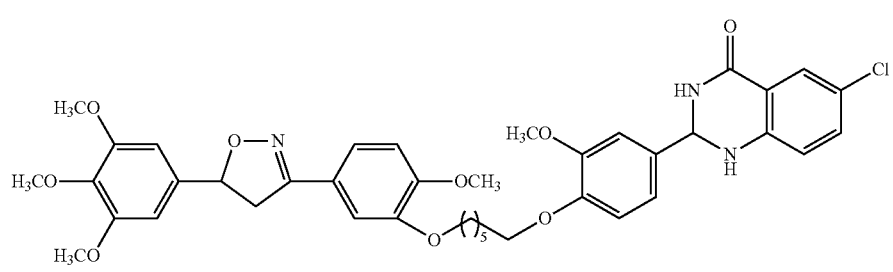
4e
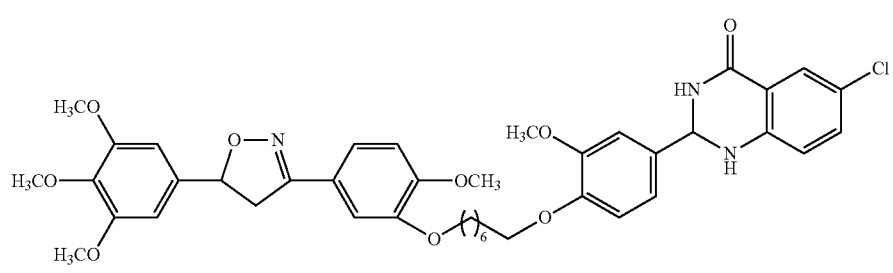
4f
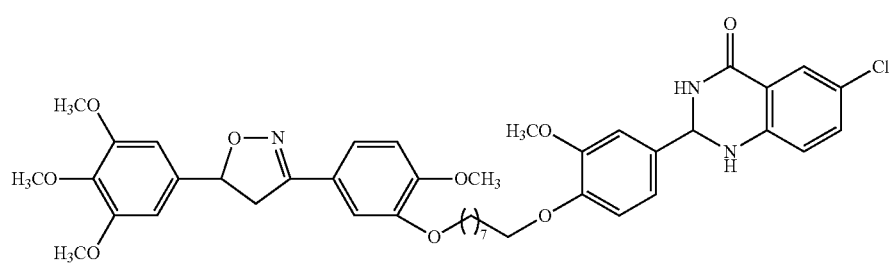
4g
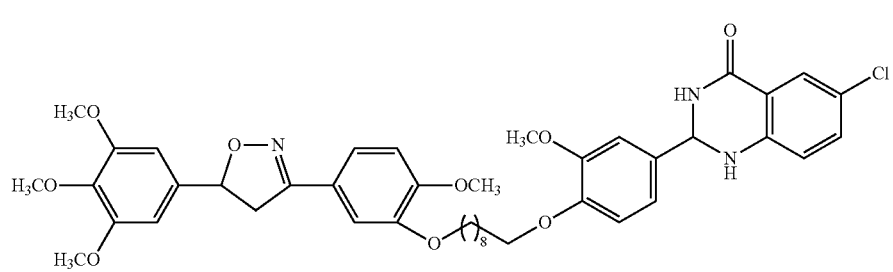
4h -continued
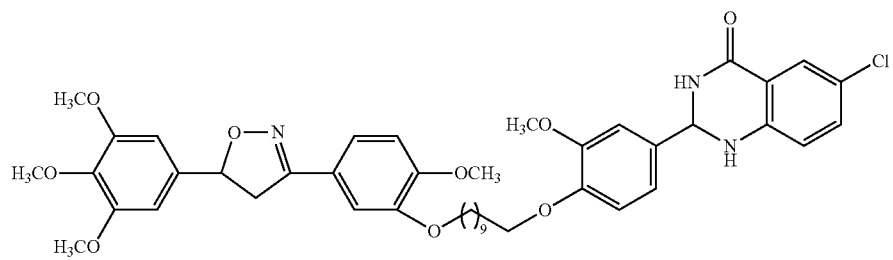
4i
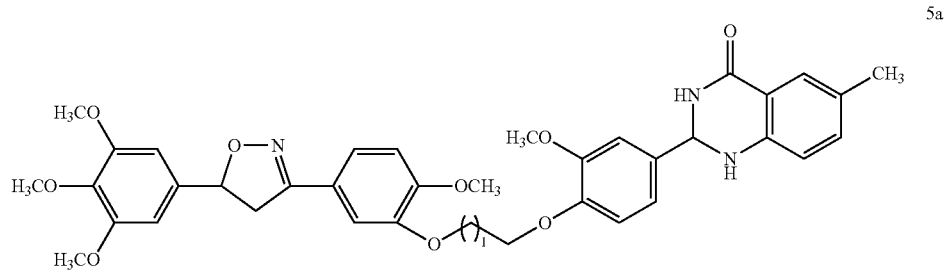
5a
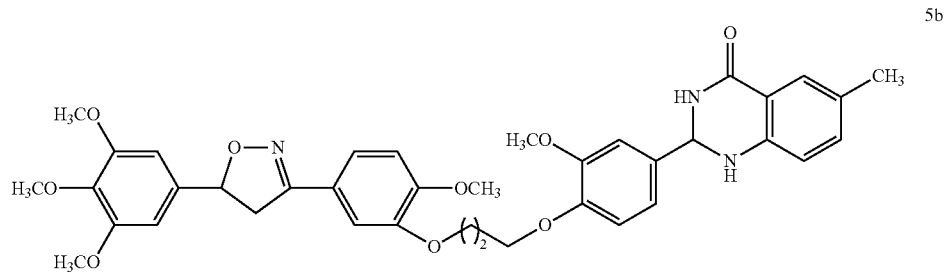
5b
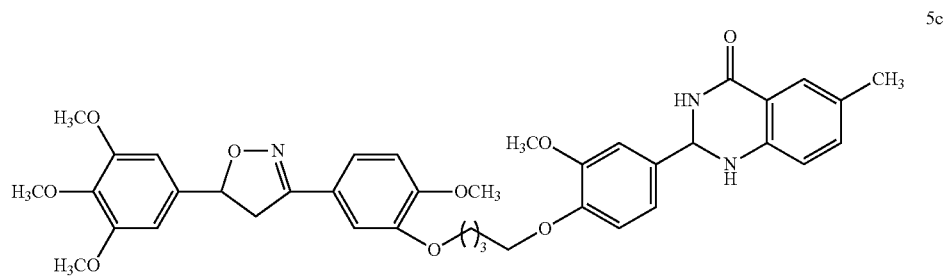
5c
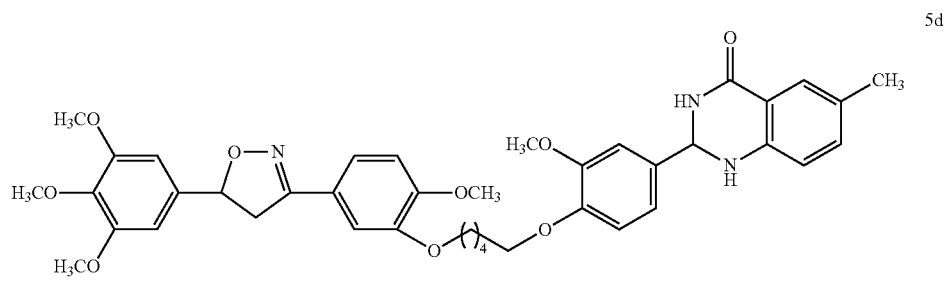
5d
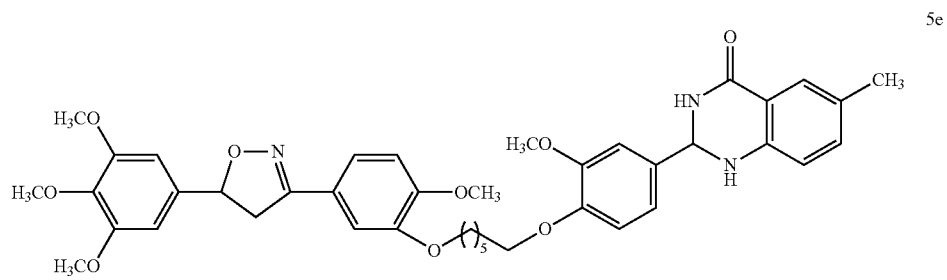
5e

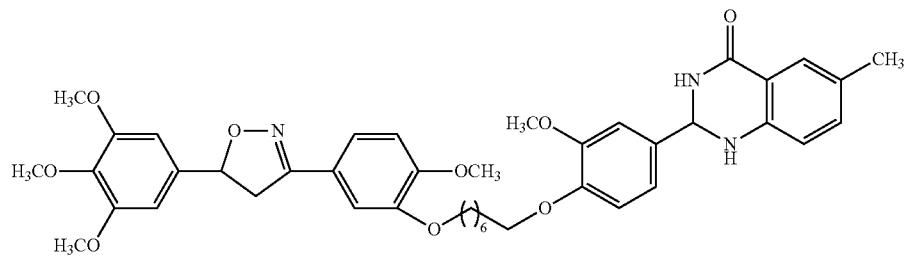
5f
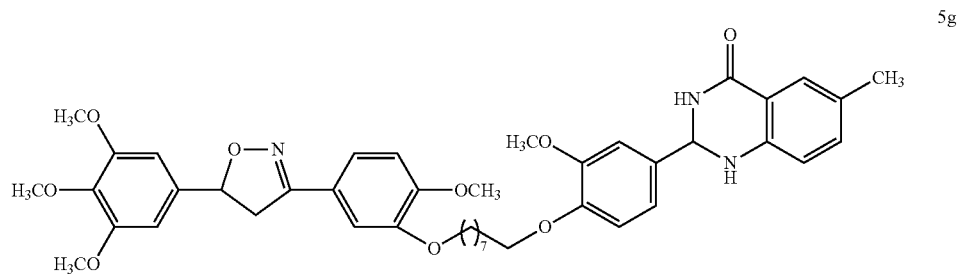
5g
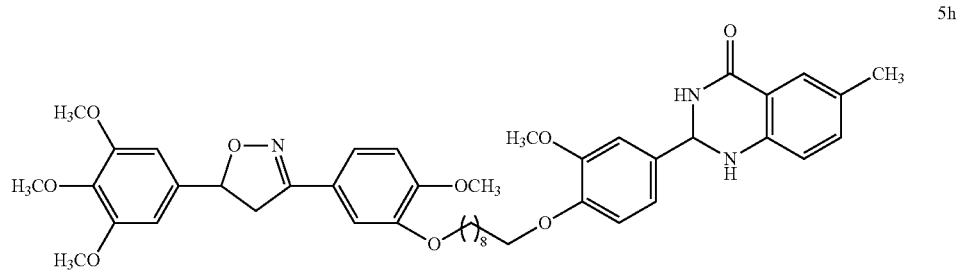
5h
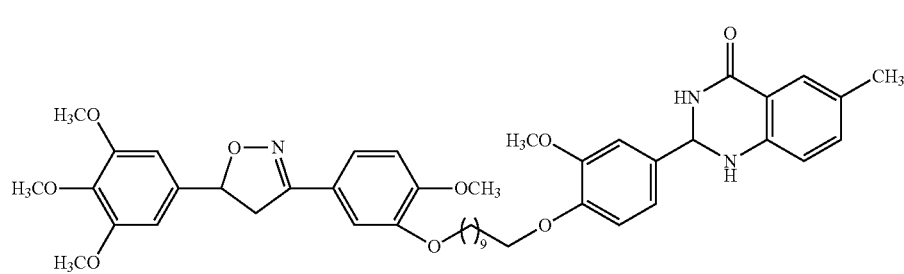
5i
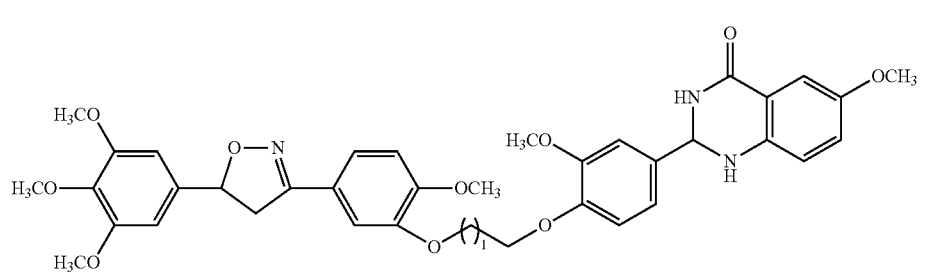
6a
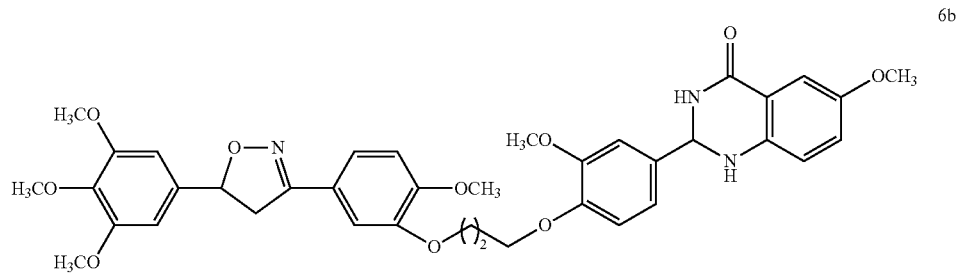
6b

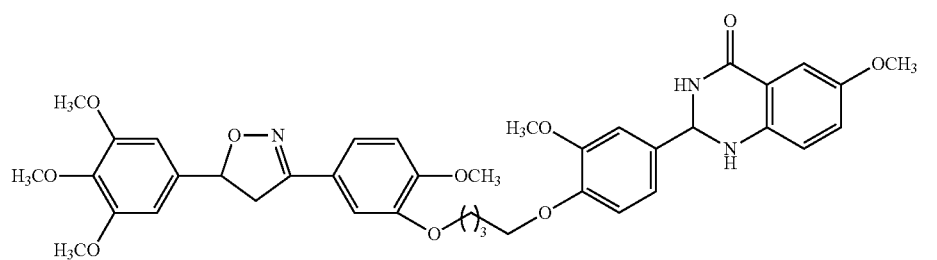
6c
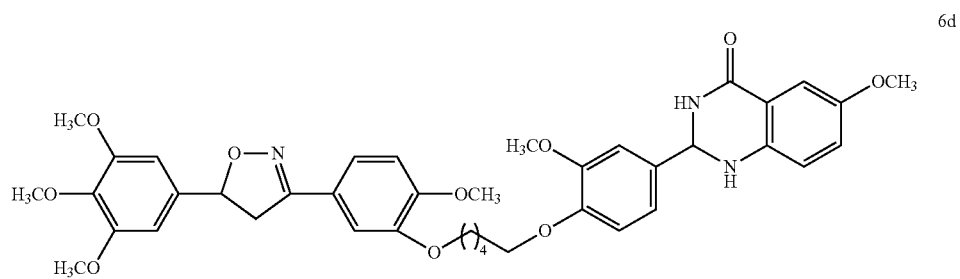
6d
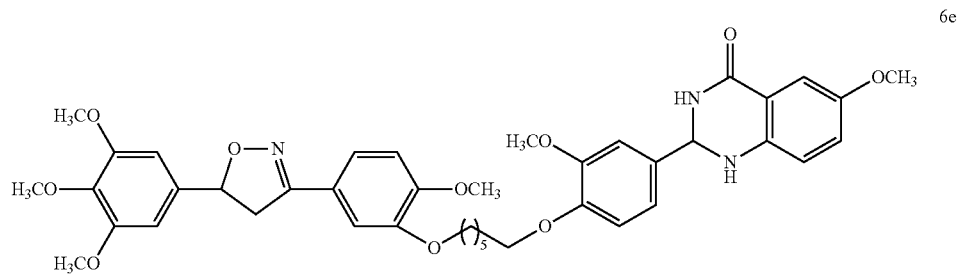
6e
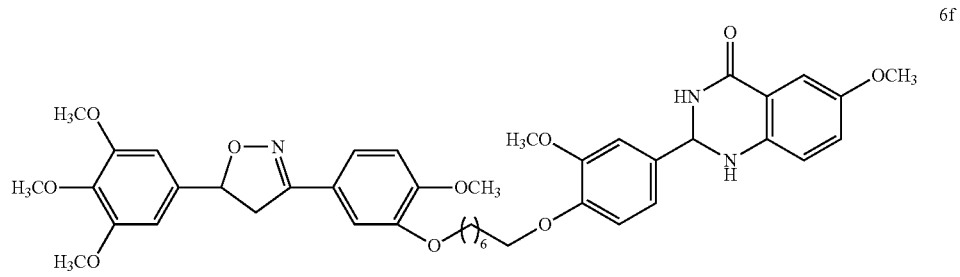
6f
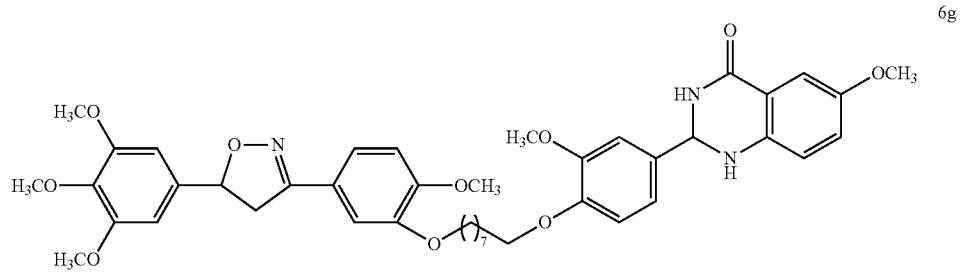
6g
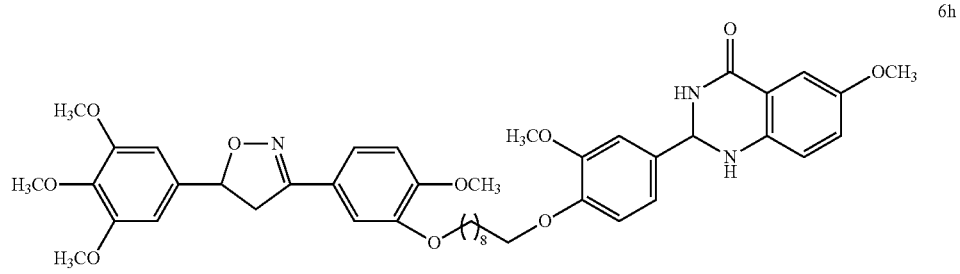
6h

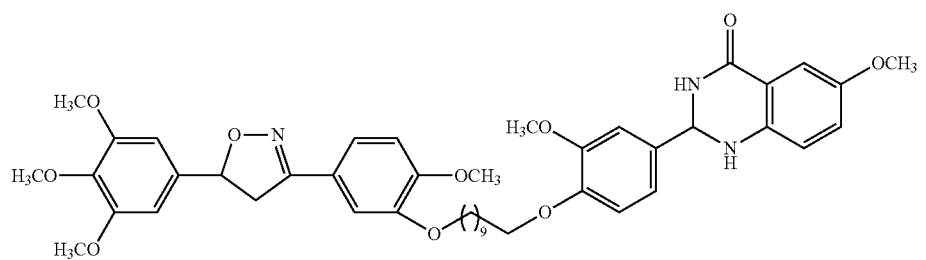
6i
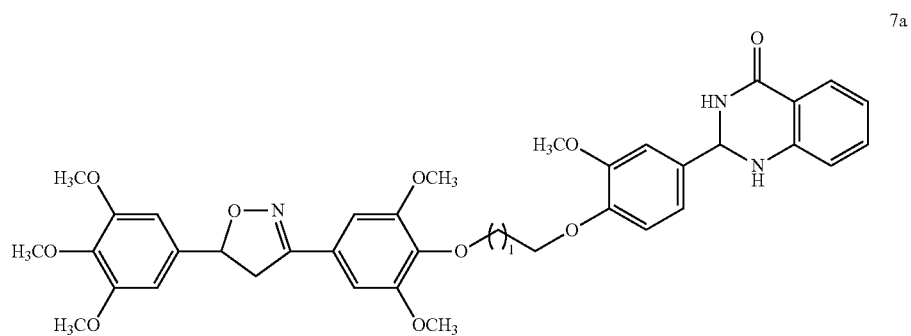
7a
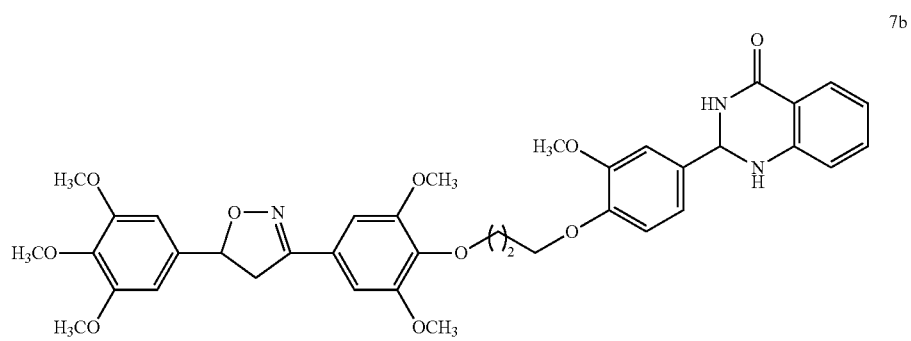
7b
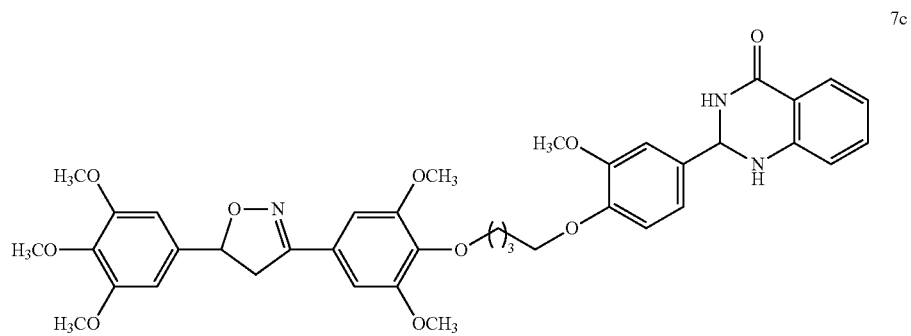
7c
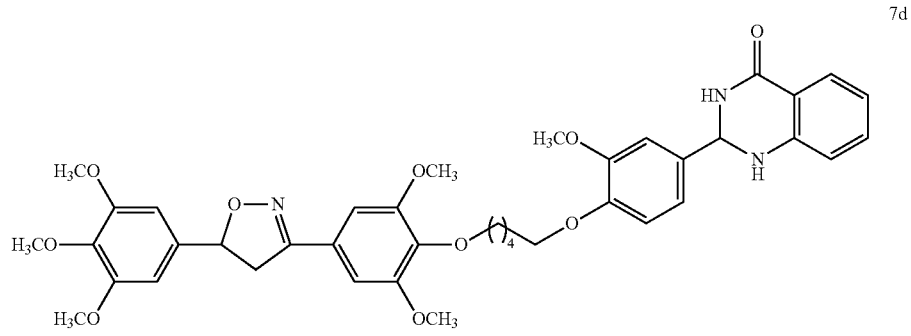
7d

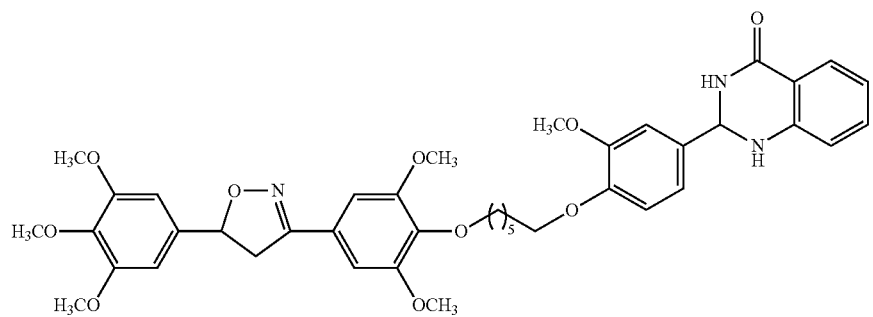
7e
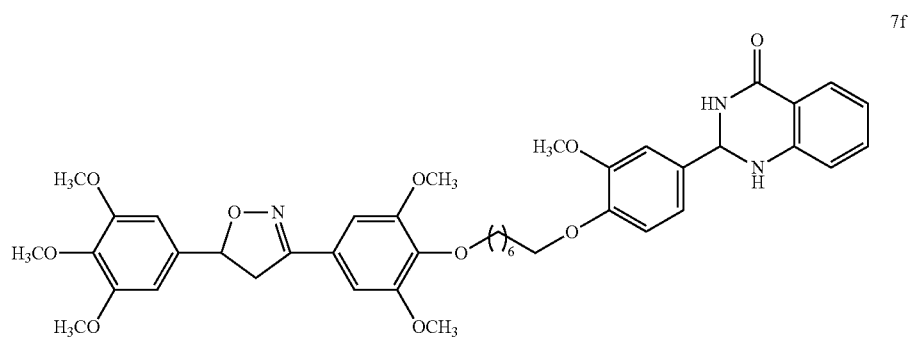
7f
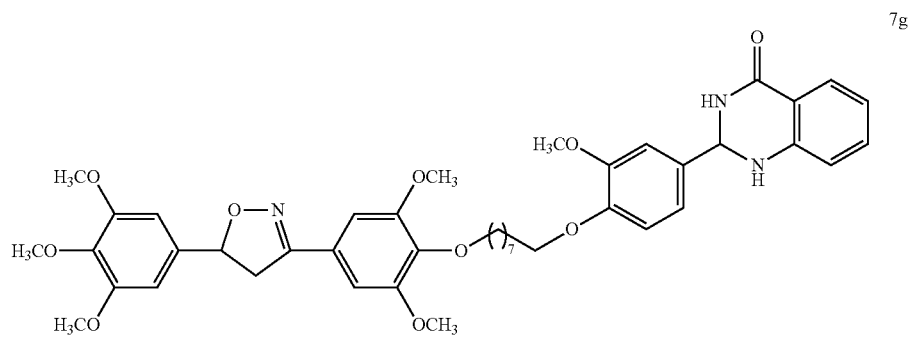
7g
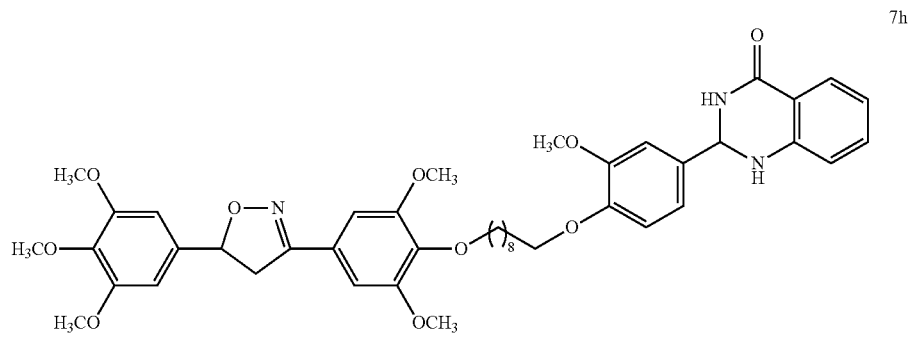
7h
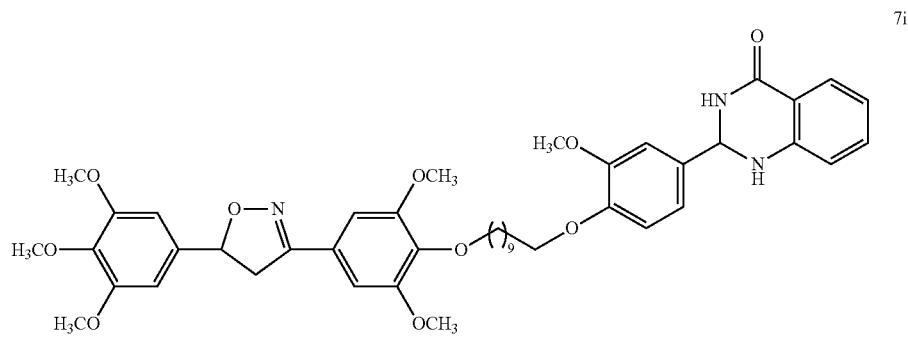
7i

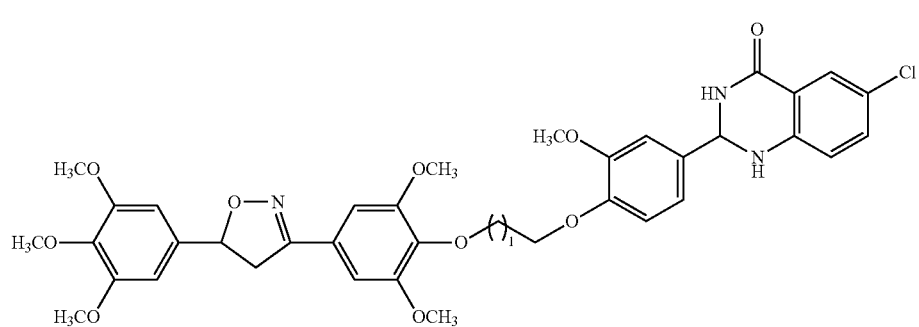
8a
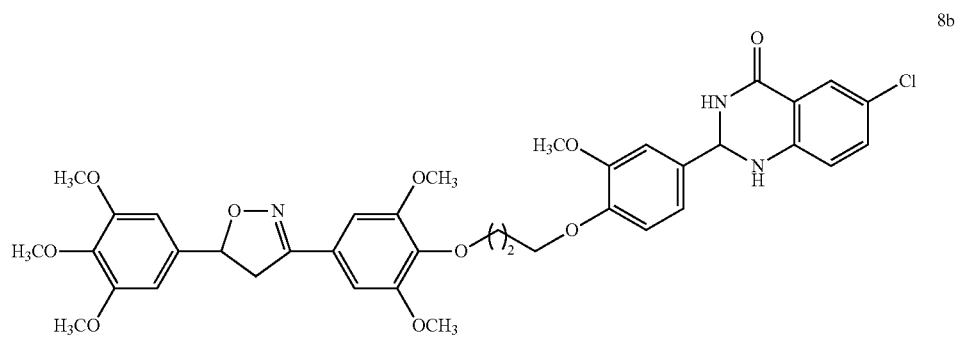
8b
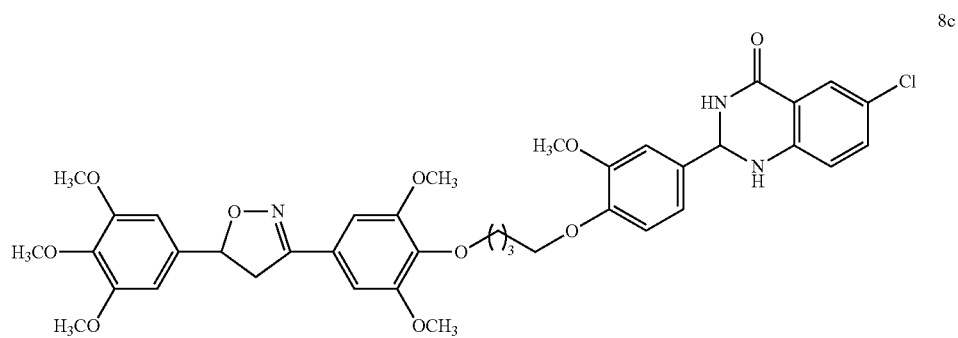
8c
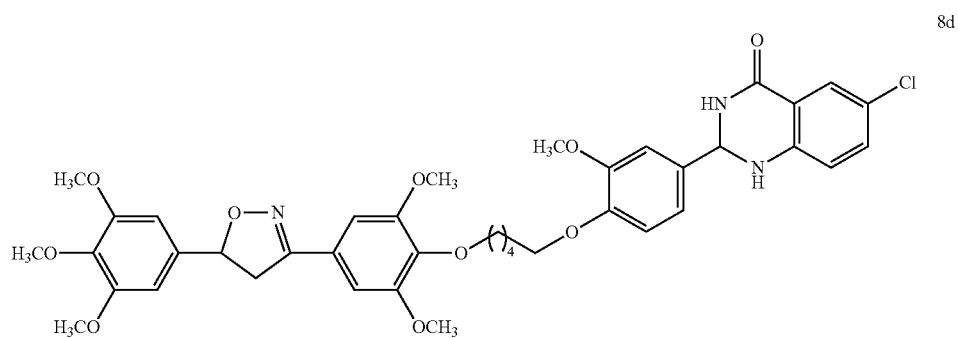
8d
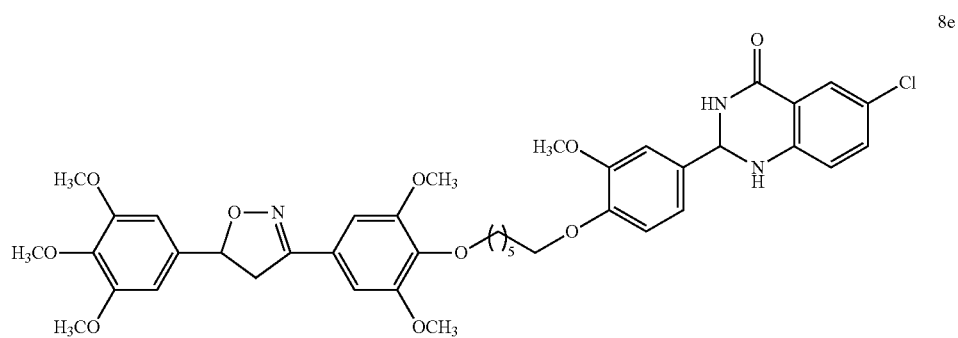
8e

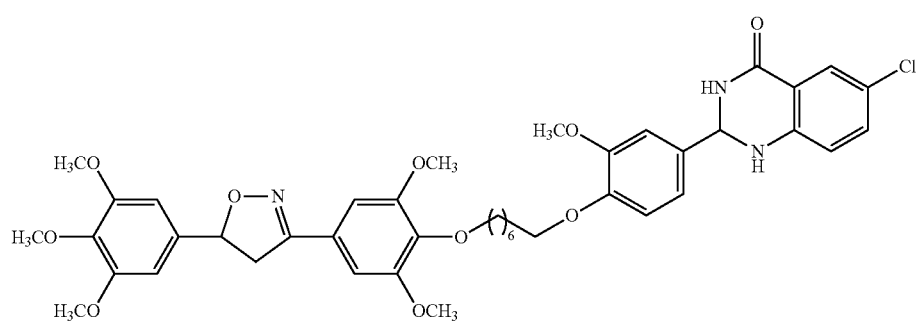
8f
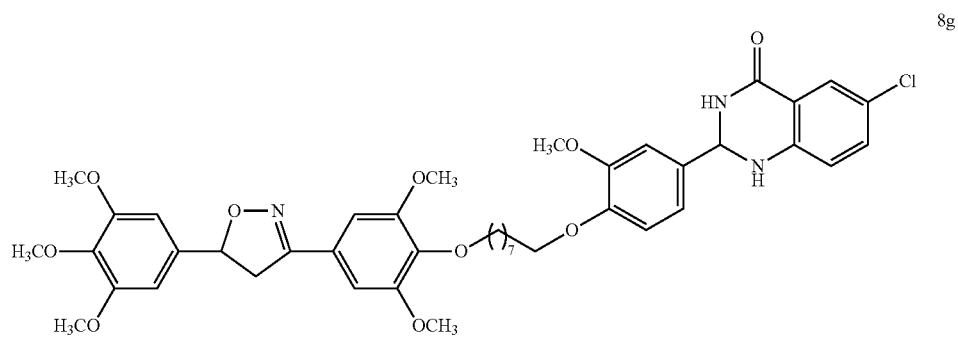
8g
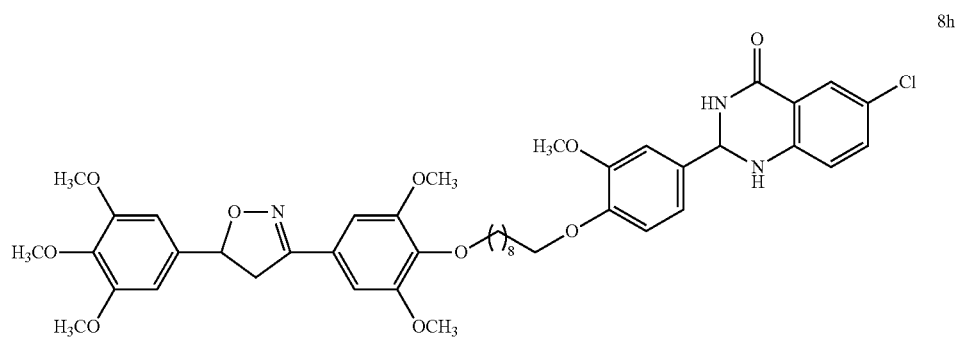
8h
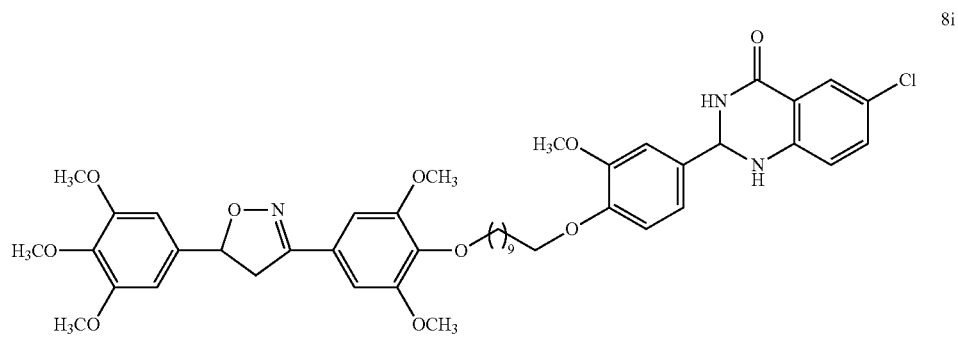
8i
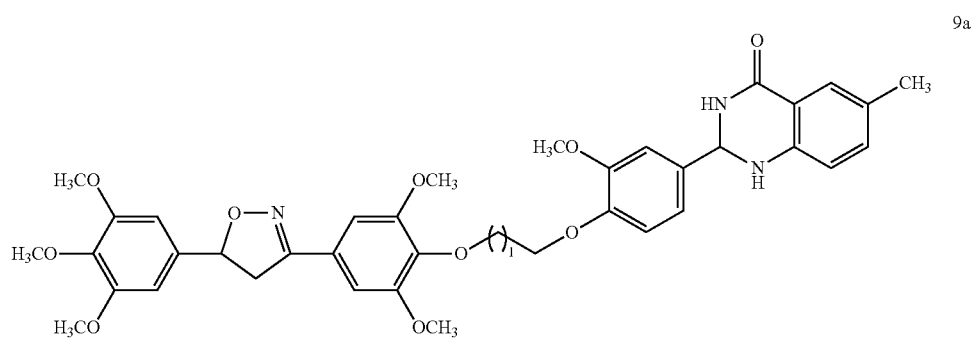
9a

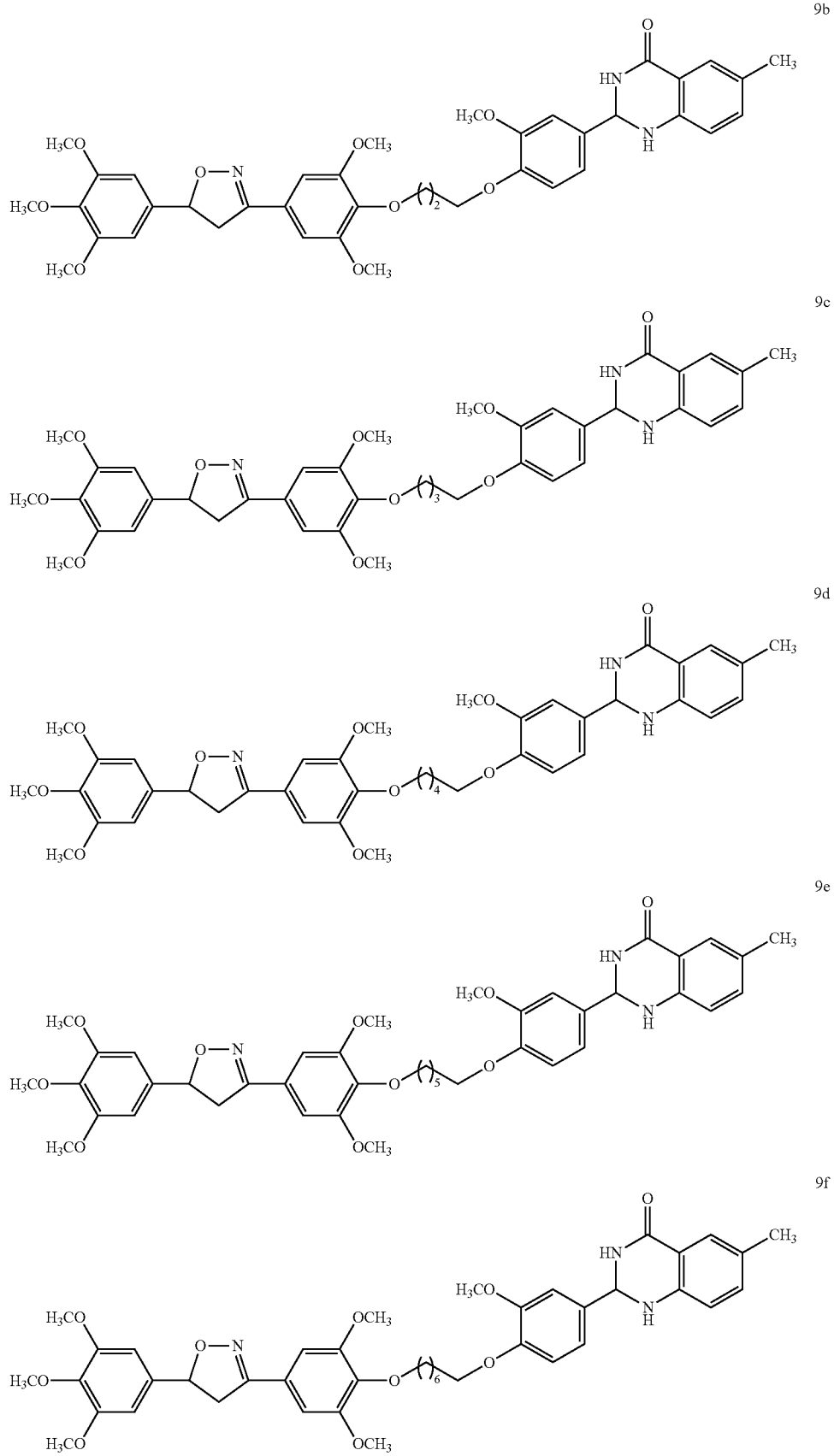

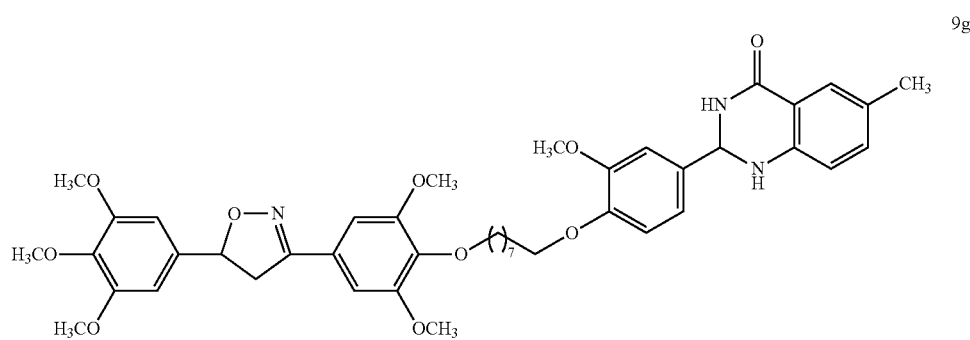
9g
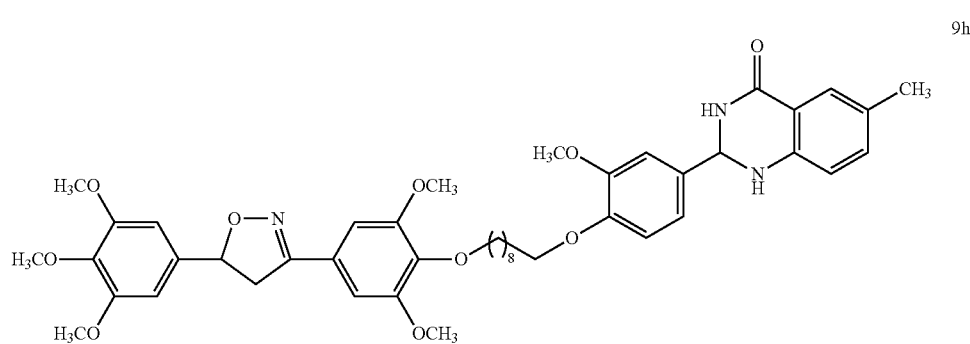
9h
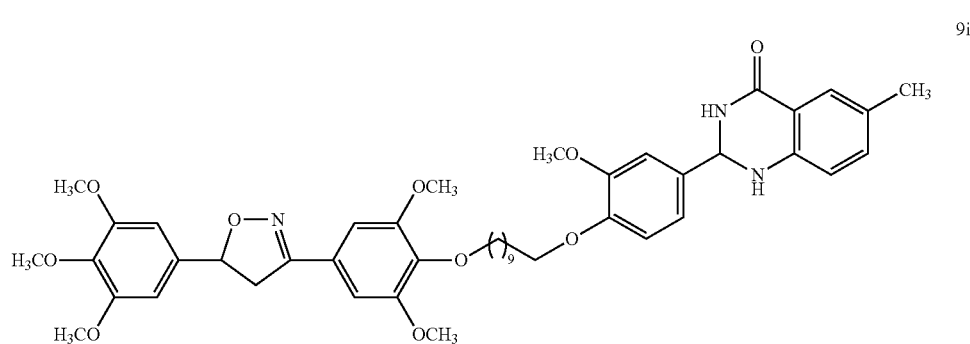
9i
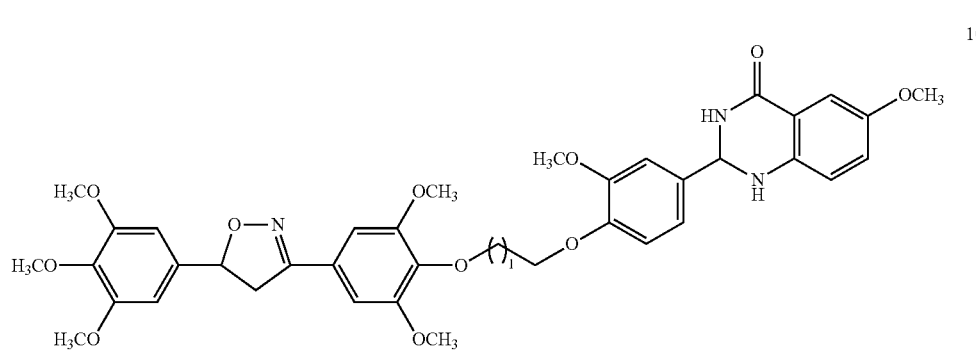
10a
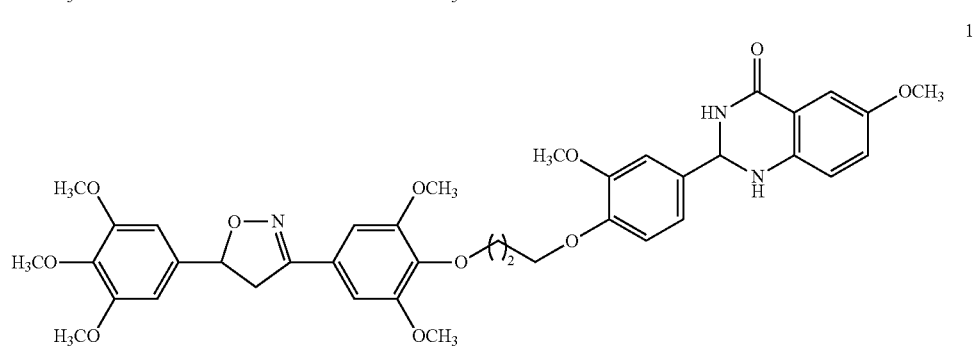
10b

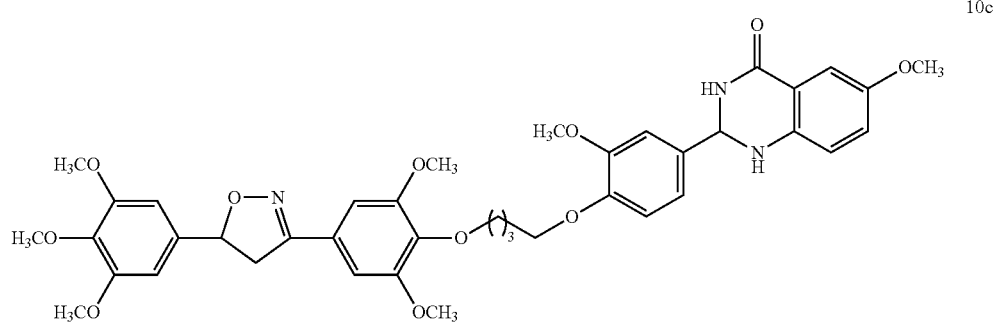
10c
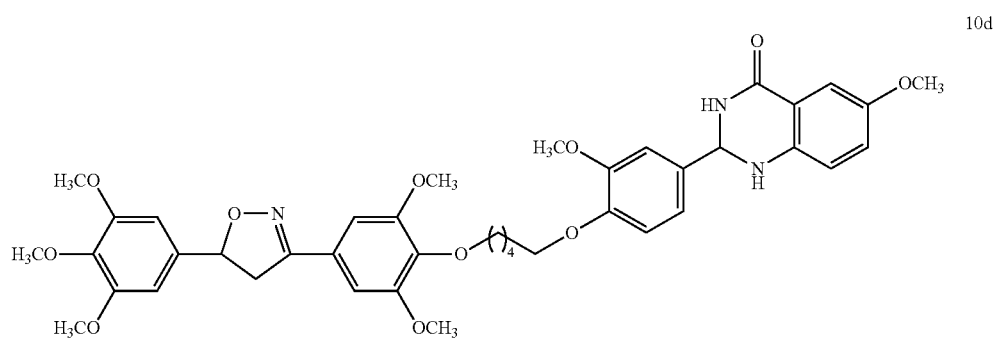
10d
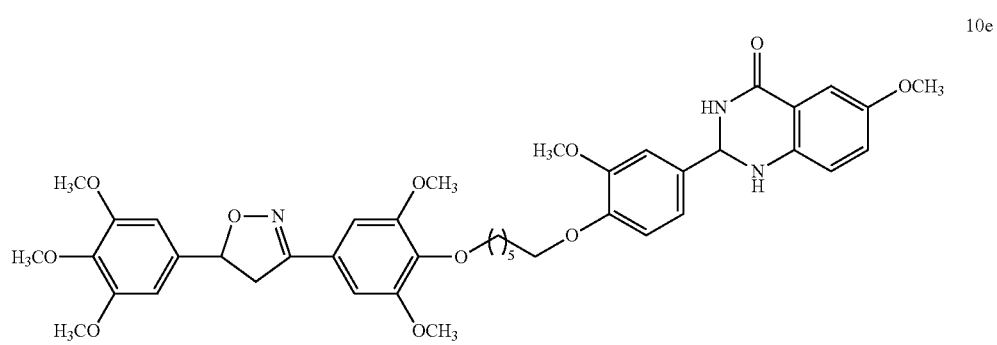
10e
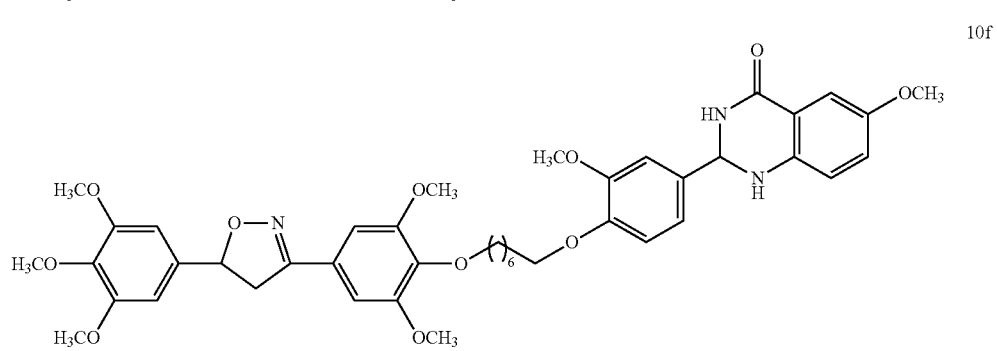
10f
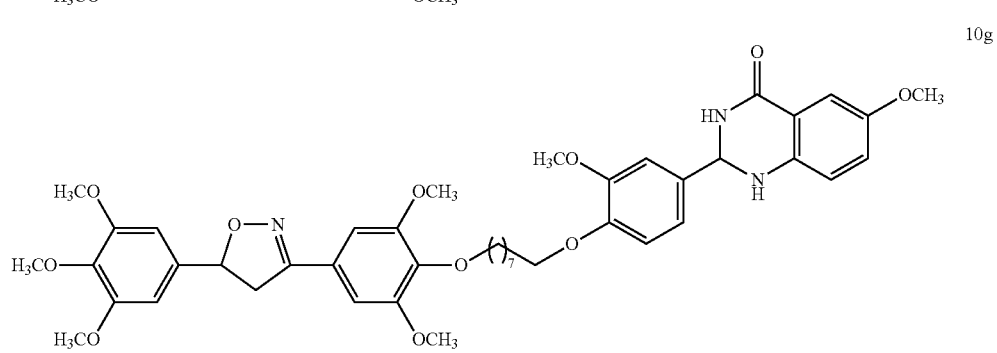
10g

-continued
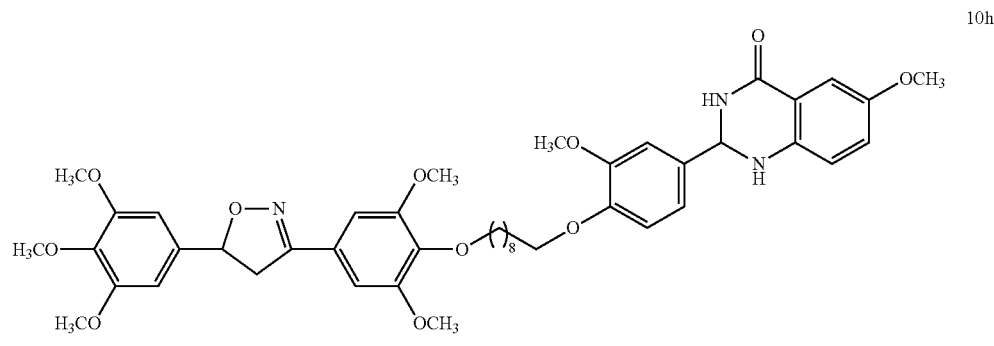
10h
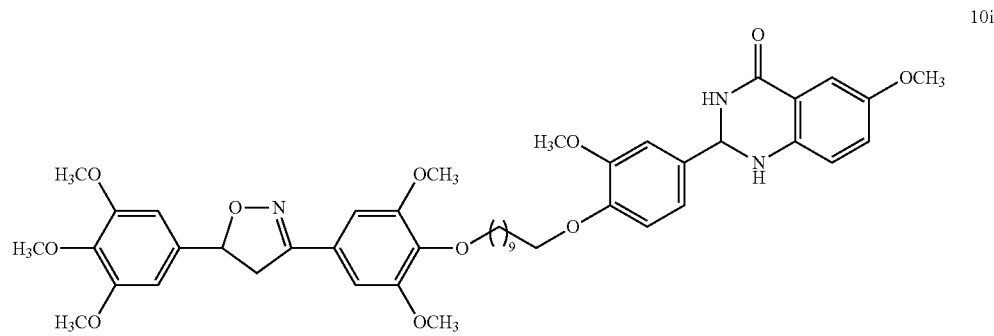
10i
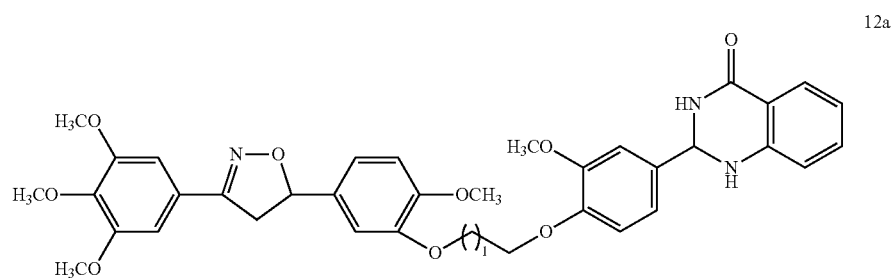
12a
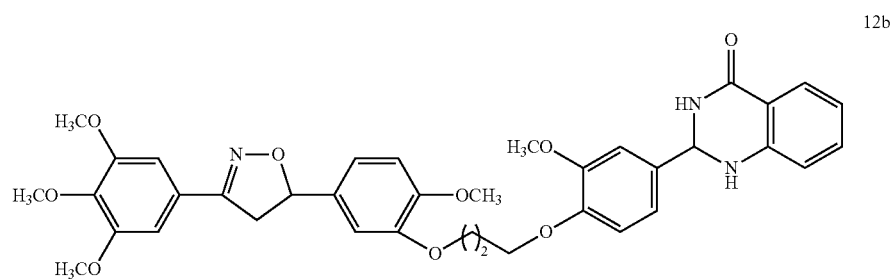
12b
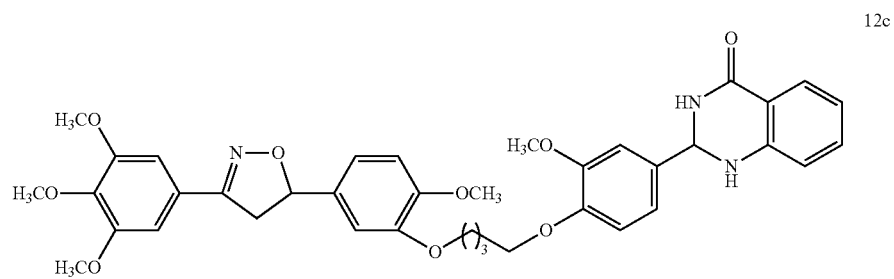
12c -continued
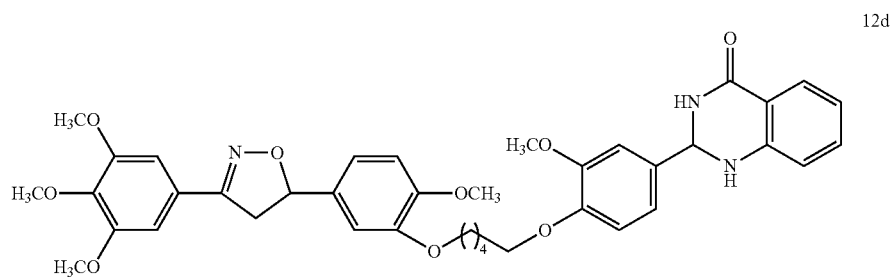
12d
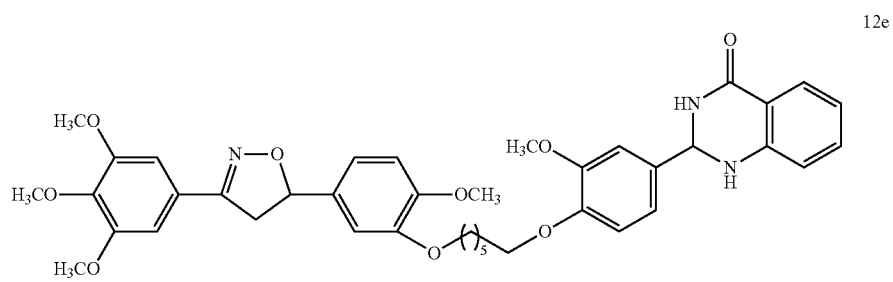
12e
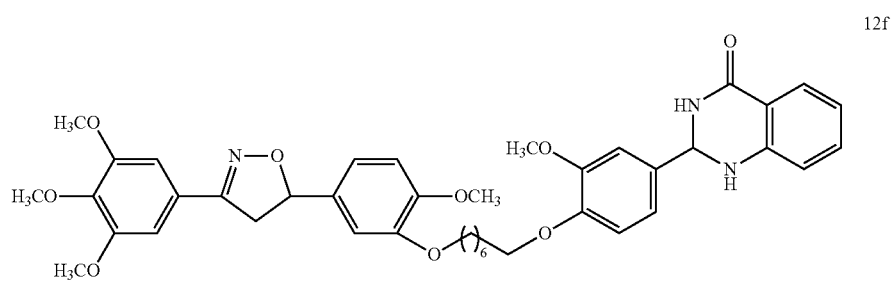
12f
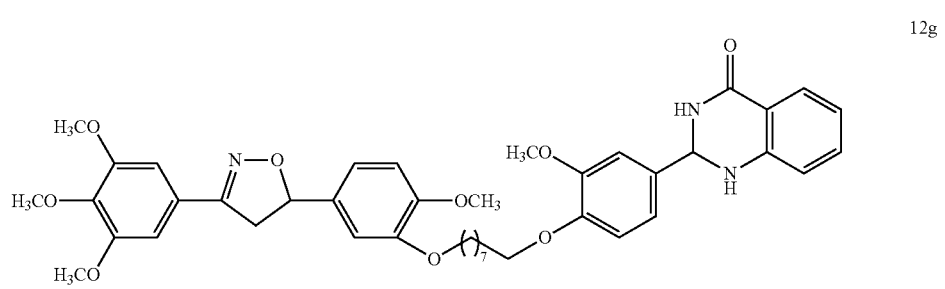
12g
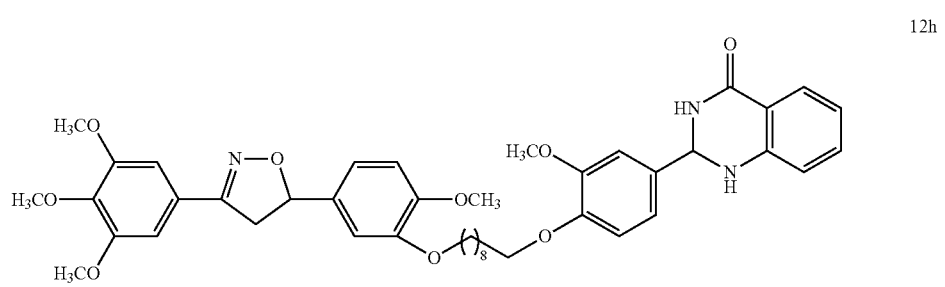
12h
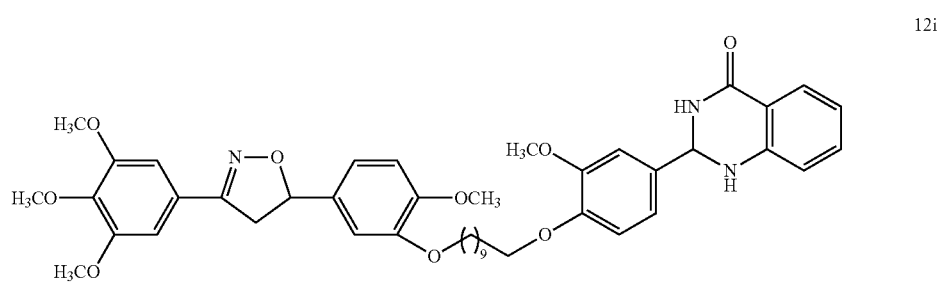
12i -continued
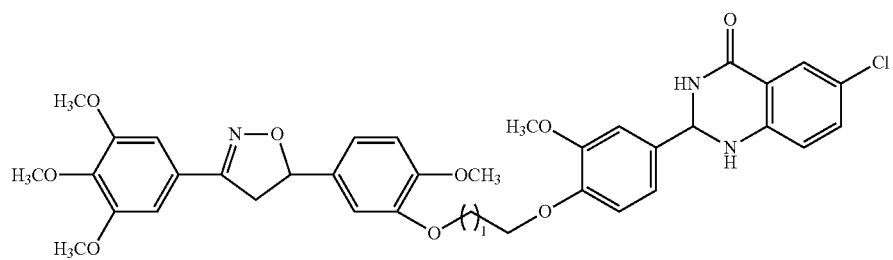
13a
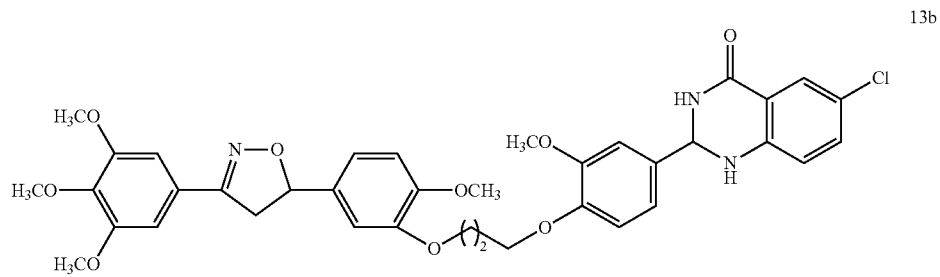
13b
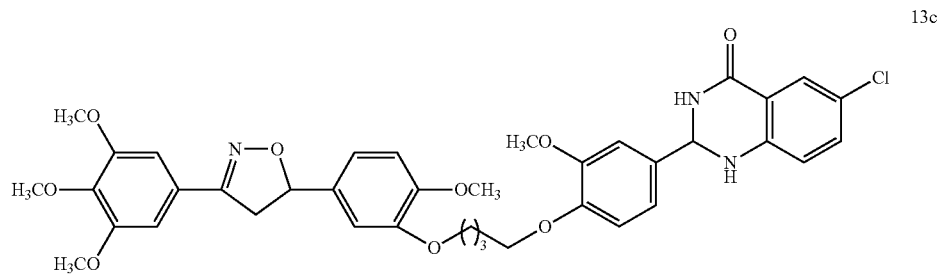
13c
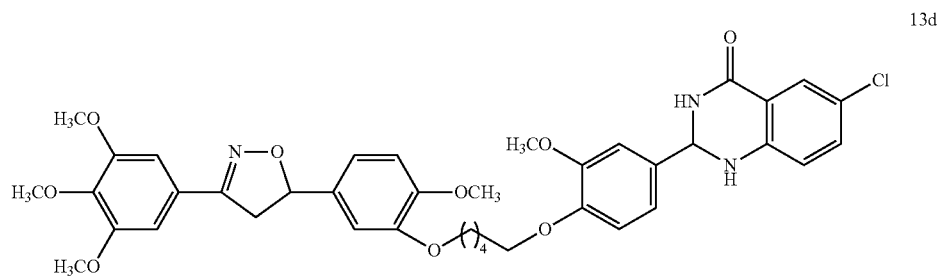
13d
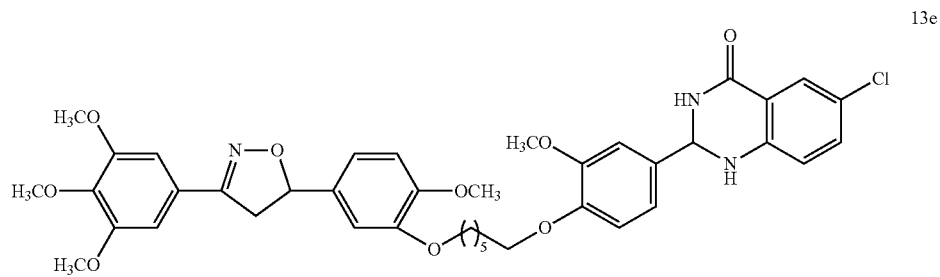
13e
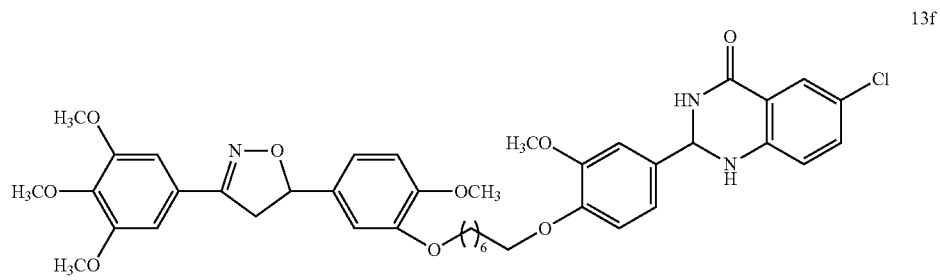
13f -continued
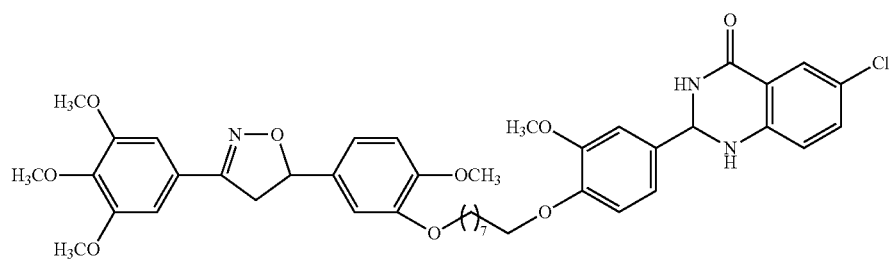
13g
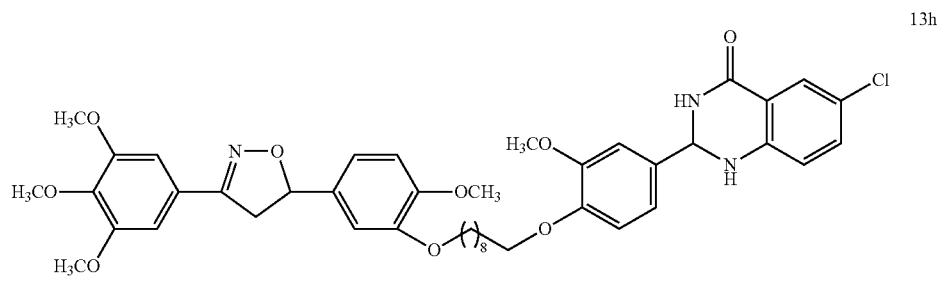
13h
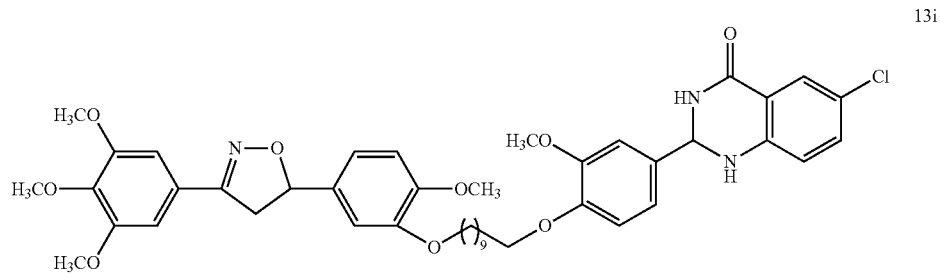
13i
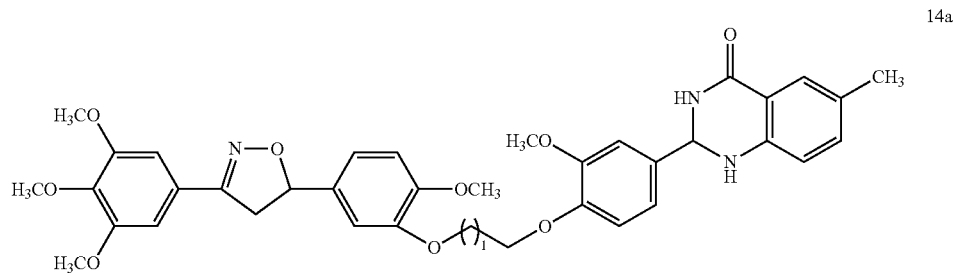
14a
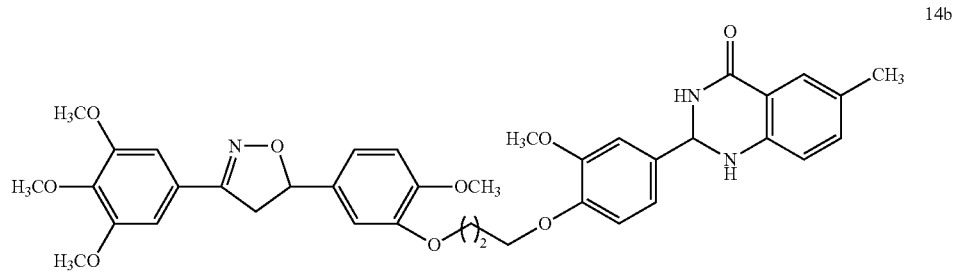
14b
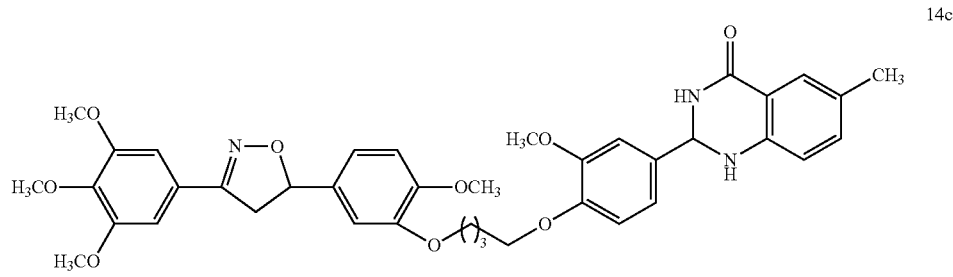
14c -continued
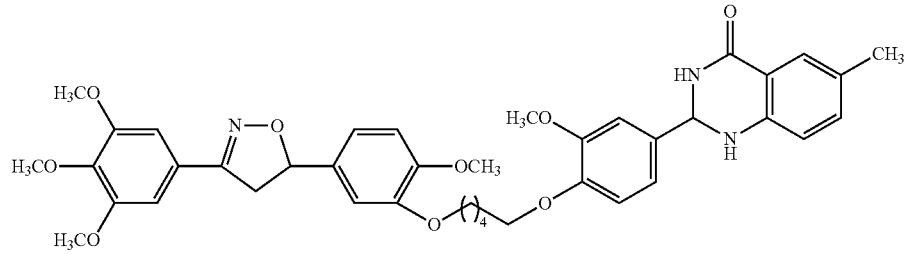
14d
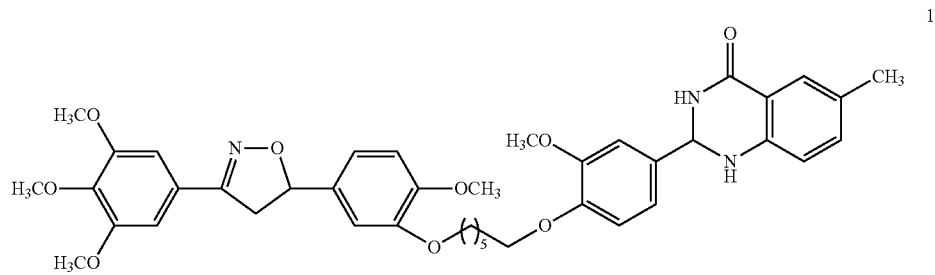
14e
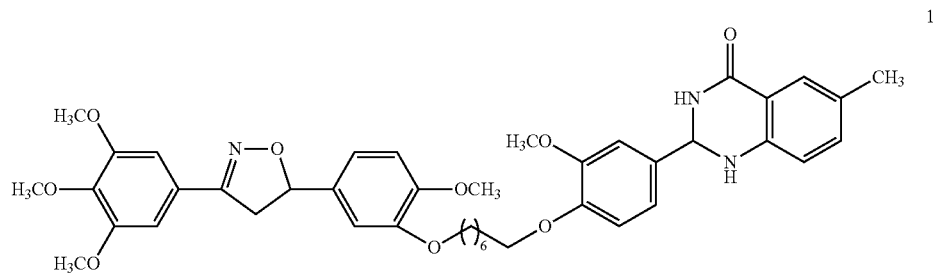
14f
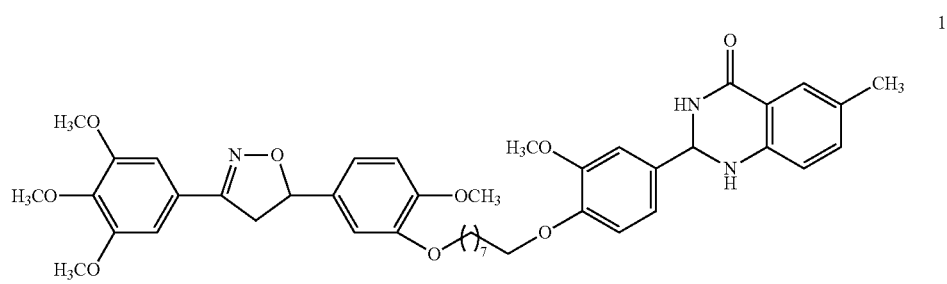
14g
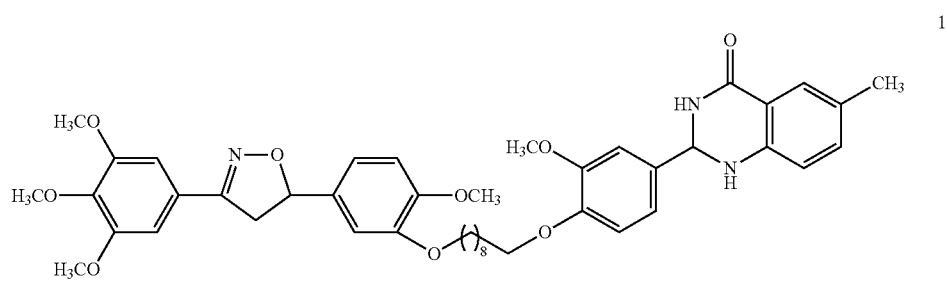
14h
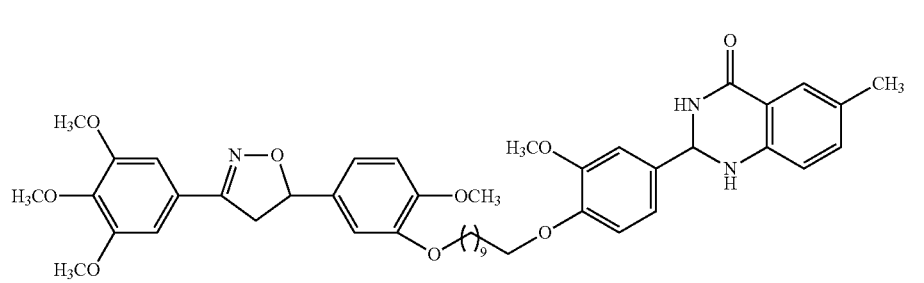
14i

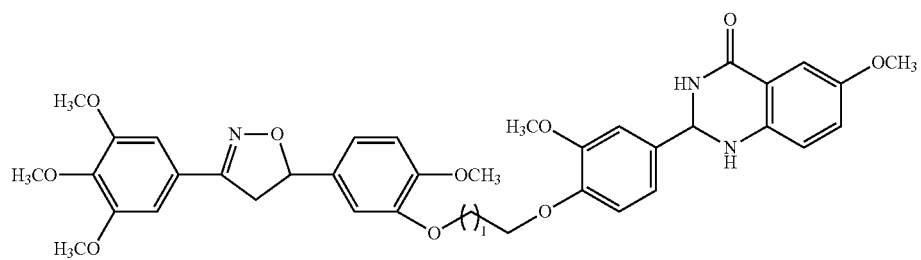
15a
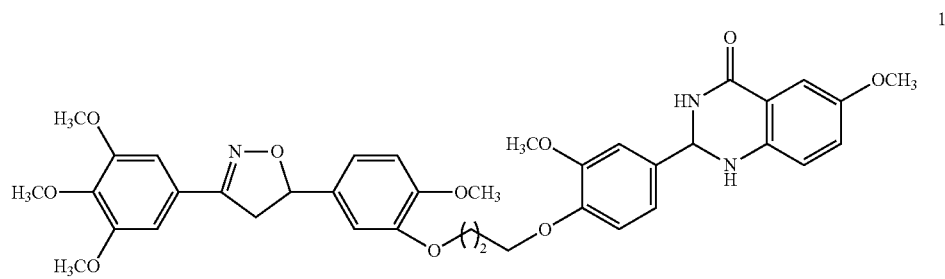
15b
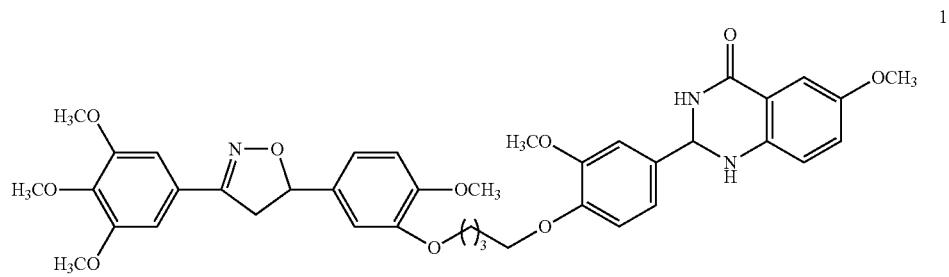
15c
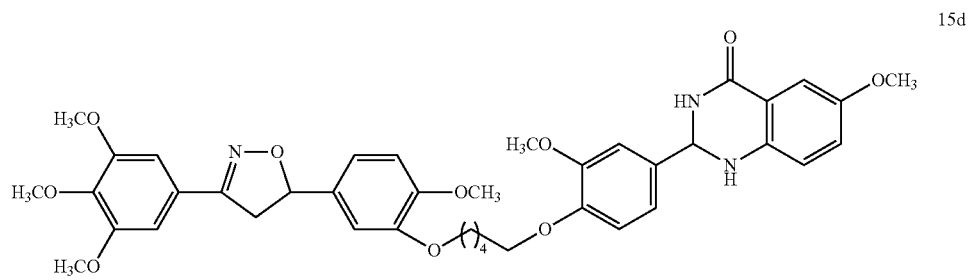
15d
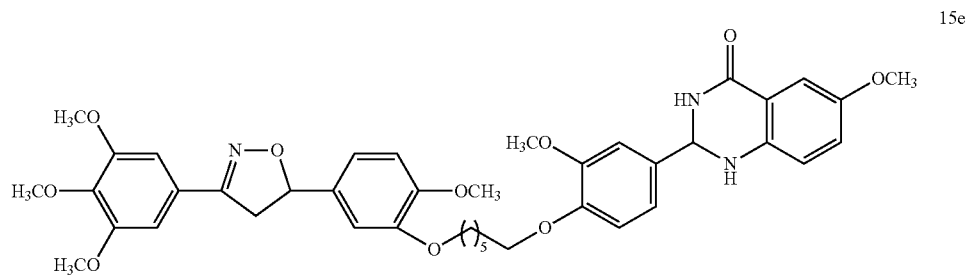
15e
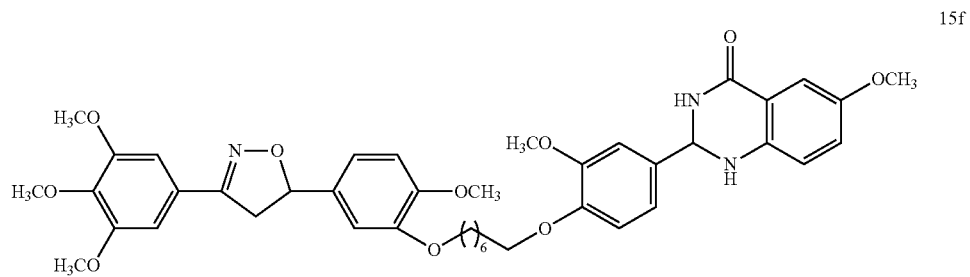
15f

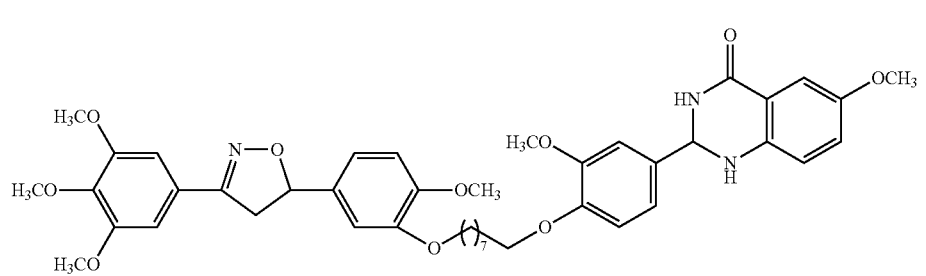
15g
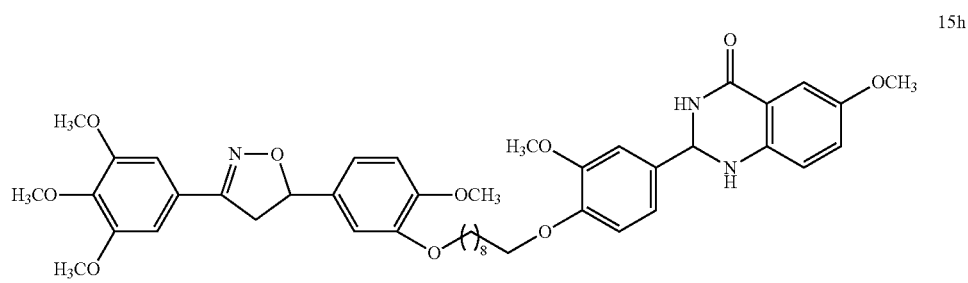
15h
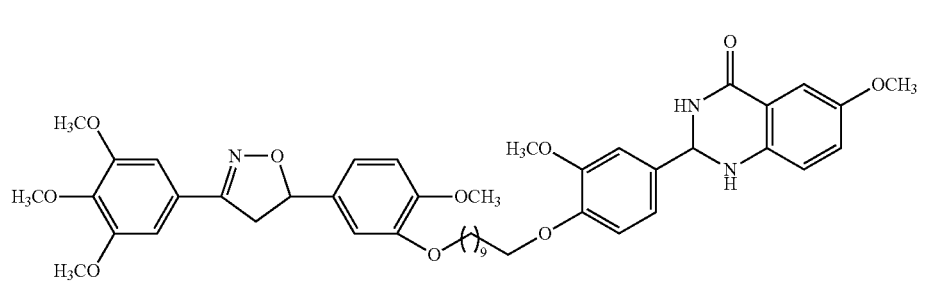
15i
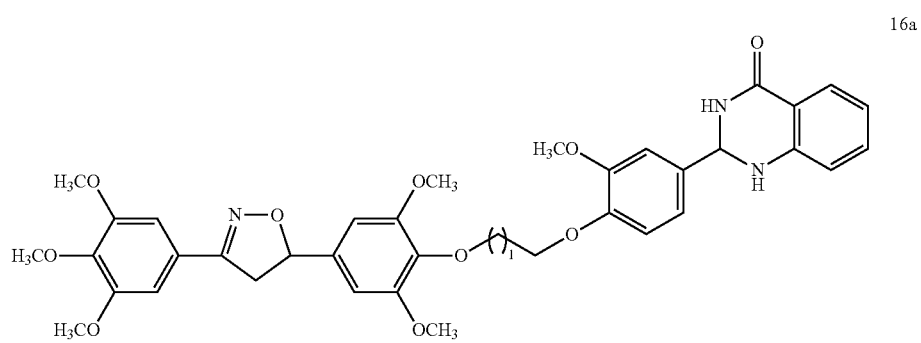
16a
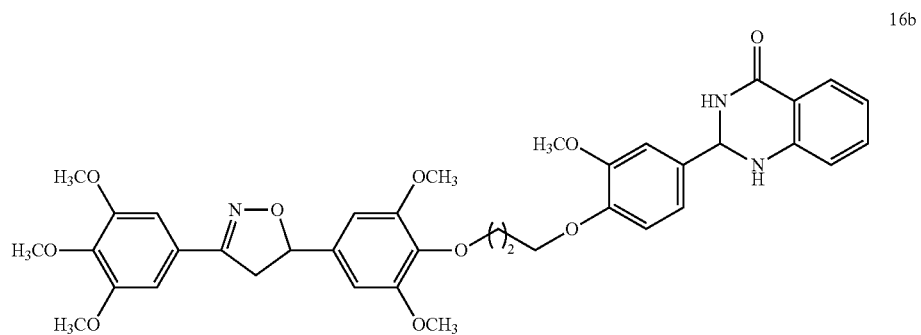
16b

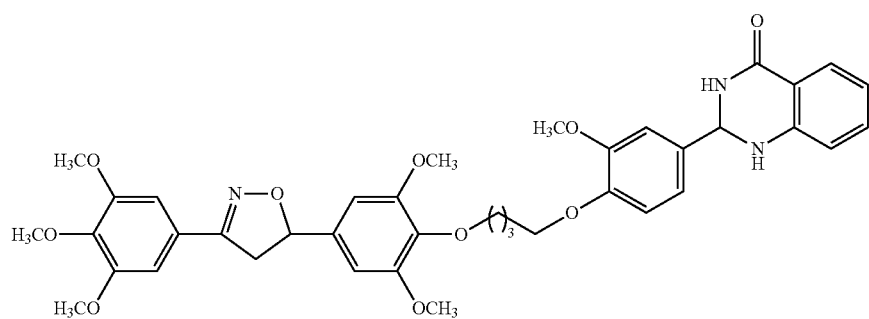
16c
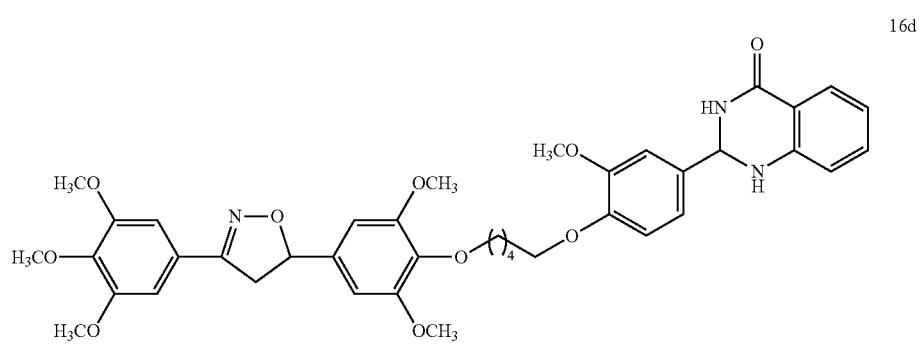
16d
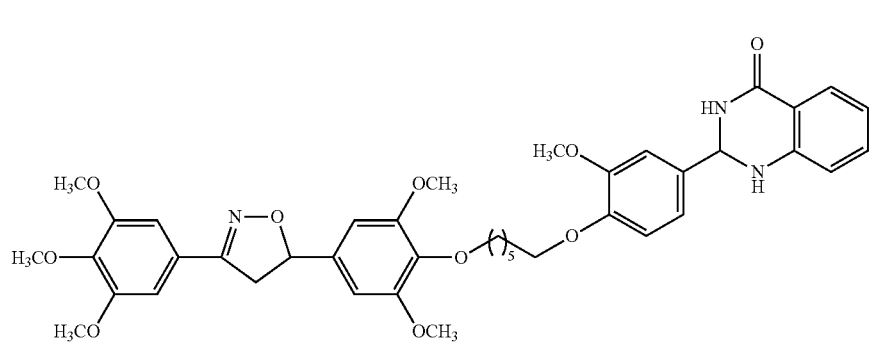
16e
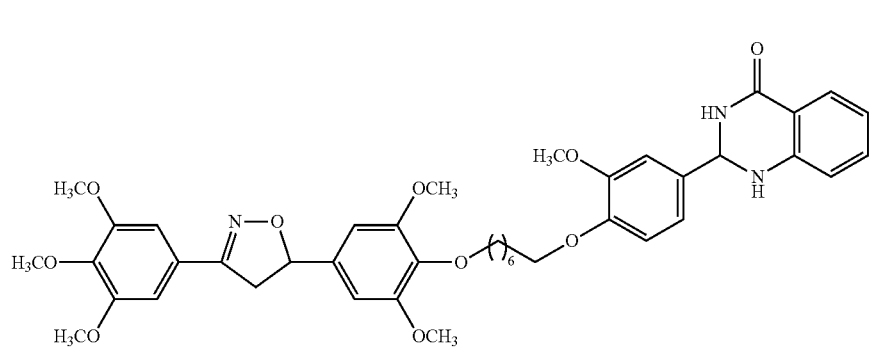
16f
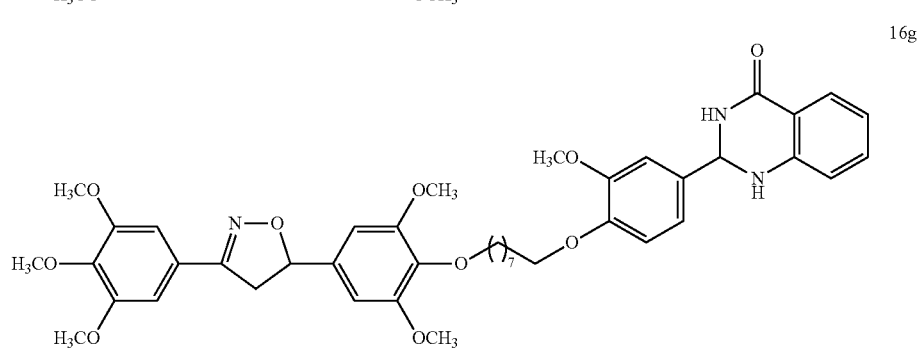
16g

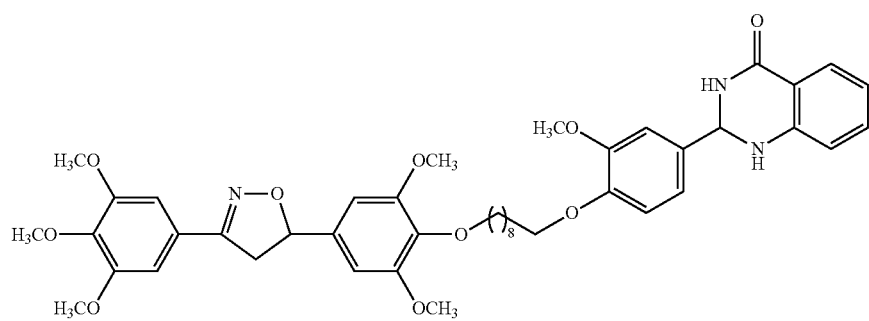
16h
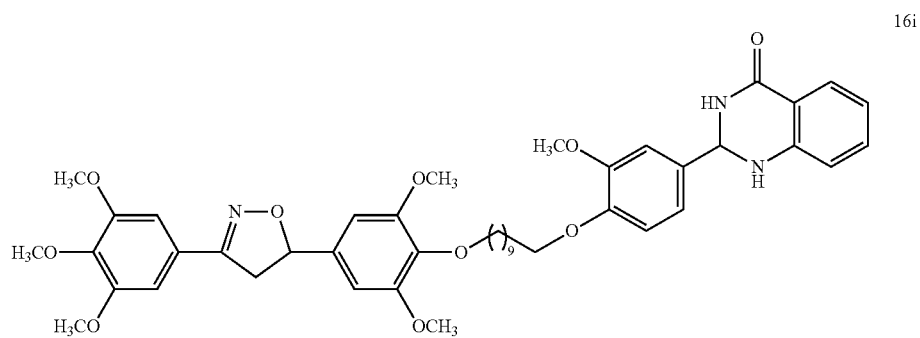
16i
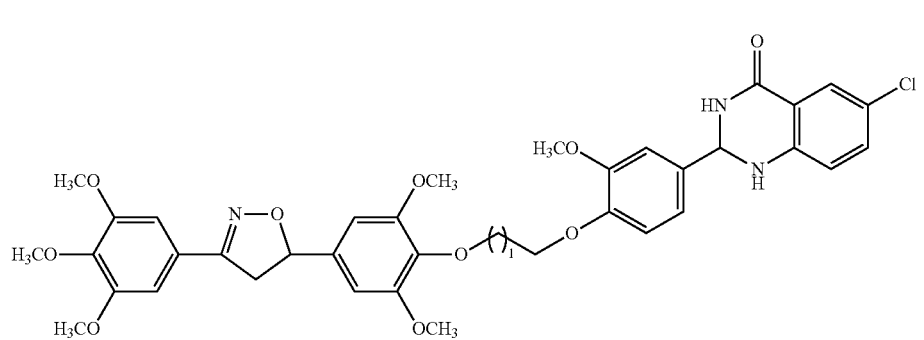
17a
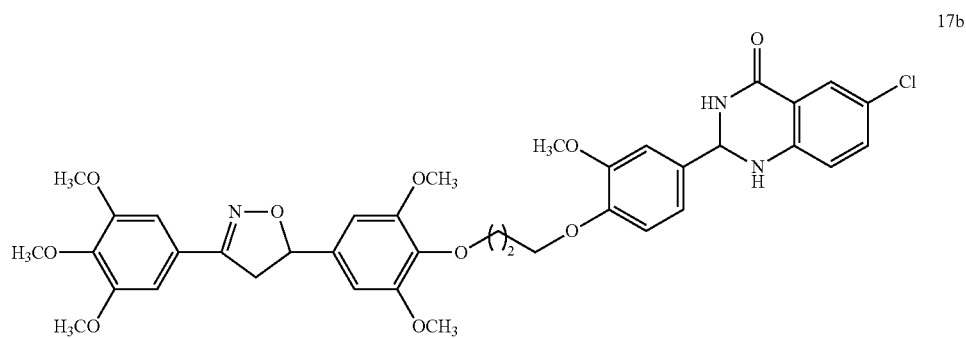
17b
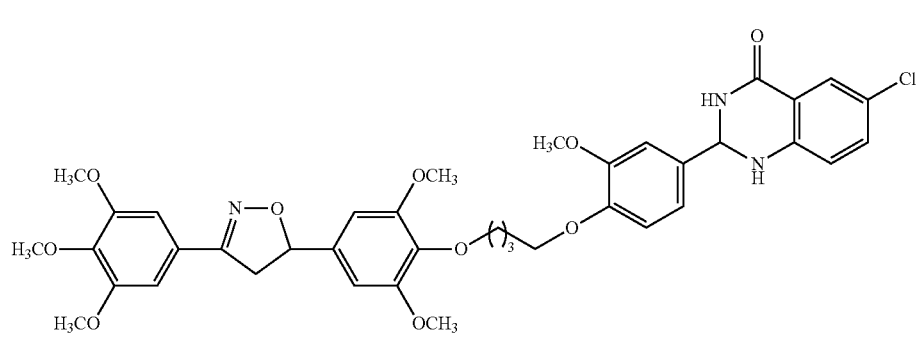
17c

-continued
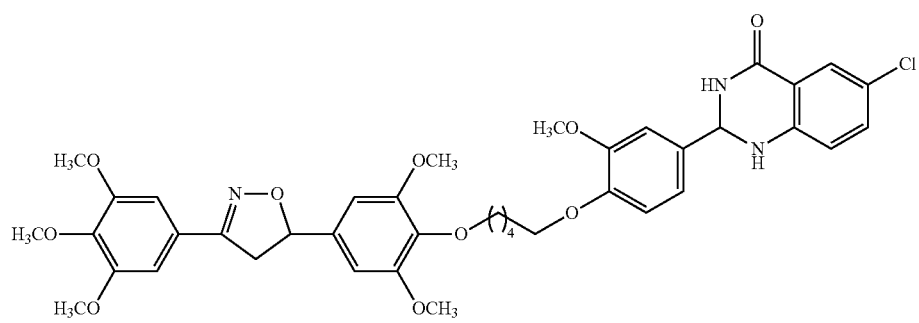
17d
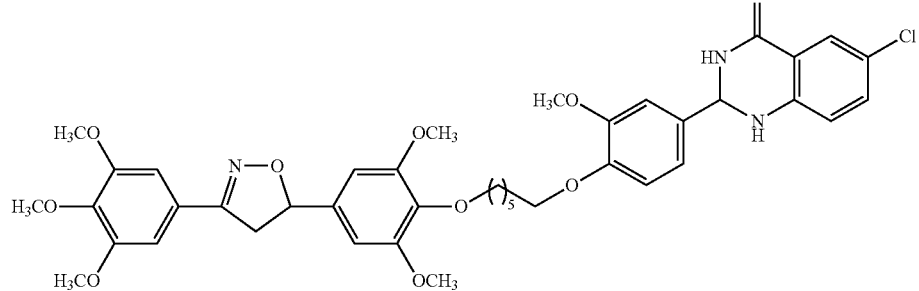
17e
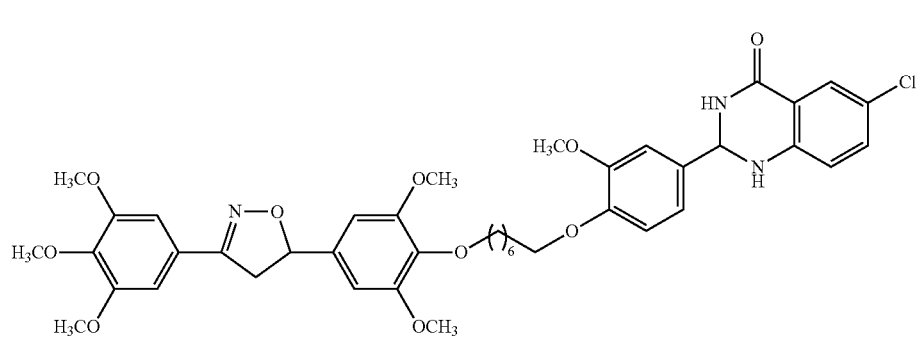
17f
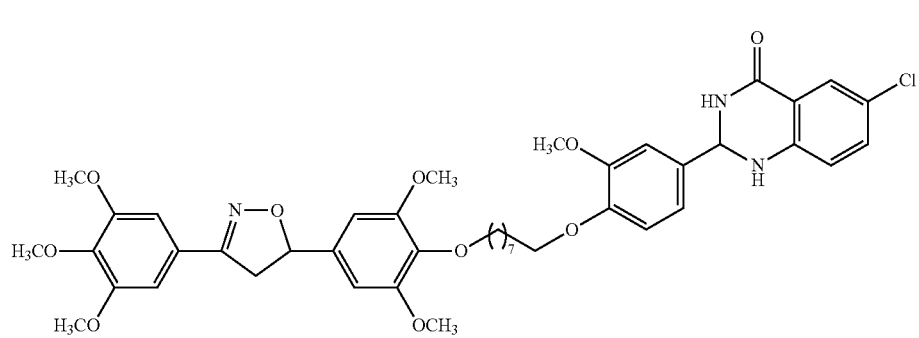
17g
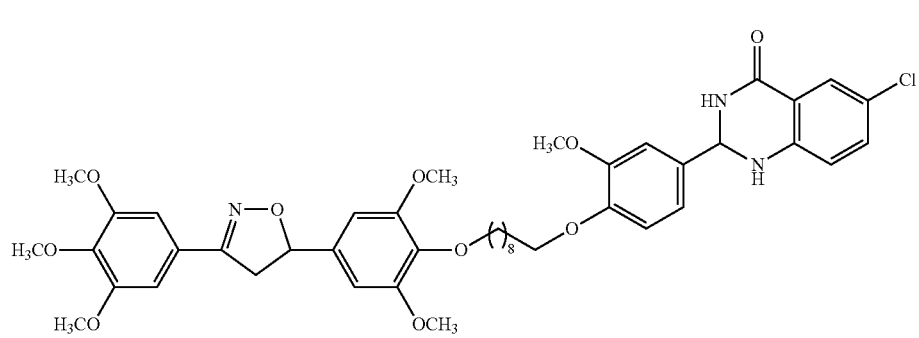
17h -continued
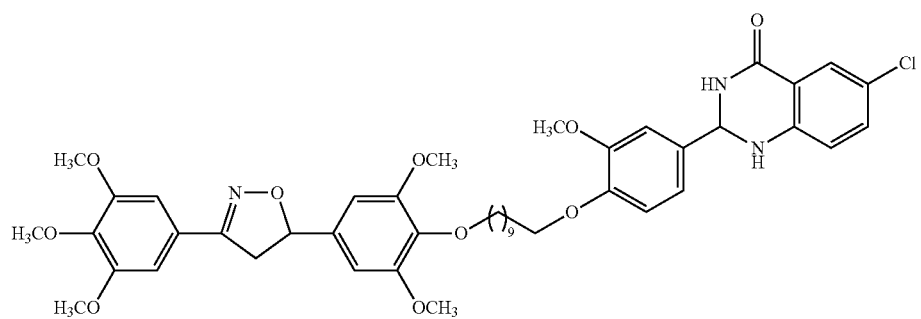
17i
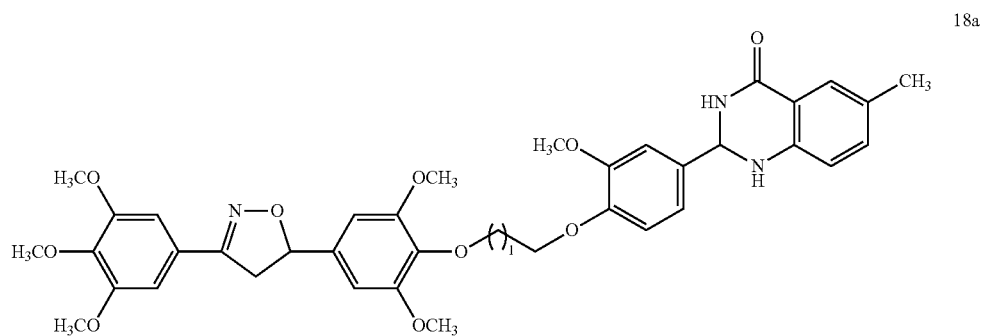
18a
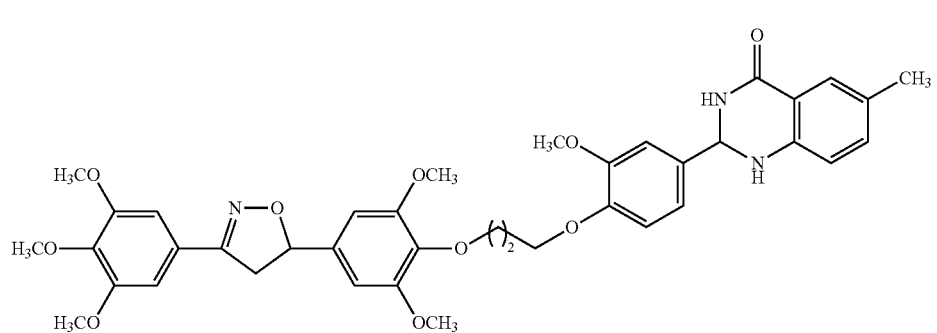
18b
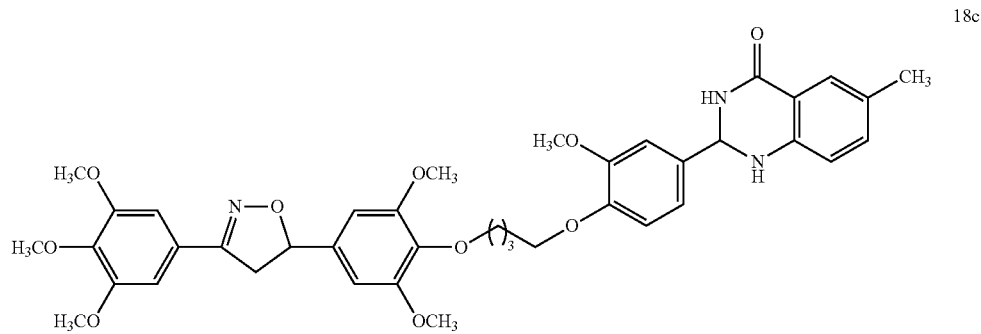
18c
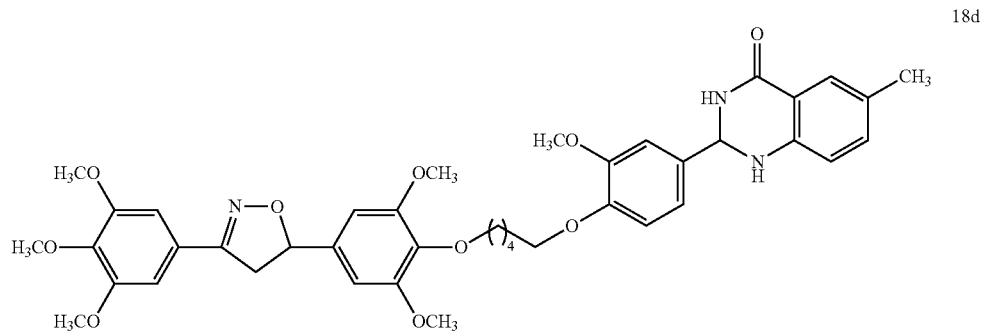
18d -continued
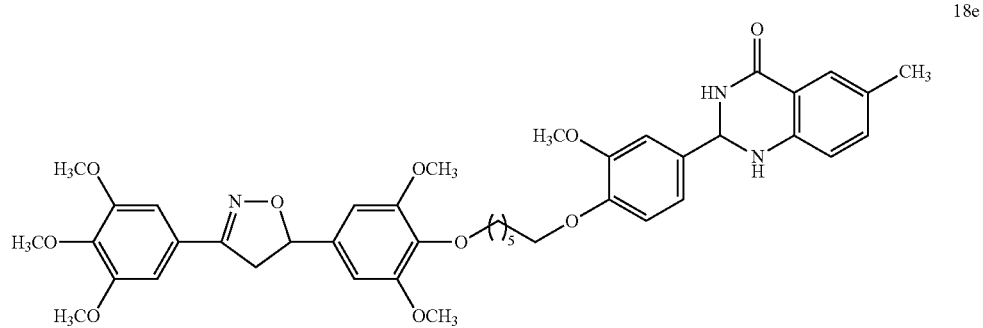
18e
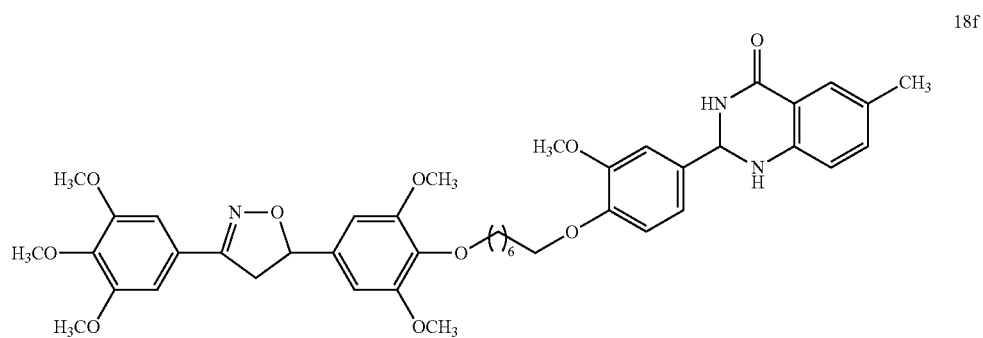
18f
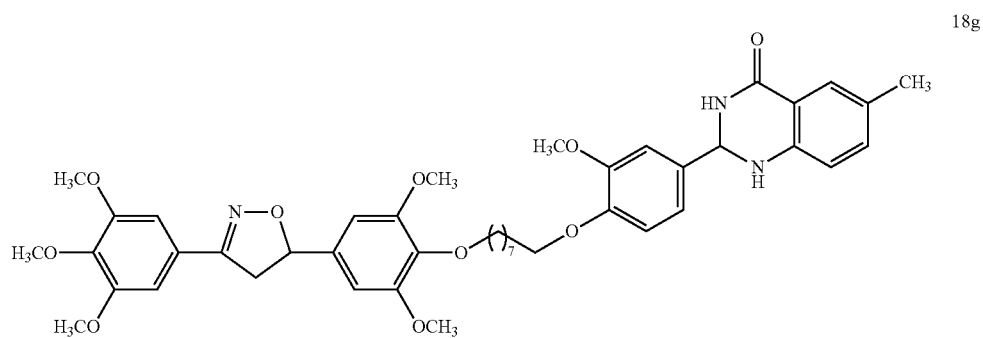
18g
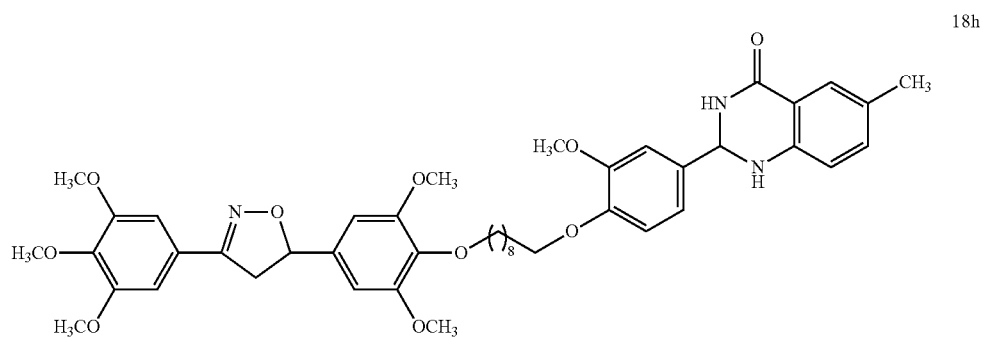
18h
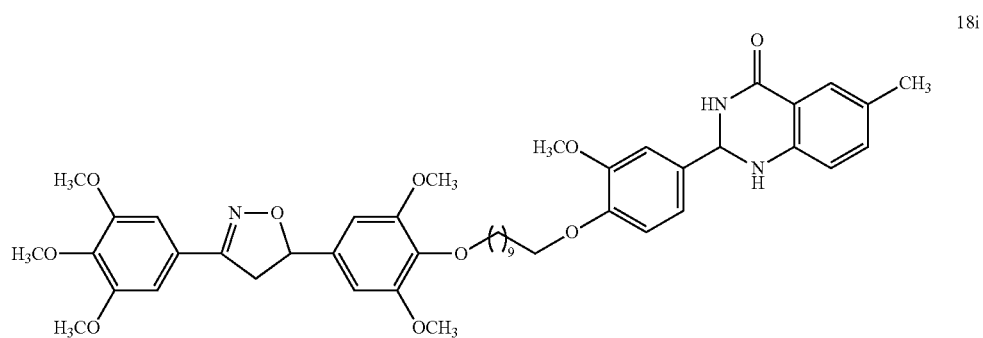
18i

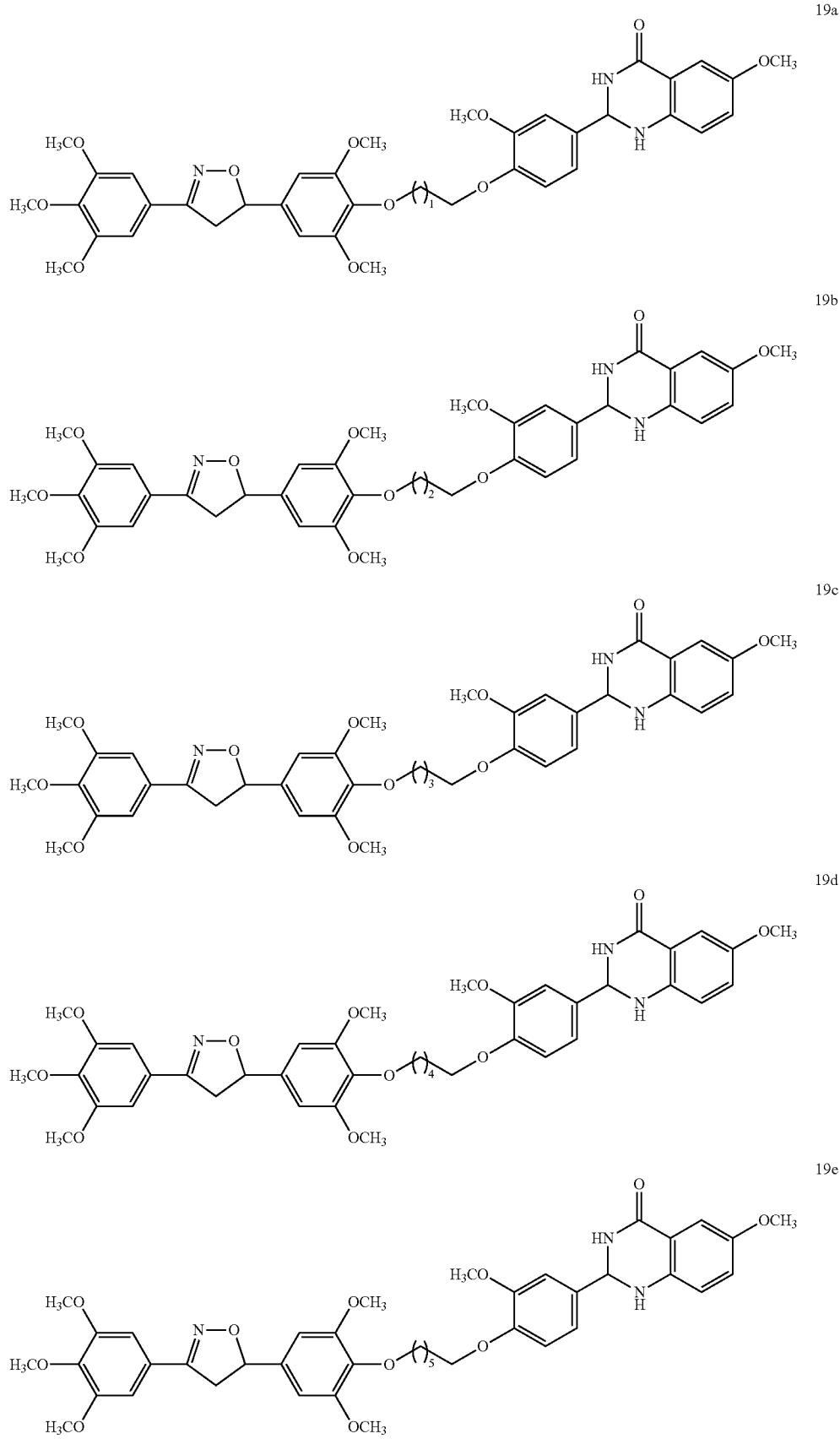

-continued
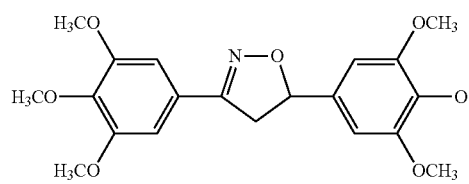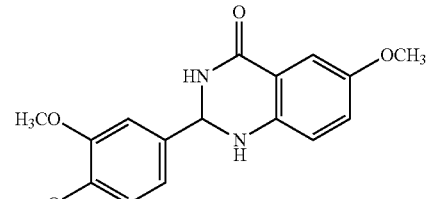
19f
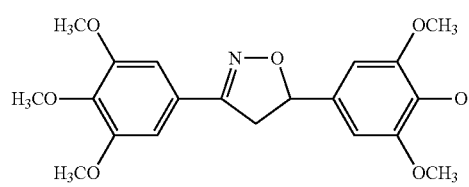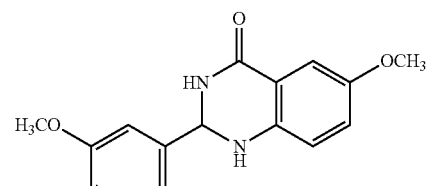
19g
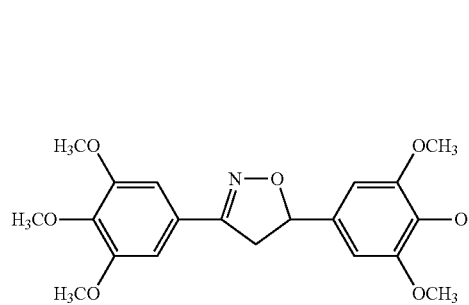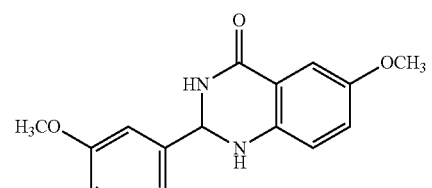
19h
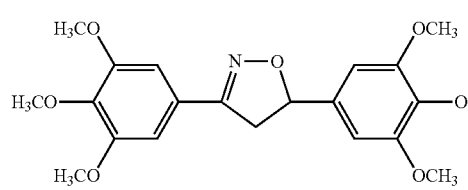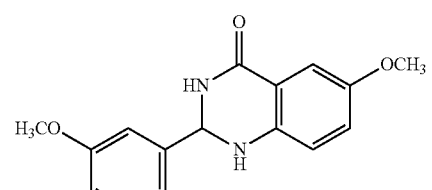
19i
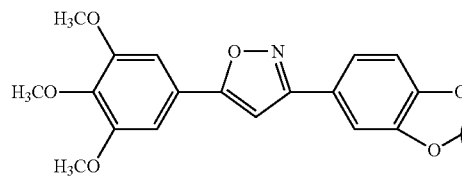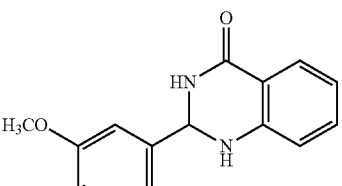
21a -continued
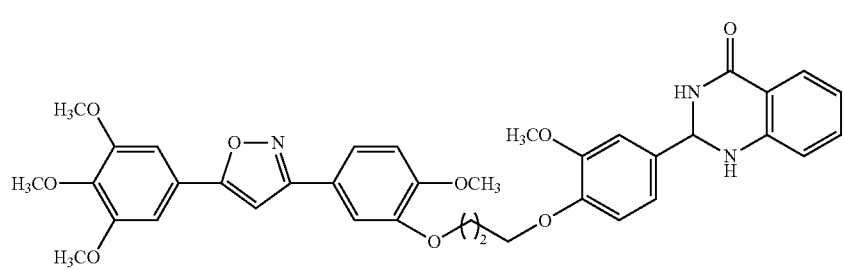
21b
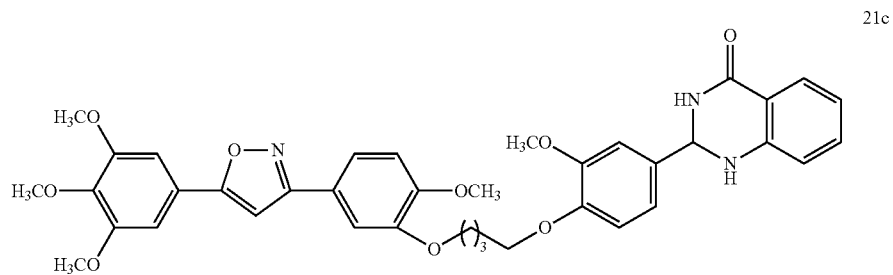
21c
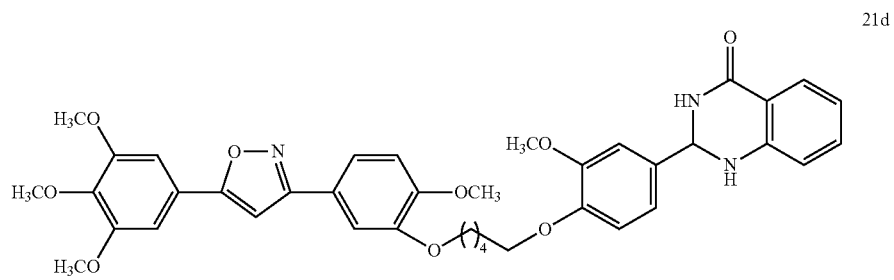
21d
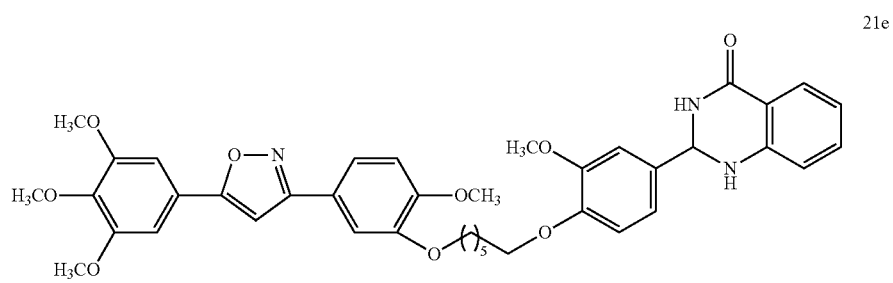
21e
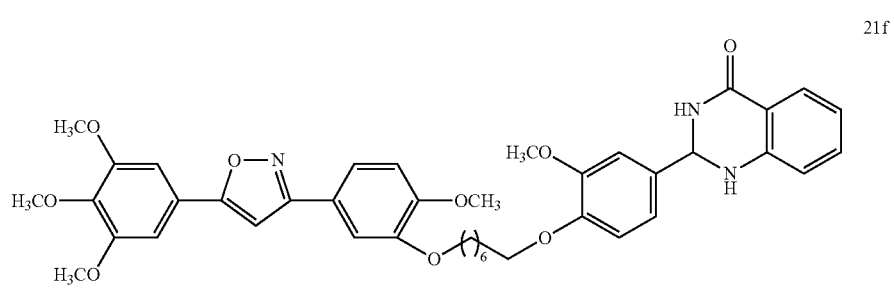
21f
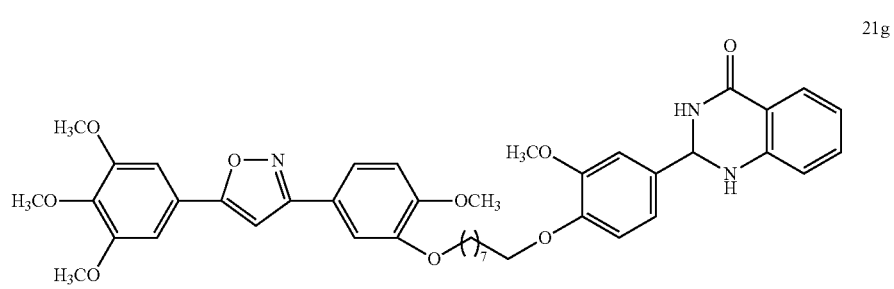
21g

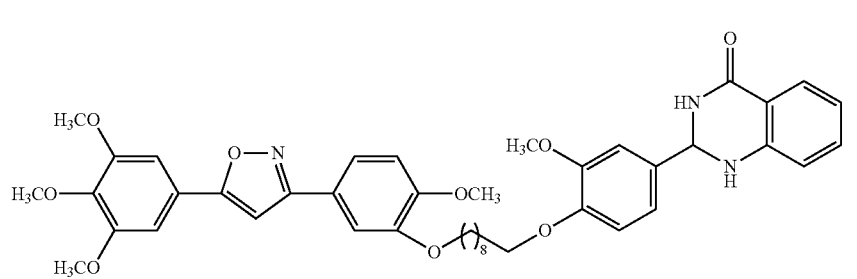
21h
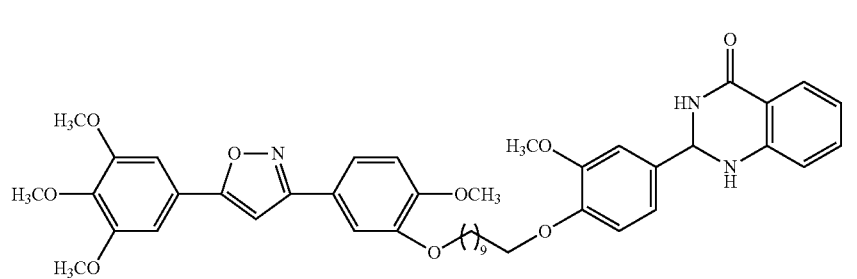
21i
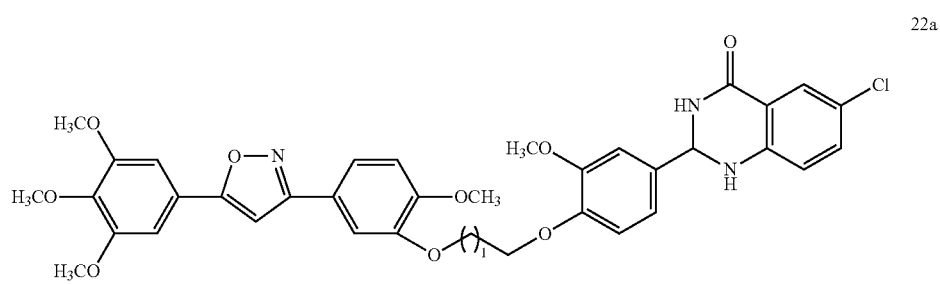
22a
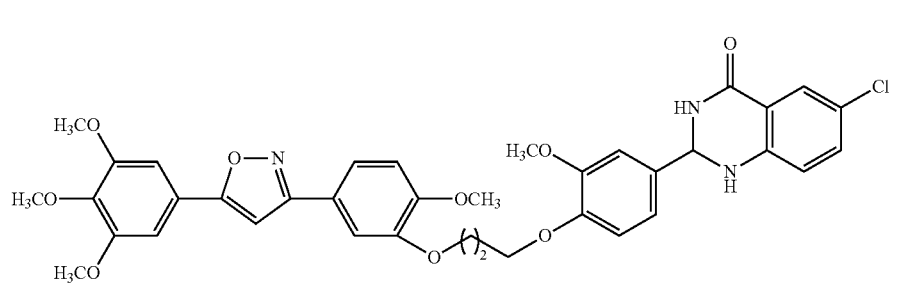
22b
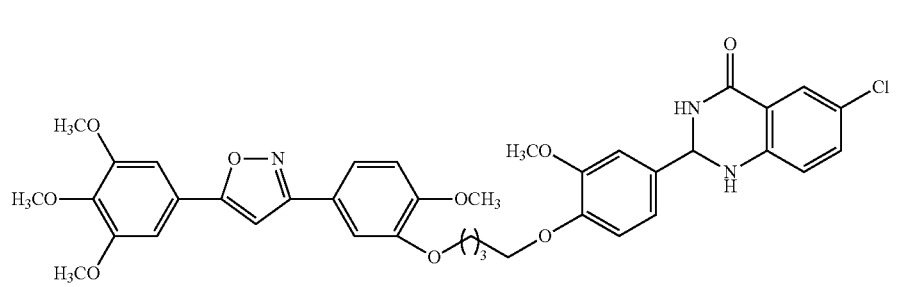
22c
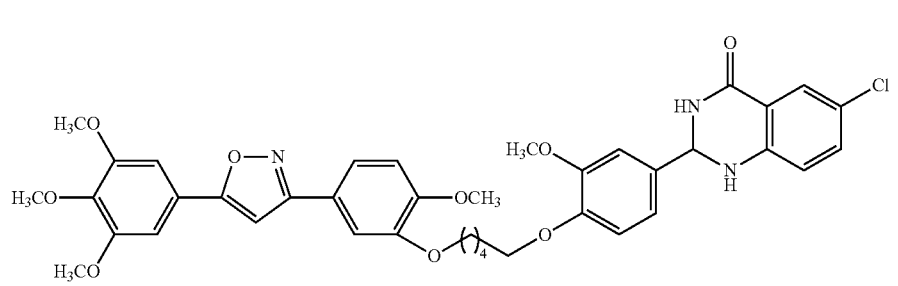
22d -continued
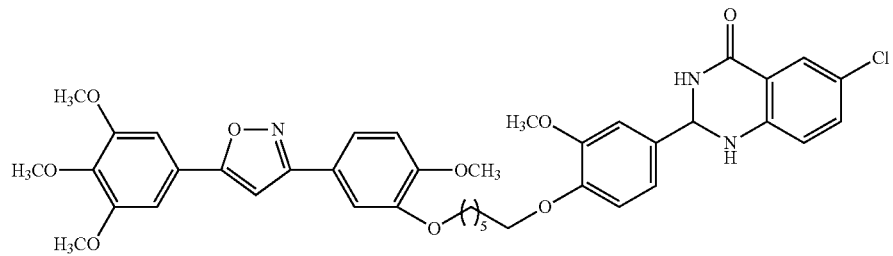
22e
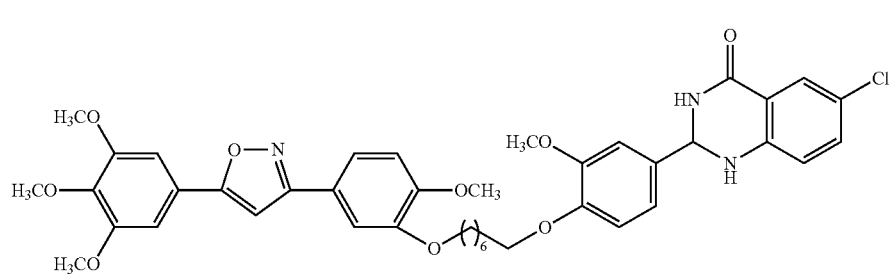
22f
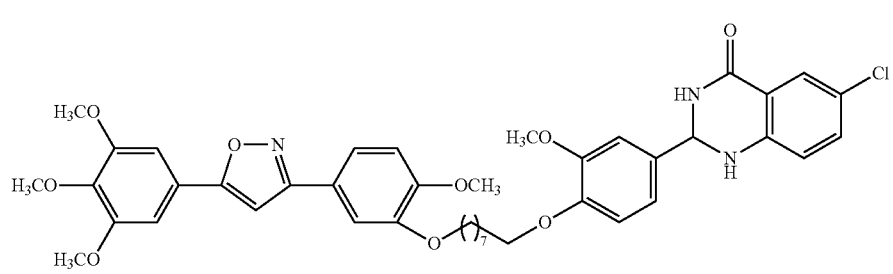
22g
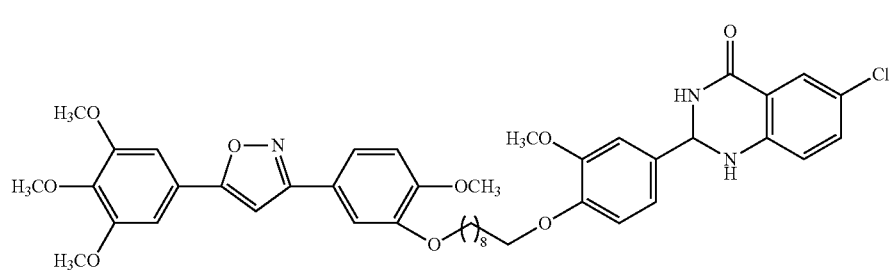
22h
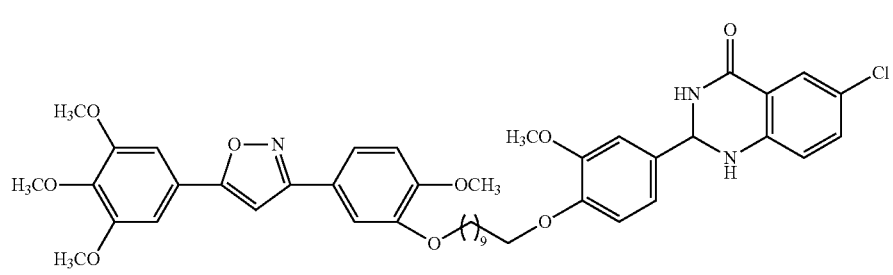
22i
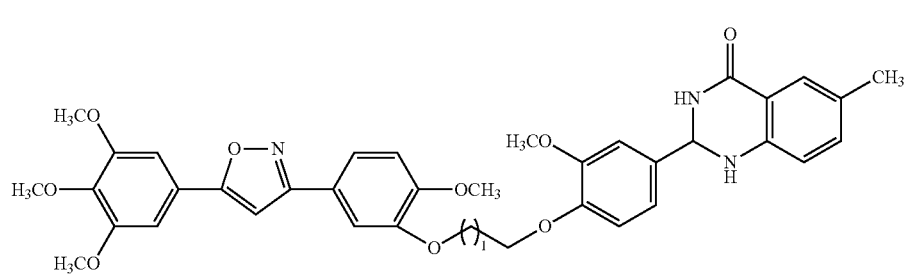
23a -continued
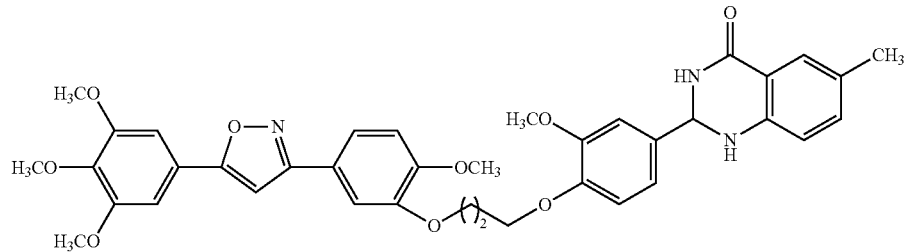
23b
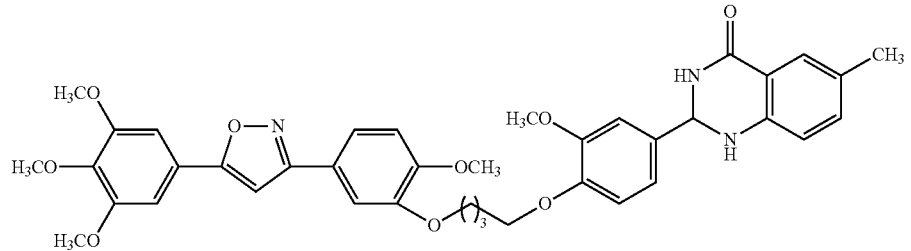
23c
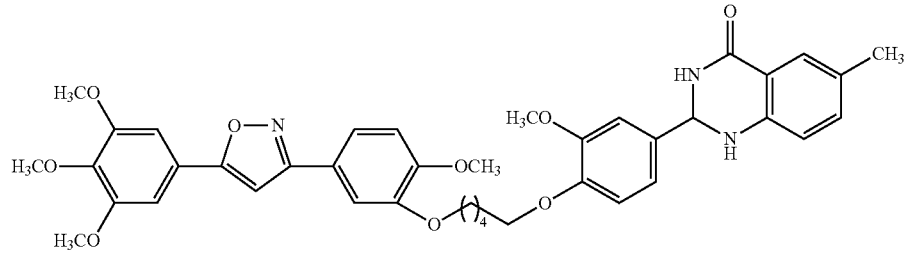
23d
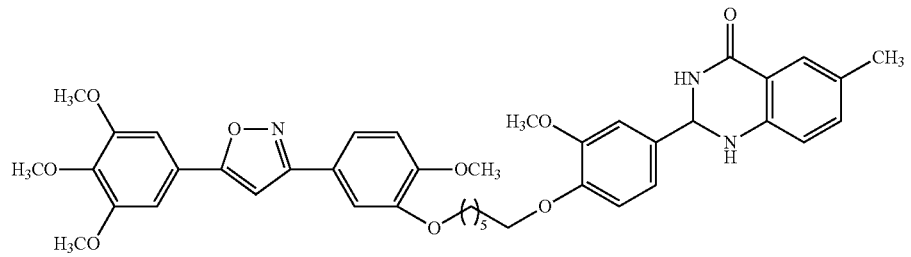
23e
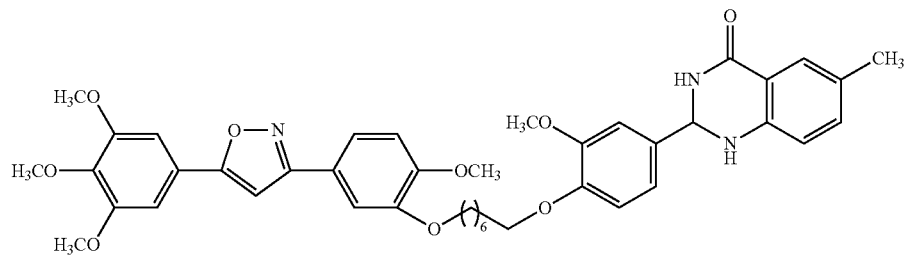
23f
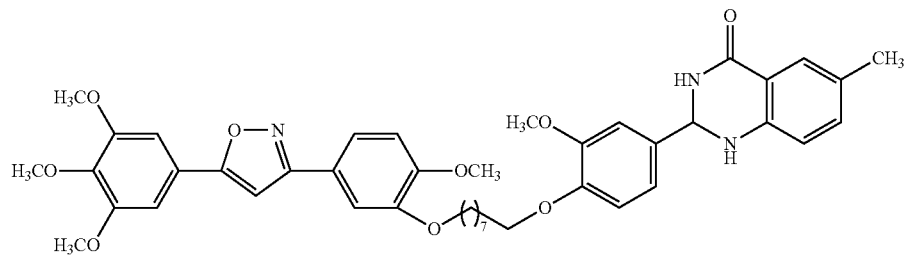
23g

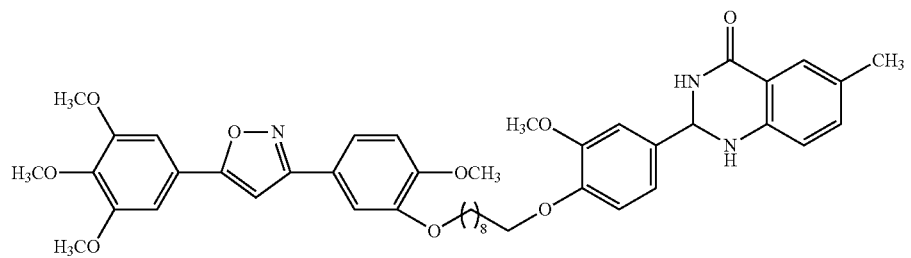
23h
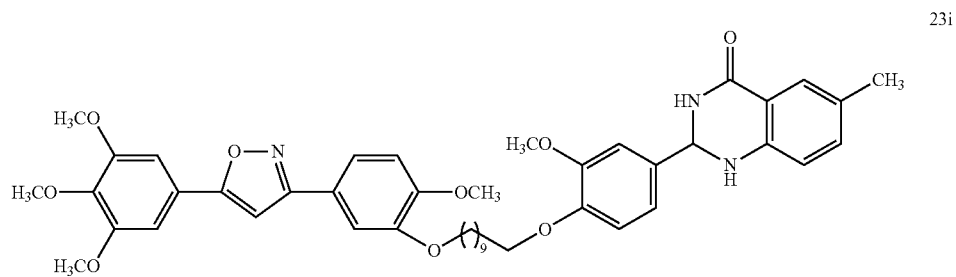
23i
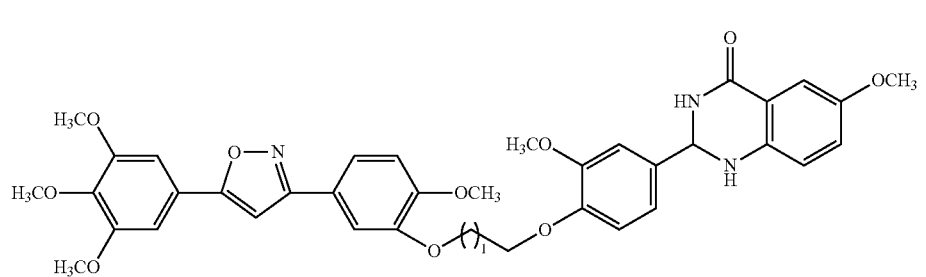
24a
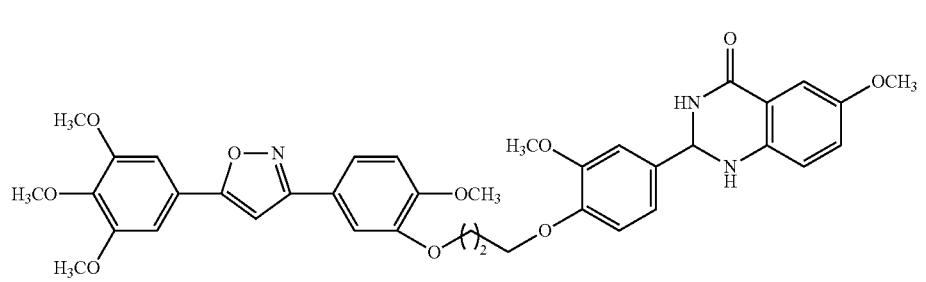
24b
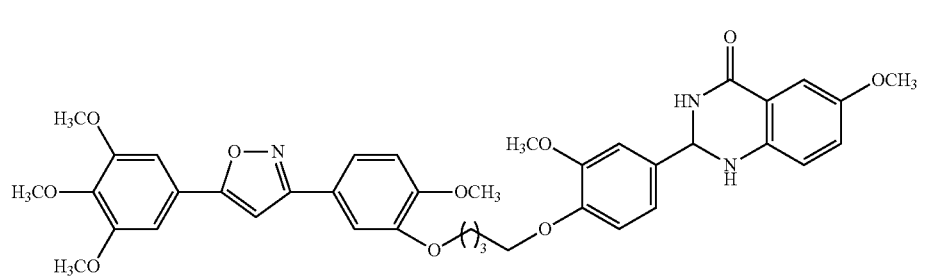
24c
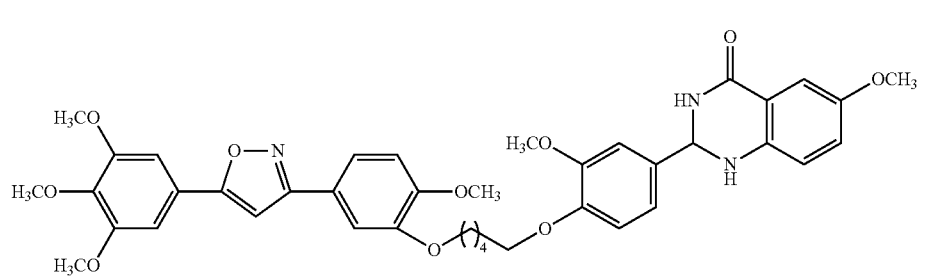
24d

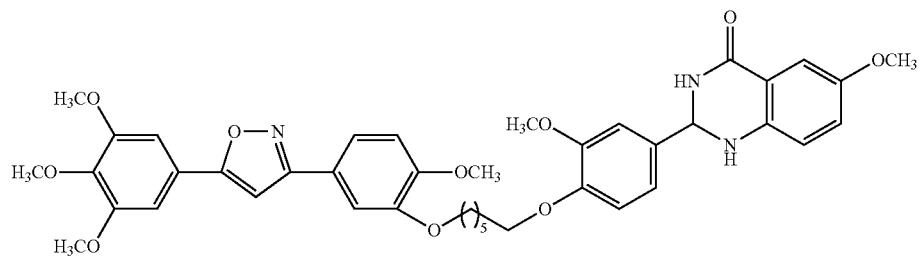
24e
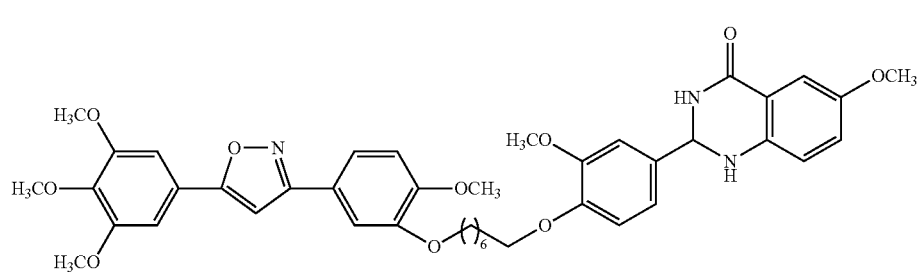
24f
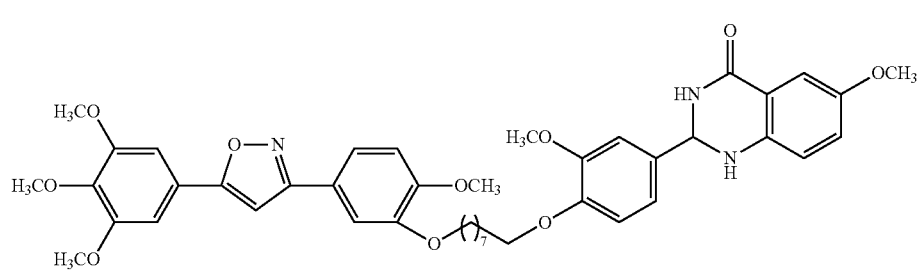
24g
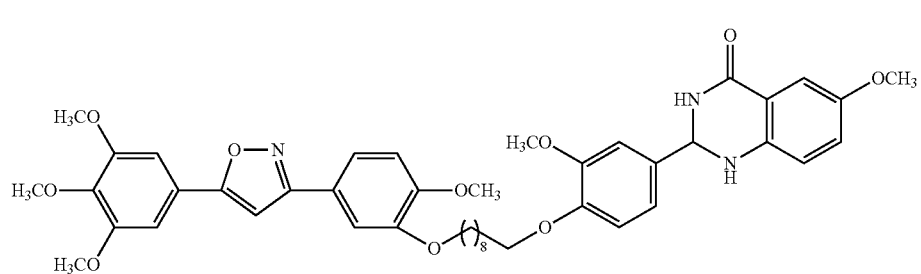
24h
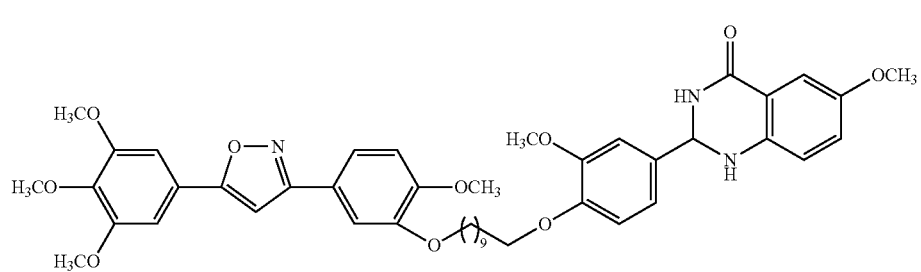
24i
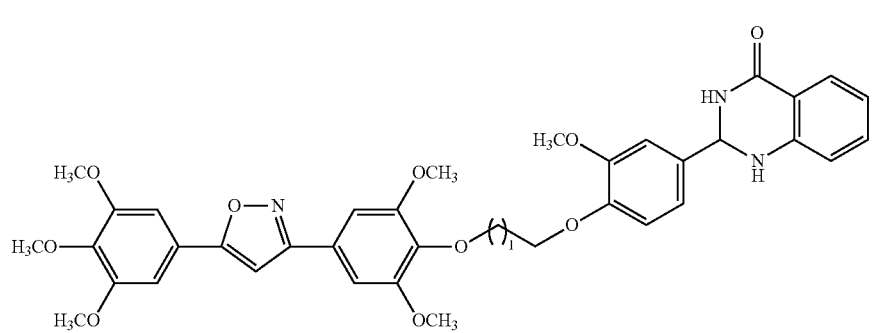
25a

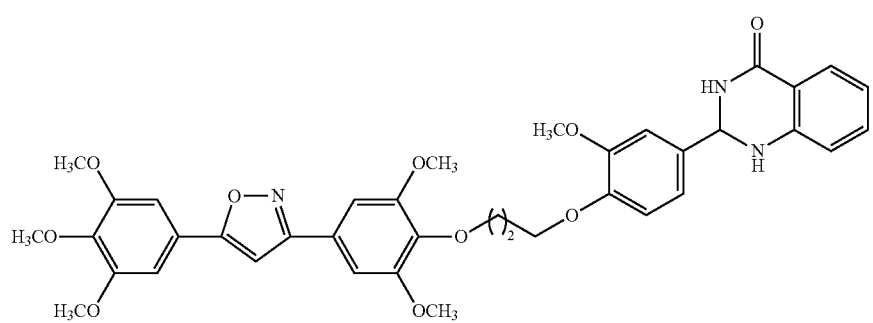
25b
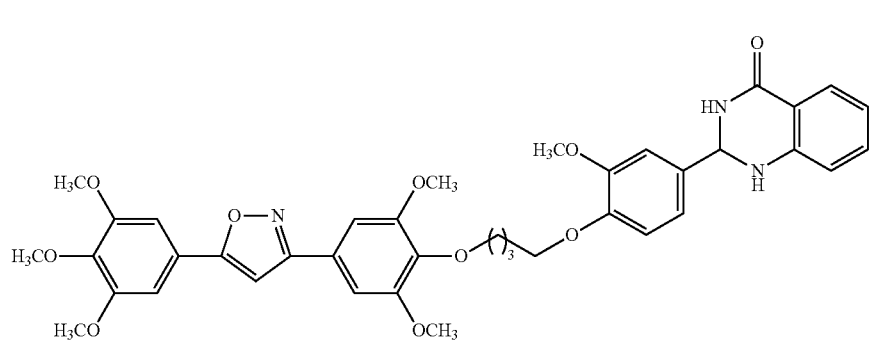
25c
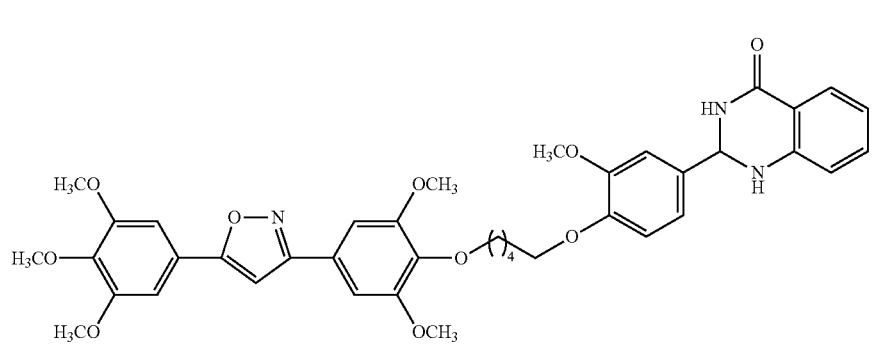
25d
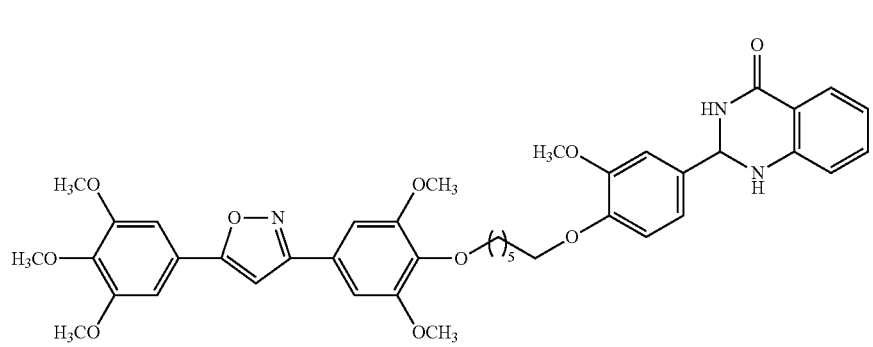
25e
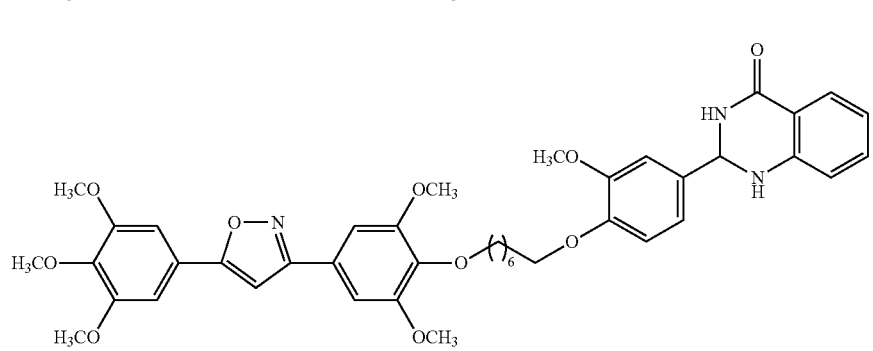
25f

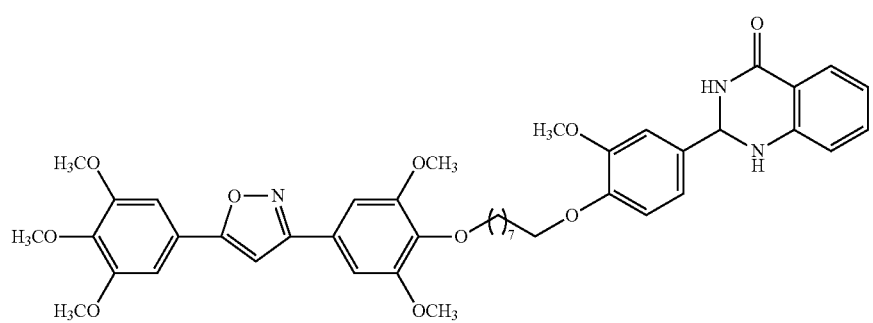
25g
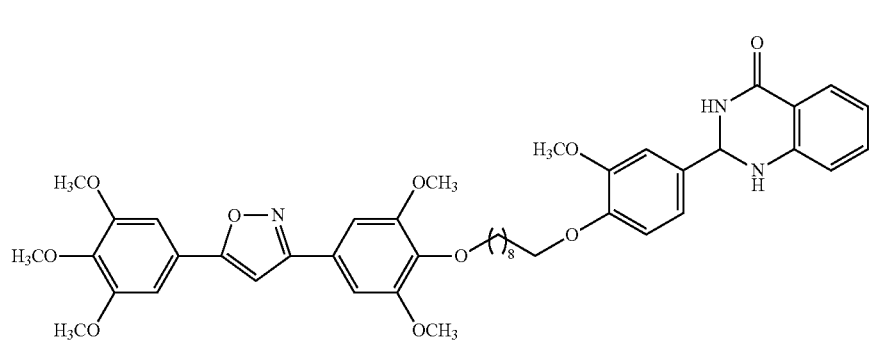
25h
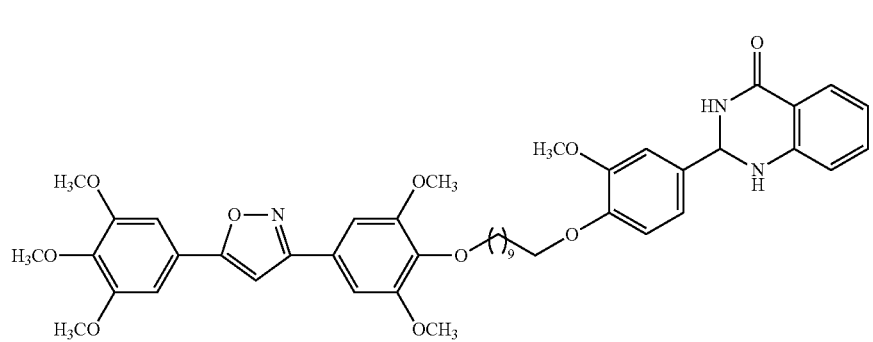
25i
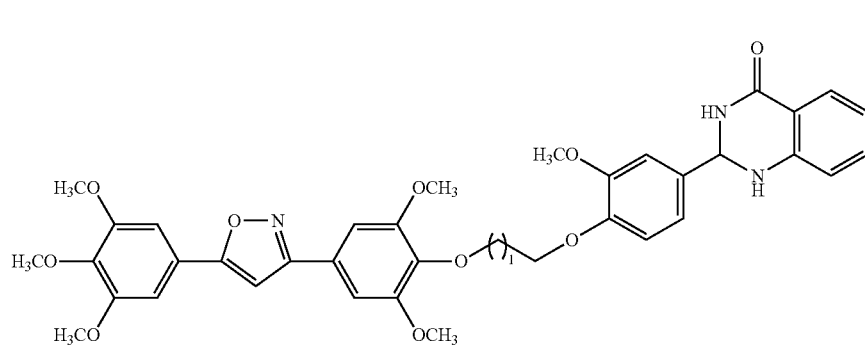
26a
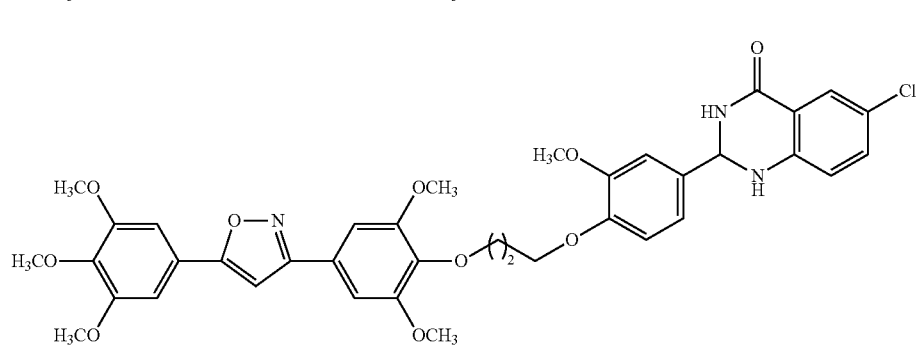
26b

-continued
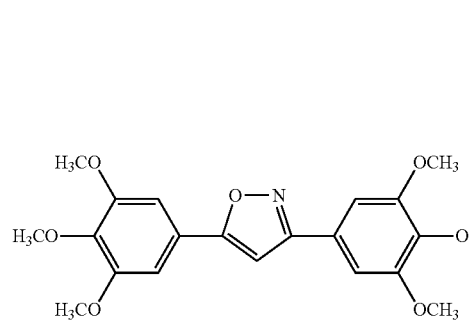
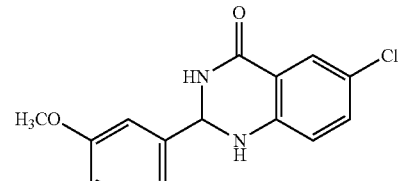
26c
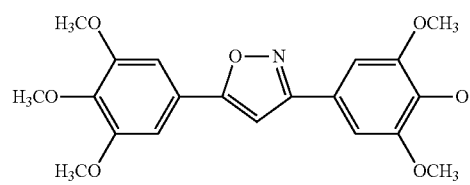
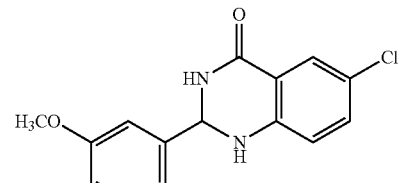
26d
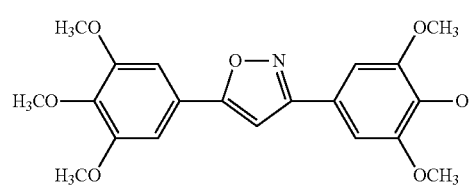
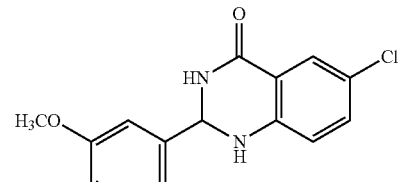
26e
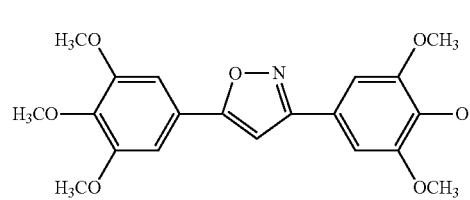
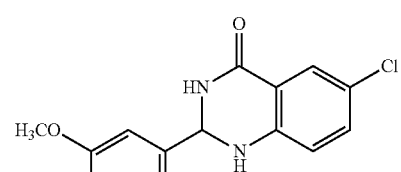
26f
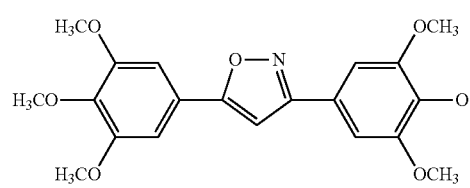
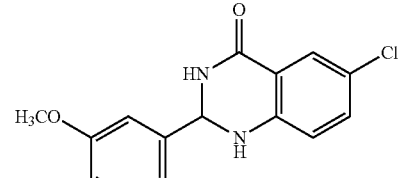
26g -continued
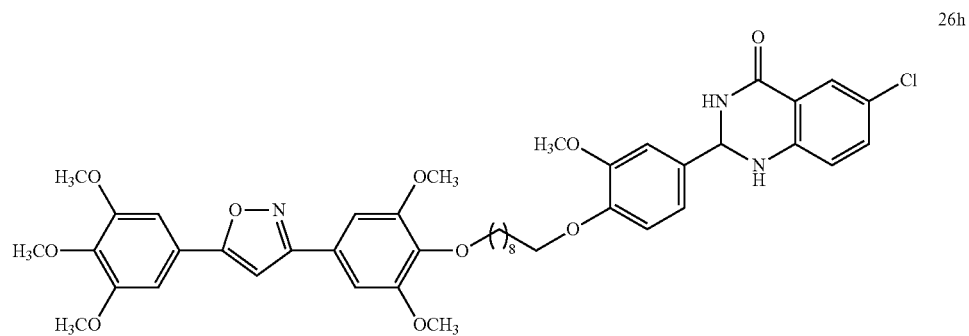
26h
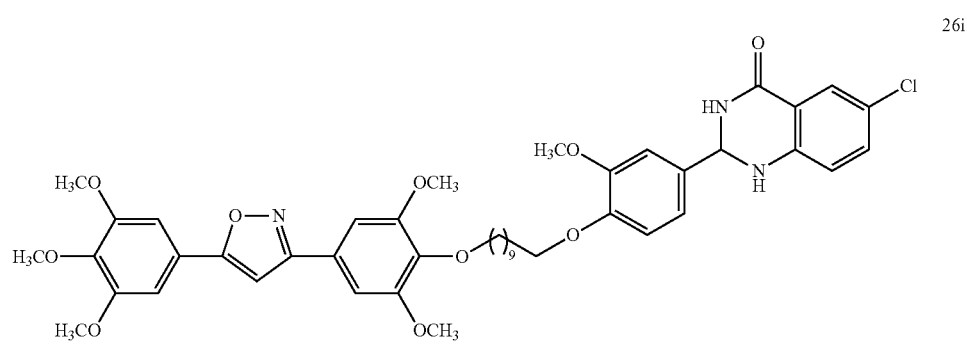
26i
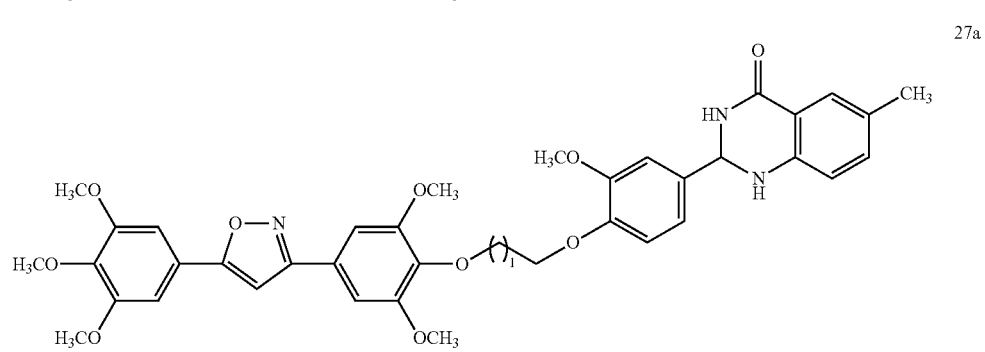
27a
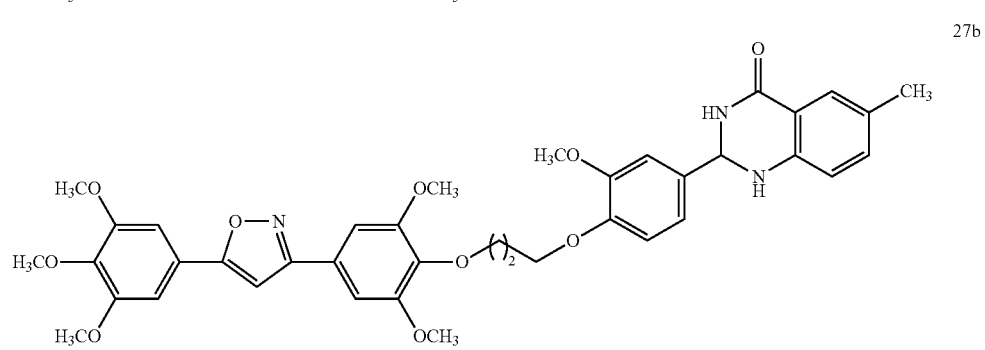
27b
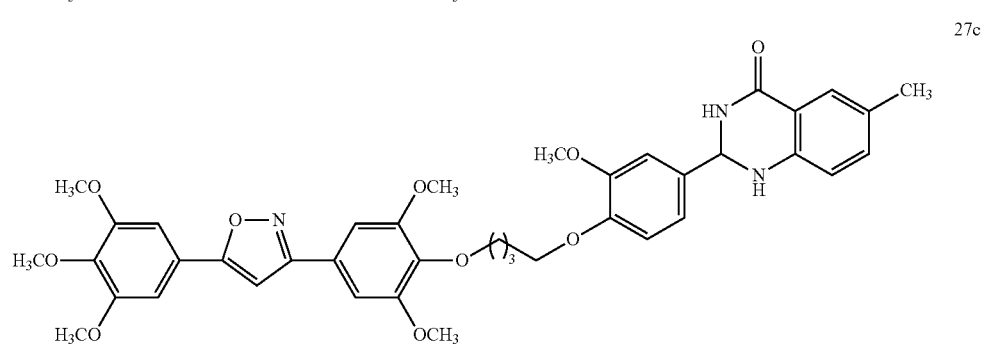
27c

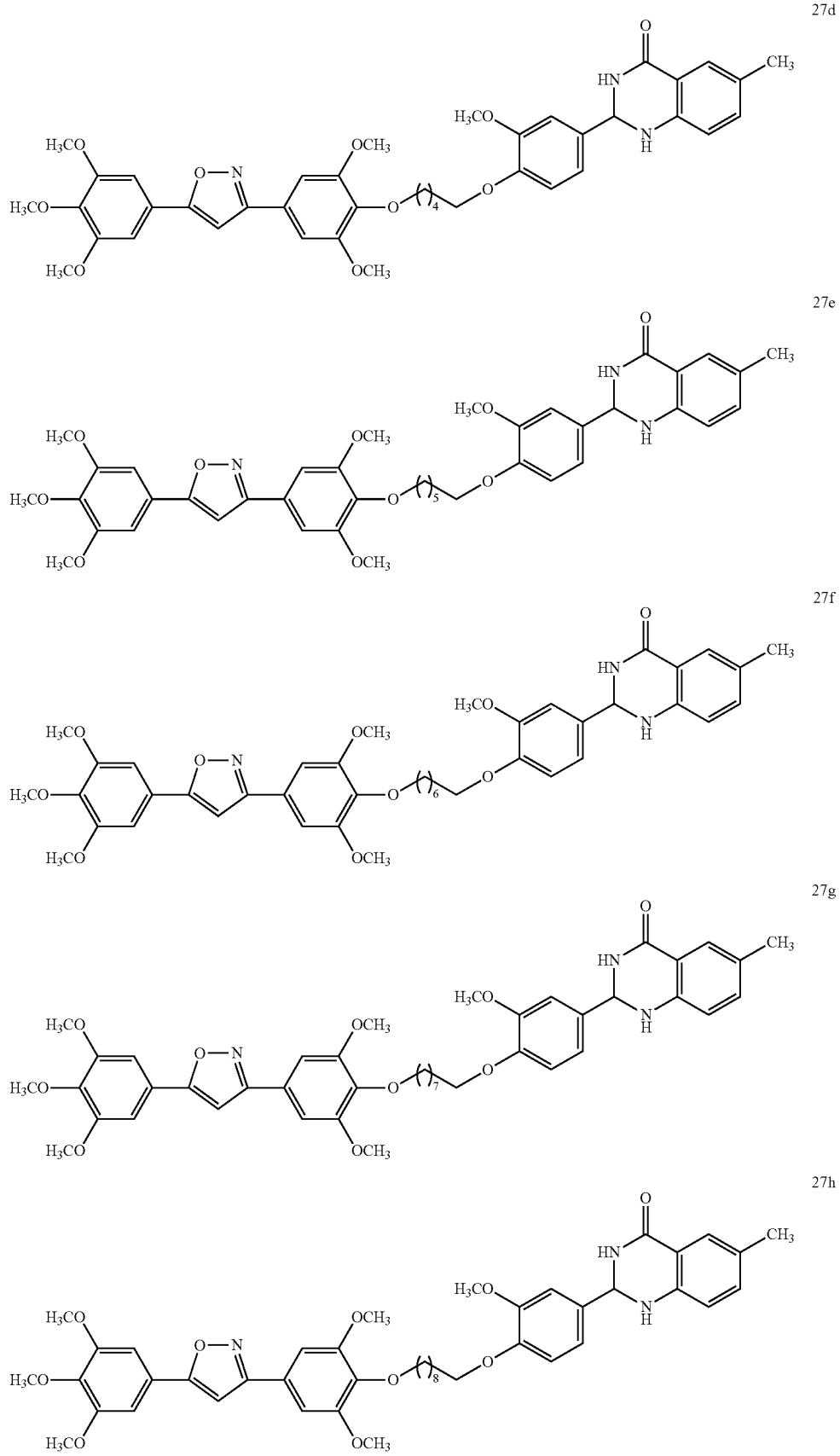

-continued
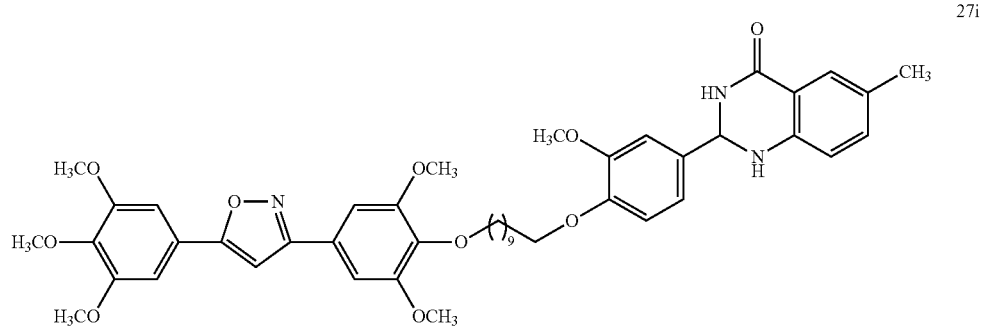
27i
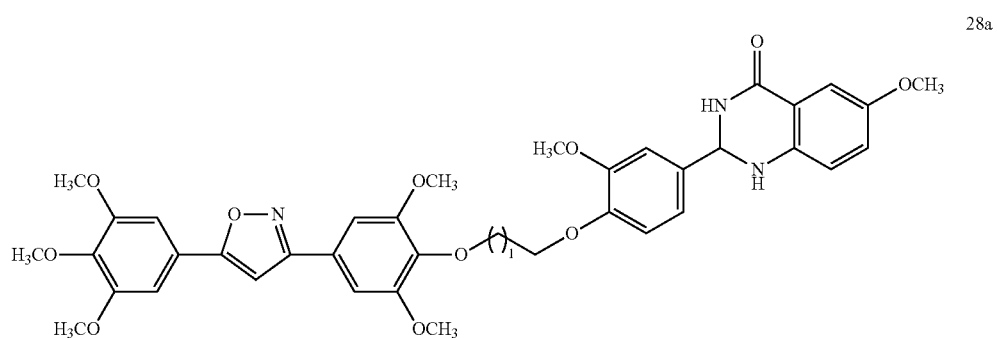
28a
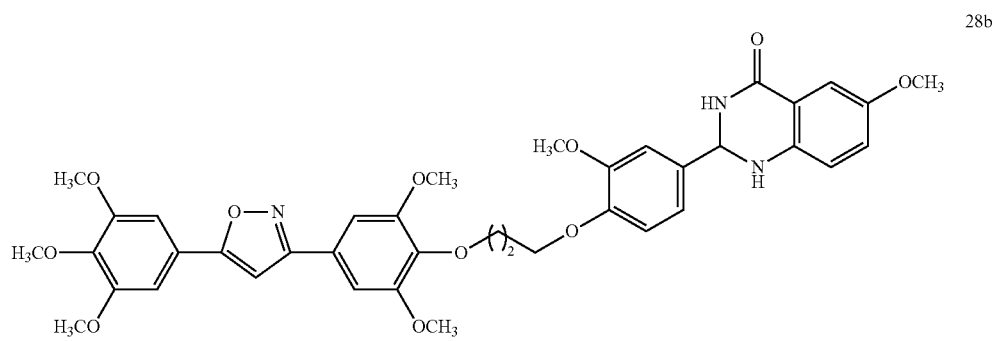
28b
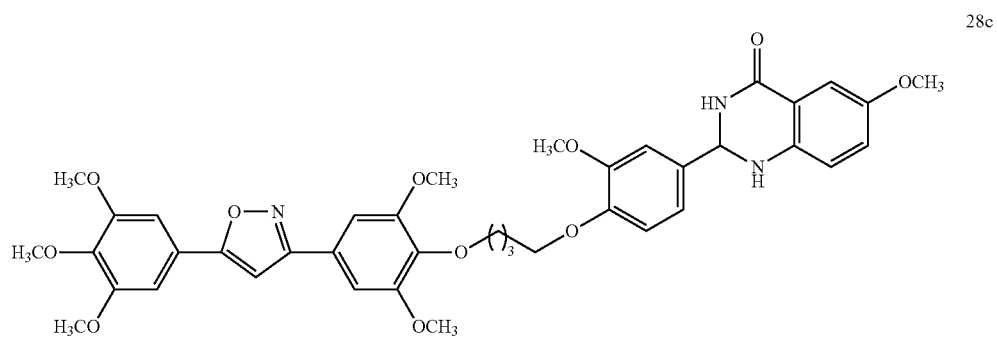
28c
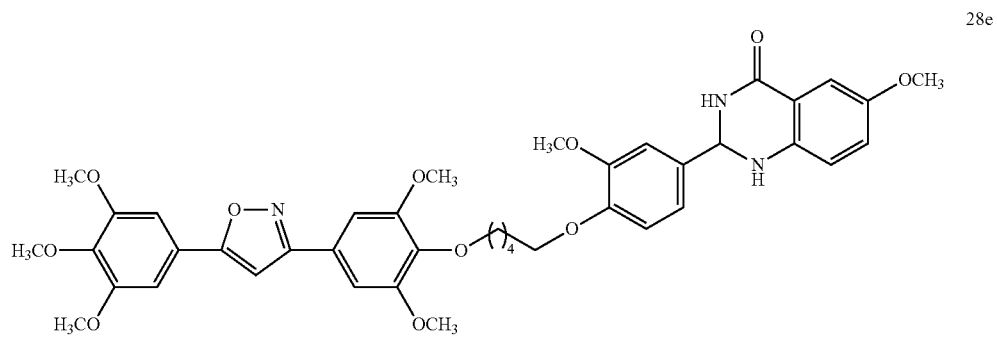
28e -continued
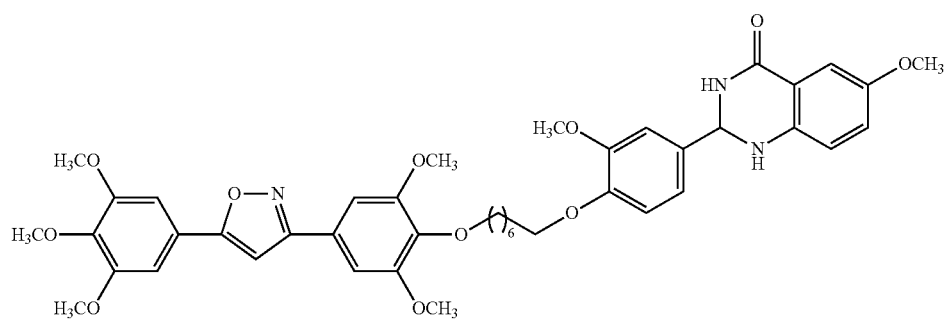
28f
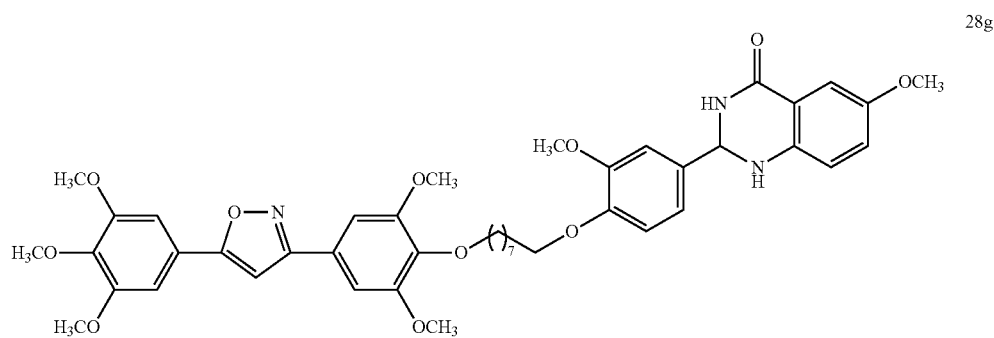
28g
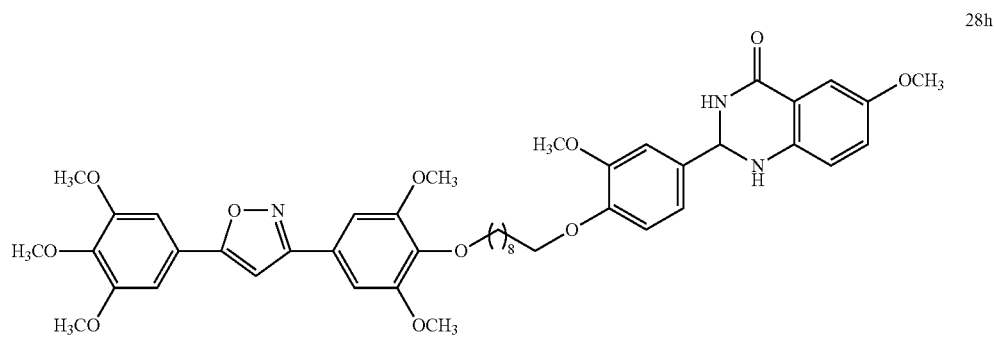
28h
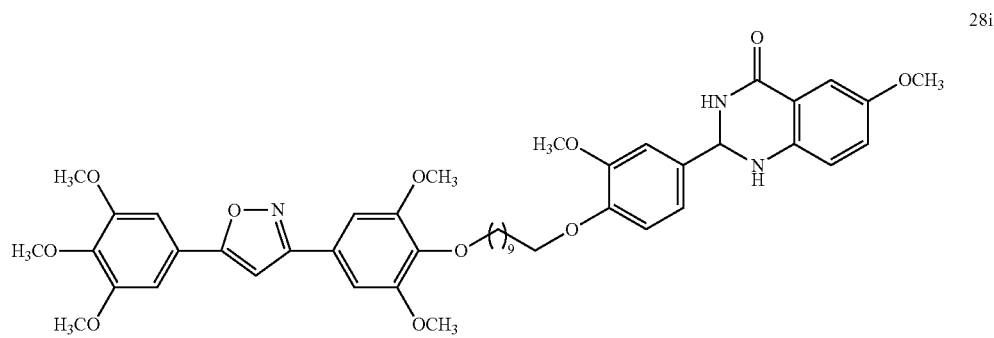
28i
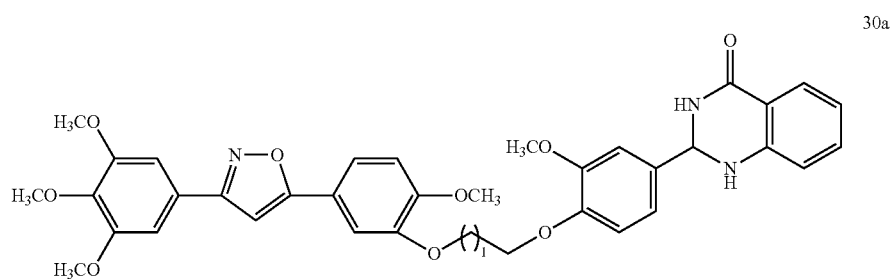
30a -continued
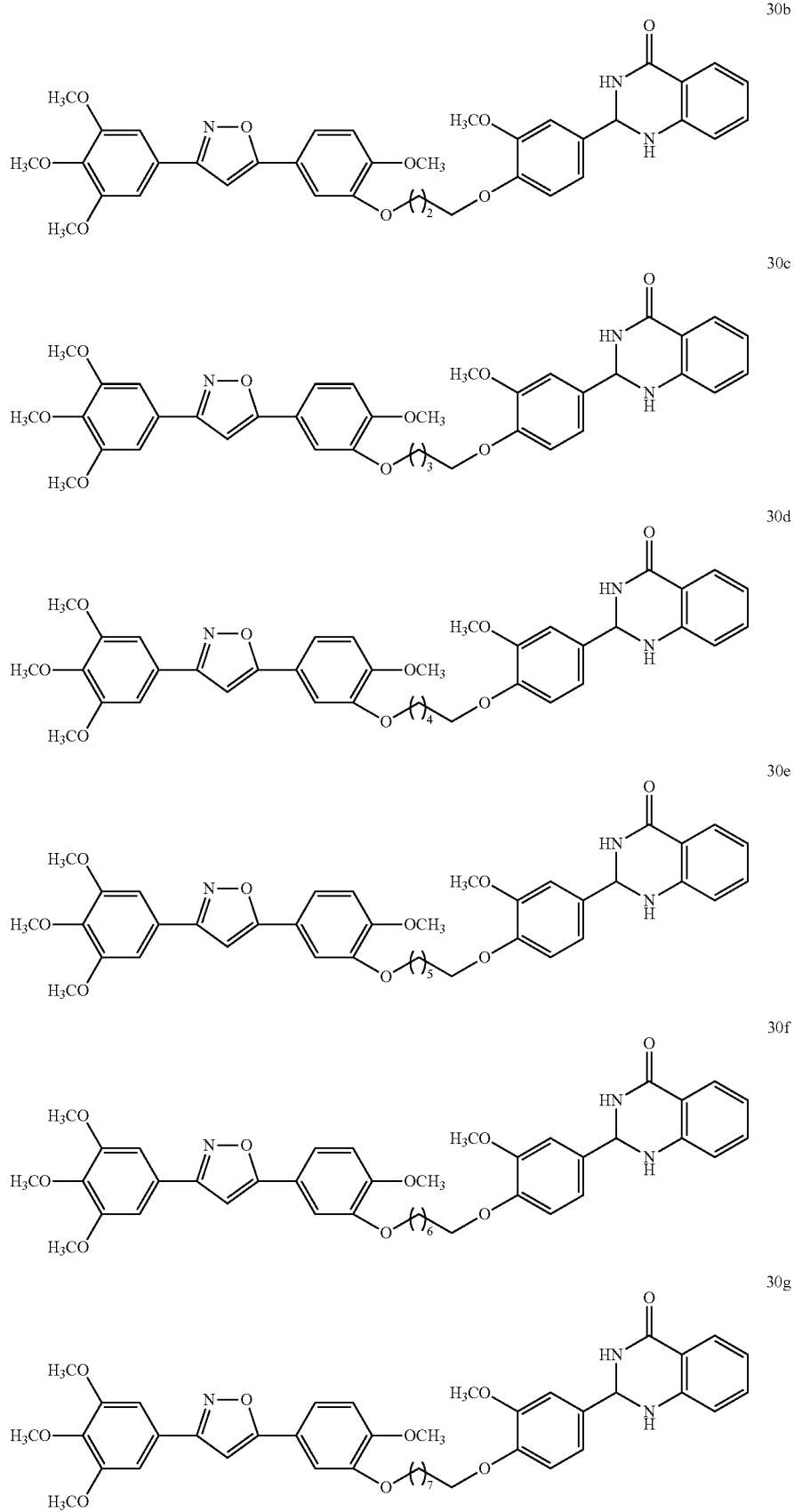

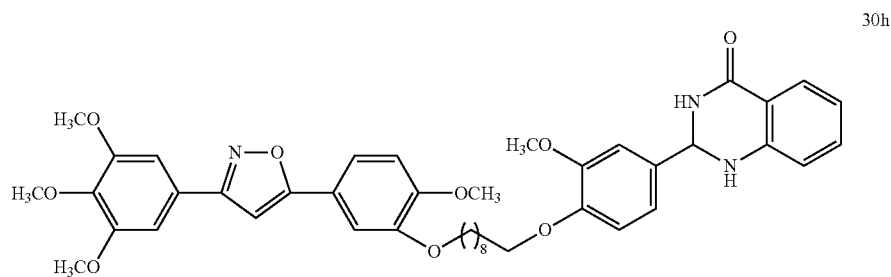
30h
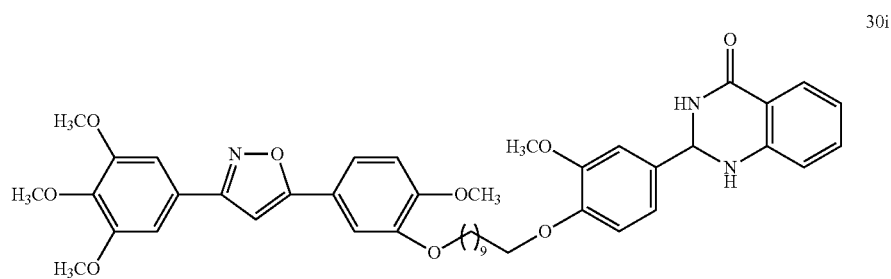
30i
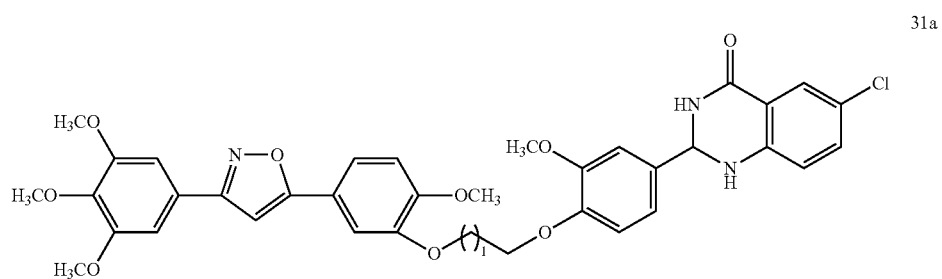
31a
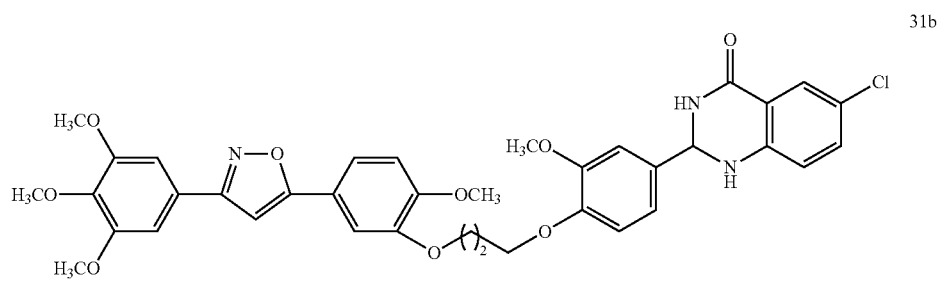
31b
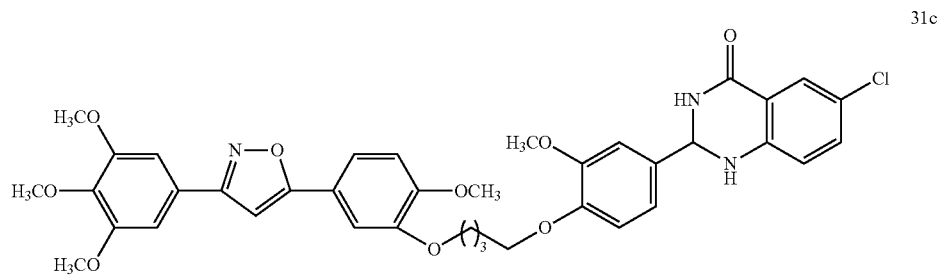
31c
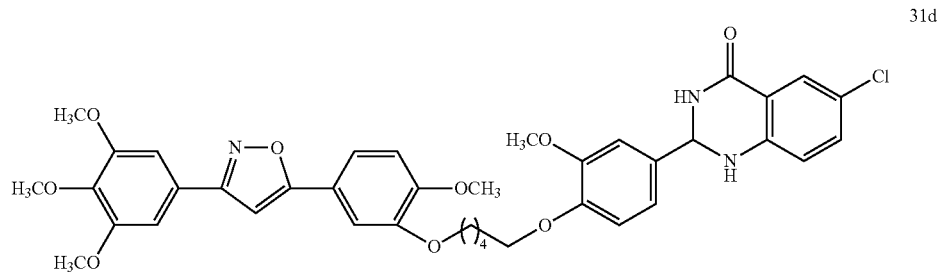
31d

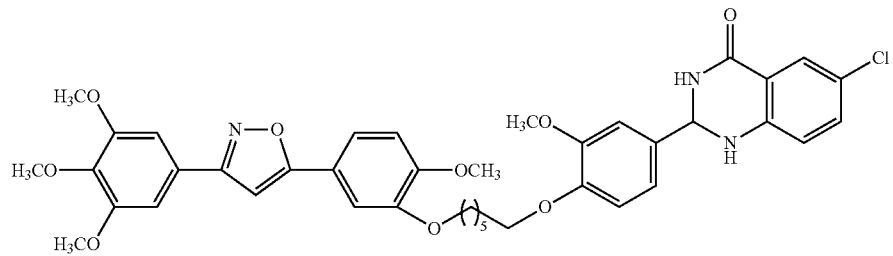
31e
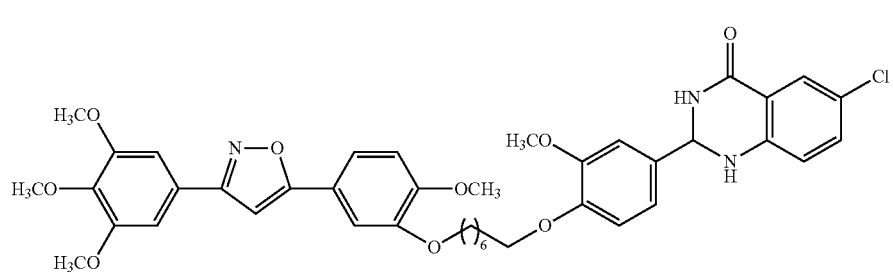
31f
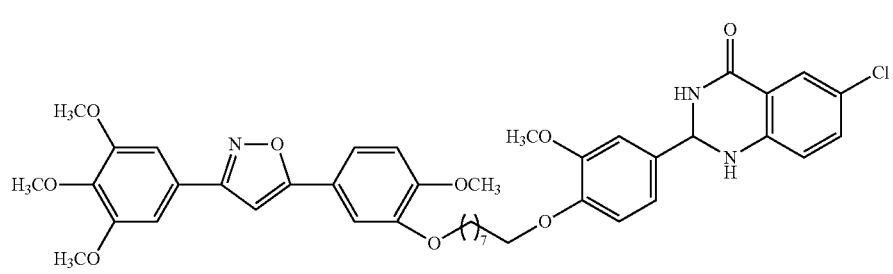
31g
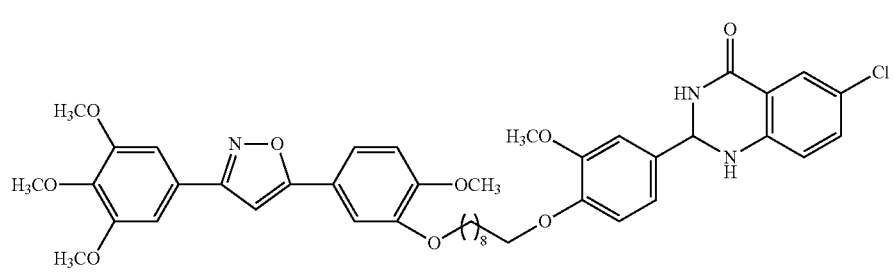
31h
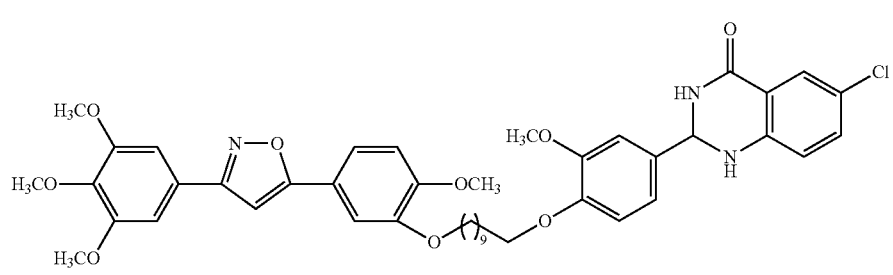
31i
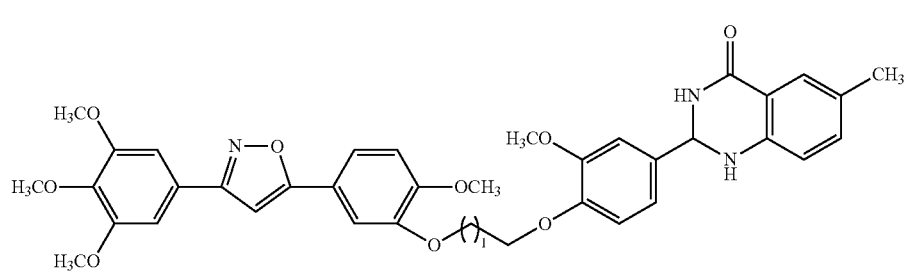
32a

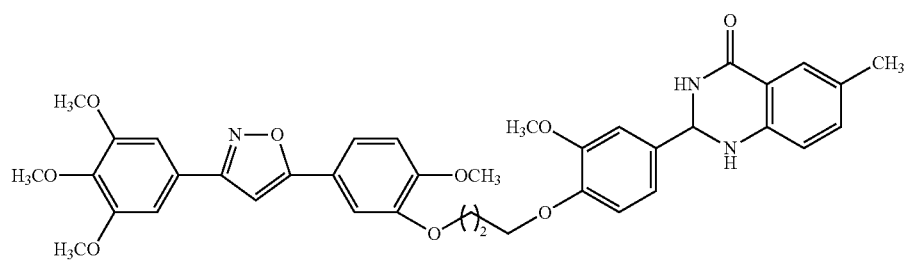
32b
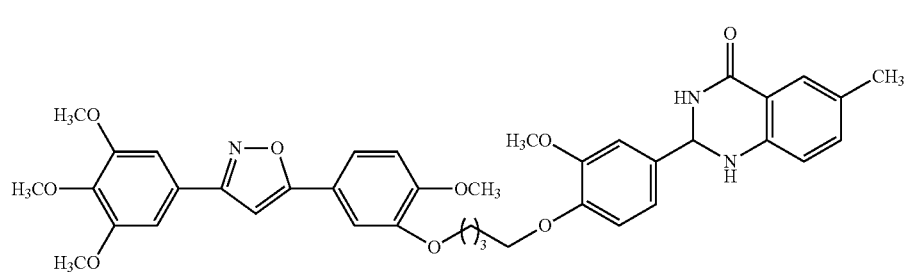
32c
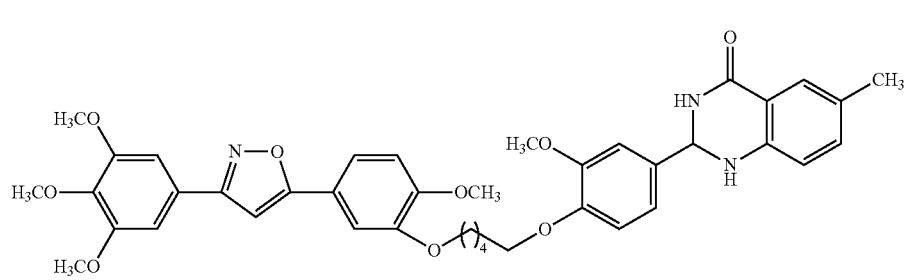
32d
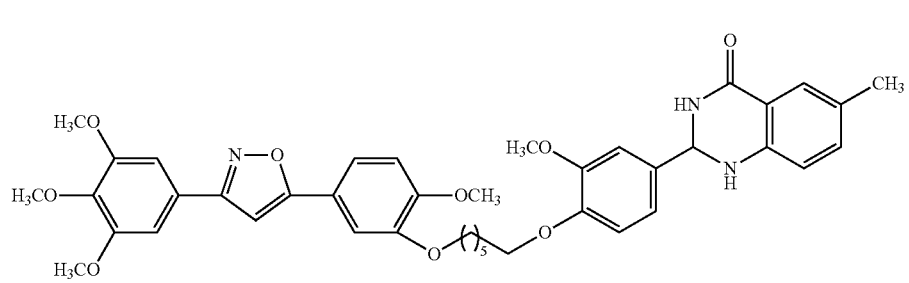
32e
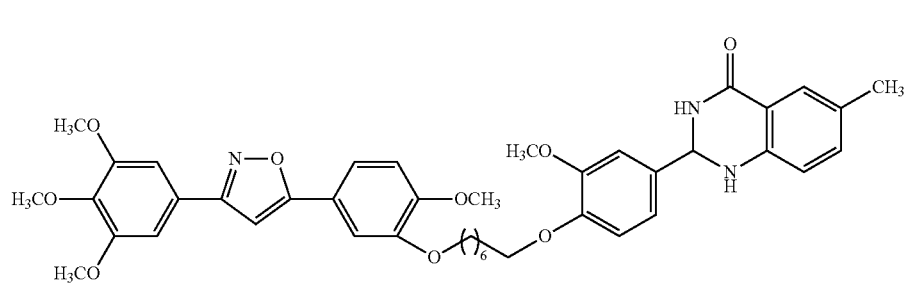
32f
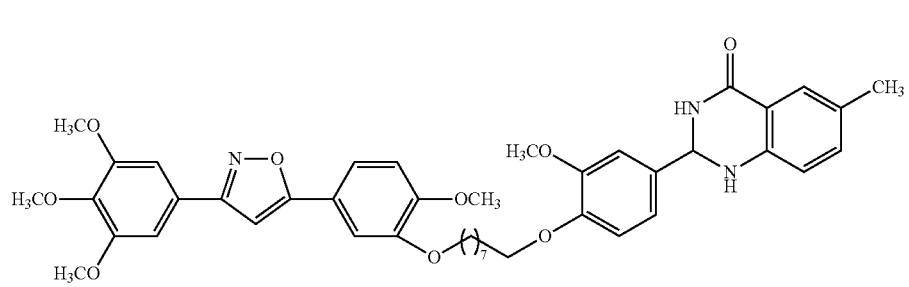
32g 32h
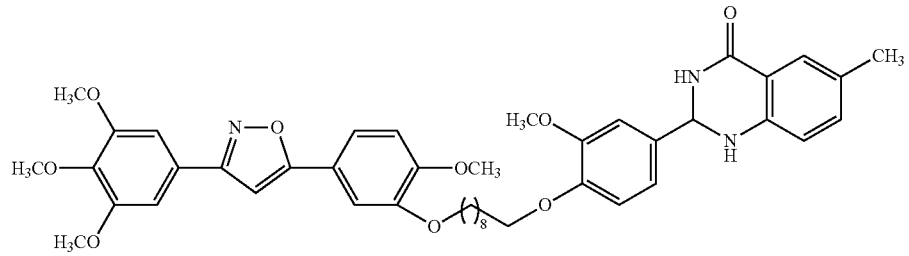
32i
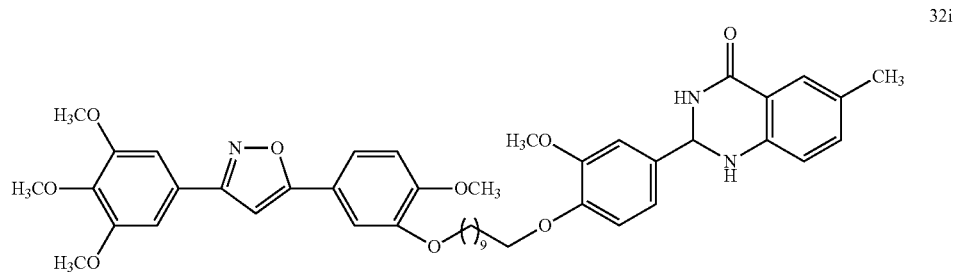
33a
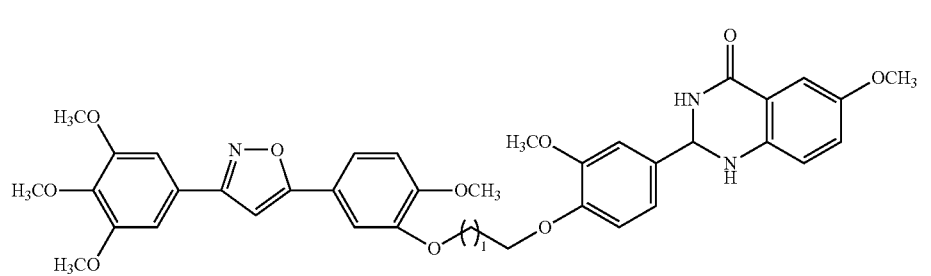
33b
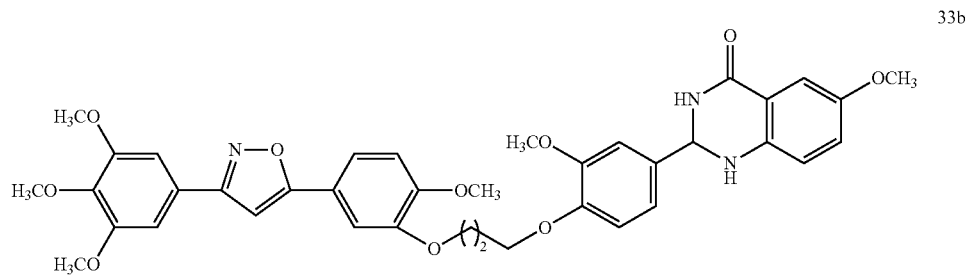
33c
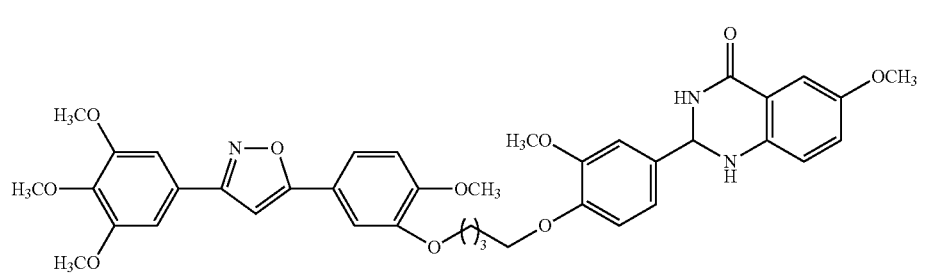
33d
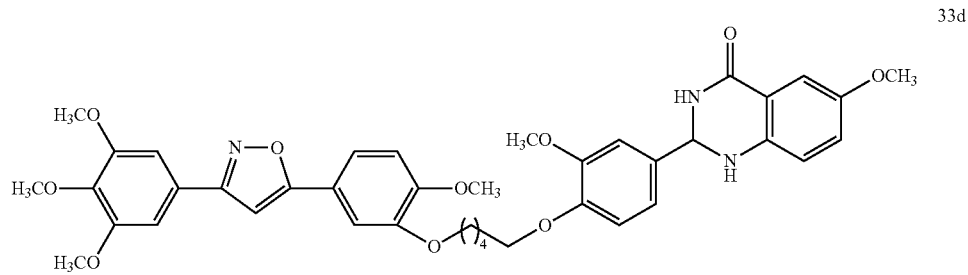

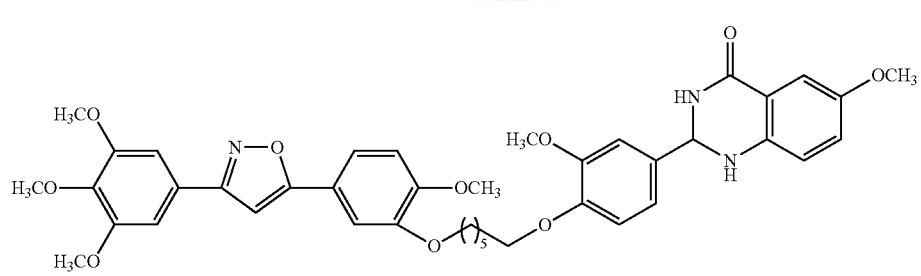
33e
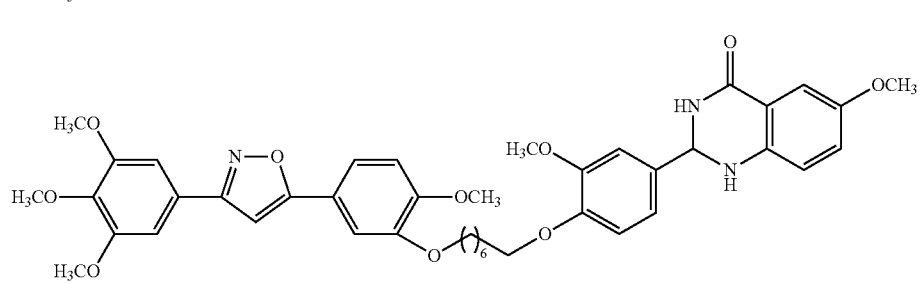
33f
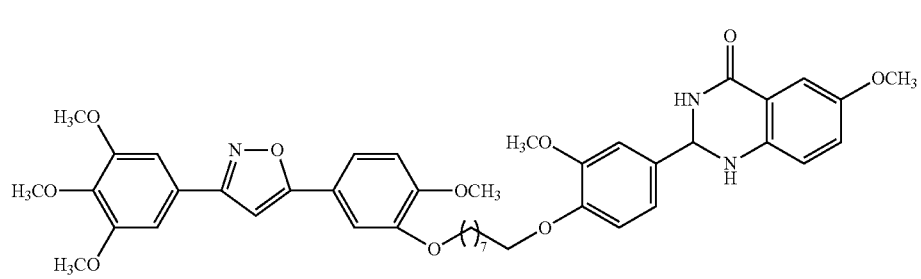
33g
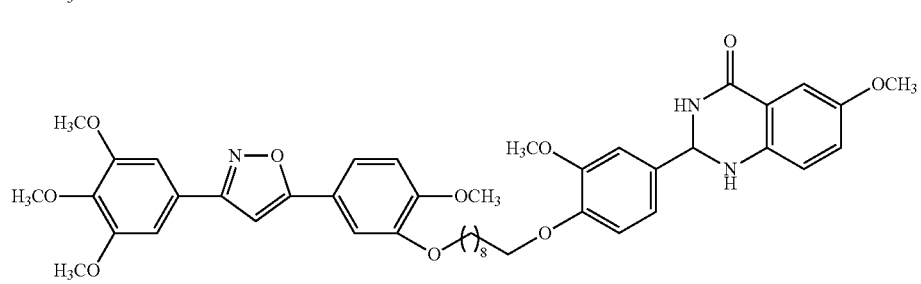
33h
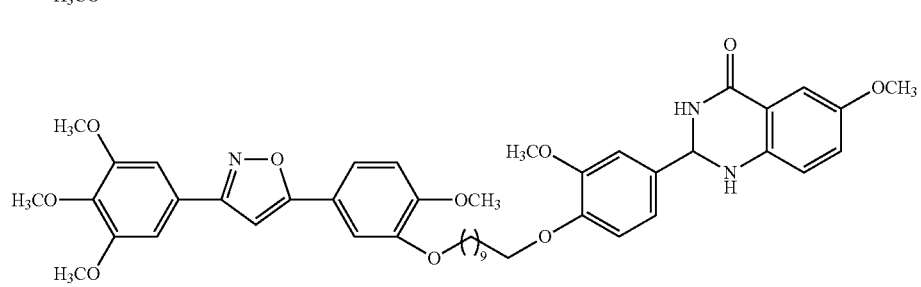
33i
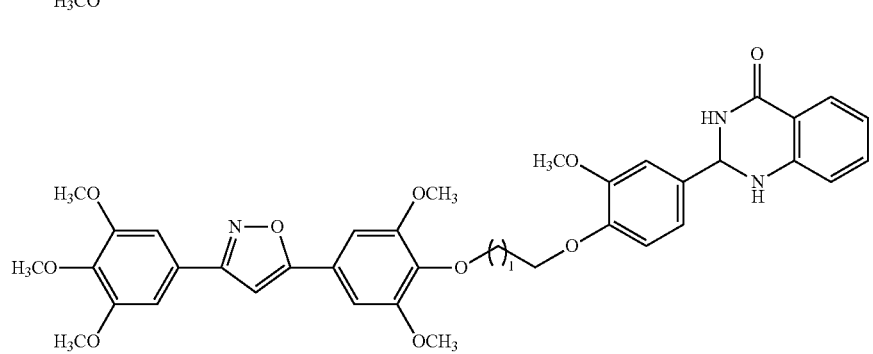
34a

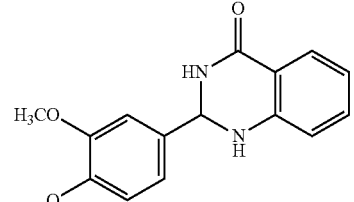
34b
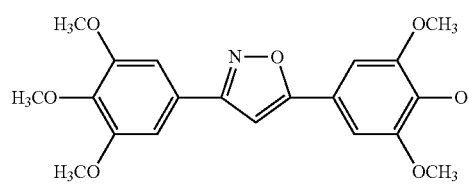
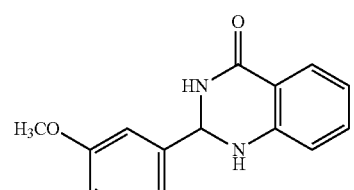
34c
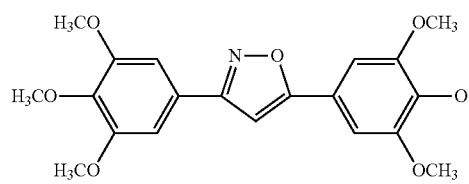
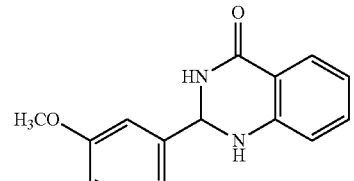
34d
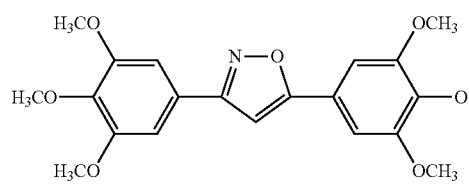
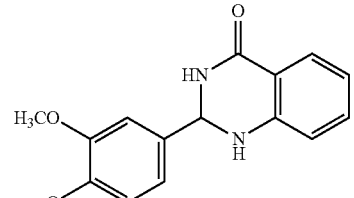
34e
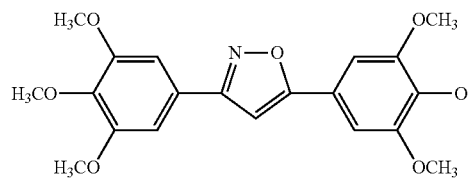
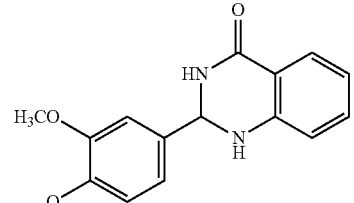
34f
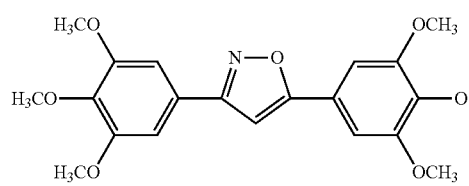

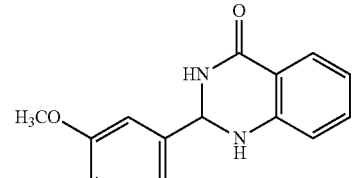
34g
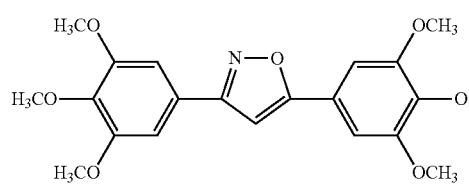
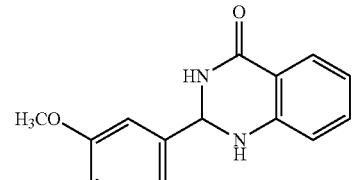
34h
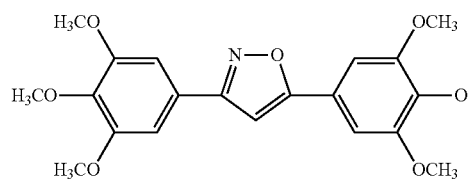
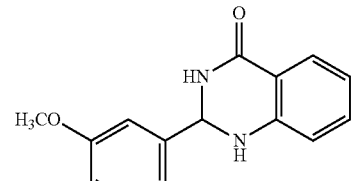
34i
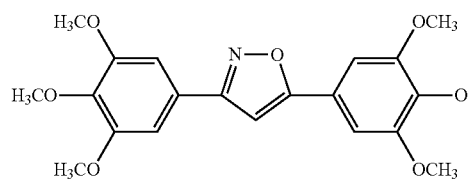
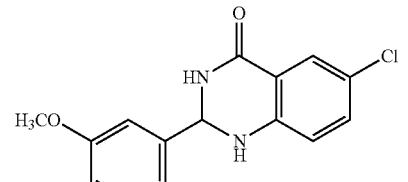
35a
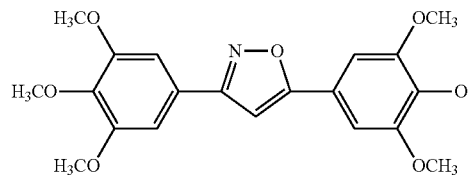
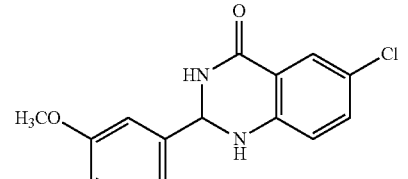
35b
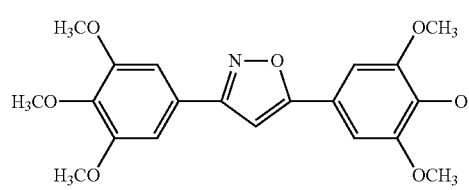

-continued
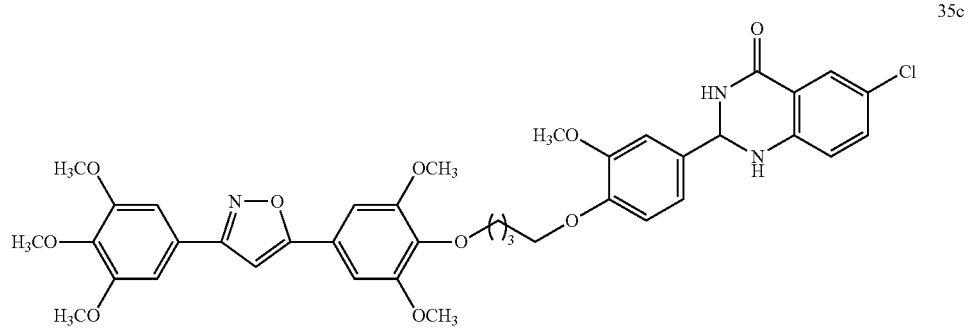
35c
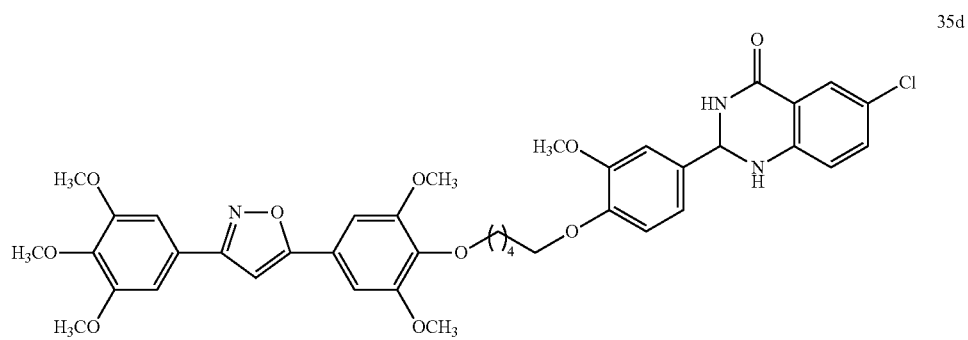
35d
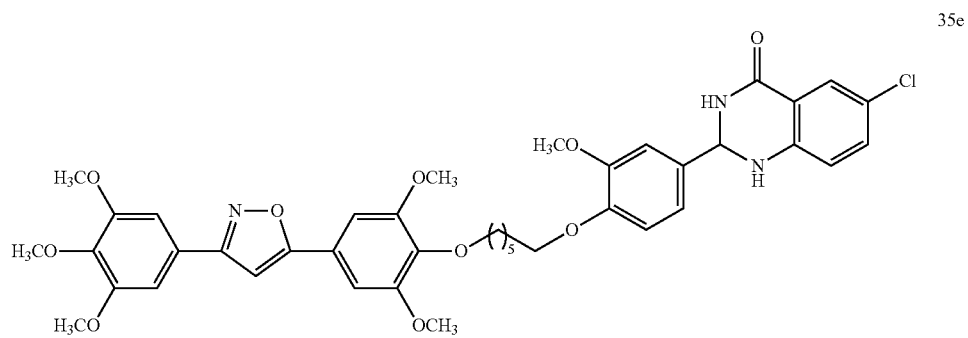
35e
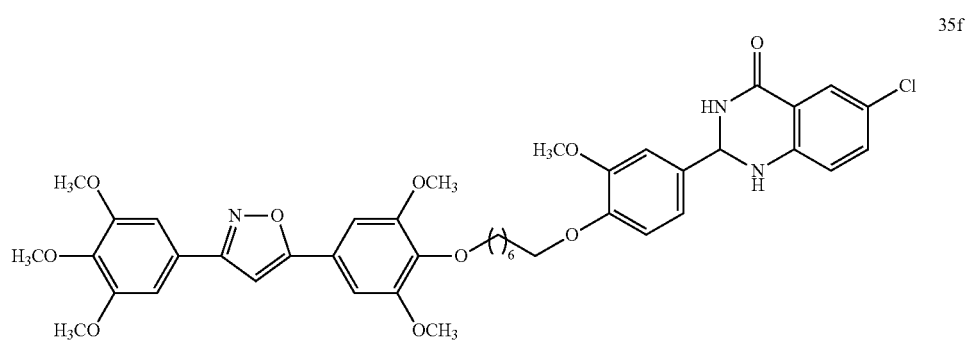
35f
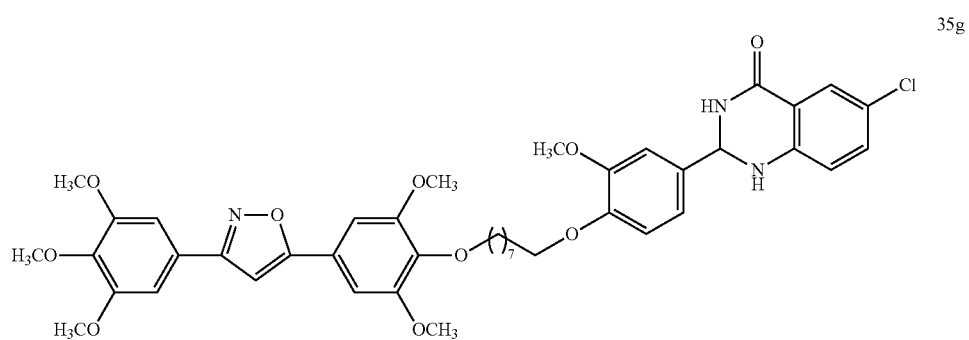
35g

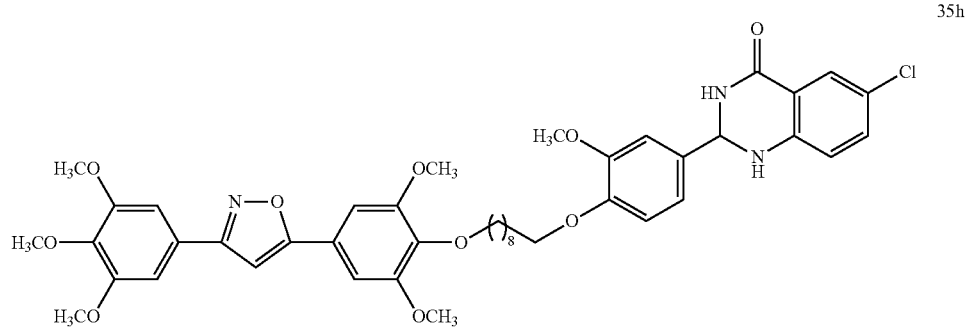
35h
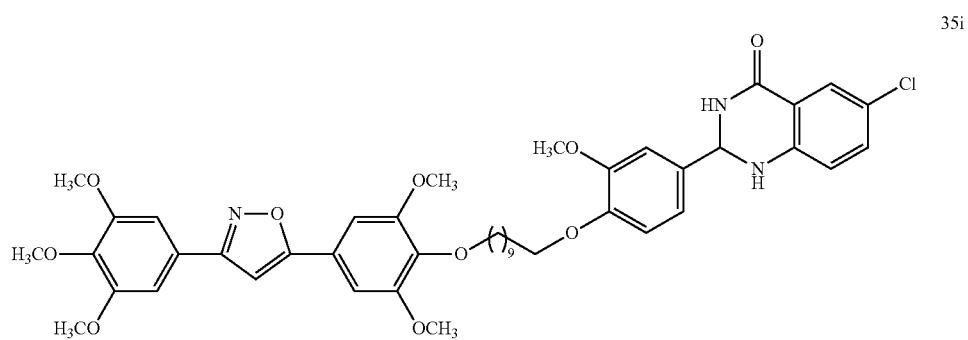
35i
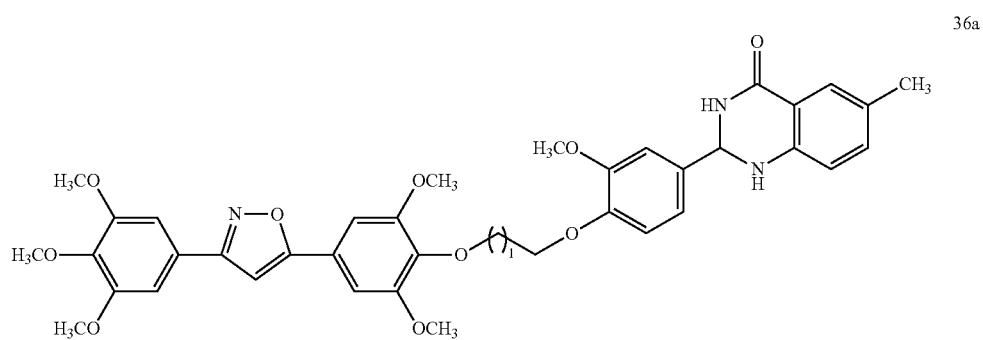
36a
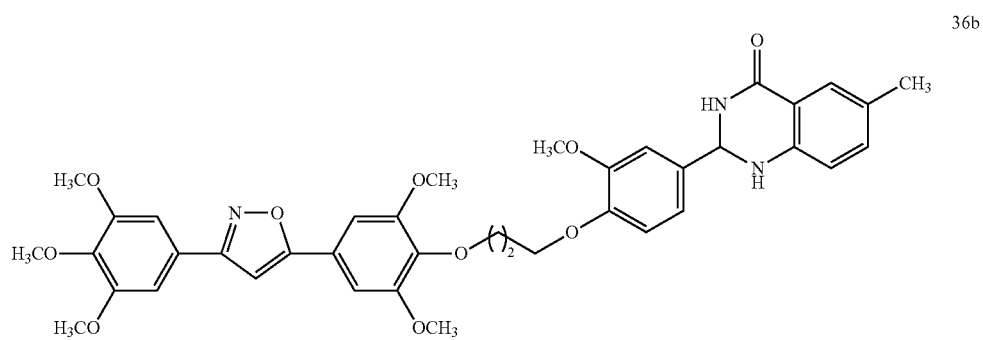
36b
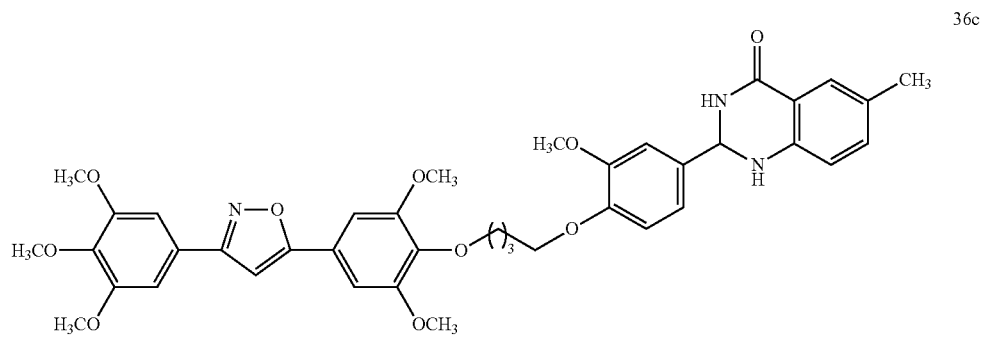
36c

36d
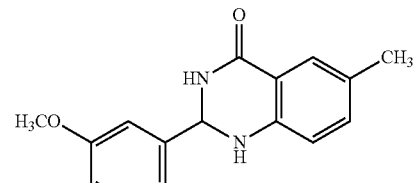
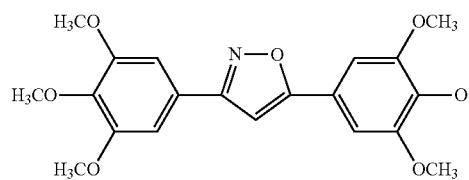
36e
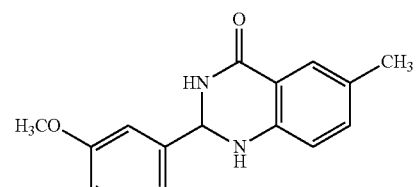
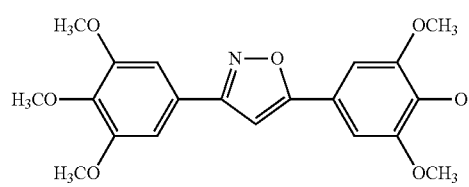
36f
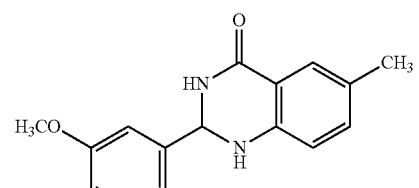
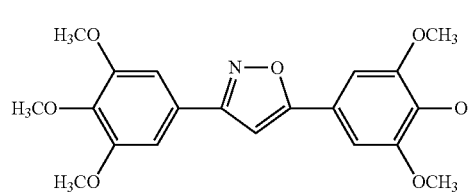
36g
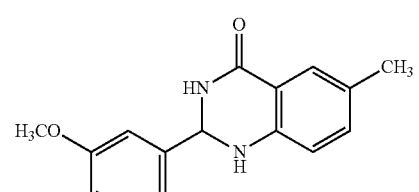
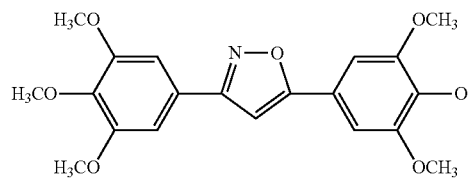
36h
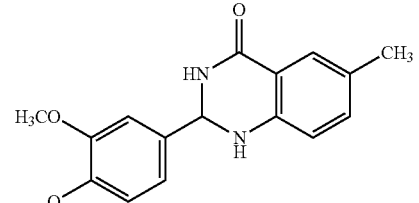
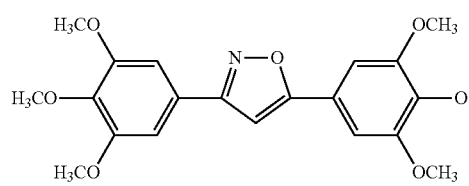

-continued
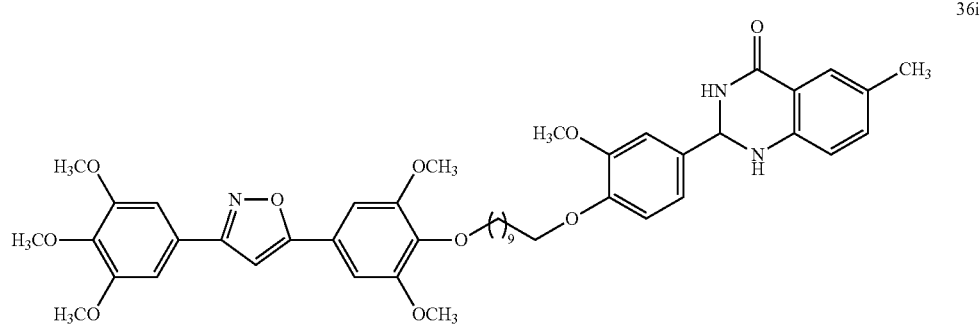
36i
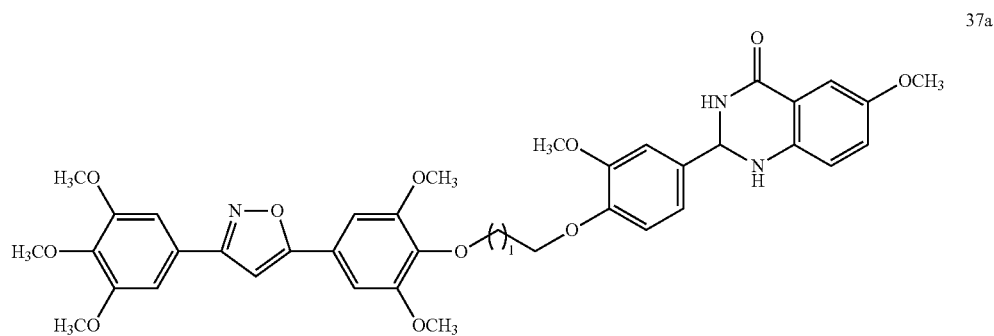
37a
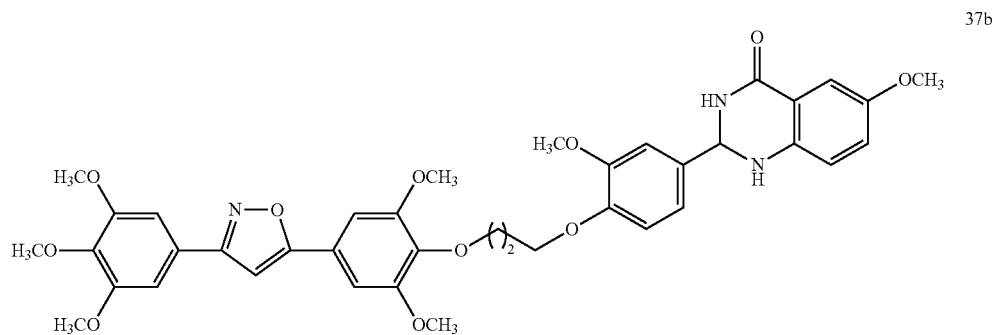
37b
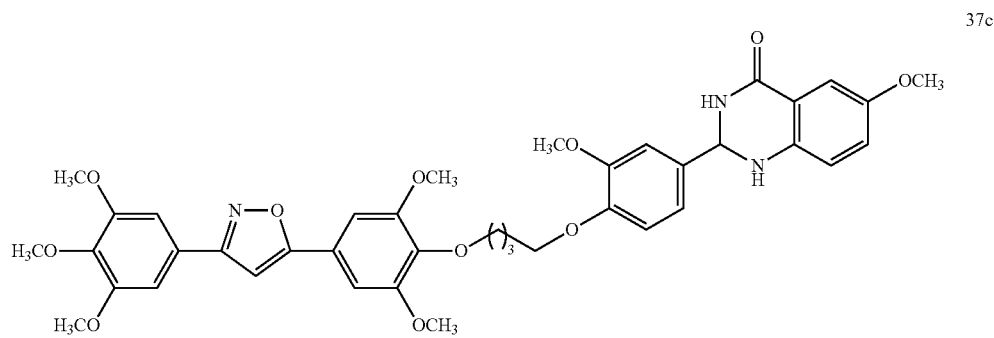
37c
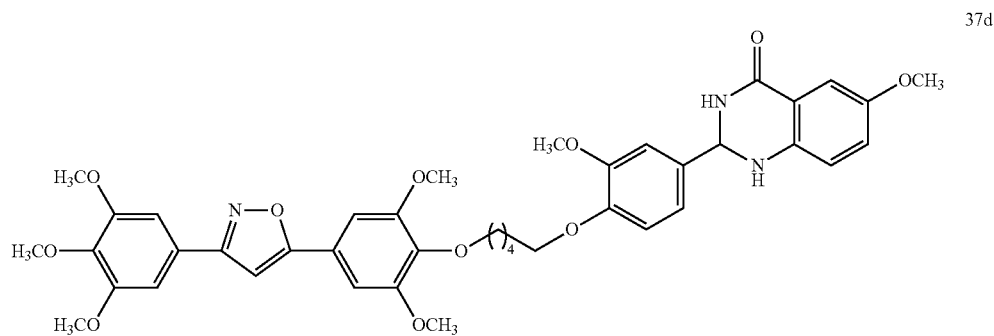
37d -continued
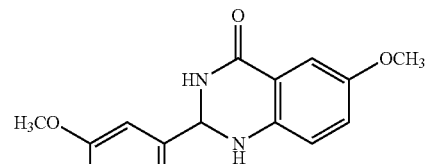
37e
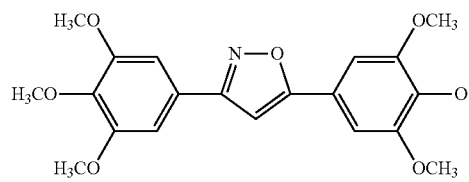
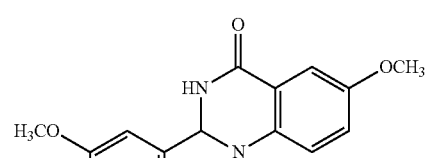
37f
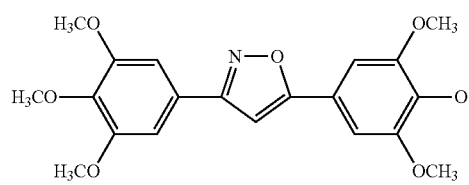
37g
37h
37i
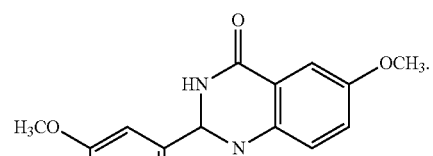
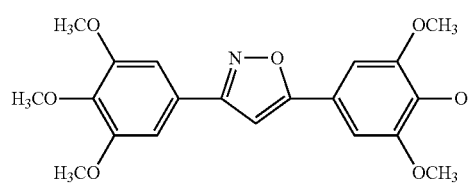
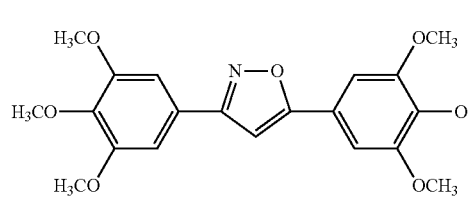

5. A process for the preparation of a isoxazole/isoxazoline/combretastatin linked dihydroquinazolinone compound of general formulae A

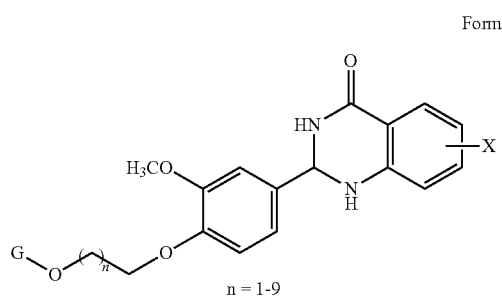

Formula A n = 1-9

Where in G=

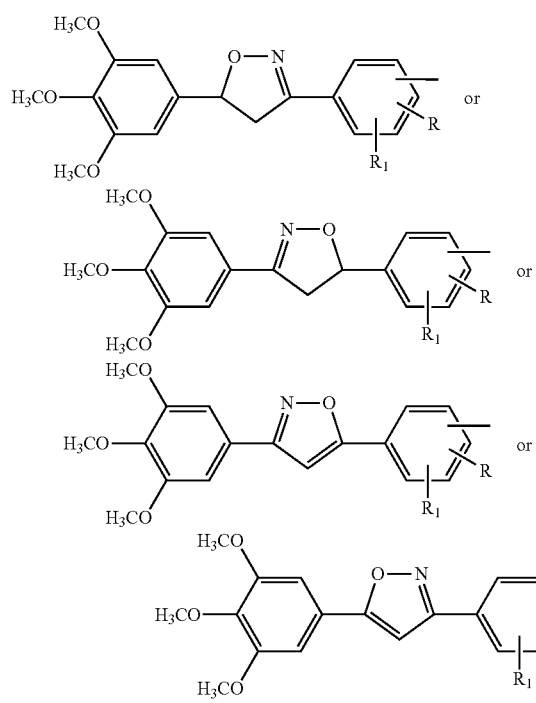

If R = 3——OCH₃, R₁ = 5——OCH₃
If R = 4——OCH₃, R₁ = 5——H
X = H, Cl, CH₃, OCH₃ said process comprising:
reacting a 2-[4-(n-Bromo-alkyloxy)-3-methoxy-phenyl]-2,3-dihydro-1H-quinazolin-4-one of formula 2

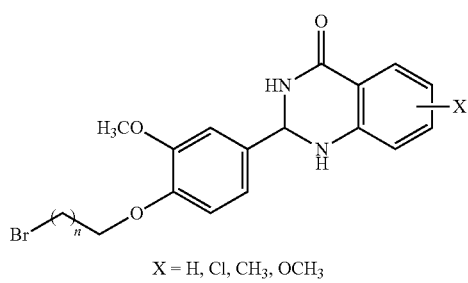

X = H, Cl, CH₃, OCH₃
n = 1-9 with a compound of formulae 1a, 1b, 11a, 11b, 20a, 20b, 29a, or 29b,

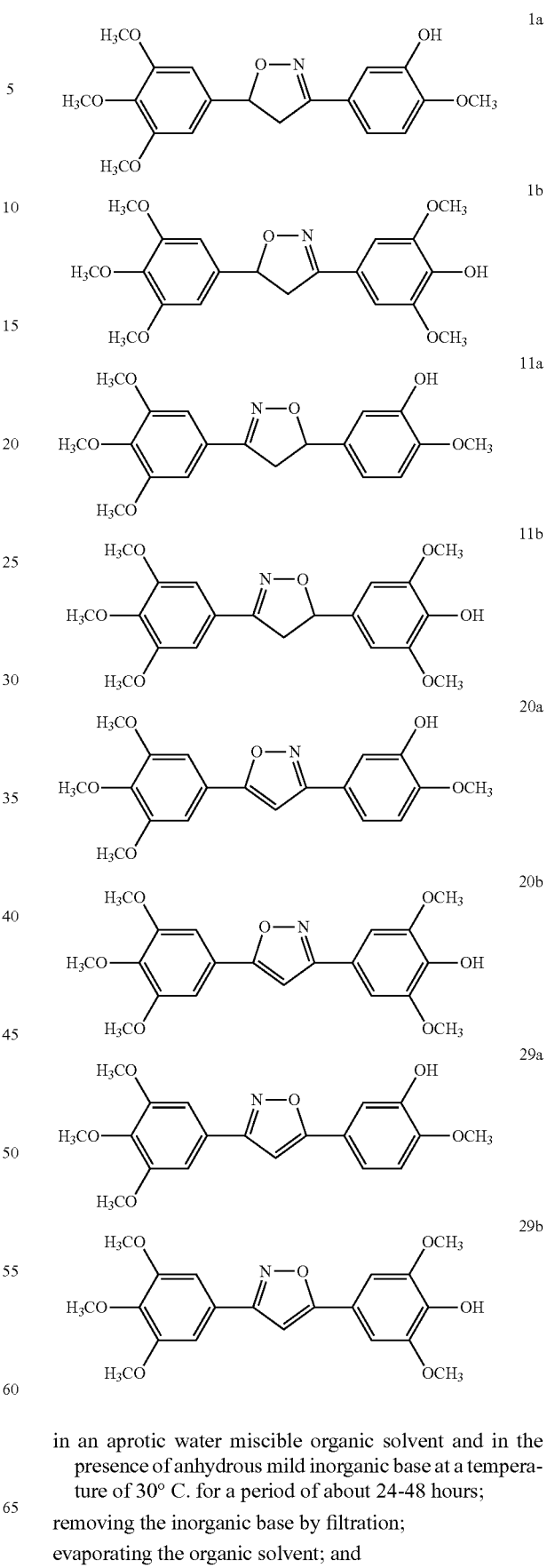

in an aprotic water miscible organic solvent and in the presence of anhydrous mild inorganic base at a temperature of 30° C. for a period of about 24-48 hours;
removing the inorganic base by filtration;
evaporating the organic solvent; and purifying the resultant crude product by column chromatography to obtain an isoxazole/isoxazoline/combretastatin linked dihydroquinazolinone compound of general formula A.

6. The process as claimed in claim 5, wherein the aprotic water miscible organic solvent is selected from the group consisting of dimethylformamide, acetone, acetonitrile and dimethyl sulfoxide.

7. The process as claimed in claim 5, wherein the anhydrous mild inorganic base is selected from the group consisting of sodium carbonate or potassium carbonate.

8. A pharmaceutical composition comprising a compound of formula A according to claim 1 and a pharmaceutically acceptable carrier.

\* \* \* \* \*